(12) United States Patent
Alam

(10) Patent No.: US 12,275,796 B2
(45) Date of Patent: Apr. 15, 2025

(54) INTERFERON-ASSOCIATED ANTIGEN BINDING PROTEINS AND USES THEREOF

(71) Applicants: EVOTEC INTERNATIONAL GmbH, Hamburg (DE); SANOFI, Paris (FR)

(72) Inventor: Antoine Alam, Lyons (FR)

(73) Assignees: EVOTEC INTERNATIONAL GmbH, Hamburg (DE); SANOFI, Paris (FR)

( * ) Notice: Subject to any disclaimer, the term of this patent is extended or adjusted under 35 U.S.C. 154(b) by 0 days.

(21) Appl. No.: 18/152,969

(22) Filed: Jan. 11, 2023

(65) Prior Publication Data

US 2023/0279137 A1 Sep. 7, 2023

Related U.S. Application Data

(63) Continuation of application No. 17/756,803, filed as application No. PCT/EP2020/083745 on Nov. 27, 2020.

(30) Foreign Application Priority Data

Dec. 3, 2019 (EP) .................................... 19306552
Dec. 4, 2019 (EP) .................................... 19306573

(51) Int. Cl.
*A61K 39/395* (2006.01)
*A61K 38/21* (2006.01)
(Continued)

(52) U.S. Cl.
CPC .......... *C07K 16/2878* (2013.01); *A61P 31/20* (2018.01); *C07K 14/555* (2013.01);
(Continued)

(58) Field of Classification Search
None
See application file for complete search history.

(56) References Cited

U.S. PATENT DOCUMENTS 4,868,116 A 9/1989 Morgan et al.
4,980,286 A 12/1990 Morgan et al.
(Continued)

FOREIGN PATENT DOCUMENTS

CN 104379169 A 2/2015
CN 106701825 A 5/2017
(Continued)

OTHER PUBLICATIONS

Vonderheide et al., Clinical activity and immune modulation in cancer patients treated with CP-870,893, a novel CD40 agonist monoclonal antibody, J Clin Oncol. 25, 876-83, 2007.*
(Continued)

*Primary Examiner* — Claire Kaufman
(74) *Attorney, Agent, or Firm* — MH2 Technology Law Group, LLP

(57) ABSTRACT

The present invention relates to novel interferon-associated antigen binding proteins as well as nucleic acids, vectors and vector systems encoding such interferon-associated antigen binding proteins. The present invention also relates to compositions comprising such interferon-associated antigen binding proteins, nucleic acids, vectors and vector systems. The novel interferon-associated antigen binding proteins afford beneficial improvements over the current state of the art, for example inthat they effectively disrupt viral replication and thereby reduce HBV viral load. Thus, the present invention also provides medical uses of such interferon-associated antigen binding proteins, nucleic acids, vectors, vector systems and compositions, e.g., in the treatment of hepatitis B virus (HBV) infection and/or for decreasing one or more symptoms of HBV infection in a subject. The present invention further provides host cells comprising such nucleic acids, vectors and vector systems as well as
(Continued)

methods of making the interferon-associated antigen binding proteins according to the invention using said host cells.

31 Claims, 14 Drawing Sheets

Specification includes a Sequence Listing.

(51) Int. Cl.
- *A61P 31/20* (2006.01)
- *C07K 14/555* (2006.01)
- *C07K 16/28* (2006.01)
- *C12N 15/63* (2006.01)

(52) U.S. Cl.
CPC .......... *C12N 15/63* (2013.01); *C07K 2317/55* (2013.01); *C07K 2317/565* (2013.01); *C07K 2319/33* (2013.01)

(56) References Cited

U.S. PATENT DOCUMENTS

| | | | |
|---|---|---|---|
| 5,328,470 A | 7/1994 | Nabel et al. | |
| 6,193,980 B1 | 2/2001 | Efstathiou et al. | |
| 7,288,251 B2* | 10/2007 | Bedian | C07K 16/2878 424/153.1 |
| 7,993,648 B2* | 8/2011 | Kedl | A61P 31/18 424/85.4 |
| 8,388,971 B2 | 3/2013 | Bedian et al. | |
| 8,629,274 B2 | 1/2014 | Hartman et al. | |
| 8,906,681 B2 | 12/2014 | Kelly et al. | |
| 9,091,679 B2* | 7/2015 | Mallone | G01N 33/505 |
| 9,107,886 B2 | 8/2015 | Chakraborty et al. | |
| 9,534,057 B2 | 1/2017 | Grewal et al. | |
| 9,814,760 B2 | 11/2017 | Bancel et al. | |
| 10,202,464 B2 | 2/2019 | Ast et al. | |
| 10,941,201 B2* | 3/2021 | Keler | A61K 39/385 |
| 11,535,673 B2* | 12/2022 | Silver | A61K 47/6853 |
| 2004/0146991 A1 | 7/2004 | Tsuji et al. | |
| 2004/0197876 A1 | 10/2004 | Tschopp | |
| 2005/0112119 A1 | 5/2005 | Qin et al. | |
| 2006/0269516 A1 | 11/2006 | Presta et al. | |
| 2007/0190051 A1 | 8/2007 | Bedian et al. | |
| 2009/0074711 A1 | 3/2009 | Glennie | |
| 2010/0068151 A1 | 3/2010 | Rosenblum et al. | |
| 2011/0076233 A1 | 3/2011 | McBride et al. | |
| 2011/0110956 A1 | 5/2011 | Rothe et al. | |
| 2012/0087927 A1 | 4/2012 | Matsushima et al. | |
| 2013/0034547 A1 | 2/2013 | Kelly et al. | |
| 2014/0004079 A1 | 1/2014 | Gehring et al. | |
| 2014/0050660 A1 | 2/2014 | Chang et al. | |
| 2015/0203560 A1 | 7/2015 | Grewal | |
| 2016/0129086 A1 | 5/2016 | Chang et al. | |
| 2016/0159920 A1 | 6/2016 | Wang et al. | |
| 2017/0073388 A1 | 3/2017 | Grewal et al. | |
| 2017/0158772 A1 | 6/2017 | Thompson et al. | |
| 2017/0202962 A1 | 7/2017 | Pogue et al. | |
| 2017/0253659 A1 | 9/2017 | Ravetch et al. | |
| 2018/0311371 A1 | 11/2018 | Dengl et al. | |
| 2018/0311381 A1 | 11/2018 | Bancel et al. | |
| 2018/0355059 A1 | 12/2018 | Liu et al. | |
| 2019/0004060 A1 | 1/2019 | Ren et al. | |
| 2019/0071500 A1 | 3/2019 | Kley et al. | |
| 2019/0071509 A1 | 3/2019 | Cohen et al. | |
| 2019/0144553 A1 | 5/2019 | Kley et al. | |
| 2019/0151447 A1 | 5/2019 | Pogue et al. | |
| 2019/0184008 A1 | 6/2019 | Inserm et al. | |
| 2019/0194713 A1 | 6/2019 | Mandell et al. | |
| 2019/0263918 A1 | 8/2019 | Li et al. | |
| 2019/0336615 A1 | 11/2019 | Thompson et al. | |
| 2021/0260165 A1 | 8/2021 | Alam | |
| 2023/0028476 A1 | 1/2023 | Alam | |
| 2023/0242655 A1* | 8/2023 | Alam | C07K 16/2878 424/130.1 |

FOREIGN PATENT DOCUMENTS

| | | | |
|---|---|---|---|
| EP | 2589654 A1 | 5/2013 | |
| EP | 3150218 A1 | 4/2017 | |
| WO | 8902468 A1 | 3/1989 | |
| WO | 8905345 A1 | 6/1989 | |
| WO | 8907136 A2 | 8/1989 | |
| WO | 9207573 A1 | 5/1992 | |
| WO | 9316107 A1 | 8/1993 | |
| WO | 0069913 A1 | 11/2000 | |
| WO | 0197844 A1 | 12/2001 | |
| WO | 0228481 A2 | 4/2002 | |
| WO | 03092737 A1 | 11/2003 | |
| WO | 03093478 A1 | 11/2003 | |
| WO | 2004058298 A1 | 7/2004 | |
| WO | 2005014618 A2 | 2/2005 | |
| WO | 2005044304 A2 | 5/2005 | |
| WO | 2005063289 A1 | 7/2005 | |
| WO | 2006029078 A2 | 3/2006 | |
| WO | 2006119128 A2 | 11/2006 | |
| WO | 2006133089 A2 | 12/2006 | |
| WO | 2007071777 A2 | 6/2007 | |
| WO | 2007089871 A2 | 8/2007 | |
| WO | 2007130493 A2 | 11/2007 | |
| WO | 2008065053 A1 | 6/2008 | |
| WO | 2008091954 A2 | 7/2008 | |
| WO | 2008124086 A2 | 10/2008 | |
| WO | 2008157473 A1 | 12/2008 | |
| WO | 2009023270 A2 | 2/2009 | |
| WO | 2010104747 A2 | 9/2010 | |
| WO | 2010108154 A2 | 9/2010 | |
| WO | 2011020783 A2 | 2/2011 | |
| WO | 2011064758 A2 | 6/2011 | |
| WO | 2011075605 A2 | 6/2011 | |
| WO | 2011144756 A1 | 11/2011 | |
| WO | WO-2012017003 A1 * | 2/2012 | ........... C07K 16/082 |
| WO | 2012135132 A1 | 10/2012 | |
| WO | 2012146628 A1 | 11/2012 | |
| WO | 2012162583 A1 | 11/2012 | |
| WO | 2012170072 A1 | 12/2012 | |
| WO | 2012170438 A2 | 12/2012 | |
| WO | 2012178137 A1 | 12/2012 | |
| WO | 2013059885 A2 | 5/2013 | |
| WO | 2013090648 A1 | 6/2013 | |
| WO | 2013134138 A1 | 9/2013 | |
| WO | 2013151666 A2 | 10/2013 | |
| WO | 2013164754 A2 | 11/2013 | |
| WO | 2014012479 A1 | 1/2014 | |
| WO | 2014028502 A1 | 2/2014 | |
| WO | 2014062963 A1 | 4/2014 | |
| WO | 2014100913 A1 | 7/2014 | |
| WO | 2014101287 A1 | 7/2014 | |
| WO | 2014139468 A1 | 9/2014 | |
| WO | 2014163684 A1 | 10/2014 | |
| WO | 2015006744 A1 | 1/2015 | |
| WO | 2015063647 A1 | 5/2015 | |
| WO | 2015181641 A2 | 12/2015 | |
| WO | 2016065409 A1 | 5/2016 | |
| WO | 2016077505 A2 | 5/2016 | |
| WO | 2016082677 A1 | 6/2016 | |
| WO | 2016113395 A1 | 7/2016 | |
| WO | 2016201251 A1 | 12/2016 | |
| WO | 2016201337 A1 | 12/2016 | |
| WO | 2016201350 A1 | 12/2016 | |
| WO | 2017023779 A1 | 2/2017 | |
| WO | 2017086627 A1 | 5/2017 | |
| WO | 2017100305 A2 | 6/2017 | |
| WO | 2017123548 A1 | 7/2017 | |
| WO | 2017134301 A1 | 8/2017 | |
| WO | 2017134302 A2 | 8/2017 | |
| WO | 2017134305 A1 | 8/2017 | |
| WO | 2017180587 A2 | 10/2017 | |
| WO | 2017180764 A1 | 10/2017 | |
| WO | 2017184619 A2 | 10/2017 | |
| WO | 2017186928 A1 | 11/2017 | |
| WO | 2017189959 A1 | 11/2017 | |
| WO | 2017194782 A2 | 11/2017 | |
| WO | 2017205742 A1 | 11/2017 | |
| WO | 2018014067 A1 | 1/2018 | |

(56) References Cited

FOREIGN PATENT DOCUMENTS

| | | |
|---|---|---|
| WO | 2018014068 A1 | 1/2018 |
| WO | 2018023093 A1 | 2/2018 |
| WO | 2018064307 A2 | 4/2018 |
| WO | 2018067987 A1 | 4/2018 |
| WO | 2018077893 A1 | 5/2018 |
| WO | 2018087345 A1 | 5/2018 |
| WO | 2018140831 A2 | 8/2018 |
| WO | 2018141964 A1 | 8/2018 |
| WO | 2018144955 A1 | 8/2018 |
| WO | 2018144999 A1 | 8/2018 |
| WO | 2018185045 A1 | 10/2018 |
| WO | 2018189220 A1 | 10/2018 |
| WO | 2018200533 A1 | 11/2018 |
| WO | 2018201047 A1 | 11/2018 |
| WO | 2018201064 A1 | 11/2018 |
| WO | 2018227023 A1 | 12/2018 |
| WO | 2018228442 A1 | 12/2018 |
| WO | 2019010219 A1 | 1/2019 |
| WO | 2019028187 A1 | 2/2019 |
| WO | 2019028191 A1 | 2/2019 |
| WO | 2019032661 A1 | 2/2019 |
| WO | 2019032662 A1 | 2/2019 |
| WO | 2019032663 A1 | 2/2019 |
| WO | 2019084060 A1 | 5/2019 |
| WO | 2019129644 A1 | 7/2019 |
| WO | 2019148089 A1 | 8/2019 |
| WO | 2019152979 A1 | 8/2019 |
| WO | 2019182996 A1 | 9/2019 |
| WO | 2019191519 A1 | 10/2019 |
| WO | 2019199689 A1 | 10/2019 |
| WO | 2019229264 A1 | 12/2019 |
| WO | 2019236567 A2 | 12/2019 |
| WO | 2020065096 A1 | 4/2020 |
| WO | 2020097350 A1 | 5/2020 |
| WO | 2020198654 A1 | 10/2020 |
| WO | 2020205808 A1 | 10/2020 |
| WO | 2021062181 A1 | 4/2021 |
| WO | 2021067458 A1 | 4/2021 |
| WO | 2021097376 A1 | 5/2021 |
| WO | 2021110561 A1 | 6/2021 |
| WO | 2021110562 A1 | 6/2021 |
| WO | 2021146590 A2 | 7/2021 |
| WO | 2021231773 A1 | 11/2021 |
| WO | 2022258720 A9 | 12/2022 |

OTHER PUBLICATIONS

Luft et al., IIFN-a enhances CD40 ligand-mediated activation of immature monocyte-derived dendritic cellsnt. Immunol. 14(4):367-380, 2002.*

Hamza et al., Interleukin 12 a Key Immunoregulatory Cytokine in Infection Applications, Int. J. Mol. Sci. 11: 789-806; doi: 10.3390/ijms11030789, 2010.*

Shimabukuro-Vornhagen et al., Cytokine release syndrome, J. Immuno Ther. Canc. 6:56, 14 pages, Jun. 15, 2018.*

Alam A., A bifunctional immune modulator exhibits potent antiviral activity in HBV infection models. Meeting report: 35th Intl. Conf. Antiviral Res. Seattle, Washington, USA—Mar. 21-25, 2022, Antiviral Res. 211:105521, Abst. 10.2, p. 1 and 19, 2023.*

Fleitmann, J. (Authorized Officer), International Search Report and Written Opinion (Forms PCT/ISA/210 and PCT/ISA/237) dated Feb. 18, 2021 for International Application No. PCT/EP2020/083745, 12 pages.

Wu et al., "Construction of the HBV S-ecdCD40L fusion gene and effects of HBV S-ecdCD40L modification on function of dendritic cells," Journal of Viral Hepatitis, vol. 18, Issue 10, Oct. 2011 (First published Jun. 1, 2011), pp. e461-e467.

Armentano et al., "Expression of Human Factor IX in Rabbit Hepatocytes by Retrovirus-Mediated Gene Transfer: Potential for Gene Therapy of Hemophilia B," Proceedings of the National Academy of Sciences of the United States of America, vol. 87, No. 16, Aug. 1990, pp. 6141-6145 (6 pages total).

Bachmann et al., "Maintenance of Memory CTL Responses by T Helper Cells and CD40-CD40 Ligand: Antibodies Provide the Key," European Journal of Immunology, vol. 34, No. 2, Feb. 3, 2004, pp. 317-326.

Bissig et al., "Human Liver Chimeric Mice Provide a Model for Hepatitis B and C Virus Infection and Treatment," The Journal of Clinical Investigation, vol. 120, No. 3, Mar. 1, 2010 (Published online Feb. 22, 2010), pp. 924-930.

Bremer, "Targeting of the Tumor Necrosis Factor Receptor Superfamily for Cancer Immunotherapy," International Scholarly Research Notices, Oncology, vol. 2013, Article ID 371854, Jun. 11, 2013, pp. 1-25 (25 pages total).

Chen et al., "Gene Therapy For Brain Tumors: Regression Of Experimental Gliomas By Adenovirus-Mediated Gene Transfer In Vivo," Proceedings of the National Academy of Sciences of the United States of America, vol. 91, No. 8, Apr. 12, 1994, pp. 3054-3057.

Chowdhury et al., "Long-Term Improvement Of Hypercholesterolemia After Ex Vivo Gene Therapy In LDLR-Deficient Rabbits," Science, vol. 254, No. 5039, Dec. 20, 1991, pp. 1802-1805 (5 pages total).

Cohen et al., "Sustained Delivery and Expression of DNA Encapsulated in Polymeric Nanoparticles," Gene Therapy, vol. 7, No. 22, Dec. 2000, pp. 1896-1905.

Dai et al., "Gene Therapy Via Primary Myoblasts: Long-Term Expression Of Factor IX Protein Following Transplantation In Vivo," Proceedings of the National Academy of Sciences of the United States of America, vol. 89, No. 22, Nov. 15, 1992, pp. 10892-10895 (5 pages total).

Dandri et al., "Animal Models of HBV Infection," Best Practice & Research Clinical Gastroenterology, vol. 31, Issue 3, Jun. 2017, pp. 273-279.

Danos et al., "Safe and Efficient Generation of Recombinant Retroviruses with Amphotropic and Ecotropic Host Ranges," Proceedings of the National Academy of Sciences of the United States of America, vol. 85, No. 17, Sep. 1, 1988, pp. 6460-6464 (6 pages total).

Dion et al., "Adeno-Associated Virus-Mediated Gene Transfer Leads to Persistent Hepatitis B Virus Replication in Mice Expressing HLA-A2 and HLA-DR1 Molecules," Journal of Virology, vol. 87, No. 10, May 2013 (Published ahead of print Mar. 6, 2013), pp. 5554-5563.

Eglitis et al., "Gene Expression in Mice after High Efficiency Retroviral-Mediated Gene Transfer," Science, vol. 230, No. 4732, Dec. 20, 1985, pp. 1395-1398 (5 pages total).

Ferry et al., "Retroviral-Mediated Gene Transfer into Hepatocytes in Vivo," Proceedings of the National Academy of Sciences of the United States of America, vol. 88, No. 19, Oct. 1, 1991, pp. 8377-8381.

Fleitmann, J. (Authorized Officer), International Search Report and Written Opinion (Forms PCT/ISA/210 and PCT/ISA/237) dated Feb. 18, 2021 for International Application No. PCT/EP2020/083737, 12 pages.

Flotte et al., "Expression of the Cystic Fibrosis Transmembrane Conductance Regulator from a Novel Adeno-associated Virus Promoter," Journal of Biological Chemistry, vol. 268, No. 5, Feb. 15, 1993, pp. 3781-3790.

Flotte et al., "Gene Expression from Adeno-Associated Virus Vectors in Airway Epithelial Cells," American Journal of Respiratory Cell and Molecular Biology, vol. 7, No. 3, Sep. 1992, pp. 349-356.

Giersch et al., "Both Interferon Alpha and Lambda can Reduce all Intrahepatic HDV Infection Markers in HBV/HDV Infected Humanized Mice," Scientific Reports, vol. 7, Article No. 3757, 2017 (Published online Jun. 16, 2017), pp. 1-11.

Gray et al., "Genenames.org: The HGNC Resources in 2015," Nucleic Acids Research, vol. 43, Issue D1, Jan. 28, 2015 (Published online Oct. 31, 2014), pp. D1079-D1085.

Guan et al., "Effect of the Hepatitis B Virus S-ecdCD40L Vaccine Therapy in HBV Transgenic Mice: A Vaccine-Induced Activation of Antigen Presenting Dendritic Cells," Molecular Medicine Reports, vol. 16, No. 5, Nov. 2017 (Published online Aug. 22, 2017), pp. 6102-6108.

(56) References Cited

OTHER PUBLICATIONS

Haj-Ahmad et al., "Development of a Helper-Independent Human Adenovirus Vector and Its Use in the Transfer of the Herpes Simplex Virus Thymidine Kinase Gene," Journal of Virology, vol. 57, No. 1, Jan. 1986, pp. 267-274.

Hermonat et al., "Use of adeno-associated virus as a mammalian DNA cloning vector: Transduction of neomycin resistance into mammalian tissue culture cells," Proceedings of the National Academy of Sciences of the United States of America, vol. 81, No. 20, Oct. 1, 1984, pp. 6466-6470.

Huber et al., "Retroviral-Mediated Gene Therapy For The Treatment Of Hepatocellular Carcinoma: An Innovative Approach For Cancer Therapy," Proceedings of the National Academy of Sciences of the United States of America, vol. 88, No. 18, Sep. 15, 1991, pp. 8039-8043.

Hwu et al., "Functional And Molecular Characterization Of Tumor-Infiltrating Lymphocytes Transduced With Tumor Necrosis Factor-$\alpha$ cDNA For The Gene Therapy Of Cancer In Humans," The Journal of Immunology, vol. 150, No. 9, May 1, 1993, pp. 4104-4115 (13 pages total).

Jones, "Proteinase Mutants of *Saccharomyces cerevisiae*," Genetics, vol. 85, No. 1, Jan. 28, 1977, pp. 23-33.

Kay et al., "Hepatic Gene Therapy: Persistent Expression of Human $\alpha$1-Antitrypsin in Mice after Direct Gene Delivery In Vivo," Human Gene Therapy, vol. 3, No. 6, Dec. 1992 (Published online Jun. 13, 2008), pp. 641-647.

Kingsman et al., "Replication In *Saccharomyces cerevisiae* Of Plasmid pBR313 Carrying DNA From The Yeast trpl Region," Gene, vol. 7, No. 2, Oct. 1979, pp. 141-152.

Kosaka et al., "A Novel TK-NOG Based Humanized Mouse Model for the Study of HBV and HCV Infections," Biochemical and Biophysical Research Communications, vol. 441, No. 1, Nov. 8, 2013 (Available online Oct. 16, 2013), pp. 230-235.

Lindner, N. (Authorized Officer), International Preliminary Report on Patentability and Written Opinion (Forms PCT/IB/326, PCT/IB/373 and PCT/ISA/237) dated Dec. 10, 2020, for International Application No. PCT/EP2019/064239, 10 pages.

Lucifora et al., "Detection of the Hepatitis B Virus (HBV) Covalently-Closed-Circular DNA (cccDNA) in Mice Transduced with a Recombinant AAV-HBV Vector," Antiviral Research, vol. 145, Sep. 2017, pp. 14-19 (25 pages total).

McLaughlin et al., "Adeno-Associated Virus General Transduction Vectors: Analysis of Proviral Structures," Journal of Virology, vol. 62, No. 6, Jun. 1988, pp. 1963-1973.

Meuli et al., "Efficient Gene Expression in Skin Wound Sites Following Local Plasmid Injection," Journal of Investigative Dermatology, vol. 116, No. 1, Jan. 2001, pp. 131-135.

Miller, "Progress Toward Human Gene Therapy," Blood, vol. 76, No. 2, Jul. 15, 1990, pp. 271-278.

Muzyczka, "Use of Adeno-Associated Virus as a General Transduction Vector for Mammalian Cells," Current Topics in Microbiology and Immunology, vol. 158, Jan. 1, 1992, pp. 97-129.

Ridgway, "Mammalian Expression Vectors," Chapter 24.2—Introduction of Vector into Host Cells, Rodriguez and Denhardt, Eds., Butterworths, Boston, Mass., 1988, pp. 470-472.

Rosenfeld et al., "Adenovirus-Mediated Transfer of a Recombinant $\alpha$1-Antitrypsin Gene to the Lung Epithelium In Vivo," Science, vol. 252, Issue 5004, Apr. 19, 1991, pp. 431-434 (5 pages).

Rosenfeld et al., "In Vivo Transfer of the Human Cystic Fibrosis Transmembrane Conductance Regulator Gene to the Airway Epithelium," Cell, vol. 68, No. 1, Jan. 10, 1992, pp. 143-155.

Samulski et al., "Helper-Free Stocks of Recombinant Adeno-Associated Viruses: Normal Integration Does Not Require Viral Gene Expression," Journal of Virology, vol. 63, No. 9, Sep. 1989, pp. 3822-3828.

Stinchcomb et al., "Isolation And Characterisation Of A Yeast Chromosomal Replicator," Nature, vol. 282, Nov. 1, 1979, pp. 39-43.

Stoltner, A. (Authorized Officer), International Search Report and Written Opinion (Forms PCT/ISA/210 and PCT/ISA/237) dated Jul. 19, 2019 for International Application No. PCT/EP2019/064239, 13 pages.

Tam et al., "Stabilized Plasmid-Lipid Particles For Systemic Gene Therapy," Gene Therapy, vol. 7, No. 21, Nov. 2000, pp. 1867-1874.

Tratschin et al., "A Human Parvovirus, Adeno-Associated Virus, as a Eucaryotic Vector: Transient Expression and Encapsidation of the Procaryotic Gene for Chloramphenicol Acetyltransferase," Molecular And Cellular Biology, vol. 4, No. 10, Oct. 1984, pp. 2072-2081.

Tratschin et al., "Adeno-Associated Virus Vector for High-Frequency Integration, Expression, and Rescue of Genes In Mammalian Cells," Molecular and Cellular Biology, vol. 5, No. 11, Nov. 1985, pp. 3251-3260.

Tratschin et al., "Genetic Analysis of Adeno-Associated Virus: Properties of Deletion Mutants Constructed In Vitro and Evidence for an Adeno-Associated Virus Replication Function," Journal of Virology, vol. 51, No. 3, Sep. 1984, pp. 611-619.

Tschumper et al., "Sequence Of A Yeast DNA Fragment Containing A Chromosomal Replicator And The TRP1 Gene," Gene, vol. 10, No. 2, Jul. 1980, pp. 157-166.

Tsuge et al., "Development of a Novel Site-Specific Pegylated Interferon Beta for Antiviral Therapy of Chronic Hepatitis B Virus," Antimicrobial Agents and Chemotherapy, vol. 61, Issue 6, e00183-17, Jun. 2017, pp. 1-10.

Van Beusechem et al., "Long-term expression of human adenosine deaminase in rhesus monkeys transplanted with retrovirus-infected bone-marrow cells," Proceedings of the National Academy of Sciences of the United States of America, vol. 89, No. 16, Aug. 15, 1992, pp. 7640-7644.

Wilson et al., "Retrovirus-Mediated Transduction of Adult Hepatocytes," Proceedings of the National Academy of Sciences of the United States of America, vol. 85, No. 9, May 1, 1988, pp. 3014-3018 (6 pages total).

Wondisford et al., "Cloning of the Human Thyrotropin $\beta$-Subunit Gene and Transient Expression of Biologically Active Human Thyrotropin after Gene Transfection," Molecular Endocrinology, vol. 2, No. 1, Jan. 1, 1988, pp. 32-39.

Xia et al., "Interferon-$\gamma$ and Tumor Necrosis Factor-$\alpha$ Produced by T Cells Reduce the HBV Persistence Form, cccDNA, Without Cytolysis," Gastroenterology, vol. 150, No. 1, Jan. 2016 (Available online Sep. 28, 2015), pp. 194-205.

Yang et al., "A Mouse Model for HBV Immunotolerance and Immunotherapy," Cellular & Molecular Immunology, vol. 11, No., 1, Jan. 2014 (Published online Sep. 30, 2013), pp. 71-78.

Trinh et al., "Optimization of codon pair use within the (GGGGS)3 linker sequence results in enhanced protein expression", Molecular Immunology, 2004, vol. 40, No. 10, pp. 717-722, https://doi.org/10.1016/j.molimm.2003.08.006.

Graslund et al. Protein production and purification. Nat Methods 5, 135-146 (2008). https://doi.org/10.1038/nmeth.f.202 [published correction appears in Nat Methods. Apr. 2008;5(4):369].

Elgueta et al., "Molecular mechanism and function of CD40/CD40L engagement in the immune system", Immunological Reviews, vol. 229, No. 1, May 1, 2009, pp. 152-172.

Park et al:, "Type I and Type III Interferons—Induction, Signaling, Evasion, and Application to Combat COVID-19", Cell Host & Microbe, vol. 27, No. 6, May 27, 2020, pp. 870-878.

Darazam et al., "Role of interferon therapy in severe COVID-19: the COVIFERON randomized controlled trial", Scientific Reports, vol. 11, No. 1, Apr. 19, 2021, 11 pages.

Murer et al., "Antibody-cytokine fusion proteins: A novel class of biopharmaceuticals for the therapy of cancer and of chronic inflammation", New Biotechnology, vol. 52, Apr. 13, 2019, pp. 42-53.

International Search Report dated Sep. 12, 2022 for corresponding International Application No. PCT/EP2022/065610, 5 pages.

Moustaqil et al., "SARS-COV-2 proteases PLpro and 3CLpro cleave IRF3 and critical modulators of inflammatory pathways (NLRP12 and TAB1): implications for disease presentation across species", Emerging Microbes & Infections, 2021, vol. 10, pp. 178-195.

(56) References Cited

OTHER PUBLICATIONS

Shin et al., "Papain-like protease regulates SARS-CoV-2 viral spread and innate immunity," Nature, Nov. 1, 2020, vol. 587(7835): 39 pages. doi:10.1038/s41586-020-2601-5, Published online Jul. 29, 2020.
Yuen et al., "SARS-CoV-2 nsp13, nsp14, nsp15 and orf6 function as potent interferon antagonists," Emerging Microbes & Infections, 2020, vol. 9, pp. 1418-1428.
Xia et al., "Evasion of Type I Interferons by SARS-CoV-2," Cell Reports, 2020, 108234, vol. 33, 19 pages published online Sep. 19, 2020.
Lei et al., "Activation and evasion of type I interferon responses by SARS-CoV-2," Nature Communications, 2020, vol. 11, 12 pages.
Xia et al., "Antagonism of Type I Interferon by Severe Acute Respiratory Syndrome Coronavirus 2," Journal of Interferon & Cytokine Research, vol. 40, No. 12, 2020, pp. 543-548.
Aagaard et al., "RNAi therapeutics: Principles, prospects and challenges", Adv. Drug Delivery Rev., vol. 59, Issues 2-3, 2007, pp. 75-86.
Bouchlaka et al., "Aging predisposes to acute inflammatory induced pathology after tumor immunotherapy", J. Exp. Med., 2013, vol. 210, No. 11, pp. 2223-2237.
Bork, "Powers and Pitfalls in sequence analysis: the 70% hurdle", Genome Research, 2000, vol. 10, pp. 398-400.
Bowie et al., "Deciphering the message in protein sequences: tolerance to amino acid substitutions", Science, 1990, 247, pp. 1306-1310.
Brown et al., "Tolerance of single, but not multiple, amino acid replacements in antibody VH CDR 2: a means of minimizing B cell wastage from somatic hypermutation?", J Immunol., May 1, 1996, vol. 156, No. 9, pp. 3285-3291.
Burgess et al., "Possible dissociation of the heparin-binding and mitogenic activities of heparin-binding (acidic fibroblast) growth factor-1 from its receptor-binding activities by site-directed mutagenesis of a single lysine residue", 1990, J. Cell Biol. vol. 111, pp. 2129-2138.
Byrne et al., "CSF-1R-dependent lethal hepatotoxicity when agonistic CD40 antibody is given before but not after chemotherapy", J. Immunol., 2016, 197:179-187. doi: 10.4049/jimmunol.1600146.
Caselmann et al., "Beta and Gamma-Interferon in Chronic Active Hepatitis B. A pilot trial of short-term combination therapy", Gastroenterology, 1989; vol. 96 (2 Pt 1):449-455.
Clark et al., "Discovery and development of Janus kinase (JAK) inhibitors for inflammatory diseases",J. Med. Chem., 2014, vol. 57, pp. 5023-5038. doi: 10.1021/jm401490p. Epub Jan. 23, 2014.
Ferrara et al., "Recombinant renewable polyclonal antibodies", Mabs, 2015, vol. 7, No. 1, pp. 32-41. doi: 10.4161/19420862.2015. 989047.
Greene et al., "In vivo and In vitro Regulation of Type I IFN Synthesis by Synergistic Effects of CD40 and Type II IFN", J. Immunol., 2006, vol. 176, No. 10, pp. 599-6003.
Guido et al., "Virtual Screening and Its Integration with Modern Drug Design Technologies", Current Medicinal Chemistry, 2008, vol. 15, No. 1, pp. 37-46.
Author unknown, Creative Biolabs, Inc. , "Human Anti-CD40 Recombinant Antibody (clone 21.4.1) CAT#: HPAB-1834-FY" obtained from the world wide web at https://www.creativebiolabs. net/anti-cd40-recombinant-antibody-clone-21-4-1-129069.htm on Jun. 10, 2024.
Jiang et al., "Immunization with adenovirus LIGHT-engineered dendritic cells induces potent T cell responses and therapeutic immunity in HBV transgenic mice," Vaccine, Jul. 31, 2014, vol. 32, No. 35, pp. 4565-4570, ePublished Jun. 18, 2014.
Karki et al., "Synergism of TNF-α and IFN-γ Triggers Inflammatory Cell Death, Tissue Damage, and Mortality in SARS-CoV-2 Infection and Cytokine Shock Syndromes", Cell, Jan. 7, 2021, vol. 184, No. 1, pp. 149-168.e17. doi: 10.1016/j.cell.2020.11.025. Epub Nov. 19, 2020.
Kimura al., "Activated intrahepatic antigen / presenting cells inhibit hepatitis B virus replication in the liver of transgenic mice", Journal of Immunology, 2002 , vol. 169, No. 9 , p. 5188-5195. doi:10.4049/jimmunol. 169.9.5188.
Lazar et al., "Transforming growth factor alpha: mutation of aspartic acid 47 and leucine 48 results in different biological activities", Mol. Cell. Biol., 1988, vol. 8, pp. 1247-1252.
Le et al., "FDA Approval Summary: Tocilizumab for Treatment of Chimeric Antigen Receptor T Cell-Induced Severe or Life-Threatening Cytokine Release Syndrome", Oncologist, 2018, vol. 23, pp. 9443-9947. DOI: 10.1634/theoncologist.2018-0028.
Lee et al., "Current concepts in the diagnosis and management of cytokine release syndrome", Blood, Jul. 10, 2014; vol. 124, No. 2, pp. 188-195.
Milling et al., "Delivering safer immunotherapies for cancer", Advanced Drug Delivery Reviews 114 (2017) 79-101.
Murthy et al., "Cytokine Release Syndrome: Current Perspectives", Immuno Targets Ther., 2019, vol. 8 pp. 43-52.
Nishimoto et al., "Clinical Impacts of Using Serum IL-6 Level as an Indicator of Cytokine Release Syndrome after HLA-Haploidentical Transplantation with Post-Transplantation Cyclophosphamide", Biol. Blood Marrow Transplant., vol. 25, 2019, pp. 2061-2069. Epub Jun. 10, 2019.
Ruby et al., "CD40 ligand has potent antiviral activity", Nature Medicine, 1995, vol. 1, No. 5, p. 437-441, doi: 10.1038/nm0595-437.
Soin et al., "Tocilizumab plus standard care versus standard care in patients in India with moderate to severe COVID-19-associated cytokine release syndrome (COVINTOC): an open-label, multicentre, randomised, controlled, phase 3 trial", Lancet Respir. Med., 2021, vol. 9, pp. 511-521.
Vajdos et al., "Comprehensive functional maps of the antigen-binding site of an anti-ErbB2 antibody obtained with shotgun scanning mutagenesis", J Mol Biol., Jul. 5, 2002, vol. 320, No. 2, pp. 415-428. doi: 10.1016/S0022-2836(02)00264-4.
Vonderheide et al., "CD40 Agonist Antibodies in Cancer Immunotherapy", Annu. Rev. Med., 2020, vol. 71, pp. 47-58. Epub Aug. 14, 2019.
Warzocha et al., "Antisense Strategy: Biological Utility and Prospects in the Treatment of Hematological Malignancies," Leuk. Lymphoma., 1997, vol. 24. pp. 267-281.
Wieland et al., "Interferon prevents formation of replication-competent hepatitis B virus RNA-containing nucleocapsids," Proc. Natl. Acad. Sci. U S A, Jul. 12, 2005, vol. 102, No. 28, pp. 9913-9917. doi: 10.1073/pnas.0504273102. Epub Jul. 1, 2005.
Winkler, "Oligonucleotide conjugates for therapeutic applications", Ther Deliv., Jul. 2013, vol. 4, No. 7, pp. 791-809. doi: 10.4155/tde.13.47.
Unknown author, "Cytokine Release Syndrome (CRS) After Immunotherapy," Mar. 2019, St. Jude's Hospital, obtained from the world wide web on Jun. 10, 2024 at https://together.stjude.org/en-us/diagnosis-treatment/side-effects/cytokine-release-syndrome-crs.html.
Berkner, "Development of adenovirus vectors for the expression of heterologous genes" Biotechniques. Jul.-Aug. 1988, vol. 6, No. (7), pp. 616-629.
Leng et al.: "The effect of HBV transfection on apoptosis induced by TNF-like weak inducer of apoptosis and the regulatory effect of IFN-γ on apoptosis", Chinese Journal of Pathophysiology, 2010, vol. 26, No. 02, 341-344 with English language Abstract.
Liang, "Hepatitis B: the virus and disease", Hepatology, 2009, May, vol. 49 (5 Suppl), S13-21. doi: 10.1002/hep.22881 (pp. 1-17).
Sun et al., "Synergetic effects of Tweak and IFN-γ in inducing apoptosis to the HBV expression HepG2.2.15 cell line," Basic Medical Sciences and Clinics, [online],2003 , vol. 23, No. 5 , [retrieved on Nov. 9, 2023], Retrieved from the Internet: <URL: https://europepmc.org/article/cba/362809, 16 pages with English language abstract; machine English language translation of article also attached.
Arase, Yasuji, "Chronic Hepatitis Efficacy of Natural Interferon-beta for Patients With Hepatitis B And C Virus-Induced" Hepatic-Biliary Pancreatic, vol. 61, No. 6, 2010, 8 pages, partial English Translation.

(56) References Cited

OTHER PUBLICATIONS

Imanishi, Yojiro, "Characteristics and History of natural IFN-β," Interferons, Clinical and Viruses, Dec. 2009, 37 (5): 409-416, 12 pages with partial English language translation.

* cited by examiner

Fig. 2A

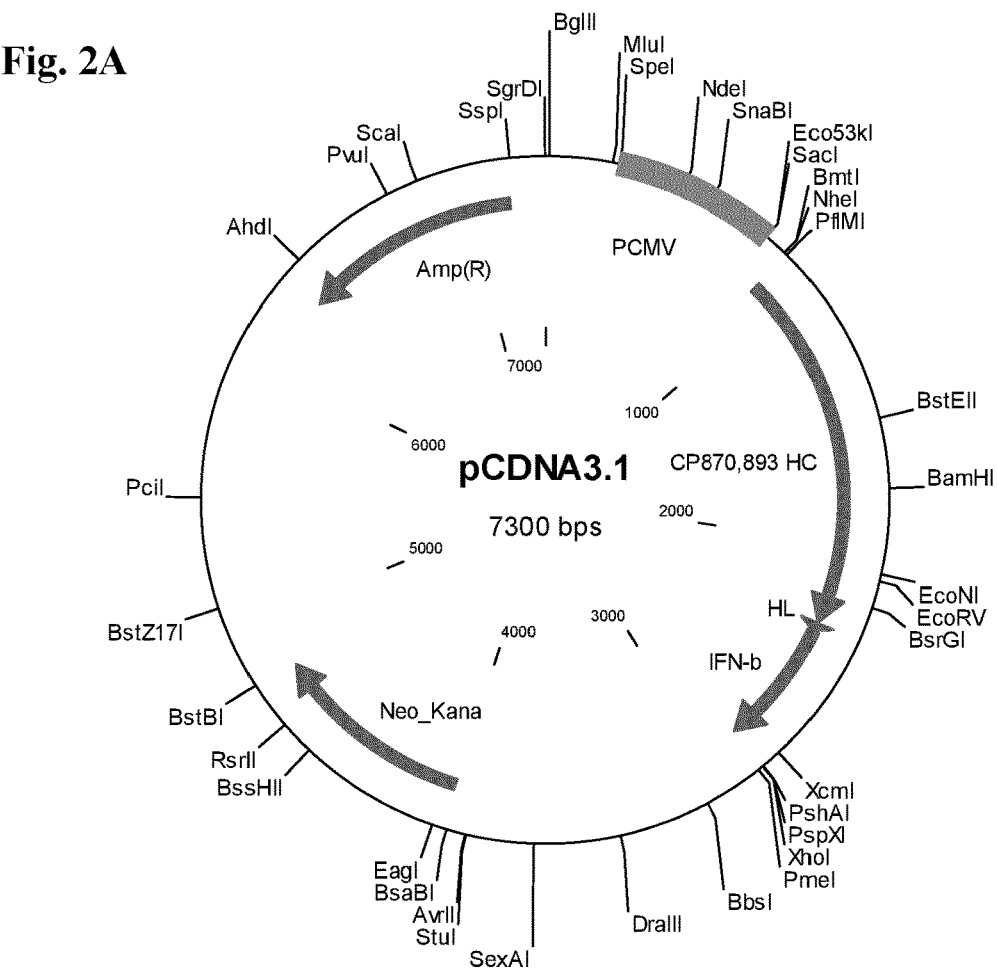

Nucleic acid sequence encoding seq ID NO 32

*ATGGGCTGGTCCTGCATCATTCTGTTTCTGGTGGCCACAGCCACAGGCGTGCACTCT*CAGGTTCAACTGGTTCAGTCTGGCGCCGA
AGTGAAGAAACCAGGCGCCAGCGTGAAGGTGTCCTGTAAAGCCAGCGGCTACACCTTTACCGGCTACTACATGCACTGGGTCCG
ACAGGCTCCAGGACAGGGACTTGAGTGGATGGGCTGGATCAATCCTGACAGCGGCGGCACCAACTACGCCCAGAAATTCCAGG
GCAGAGTGACCATGACCAGAGACACCAGCATCAGCACCGCCTACATGGAACTGAACCGGCTGAGATCCGACGACACCGCCGTGT
ACTATTGCGCCAGAGATCAGCCTCTGGGCTACTGCACAAATGGCGTGTGCAGCTACTTCGACTACTGGGGCCAGGGCACACTGG
TTACAGTGTCTAGCGCCTCTACAAAGGGCCCCTCCGTTTTTCCTCTGGCTCCTTGTTCTAGAAGCACCAGCGAGTCTACAGCCGCTC
TGGGCTGTCTGGTCAAGGACTACTTTCCTGAGCCTGTGACCGTGTCCTGGAATAGCGGAGCACTGACATCCGGCGTGCACACATT
TCCAGCTGTGCTGCAGAGCAGCGGCCTGTACTCTCTGTCTAGCGTGGTCACCGTGCCTAGCAGCAATTTCGGCACCCAGACCTAC
ACCTGTAACGTGGACCACAAGCCTAGCAACACCAAGGTGGACAAGACCGTGGAACGGAAGTGCTGCGTGGAATGCCCTCCTTGT
CCTGCTCCTCCAGTGGCCGGACCTTCCGTGTTTCTGTTCCCTCCAAAGCCTAAGGACACCCTGATGATCAGCAGAACCCCTGAAGT
GACCTGCGTGGTGGTGGATGTGTCTCACGAGGATCCCGAGGTGCAGTTCAATTGGTACGTGGACGGCGTGGAAGTGCACAACG
CCAAGACCAAGCCTAGAGAGGAACAGTTCAACAGCACCTTCAGAGTGGTGTCCGTGCTGACCGTGGTGCATCAGGACTGGCTGA
ACGGCAAAGAGTACAAGTGCAAGGTGTCCAACAAGGGCCTGCCTGCTCCTATCGAGAAAACCATCAGCAAGACCAAAGGCCAGC
CTCGCGAGCCTCAGGTTTACACACTGCCTCCAAGCCGGGAAGAGATGACCAAGAATCAGGTGTCCCTGACCTGCCTCGTGAAGG
GCTTCTACCCTTCCGATATCGCCGTGGAATGGGAGAGCAATGGCCAGCCTGAGAACAACTACAAGACCACACCTCCTATGCTGGA
CAGCGACGGCTCATTCTTCCTGTACAGCAAGCTGACAGTGGACAAGTCCAGATGGCAGCAGGGCAACGTGTTCAGCTGTTCTGT
GATGCACGAGGCCCTGCACAACCACTACACCCAGAAGTCTCTGTCTCTGAGCCCTGGC<u>GCTGAAGCCGCTGCTAAAGAAGCTGCC
GCCAAGGCC</u>ATGAGCTACAACCTGCTGGGCTTTCTGCAGCGGAGCAGCAACTTCCAGTGCCAGAAACTGCTGTGGCAGCTGAA
TGGCCGGCTGGAATACTGCCTGAAGGACCGGATGAACTTCGACATCCCCGAGGAAATCAAGCAGCTGCAGCAGTTCCAGAAA
GAGGACGCCGCTCTGACCATCTACGAGATGCTGCAGAACATCTTCGCCATCTTCCGGCAGGATAGCAGCAGCACCGGATGGAA
CGAGACAATCGTGGAAAATCTGCTGGCCAACGTGTACCACCAGATCAACCACCTGAAAACCGTGCTGGAAGAGAAGCTGGAA
AAAGAGGACTTCACCCGGGGCAAGCTGATGAGCAGCCTGCACCTGAAGCGGTACTACGGCAGAATCCTGCACTACCTCAAGG
CCAAAGAGTATAGCCACTGCGCCTGGACCATCGTGCGCGTGGAAATCCTGCGGAACTTCTACTTCATCAACAGACTGACCGGCT
ACCTGCGCAACTGA

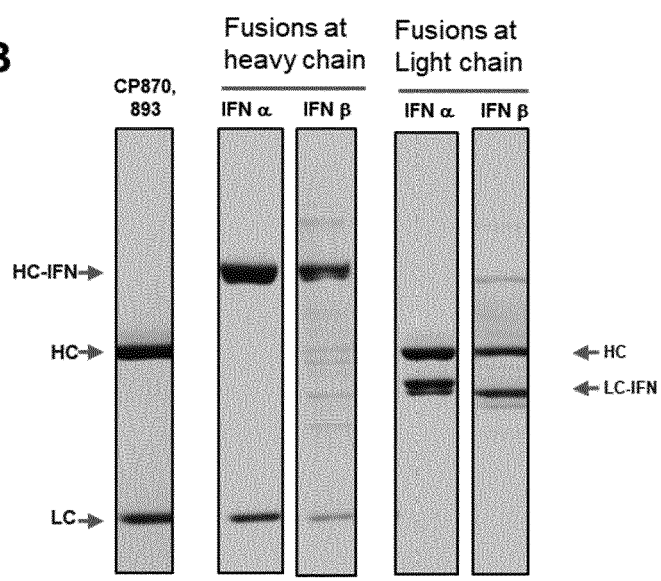

Fig. 3A
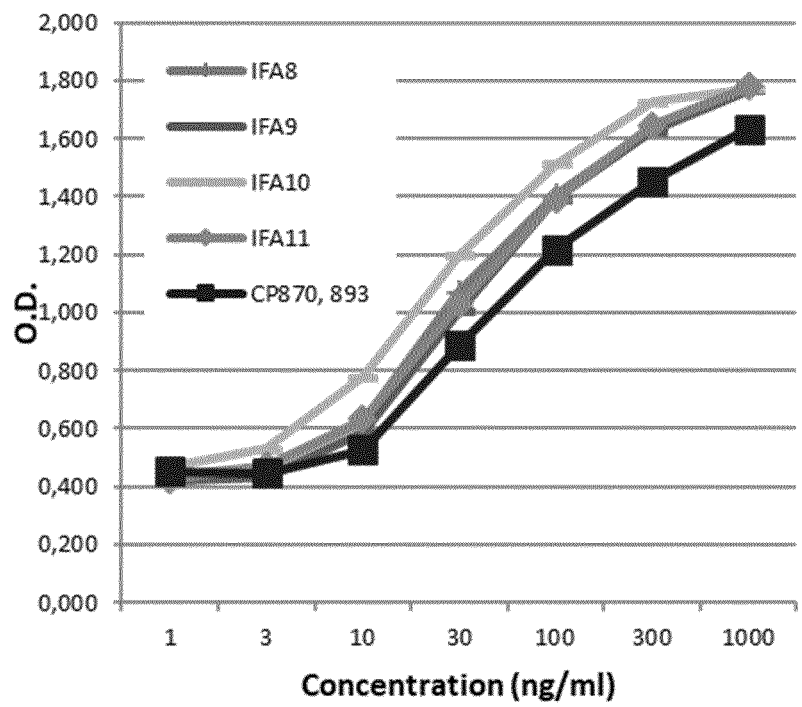
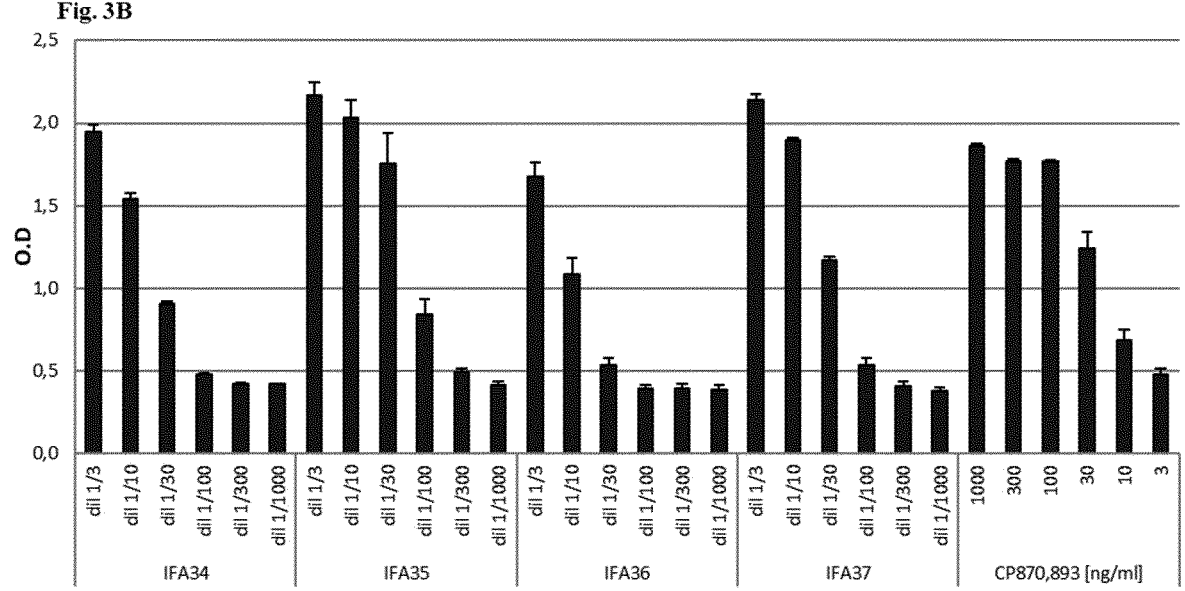
Fig. 3B

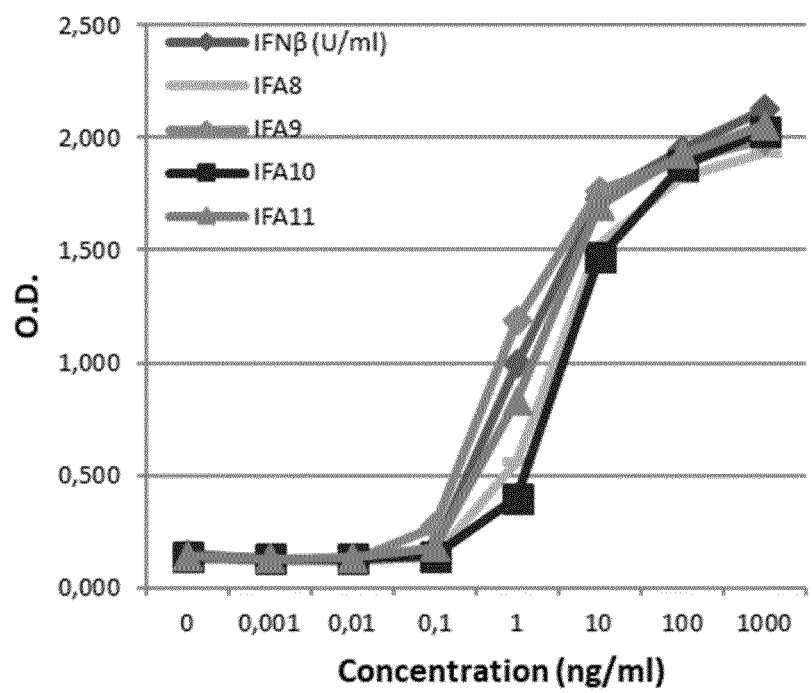
Fig. 3C
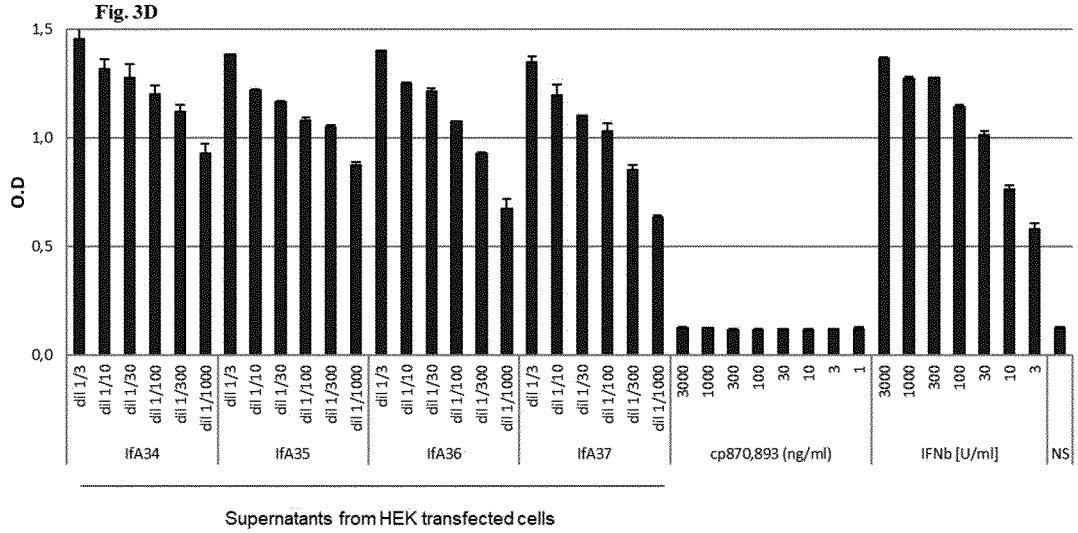

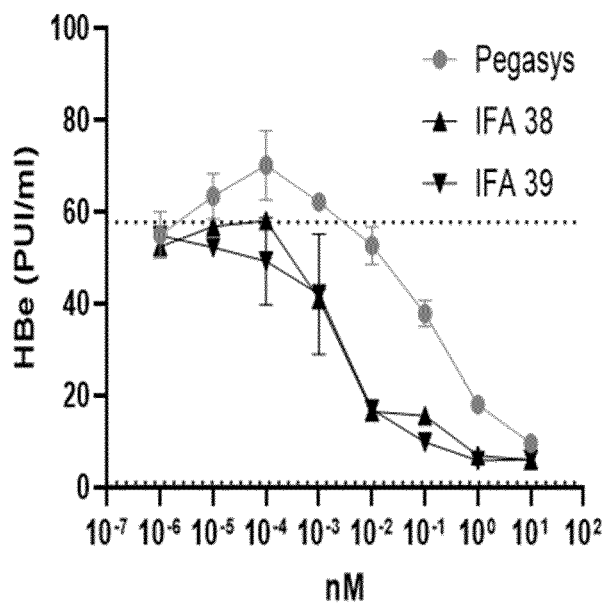

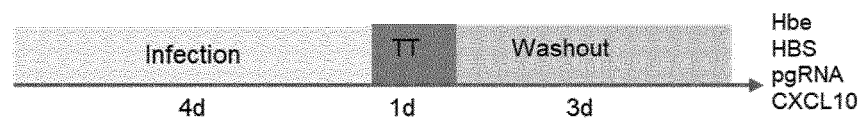
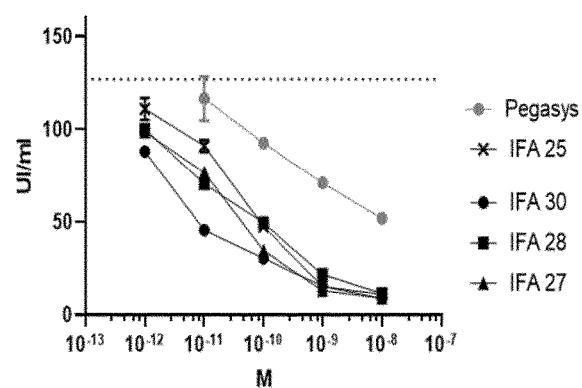
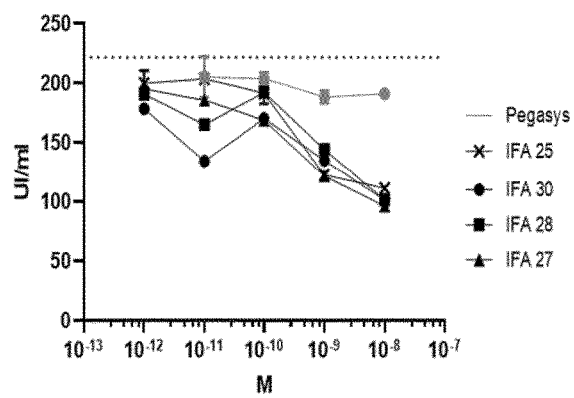
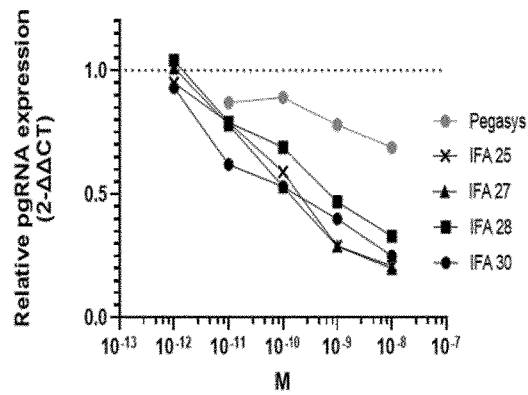
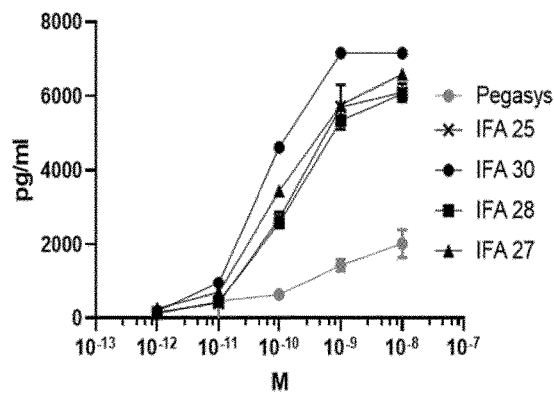

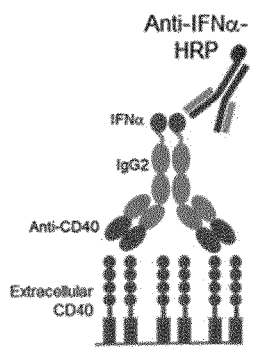
Fig. 8A
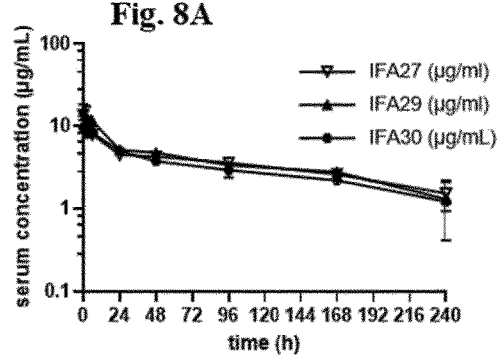
Fig. 8B
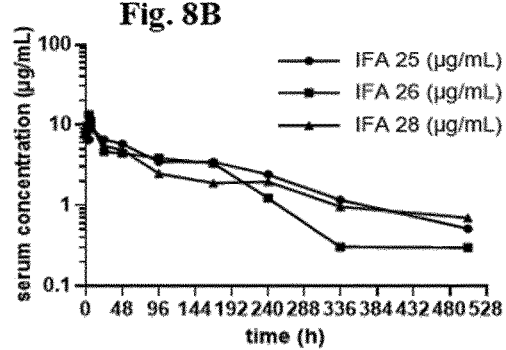
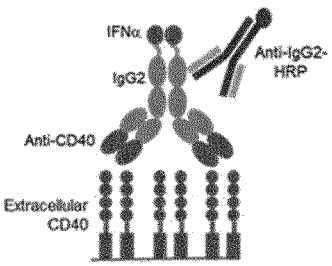
Fig. 8C
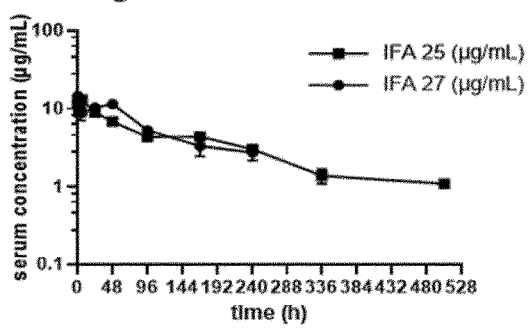
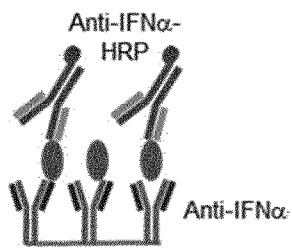
Fig. 8D
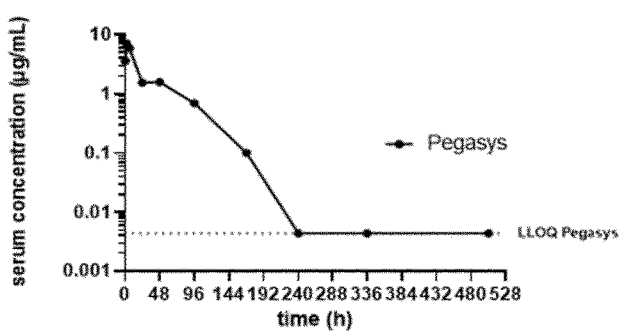

```
                        SEQUENCE LISTING

Sequence total quantity: 72
SEQ ID NO: 1           moltype = AA   length = 19
FEATURE                Location/Qualifiers
REGION                 1..19
                       note = Signal peptide 1
source                 1..19
                       mol_type = protein
                       organism = synthetic construct
SEQUENCE: 1
MGWSCIILFL VATATGVHS                                                 19

SEQ ID NO: 2           moltype = AA   length = 22
FEATURE                Location/Qualifiers
REGION                 1..22
                       note = Signal peptide 2
source                 1..22
                       mol_type = protein
                       organism = synthetic construct
SEQUENCE: 2
MDMRVPAQLL GLLLLWLRGA RC                                             22

SEQ ID NO: 3           moltype = AA   length = 214
FEATURE                Location/Qualifiers
REGION                 1..214
                       note = antiCD40 antibody light chain
source                 1..214
                       mol_type = protein
                       organism = synthetic construct
SEQUENCE: 3
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 4           moltype = AA   length = 233
FEATURE                Location/Qualifiers
REGION                 1..233
                       note = antiCD40 antibody light chain with signal peptide 1
source                 1..233
                       mol_type = protein
                       organism = synthetic construct
SEQUENCE: 4
MGWSCIILFL VATATGVHSD IQMTQSPSSV SASVGDRVTI TCRASQGIYS WLAWYQQKPG    60
KAPNLLIYTA STLQSGVPSR FSGSGSGTDF TLTISSLQPE DFATYYCQQA NIFPLTFGGG   120
TKVEIKRTVA APSVFIFPPS DEQLKSGTAS VVCLLNNFYP REAKVQWKVD NALQSGNSQE   180
SVTEQDSKDS TYSLSSTLTL SKADYEKHKV YACEVTHQGL SSPVTKSFNR GEC          233

SEQ ID NO: 5           moltype = AA   length = 236
FEATURE                Location/Qualifiers
REGION                 1..236
                       note = antiCD40 antibody light chain with signal peptide 2
source                 1..236
                       mol_type = protein
                       organism = synthetic construct
SEQUENCE: 5
MDMRVPAQLL GLLLLWLRGA RCDIQMTQSP SSVSASVGDR VTITCRASQG IYSWLAWYQQ    60
```

```
KPGKAPNLLI YTASTLQSGV PSRFSGSGSG TDFTLTISSL QPEDFATYYC QQANIFPLTF    120
GGGTKVEIKR TVAAPSVFIF PPSDEQLKSG TASVVCLLNN FYPREAKVQW KVDNALQSGN    180
SQESVTEQDS KDSTYSLSST LTLSKADYEK HKVYACEVTH QGLSSPVTKS FNRGEC        236

SEQ ID NO: 6            moltype = AA   length = 451
FEATURE                 Location/Qualifiers
REGION                  1..451
                        note = antiCD40 antibody heavy chain hIgG2 dK
source                  1..451
                        mol_type = protein
                        organism = synthetic construct
SEQUENCE: 6
QVQLVQSGAE VKKPGASVKV SCKASGYTFT GYYMHWVRQA PGQGLEWMGW INPDSGGTNY     60
AQKFQGRVTM TRDTSISTAY MELNRLRSDD TAVYYCARDQ PLGYCTNGVC SYFDYWGQGT    120
LVTVSSASTK GPSVFPLAPC SRSTSESTAA LGCLVKDYFP EPVTVSWNSG ALTSGVHTFP    180
AVLQSSGLYS LSSVVTVPSS NFGTQTYTCN VDHKPSNTKV DKTVERKCCV ECPPCPAPPV    240
AGPSVFLFPP KPKDTLMISR TPEVTCVVVD VSHEDPEVQF NWYVDGVEVH NAKTKPREEQ    300
FNSTFRVVSV LTVVHQDWLN GKEYKCKVSN KGLPAPIEKT ISKTKGQPRE PQVYTLPPSR    360
EEMTKNQVSL TCLVKGFYPS DIAVEWESNG QPENNYKTTP PMLDSDGSFF LYSKLTVDKS    420
RWQQGNVFSC SVMHEALHNH YTQKSLSLSP G                                   451

SEQ ID NO: 7            moltype = AA   length = 470
FEATURE                 Location/Qualifiers
REGION                  1..470
                        note = antiCD40 antibody heavy chain hIgG2 dK with signal
                         peptide 1
source                  1..470
                        mol_type = protein
                        organism = synthetic construct
SEQUENCE: 7
MGWSCIILFL VATATGVHSQ VQLVQSGAEV KKPGASVKVS CKASGYTFTG YYMHWVRQAP     60
GQGLEWMGWI NPDSGGTNYA QKFQGRVTMT RDTSISTAYM ELNRLRSDDT AVYYCARDQP    120
LGYCTNGVCS YFDYWGQGTL VTVSSASTKG PSVFPLAPCS RSTSESTAAL GCLVKDYFPE    180
PVTVSWNSGA LTSGVHTFPA VLQSSGLYSL SSVVTVPSSN FGTQTYTCNV DHKPSNTKVD    240
KTVERKCCVE CPPCPAPPVA GPSVFLFPPK PKDTLMISRT PEVTCVVVDV SHEDPEVQFN    300
WYVDGVEVHN AKTKPREEQF NSTFRVVSVL TVVHQDWLNG KEYKCKVSNK GLPAPIEKTI    360
SKTKGQPREP QVYTLPPSRE EMTKNQVSLT CLVKGFYPSD IAVEWESNGQ PENNYKTTPP    420
MLDSDGSFFL YSKLTVDKSR WQQGNVFSCS VMHEALHNHY TQKSLSLSPG               470

SEQ ID NO: 8            moltype = AA   length = 473
FEATURE                 Location/Qualifiers
REGION                  1..473
                        note = antiCD40 antibody heavy chain hIgG2 dK with signal
                         peptide 2
source                  1..473
                        mol_type = protein
                        organism = synthetic construct
SEQUENCE: 8
MDMRVPAQLL GLLLLWLRGA RCQVLVQSG AEVKKPGASV KVSCKASGYT FTGYYMHWVR      60
QAPGQGLEWM GWINPDSGGT NYAQKFQGRV TMTRDTSIST AYMELNRLRS DDTAVYYCAR    120
DQPLGYCTNG VCSYFDYWGQ GTLVTVSSAS TKGPSVFPLA PCSRSTSEST AALGCLVKDY    180
FPEPVTVSWN SGALTSGVHT FPAVLQSSGL YSLSSVVTVP SSNFGTQTYT CNVDHKPSNT    240
KVDKTVERKC CVECPPCPAP PVAGPSVFLF PPKPKDTLMI SRTPEVTCVV VDVSHEDPEV    300
QFNWYVDGVE VHNAKTKPRE EQFNSTFRVV SVLTVVHQDW LNGKEYKCKV SNKGLPAPIE    360
KTISKTKGQP REPQVYTLPP SREEMTKNQV SLTCLVKGFY PSDIAVEWES NGQPENNYKT    420
TPPMLDSDGS FFLYSKLTVD KSRWQQGNVF SCSVMHEALH NHYTQKSLSL SPG           473

SEQ ID NO: 9            moltype = AA   length = 452
FEATURE                 Location/Qualifiers
REGION                  1..452
                        note = antiCD40 antibody heavy chain hIgG2
source                  1..452
                        mol_type = protein
                        organism = synthetic construct
SEQUENCE: 9
QVQLVQSGAE VKKPGASVKV SCKASGYTFT GYYMHWVRQA PGQGLEWMGW INPDSGGTNY     60
AQKFQGRVTM TRDTSISTAY MELNRLRSDD TAVYYCARDQ PLGYCTNGVC SYFDYWGQGT    120
LVTVSSASTK GPSVFPLAPC SRSTSESTAA LGCLVKDYFP EPVTVSWNSG ALTSGVHTFP    180
AVLQSSGLYS LSSVVTVPSS NFGTQTYTCN VDHKPSNTKV DKTVERKCCV ECPPCPAPPV    240
AGPSVFLFPP KPKDTLMISR TPEVTCVVVD VSHEDPEVQF NWYVDGVEVH NAKTKPREEQ    300
FNSTFRVVSV LTVVHQDWLN GKEYKCKVSN KGLPAPIEKT ISKTKGQPRE PQVYTLPPSR    360
EEMTKNQVSL TCLVKGFYPS DIAVEWESNG QPENNYKTTP PMLDSDGSFF LYSKLTVDKS    420
RWQQGNVFSC SVMHEALHNH YTQKSLSLSP GK                                  452

SEQ ID NO: 10           moltype = AA   length = 471
FEATURE                 Location/Qualifiers
REGION                  1..471
                        note = antiCD40 antibody heavy chain hIgG2 with signal
                         peptide 1
```

```
source                  1..471
                        mol_type = protein
                        organism = synthetic construct
SEQUENCE: 10
MGWSCIILFL VATATGVHSQ VQLVQSGAEV KKPGASVKVS CKASGYTFTG YYMHWVRQAP   60
GQGLEWMGWI NPDSGGTNYA QKFQGRVTMT RDTSISTAYM ELNRLRSDDT AVYYCARDQP  120
LGYCTNGVCS YFDYWGQGTL VTVSSASTKG PSVFPLAPCS RSTSESTAAL GCLVKDYFPE  180
PVTVSWNSGA LTSGVHTFPA VLQSSGLYSL SSVVTVPSSN FGTQTYTCNV DHKPSNTKVD  240
KTVERKCCVE CPPCPAPPVA GPSVFLFPPK PKDTLMISRT PEVTCVVVDV SHEDPEVQFN  300
WYVDGVEVHN AKTKPREEQF NSTFRVVSVL TVVHQDWLNG KEYKCKVSNK GLPAPIEKTI  360
SKTKGQPREP QVYTLPPSRE EMTKNQVSLT CLVKGFYPSD IAVEWESNGQ PENNYKTTPP  420
MLDSDGSFFL YSKLTVDKSR WQQGNVFSCS VMHEALHNHY TQKSLSLSPG K           471

SEQ ID NO: 11           moltype = AA   length = 474
FEATURE                 Location/Qualifiers
REGION                  1..474
                        note = antiCD40 antibody heavy chain hIgG2 with signal
                         peptide 2
source                  1..474
                        mol_type = protein
                        organism = synthetic construct
SEQUENCE: 11
MDMRVPAQLL GLLLLWLRGA RCQVQLVQSG AEVKKPGASV KVSCKASGYT FTGYYMHWVR   60
QAPGQGLEWM GWINPDSGGT NYAQKFQGRV TMTRDTSIST AYMELNRLRS DDTAVYYCAR  120
DQPLGYCTNG VCSYFDYWGQ GTLVTVSSAS TKGPSVFPLA PCSRSTSEST AALGCLVKDY  180
FPEPVTVSWN SGALTSGVHT FPAVLQSSGL YSLSSVVTVP SSNFGTQTYT CNVDHKPSNT  240
KVDKTVERKC CVECPPCPAP PVAGPSVFLF PPKPKDTLMI SRTPEVTCVV VDVSHEDPEV  300
QFNWYVDGVE VHNAKTKPRE EQFNSTFRVV SVLTVVHQDW LNGKEYKCKV SNKGLPAPIE  360
KTISKTKGQP REPQVYTLPP SREEMTKNQV SLTCLVKGFY PSDIAVEWES NGQPENNYKT  420
TPPMLDSDGS FFLYSKLTVD KSRWQQGNVF SCSVMHEALH NHYTQKSLSL SPGK        474

SEQ ID NO: 12           moltype = AA   length = 231
FEATURE                 Location/Qualifiers
REGION                  1..231
                        note = antiCD40 antibody hIgG2 Fab region heavy chain
source                  1..231
                        mol_type = protein
                        organism = synthetic construct
SEQUENCE: 12
QVQLVQSGAE VKKPGASVKV SCKASGYTFT GYYMHWVRQA PGQGLEWMGW INPDSGGTNY   60
AQKFQGRVTM TRDTSISTAY MELNRLRSDD TAVYYCARDQ PLGYCTNGVC SYFDYWGQGT  120
LVTVSSASTK GPSVFPLAPC SRSTSESTAA LGCLVKDYFP EPVTVSWNSG ALTSGVHTFP  180
AVLQSSGLYS LSSVVTVPSS NFGTQTYTCN VDHKPSNTKV DKTVERKCCV E           231

SEQ ID NO: 13           moltype = AA   length = 250
FEATURE                 Location/Qualifiers
REGION                  1..250
                        note = antiCD40 antibody hIgG2 Fab region heavy chain with
                         signal peptide 1
source                  1..250
                        mol_type = protein
                        organism = synthetic construct
SEQUENCE: 13
MGWSCIILFL VATATGVHSQ VQLVQSGAEV KKPGASVKVS CKASGYTFTG YYMHWVRQAP   60
GQGLEWMGWI NPDSGGTNYA QKFQGRVTMT RDTSISTAYM ELNRLRSDDT AVYYCARDQP  120
LGYCTNGVCS YFDYWGQGTL VTVSSASTKG PSVFPLAPCS RSTSESTAAL GCLVKDYFPE  180
PVTVSWNSGA LTSGVHTFPA VLQSSGLYSL SSVVTVPSSN FGTQTYTCNV DHKPSNTKVD  240
KTVERKCCVE                                                         250

SEQ ID NO: 14           moltype = AA   length = 166
FEATURE                 Location/Qualifiers
REGION                  1..166
                        note = MISC_FEATURE - IFN beta
source                  1..166
                        mol_type = protein
                        organism = Homo sapiens
SEQUENCE: 14
MSYNLLGFLQ RSSNFQCQKL LWQLNGRLEY CLKDRMNFDI PEEIKQLQQF QKEDAALTIY   60
EMLQNIFAIF RQDSSSTGWN ETIVENLLAN VYHQINHLKT VLEEKLEKED FTRGKLMSSL  120
HLKRYYGRIL HYLKAKEYSH CAWTIVRVEI LRNFYFINRL TGYLRN                 166

SEQ ID NO: 15           moltype = AA   length = 166
FEATURE                 Location/Qualifiers
REGION                  1..166
                        note = IFN beta C17S
source                  1..166
                        mol_type = protein
                        organism = synthetic construct
SEQUENCE: 15
```

```
MSYNLLGFLQ RSSNFQSQKL LWQLNGRLEY CLKDRMNFDI PEEIKQLQQF QKEDAALTIY    60
EMLQNIFAIF RQDSSSTGWN ETIVENLLAN VYHQINHLKT VLEEKLEKED FTRGKLMSSL   120
HLKRYYGRIL HYLKAKEYSH CAWTIVRVEI LRNFYFINRL TGYLRN                 166

SEQ ID NO: 16          moltype = AA   length = 166
FEATURE                Location/Qualifiers
REGION                 1..166
                       note = IFN beta C17S,N80Q
source                 1..166
                       mol_type = protein
                       organism = synthetic construct
SEQUENCE: 16
MSYNLLGFLQ RSSNFQSQKL LWQLNGRLEY CLKDRMNFDI PEEIKQLQQF QKEDAALTIY    60
EMLQNIFAIF RQDSSSTGWQ ETIVENLLAN VYHQINHLKT VLEEKLEKED FTRGKLMSSL   120
HLKRYYGRIL HYLKAKEYSH CAWTIVRVEI LRNFYFINRL TGYLRN                 166

SEQ ID NO: 17          moltype = AA   length = 165
FEATURE                Location/Qualifiers
REGION                 1..165
                       note = MISC_FEATURE - IFN alpha 2a
source                 1..165
                       mol_type = protein
                       organism = Homo sapiens
SEQUENCE: 17
CDLPQTHSLG SRRTLMLLAQ MRKISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKE                  165

SEQ ID NO: 18          moltype = AA   length = 175
FEATURE                Location/Qualifiers
REGION                 1..175
                       note = MISC_FEATURE - IFN lambda 2
source                 1..175
                       mol_type = protein
                       organism = Homo sapiens
SEQUENCE: 18
VPVARLHGAL PDARGCHIAQ FKSLSPQELQ AFKRAKDALE ESLLLKDCRC HSRLFPRTWD    60
LRQLQVRERP MALEAELALT LKVLEATADT DPALVDVLDQ PLHTLHHILS QFRACIQPQP   120
TAGPRTRGRL HHWLYRLQEA PKKESPGCLE ASVTFNLFRL LTRDLNCVAS GDLCV        175

SEQ ID NO: 19          moltype = AA   length = 143
FEATURE                Location/Qualifiers
REGION                 1..143
                       note = MISC_FEATURE - IFN gamma
source                 1..143
                       mol_type = protein
                       organism = Homo sapiens
SEQUENCE: 19
QDPYVKEAEN LKKYFNAGHS DVADNGTLFL GILKNWKEES DRKIMQSQIV SFYFKLFKNF    60
KDDQSIQKSV ETIKEDMNVK FFNSNKKKRD DFEKLTNYSV TDLNVQRKAI HELIQVMAEL   120
SPAAKTGKRK RSQMLFRGRR ASQ                                          143

SEQ ID NO: 20          moltype = AA   length = 4
FEATURE                Location/Qualifiers
REGION                 1..4
                       note = RL linker
source                 1..4
                       mol_type = protein
                       organism = synthetic construct
SEQUENCE: 20
PAPA                                                                 4

SEQ ID NO: 21          moltype = AA   length = 13
FEATURE                Location/Qualifiers
REGION                 1..13
                       note = GST linker
source                 1..13
                       mol_type = protein
                       organism = synthetic construct
SEQUENCE: 21
SGGTSGSTSG TGS                                                      13

SEQ ID NO: 22          moltype = AA   length = 12
FEATURE                Location/Qualifiers
REGION                 1..12
                       note = HL linker
source                 1..12
                       mol_type = protein
                       organism = synthetic construct
```

```
SEQUENCE: 22
AEAAAKEAAA KA                                                              12

SEQ ID NO: 23           moltype = AA  length = 24
FEATURE                 Location/Qualifiers
REGION                  1..24
                        note = HL2 linker
source                  1..24
                        mol_type = protein
                        organism = synthetic construct
SEQUENCE: 23
AEAAAKEAAA KAAEAAAKEA AAKA                                                 24

SEQ ID NO: 24           moltype = AA  length = 10
FEATURE                 Location/Qualifiers
REGION                  1..10
                        note = G4S2 linker
source                  1..10
                        mol_type = protein
                        organism = synthetic construct
SEQUENCE: 24
GGGGSGGGGS                                                                 10

SEQ ID NO: 25           moltype = AA  length = 15
FEATURE                 Location/Qualifiers
REGION                  1..15
                        note = G4S3 linker
source                  1..15
                        mol_type = protein
                        organism = synthetic construct
SEQUENCE: 25
GGGGSGGGGS GGGGS                                                           15

SEQ ID NO: 26           moltype = AA  length = 20
FEATURE                 Location/Qualifiers
REGION                  1..20
                        note = G4S4 linker
source                  1..20
                        mol_type = protein
                        organism = synthetic construct
SEQUENCE: 26
GGGGSGGGGS GGGGSGGGGS                                                      20

SEQ ID NO: 27           moltype = AA  length = 13
FEATURE                 Location/Qualifiers
REGION                  1..13
                        note = TEV-6His tag
source                  1..13
                        mol_type = protein
                        organism = synthetic construct
SEQUENCE: 27
ENLYFQSHHH HHH                                                             13

SEQ ID NO: 28           moltype = AA  length = 392
FEATURE                 Location/Qualifiers
REGION                  1..392
                        note = antiCD40_LC--HL--IFN beta
source                  1..392
                        mol_type = protein
                        organism = synthetic construct
SEQUENCE: 28
DIQMTQSPSS VSASVGDRVT ITCRASQGIY SWLAWYQQKP GKAPNLLIYT ASTLQSGVPS           60
RFSGSGSGTD FTLTISSLQP EDFATYYCQQ ANIFPLTFGG GTKVEIKRTV AAPSVFIFPP          120
SDEQLKSGTA SVVCLLNNFY PREAKVQWKV DNALQSGNSQ ESVTEQDSKD STYSLSSTLT          180
LSKADYEKHK VYACEVTHQG LSSPVTKSFN RGECAEAAAK EAAAKAMSYN LLGFLQRSSN          240
FQCQKLLWQL NGRLEYCLKD RMNFDIPEEI KQLQQFQKED AALTIYEMLQ NIFAIFRQDS          300
SSTGWNETIV ENLLANVYHQ INHLKTVLEE KLEKEDFTRG KLMSSLHLKR YYGRILHYLK          360
AKEYSHCAWT IVRVEILRNF YFINRLTGYL RN                                       392

SEQ ID NO: 29           moltype = AA  length = 392
FEATURE                 Location/Qualifiers
REGION                  1..392
                        note = antiCD40_LC--HL--IFN beta_C17S
source                  1..392
                        mol_type = protein
                        organism = synthetic construct
SEQUENCE: 29
DIQMTQSPSS VSASVGDRVT ITCRASQGIY SWLAWYQQKP GKAPNLLIYT ASTLQSGVPS           60
RFSGSGSGTD FTLTISSLQP EDFATYYCQQ ANIFPLTFGG GTKVEIKRTV AAPSVFIFPP          120
```

```
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECAEAAAK EAAAKAMSYN LLGFLQRSSN  240
FQSQKLLWQL NGRLEYCLKD RMNFDIPEEI KQLQQFQKED AALTIYEMLQ NIFAIFRQDS  300
SSTGWNETIV ENLLANVYHQ INHLKTVLEE KLEKEDFTRG KLMSSLHLKR YYGRILHYLK  360
AKEYSHCAWT IVRVEILRNF YFINRLTGYL RN                               392

SEQ ID NO: 30           moltype = AA   length = 621
FEATURE                 Location/Qualifiers
REGION                  1..621
                        note = antiCD40_hIgG2_dK_HC--RL--IFN beta
source                  1..621
                        mol_type = protein
                        organism = synthetic construct
SEQUENCE: 30
QVQLVQSGAE VKKPGASVKV SCKASGYTFT GYYMHWVRQA PGQGLEWMGW INPDSGGTNY  60
AQKFQGRVTM TRDTSISTAY MELNRLRSDD TAVYYCARDQ PLGYCTNGVC SYFDYWGQGT  120
LVTVSSASTK GPSVFPLAPC SRSTSESTAA LGCLVKDYFP EPVTVSWNSG ALTSGVHTFP  180
AVLQSSGLYS LSSVVTVPSS NFGTQTYTCN VDHKPSNTKV DKTVERKCCV ECPPCPAPPV  240
AGPSVFLFPP KPKDTLMISR TPEVTCVVVD VSHEDPEVQF NWYVDGVEVH NAKTKPREEQ  300
FNSTFRVVSV LTVVHQDWLN GKEYKCKVSN KGLPAPIEKT ISKTKGQPRE PQVYTLPPSR  360
EEMTKNQVSL TCLVKGFYPS DIAVEWESNG QPENNYKTTP PMLDSDGSFF LYSKLTVDKS  420
RWQQGNVFSC SVMHEALHNH YTQKSLSLSP GPAPAMSYNL LGFLQRSSNF QCQKLLWQLN  480
GRLEYCLKDR MNFDIPEEIK QLQQFQKEDA ALTIYEMLQN IFAIFRQDSS STGWNETIVE  540
NLLANVYHQI NHLKTVLEEK LEKEDFTRGK LMSSLHLKRY YGRILHYLKA KEYSHCAWTI  600
VRVEILRNFY FINRLTGYLR N                                           621

SEQ ID NO: 31           moltype = AA   length = 621
FEATURE                 Location/Qualifiers
REGION                  1..621
                        note = antiCD40_hIgG2_dK_HC--RL--IFN beta_C17S
source                  1..621
                        mol_type = protein
                        organism = synthetic construct
SEQUENCE: 31
QVQLVQSGAE VKKPGASVKV SCKASGYTFT GYYMHWVRQA PGQGLEWMGW INPDSGGTNY  60
AQKFQGRVTM TRDTSISTAY MELNRLRSDD TAVYYCARDQ PLGYCTNGVC SYFDYWGQGT  120
LVTVSSASTK GPSVFPLAPC SRSTSESTAA LGCLVKDYFP EPVTVSWNSG ALTSGVHTFP  180
AVLQSSGLYS LSSVVTVPSS NFGTQTYTCN VDHKPSNTKV DKTVERKCCV ECPPCPAPPV  240
AGPSVFLFPP KPKDTLMISR TPEVTCVVVD VSHEDPEVQF NWYVDGVEVH NAKTKPREEQ  300
FNSTFRVVSV LTVVHQDWLN GKEYKCKVSN KGLPAPIEKT ISKTKGQPRE PQVYTLPPSR  360
EEMTKNQVSL TCLVKGFYPS DIAVEWESNG QPENNYKTTP PMLDSDGSFF LYSKLTVDKS  420
RWQQGNVFSC SVMHEALHNH YTQKSLSLSP GPAPAMSYNL LGFLQRSSNF QSQKLLWQLN  480
GRLEYCLKDR MNFDIPEEIK QLQQFQKEDA ALTIYEMLQN IFAIFRQDSS STGWNETIVE  540
NLLANVYHQI NHLKTVLEEK LEKEDFTRGK LMSSLHLKRY YGRILHYLKA KEYSHCAWTI  600
VRVEILRNFY FINRLTGYLR N                                           621

SEQ ID NO: 32           moltype = AA   length = 629
FEATURE                 Location/Qualifiers
REGION                  1..629
                        note = antiCD40_hIgG2_dK_HC--HL--IFN beta
source                  1..629
                        mol_type = protein
                        organism = synthetic construct
SEQUENCE: 32
QVQLVQSGAE VKKPGASVKV SCKASGYTFT GYYMHWVRQA PGQGLEWMGW INPDSGGTNY  60
AQKFQGRVTM TRDTSISTAY MELNRLRSDD TAVYYCARDQ PLGYCTNGVC SYFDYWGQGT  120
LVTVSSASTK GPSVFPLAPC SRSTSESTAA LGCLVKDYFP EPVTVSWNSG ALTSGVHTFP  180
AVLQSSGLYS LSSVVTVPSS NFGTQTYTCN VDHKPSNTKV DKTVERKCCV ECPPCPAPPV  240
AGPSVFLFPP KPKDTLMISR TPEVTCVVVD VSHEDPEVQF NWYVDGVEVH NAKTKPREEQ  300
FNSTFRVVSV LTVVHQDWLN GKEYKCKVSN KGLPAPIEKT ISKTKGQPRE PQVYTLPPSR  360
EEMTKNQVSL TCLVKGFYPS DIAVEWESNG QPENNYKTTP PMLDSDGSFF LYSKLTVDKS  420
RWQQGNVFSC SVMHEALHNH YTQKSLSLSP GAEAAAKEAA AKAMSYNLLG FLQRSSNFQC  480
QKLLWQLNGR LEYCLKDRMN FDIPEEIKQL QQFQKEDAAL TIYEMLQNIF AIFRQDSSST  540
GWNETIVENL LANVYHQINH LKTVLEEKLE KEDFTRGKLM SSLHLKRYYG RILHYLKAKE  600
YSHCAWTIVR VEILRNFYFI NRLTGYLRN                                   629

SEQ ID NO: 33           moltype = AA   length = 629
FEATURE                 Location/Qualifiers
REGION                  1..629
                        note = antiCD40_hIgG2_dK_HC--HL--IFN beta_C17S
source                  1..629
                        mol_type = protein
                        organism = synthetic construct
SEQUENCE: 33
QVQLVQSGAE VKKPGASVKV SCKASGYTFT GYYMHWVRQA PGQGLEWMGW INPDSGGTNY  60
AQKFQGRVTM TRDTSISTAY MELNRLRSDD TAVYYCARDQ PLGYCTNGVC SYFDYWGQGT  120
LVTVSSASTK GPSVFPLAPC SRSTSESTAA LGCLVKDYFP EPVTVSWNSG ALTSGVHTFP  180
AVLQSSGLYS LSSVVTVPSS NFGTQTYTCN VDHKPSNTKV DKTVERKCCV ECPPCPAPPV  240
AGPSVFLFPP KPKDTLMISR TPEVTCVVVD VSHEDPEVQF NWYVDGVEVH NAKTKPREEQ  300
```

```
FNSTFRVVSV LTVVHQDWLN GKEYKCKVSN KGLPAPIEKT ISKTKGQPRE PQVYTLPPSR    360
EEMTKNQVSL TCLVKGFYPS DIAVEWESNG QPENNYKTTP PMLDSDGSFF LYSKLTVDKS    420
RWQQGNVFSC SVMHEALHNH YTQKSLSLSP GAEAAAKEAA AKAMSYNLLG FLQRSSNFQS    480
QKLLWQLNGR LEYCLKDRMN FDIPEEIKQL QQFQKEDAAL TIYEMLQNIF AIFRQDSSST    540
GWNETIVENL LANVYHQINH LKTVLEEKLE KEDFTRGKLM SSLHLKRYYG RILHYLKAKE    600
YSHCAWTIVR VEILRNFYFI NRLTGYLRN                                     629

SEQ ID NO: 34           moltype = AA  length = 384
FEATURE                 Location/Qualifiers
REGION                  1..384
                        note = antiCD40_LC-- RL--IFN beta
source                  1..384
                        mol_type = protein
                        organism = synthetic construct
SEQUENCE: 34
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECPAPAMS YNLLGFLQRS SNFQCQKLLW    240
QLNGRLEYCL KDRMNFDIPE EIKQLQQFQK EDAALTIYEM LQNIFAIFRQ DSSSTGWNET    300
IVENLLANVY HQINHLKTVL EEKLEKEDFT RGKLMSSLHL KRYYGRILHY LKAKEYSHCA    360
WTIVRVEILR NFYFINRLTG YLRN                                           384

SEQ ID NO: 35           moltype = AA  length = 384
FEATURE                 Location/Qualifiers
REGION                  1..384
                        note = antiCD40_LC--RL--IFN beta_C17S
source                  1..384
                        mol_type = protein
                        organism = synthetic construct
SEQUENCE: 35
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECPAPAMS YNLLGFLQRS SNFQSQKLLW    240
QLNGRLEYCL KDRMNFDIPE EIKQLQQFQK EDAALTIYEM LQNIFAIFRQ DSSSTGWNET    300
IVENLLANVY HQINHLKTVL EEKLEKEDFT RGKLMSSLHL KRYYGRILHY LKAKEYSHCA    360
WTIVRVEILR NFYFINRLTG YLRN                                           384

SEQ ID NO: 36           moltype = AA  length = 393
FEATURE                 Location/Qualifiers
REGION                  1..393
                        note = antiCD40_LC--GST--IFN beta_C17S
source                  1..393
                        mol_type = protein
                        organism = synthetic construct
SEQUENCE: 36
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECSTSGTGSMSY NLLGFLQRS            240
NFQSQKLLWQ LNGRLEYCLK DRMNFDIPEE IKQLQQFQKE DAALTIYEML QNIFAIFRQD    300
SSSTGWNETI VENLLANVYH QINHLKTVLE EKLEKEDFTR GKLMSSLHLK RYYGRILHYL    360
KAKEYSHCAW TIVRVEILRN FYFINRLTGY LRN                                 393

SEQ ID NO: 37           moltype = AA  length = 404
FEATURE                 Location/Qualifiers
REGION                  1..404
                        note = antiCD40_LC--HL2--IFN beta_C17S
source                  1..404
                        mol_type = protein
                        organism = synthetic construct
SEQUENCE: 37
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECAEAAAK EAAAKAAEAA AKEAAAKAMS    240
YNLLGFLQRS SNFQSQKLLW QLNGRLEYCL KDRMNFDIPE EIKQLQQFQK EDAALTIYEM    300
LQNIFAIFRQ DSSSTGWNET IVENLLANVY HQINHLKTVL EEKLEKEDFT RGKLMSSLHL    360
KRYYGRILHY LKAKEYSHCA WTIVRVEILR NFYFINRLTG YLRN                    404

SEQ ID NO: 38           moltype = AA  length = 626
FEATURE                 Location/Qualifiers
REGION                  1..626
                        note = antiCD40_hIgG2_dK_HC--G4S2--IFN alpha 2A
source                  1..626
                        mol_type = protein
                        organism = synthetic construct
SEQUENCE: 38
```

```
QVQLVQSGAE VKKPGASVKV SCKASGYTFT GYYMHWVRQA PGQGLEWMGW INPDSGGTNY    60
AQKFQGRVTM TRDTSISTAY MELNRLRSDD TAVYYCARDQ PLGYCTNGVC SYFDYWGQGT   120
LVTVSSASTK GPSVFPLAPC SRSTSESTAA LGCLVKDYFP EPVTVSWNSG ALTSGVHTFP   180
AVLQSSGLYS LSSVVTVPSS NFGTQTYTCN VDHKPSNTKV DKTVERKCCV ECPPCPAPPV   240
AGPSVFLFPP KPKDTLMISR TPEVTCVVVD VSHEDPEVQF NWYVDGVEVH NAKTKPREEQ   300
FNSTFRVVSV LTVVHQDWLN GKEYKCKVSN KGLPAPIEKT ISKTKGQPRE PQVYTLPPSR   360
EEMTKNQVSL TCLVKGFYPS DIAVEWESNG QPENNYKTTP PMLDSDGSFF LYSKLTVDKS   420
RWQQGNVFSC SVMHEALHNH YTQKSLSLSP GGGGSGGGG SCDLPQTHSL GSRRTLMLLA   480
QMRKISLFSC LKDRHDFGFP QEEFGNQFQK AETIPVLHEM IQQIFNLFST KDSSAAWDET   540
LLDKFYTELY QQLNDLEACV IQGVGVTETP LMKEDSILAV RKYFQRITLY LKEKKYSPCA   600
WEVVRAEIMR SFSLSTNLQE SLRSKE                                        626

SEQ ID NO: 39           moltype = AA  length = 631
FEATURE                 Location/Qualifiers
REGION                  1..631
                        note = antiCD40_hIgG2_dK_HC--G4S3--IFN alpha 2A
source                  1..631
                        mol_type = protein
                        organism = synthetic construct
SEQUENCE: 39
QVQLVQSGAE VKKPGASVKV SCKASGYTFT GYYMHWVRQA PGQGLEWMGW INPDSGGTNY    60
AQKFQGRVTM TRDTSISTAY MELNRLRSDD TAVYYCARDQ PLGYCTNGVC SYFDYWGQGT   120
LVTVSSASTK GPSVFPLAPC SRSTSESTAA LGCLVKDYFP EPVTVSWNSG ALTSGVHTFP   180
AVLQSSGLYS LSSVVTVPSS NFGTQTYTCN VDHKPSNTKV DKTVERKCCV ECPPCPAPPV   240
AGPSVFLFPP KPKDTLMISR TPEVTCVVVD VSHEDPEVQF NWYVDGVEVH NAKTKPREEQ   300
FNSTFRVVSV LTVVHQDWLN GKEYKCKVSN KGLPAPIEKT ISKTKGQPRE PQVYTLPPSR   360
EEMTKNQVSL TCLVKGFYPS DIAVEWESNG QPENNYKTTP PMLDSDGSFF LYSKLTVDKS   420
RWQQGNVFSC SVMHEALHNH YTQKSLSLSP GGGGSGGGG SGGGGSCDLP QTHSLGSRRT   480
LMLLAQMRKI SLFSCLKDRH DFGFPQEEFG NQFQKAETIP VLHEMIQQIF NLFSTKDSSA   540
AWDETLLDKF YTELYQQLND LEACVIQGVG VTETPLMKED SILAVRKYFQ RITLYLKEKK   600
YSPCAWEVVR AEIMRSFSLS TNLQESLRSK E                                 631

SEQ ID NO: 40           moltype = AA  length = 636
FEATURE                 Location/Qualifiers
REGION                  1..636
                        note = antiCD40_hIgG2_dK_HC--G4S4--IFN alpha 2A
source                  1..636
                        mol_type = protein
                        organism = synthetic construct
SEQUENCE: 40
QVQLVQSGAE VKKPGASVKV SCKASGYTFT GYYMHWVRQA PGQGLEWMGW INPDSGGTNY    60
AQKFQGRVTM TRDTSISTAY MELNRLRSDD TAVYYCARDQ PLGYCTNGVC SYFDYWGQGT   120
LVTVSSASTK GPSVFPLAPC SRSTSESTAA LGCLVKDYFP EPVTVSWNSG ALTSGVHTFP   180
AVLQSSGLYS LSSVVTVPSS NFGTQTYTCN VDHKPSNTKV DKTVERKCCV ECPPCPAPPV   240
AGPSVFLFPP KPKDTLMISR TPEVTCVVVD VSHEDPEVQF NWYVDGVEVH NAKTKPREEQ   300
FNSTFRVVSV LTVVHQDWLN GKEYKCKVSN KGLPAPIEKT ISKTKGQPRE PQVYTLPPSR   360
EEMTKNQVSL TCLVKGFYPS DIAVEWESNG QPENNYKTTP PMLDSDGSFF LYSKLTVDKS   420
RWQQGNVFSC SVMHEALHNH YTQKSLSLSP GGGGSGGGG SGGGGSGGGG SCDLPQTHSL   480
GSRRTLMLLA QMRKISLFSC LKDRHDFGFP QEEFGNQFQK AETIPVLHEM IQQIFNLFST   540
KDSSAAWDET LLDKFYTELY QQLNDLEACV IQGVGVTETP LMKEDSILAV RKYFQRITLY   600
LKEKKYSPCA WEVVRAEIMR SFSLSTNLQE SLRSKE                             636

SEQ ID NO: 41           moltype = AA  length = 389
FEATURE                 Location/Qualifiers
REGION                  1..389
                        note = antiCD40_LC--G4S2--IFN alpha 2A
source                  1..389
                        mol_type = protein
                        organism = synthetic construct
SEQUENCE: 41
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGGGGSG GGGSCDLPQT HSLGSRRTLM   240
LLAQMRKISL FSCLKDRHDF GFPQEEFGNQ FQKAETIPVL HEMIQQIFNL FSTKDSSAAW   300
DETLLDKFYT ELYQQLNDLE ACVIQGVGVT ETPLMKEDSI LAVRKYFQRI TLYLKEKKYS   360
PCAWEVVRAE IMRSFSLSTN LQESLRSKE                                    389

SEQ ID NO: 42           moltype = AA  length = 394
FEATURE                 Location/Qualifiers
REGION                  1..394
                        note = antiCD40_LC--G4S3--IFN alpha 2A
source                  1..394
                        mol_type = protein
                        organism = synthetic construct
SEQUENCE: 42
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
```

```
LSKADYEKHK VYACEVTHQG LSSPVTKSFN RGECGGGGSG GGGSGGGGSC DLPQTHSLGS      240
RRTLMLLAQM RKISLFSCLK DRHDFGFPQE EFGNQFQKAE TIPVLHEMIQ QIFNLFSTKD      300
SSAAWDETLL DKFYTELYQQ LNDLEACVIQ GVGVTETPLM KEDSILAVRK YFQRITLYLK      360
EKKYSPCAWE VVRAEIMRSF SLSTNLQESL RSKE                                 394

SEQ ID NO: 43              moltype = AA   length = 399
FEATURE                    Location/Qualifiers
REGION                     1..399
                           note = antiCD40_LC--G4S4--IFN alpha 2A
source                     1..399
                           mol_type = protein
                           organism = synthetic construct
SEQUENCE: 43
DIQMTQSPSS VSASVGDRVT ITCRASQGIY SWLAWYQQKP GKAPNLLIYT ASTLQSGVPS      60
RFSGSGSGTD FTLTISSLQP EDFATYYCQQ ANIFPLTFGG GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGECGGGGSG GGGSGGGGSG GGGSCDLPQT     240
HSLGSRRTLM LLAQMRKISL FSCLKDRHDF GFPQEEFGNQ FQKAETIPVL HEMIQQIFNL     300
FSTKDSSAAW DETLLDKFYT ELYQQLNDLE ACVIQGVGVT ETPLMKEDSI LAVRKYFQRI     360
TLYLKEKKYS PCAWEVVRAE IMRSFSLSTN LQESLRSKE                            399

SEQ ID NO: 44              moltype = AA   length = 395
FEATURE                    Location/Qualifiers
REGION                     1..395
                           note = IFN beta--G4S3--antiCD40_LC
source                     1..395
                           mol_type = protein
                           organism = synthetic construct
SEQUENCE: 44
MSYNLLGFLQ RSSNFQCQKL LWQLNGRLEY CLKDRMNFDI PEEIKQLQQF QKEDAALTIY      60
EMLQNIFAIF RQDSSSTGWN ETIVENLLAN VYHQINHLKT VLEEKLEKED FTRGKLMSSL     120
HLKRYYGRIL HYLKAKEYSH CAWTIVRVEI LRNFYFINRL TGYLRNGGGG SGGGGSGGGG     180
SDIQMTQSPS SVSASVGDRV TITCRASQGI YSWLAWYQQK PGKAPNLLIY TASTLQSGVP     240
SRFSGSGSGT DFTLTISSLQ PEDFATYYCQ QANIFPLTFG GGTKVEIKRT VAAPSVFIFP     300
PSDEQLKSGT ASVVCLLNNF YPREAKVQWK VDNALQSGNS QESVTEQDSK DSTYSLSSTL     360
TLSKADYEKH KVYACEVTHQ GLSSPVTKSF NRGEC                                395

SEQ ID NO: 45              moltype = AA   length = 400
FEATURE                    Location/Qualifiers
REGION                     1..400
                           note = antiCD40_LC--G4S4--IFN beta
source                     1..400
                           mol_type = protein
                           organism = synthetic construct
SEQUENCE: 45
DIQMTQSPSS VSASVGDRVT ITCRASQGIY SWLAWYQQKP GKAPNLLIYT ASTLQSGVPS      60
RFSGSGSGTD FTLTISSLQP EDFATYYCQQ ANIFPLTFGG GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGECGGGGSG GGGSGGGGSG GGGSMSYNLL     240
GFLQRSSNFQ CQKLLWQLNG RLEYCLKDRM NFDIPEEIKQ LQQFQKEDAA LTIYEMLQNI     300
FAIFRQDSSS TGWNETIVEN LLANVYHQIN HLKTVLEEKL EKEDFTRGKL MSSLHLKRYY     360
GRILHYLKAK EYSHCAWTIV RVEILRNFYF INRLTGYLRN                           400

SEQ ID NO: 46              moltype = AA   length = 636
FEATURE                    Location/Qualifiers
REGION                     1..636
                           note = IFN beta--G4S3--antiCD40_HC_IgG1_NNAS_dK
source                     1..636
                           mol_type = protein
                           organism = synthetic construct
SEQUENCE: 46
MSYNLLGFLQ RSSNFQCQKL LWQLNGRLEY CLKDRMNFDI PEEIKQLQQF QKEDAALTIY      60
EMLQNIFAIF RQDSSSTGWN ETIVENLLAN VYHQINHLKT VLEEKLEKED FTRGKLMSSL     120
HLKRYYGRIL HYLKAKEYSH CAWTIVRVEI LRNFYFINRL TGYLRNGGGG SGGGGSGGGG     180
SQVQLVQSGA EVKKPGASVK VSCKASGYTF TGYYMHWVRQ APGQGLEWMG WINPDSGGTN     240
YAQKFQGRVT MTRDTSISTA YMELNRLRSD DTAVYYCARD QPLGYCTNGV CSYFDYWGQG     300
TLVTVSSAST KGPSVFPLAP SSKSTSGGTA ALGCLVKDYF PEPVTVSWNS GALTSGVHTF     360
PAVLQSSGLY SLSSVVTVPS SSLGTQTYIC NVNHKPSNTK VDKKVEPKSC DKTHTCPPCP     420
APELLGGPSV FLFPPKPKDT LMISRTPEVT CVVVDVSHED PEVKFNWYVD GVEVHNAKTK     480
PREEQYNNAS RVVSVLTVLH QDWLNGKEYK CKVSNKALPA PIEKTISKAK GQPREPQVYT     540
LPPSRDELTK NQVSLTCLVK GFYPSDIAVE WESNGQPENN YKTTPPVLDS DGSFFLYSKL     600
TVDKSRWQQG NVFSCSVMHE ALHNHYTQKS LSLSPG                               636

SEQ ID NO: 47              moltype = AA   length = 641
FEATURE                    Location/Qualifiers
REGION                     1..641
                           note = antiCD40_HC_IgG1_NNAS_dK--G4S4--IFN beta
source                     1..641
                           mol_type = protein
```

```
                        organism = synthetic construct
SEQUENCE: 47
QVQLVQSGAE VKKPGASVKV SCKASGYTFT GYYMHWVRQA PGQGLEWMGW INPDSGGTNY    60
AQKFQGRVTM TRDTSISTAY MELNRLRSDD TAVYYCARDQ PLGYCTNGVC SYFDYWGQGT   120
LVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKKVEPKSCD KTHTCPPCPA   240
PELLGGPSVF LFPPKPKDTL MISRTPEVTC VVVDVSHEDP EVKFNWYVDG VEVHNAKTKP   300
REEQYNNASR VVSVLTVLHQ DWLNGKEYKC KVSNKALPAP IEKTISKAKG QPREPQVYTL   360
PPSRDELTKN QVSLTCLVKG FYPSDIAVEW ESNGQPENNY KTTPPVLDSD GSFFLYSKLT   420
VDKSRWQQGN VFSCSVMHEA LHNHYTQKSL SLSPGGGGGS GGGGSGGGGS GGGGSMSYNL   480
LGFLQRSSNF QCQKLLWQLN GRLEYCLKDR MNFDIPEEIK QLQQFQKEDA ALTIYEMLQN   540
IFAIFRQDSS STGWNETIVE NLLANVYHQI NHLKTVLEEK LEKEDFTRGK LMSSLHLKRY   600
YGRILHYLKA KEYSHCAWTI VRVEILRNFY FINRLTGYLR N                      641

SEQ ID NO: 48           moltype = AA  length = 456
FEATURE                 Location/Qualifiers
REGION                  1..456
                        note = antiCD40 antibody hIgG1 heavy chain -NNAS
source                  1..456
                        mol_type = protein
                        organism = synthetic construct
SEQUENCE: 48
QVQLVQSGAE VKKPGASVKV SCKASGYTFT GYYMHWVRQA PGQGLEWMGW INPDSGGTNY    60
AQKFQGRVTM TRDTSISTAY MELNRLRSDD TAVYYCARDQ PLGYCTNGVC SYFDYWGQGT   120
LVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKKVEPKSCD KTHTCPPCPA   240
PELLGGPSVF LFPPKPKDTL MISRTPEVTC VVVDVSHEDP EVKFNWYVDG VEVHNAKTKP   300
REEQYNNASR VVSVLTVLHQ DWLNGKEYKC KVSNKALPAP IEKTISKAKG QPREPQVYTL   360
PPSRDELTKN QVSLTCLVKG FYPSDIAVEW ESNGQPENNY KTTPPVLDSD GSFFLYSKLT   420
VDKSRWQQGN VFSCSVMHEA LHNHYTQKSL SLSPGK                            456

SEQ ID NO: 49           moltype = AA  length = 455
FEATURE                 Location/Qualifiers
REGION                  1..455
                        note = antiCD40 antibody hIgG1 heavy chain -NNAS-dK
source                  1..455
                        mol_type = protein
                        organism = synthetic construct
SEQUENCE: 49
QVQLVQSGAE VKKPGASVKV SCKASGYTFT GYYMHWVRQA PGQGLEWMGW INPDSGGTNY    60
AQKFQGRVTM TRDTSISTAY MELNRLRSDD TAVYYCARDQ PLGYCTNGVC SYFDYWGQGT   120
LVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKKVEPKSCD KTHTCPPCPA   240
PELLGGPSVF LFPPKPKDTL MISRTPEVTC VVVDVSHEDP EVKFNWYVDG VEVHNAKTKP   300
REEQYNNASR VVSVLTVLHQ DWLNGKEYKC KVSNKALPAP IEKTISKAKG QPREPQVYTL   360
PPSRDELTKN QVSLTCLVKG FYPSDIAVEW ESNGQPENNY KTTPPVLDSD GSFFLYSKLT   420
VDKSRWQQGN VFSCSVMHEA LHNHYTQKSL SLSPG                             455

SEQ ID NO: 50           moltype = AA  length = 244
FEATURE                 Location/Qualifiers
REGION                  1..244
                        note = antiCD40 antibody hIgG2 Fab region heavy
                          chain--TEV--6His tag
source                  1..244
                        mol_type = protein
                        organism = synthetic construct
SEQUENCE: 50
QVQLVQSGAE VKKPGASVKV SCKASGYTFT GYYMHWVRQA PGQGLEWMGW INPDSGGTNY    60
AQKFQGRVTM TRDTSISTAY MELNRLRSDD TAVYYCARDQ PLGYCTNGVC SYFDYWGQGT   120
LVTVSSASTK GPSVFPLAPC SRSTSESTAA LGCLVKDYFP EPVTVSWNSG ALTSGVHTFP   180
AVLQSSGLYS LSSVVTVPSS NFGTQTYTCN VDHKPSNTKV DKTVERKCCV EENLYFQSHH   240
HHHH                                                               244

SEQ ID NO: 51           moltype = AA  length = 107
FEATURE                 Location/Qualifiers
REGION                  1..107
                        note = antiCD40 Antibody VL domain
source                  1..107
                        mol_type = protein
                        organism = synthetic construct
SEQUENCE: 51
DIQMTQSPSS VSASVGDRVT ITCRASQGIY SWLAWYQQKP GKAPNLLIYT ASTLQSVPS     60
RFSGSGSGTD FTLTISSLQP EDFATYYCQQ ANIFPLTFGG GTKVEIK                107

SEQ ID NO: 52           moltype = AA  length = 11
FEATURE                 Location/Qualifiers
REGION                  1..11
                        note = antiCD40 Antibody CDRL1
source                  1..11
```

```
                        mol_type = protein
                        organism = synthetic construct
SEQUENCE: 52
RASQGIYSWL A                                                         11

SEQ ID NO: 53           moltype = AA   length = 7
FEATURE                 Location/Qualifiers
REGION                  1..7
                        note = antiCD40 Antibody CDRL2
source                  1..7
                        mol_type = protein
                        organism = synthetic construct
SEQUENCE: 53
TASTLQS                                                              7

SEQ ID NO: 54           moltype = AA   length = 9
FEATURE                 Location/Qualifiers
REGION                  1..9
                        note = antiCD40 Antibody CDRL3
source                  1..9
                        mol_type = protein
                        organism = synthetic construct
SEQUENCE: 54
QQANIFPLT                                                            9

SEQ ID NO: 55           moltype = AA   length = 126
FEATURE                 Location/Qualifiers
REGION                  1..126
                        note = antiCD40 Antibody VH domain
source                  1..126
                        mol_type = protein
                        organism = synthetic construct
SEQUENCE: 55
QVQLVQSGAE VKKPGASVKV SCKASGYTFT GYYMHWVRQA PGQGLEWMGW INPDSGGTNY     60
AQKFQGRVTM TRDTSISTAY MELNRLRSDD TAVYYCARDQ PLGYCTNGVC SYFDYWGQGT    120
LVTVSS                                                              126

SEQ ID NO: 56           moltype = AA   length = 6
FEATURE                 Location/Qualifiers
REGION                  1..6
                        note = antiCD40 Antibody CDRH1
source                  1..6
                        mol_type = protein
                        organism = synthetic construct
SEQUENCE: 56
TGYYMH                                                               6

SEQ ID NO: 57           moltype = AA   length = 17
FEATURE                 Location/Qualifiers
REGION                  1..17
                        note = antiCD40 Antibody CDRH2
source                  1..17
                        mol_type = protein
                        organism = synthetic construct
SEQUENCE: 57
WINPDSGGTN YAQKFQG                                                   17

SEQ ID NO: 58           moltype = AA   length = 17
FEATURE                 Location/Qualifiers
REGION                  1..17
                        note = antiCD40 Antibody CDRH3
source                  1..17
                        mol_type = protein
                        organism = synthetic construct
SEQUENCE: 58
DQPLGYCTNG VCSYFDY                                                   17

SEQ ID NO: 59           moltype = DNA  length = 1947
FEATURE                 Location/Qualifiers
misc_feature            1..1947
                        note = Nucleic acid encoding SEQ ID NO 32
source                  1..1947
                        mol_type = other DNA
                        organism = synthetic construct
SEQUENCE: 59
atgggctggt cctgcatcat tctgtttctg gtggccacag ccacaggcgt gcactctcag    60
gttcaactgg ttcagtctgg cgccgaagtg aagaaaccag cgccagcgt gaaggtgtcc   120
tgtaaagcca gcggctacac ctttaccggc tactacatgc actgggtccg acaggctcca   180
ggacagggac ttgagtggat gggctggatc aatcctgaca gcggcggcac caactacgcc   240
```

```
cagaaattcc agggcagagt gaccatgacc agagacacca gcatcagcac cgcctacatg    300
gaactgaacc ggctgagatc cgacgacacc gccgtgtact attgcgccag agatcagcct    360
ctgggctact gcacaaatgg cgtgtgcagc tacttcgact actggggcca gggcacactg    420
gttacagtgt ctagcgcctc tacaaagggc ccctccgttt ttcctctggc tccttgttct    480
agaagcacca gcgagtctac agccgctctg ggctgtctgg tcaaggacta ctttcctgag    540
cctgtgaccg tgtcctggaa tagcggagca ctgacatccg gcgtgcacac atttccagct    600
gtgctgcaga gcagcggcct gtactctctg tctagcgtgg tcaccgtgcc tagcagcaat    660
ttcggcaccc agacctacac ctgtaacgtg gaccacaagc ctagcaacac caaggtggac    720
aagaccgtgg aacggaagtg ctgcgtggaa tgccctcctt gtcctgctcc tccagtggcc    780
ggaccttccg tgtttctgtt ccctccaaag cctaaggaca ccctgatgat cagcagaacc    840
cctgaagtga cctgcgtggt ggtggatgtg tctcacgagg atcccgaggt gcagttcaat    900
tggtacgtgg acggcgtgga agtgcacaac gccaagacca gcctagaga ggaacagttc    960
aacagcacct tcagagtggt gtccgtgctg accgtggtgc atcaggactg gctgaacggc    1020
aaagagtaca agtgcaaggt gtccaacaag ggcctgcctg ctcctatcga gaaaaccatc    1080
agcaagacca aaggccagcc tcgcgagcct caggtttaca cactgcctcc aagccgggaa    1140
gagatgacca gaatcaggt gtccctgacc tgcctcgtga agggcttcta ccccttccgat    1200
atcgccgtga aatgggagag caatggccag cctgagaaca actacaagac cacacctcct    1260
atgctggaca gcgacggctc attcttcctg tacagcaagc tgacagtgga caagtccaga    1320
tggcagcagg gcaacgtgtt cagctgttct gtgatgcacg aggccctgca caaccactac    1380
acccagaagt ctctgtctct gagccctggc gctgaagccg ctgctaaaga agctgccgcc    1440
aaggccatga gctacaacct gctgggcttt ctgcagcgga gcagcaactt ccagtgccag    1500
aaactgctgt ggcagctgaa tggccggctg gaatactgcc tgaaggaccg gatgaactct    1560
gacatcccg aggaaatcaa gcagctgcag cagttccaga aagaggacgc cgctctgacc    1620
atctacgaga tgctgcagaa catcttcgcc atcttccgcc aggatagcag cagcaccgga    1680
tggaacgaga caatcgtgga aaatctgctg ccaacgtgt accaccagat caaccacctg    1740
aaaaccgtgc tggaagagaa gctggaaaaa gaggacttca cccgggacaa gctgatgagc    1800
agcctgcacc tgaagcggta ctacggcaga atcctgcact acctcaaggc caaaagatat    1860
agccactgcg cctggaccat cgtgcgcgtg gaaatcctgc ggaacttcta cttcatcaac    1920
agactgaccg gctacctgcg caactga                                        1947

SEQ ID NO: 60           moltype = AA   length = 174
FEATURE                 Location/Qualifiers
REGION                  1..174
                        note = IFN omega
source                  1..174
                        mol_type = protein
                        organism = synthetic construct
SEQUENCE: 60
LGCDLPQNHG LLSRNTLVLL HQMRRISPFL CLKDRRDFRF PQEMVKGSQL QKAHVMSVLH     60
EMLQQIFSLF HTERSSAAWN MTLLDQLHTG LHQQLQHLET CLLQVVGEGE SAGAISSPAL    120
TLRRYFQGIR VYLKEKKYSD CAWEVVRMEI MKSLFLSTNM QERLRSKDRD LGSS          174

SEQ ID NO: 61           moltype = AA   length = 187
FEATURE                 Location/Qualifiers
REGION                  1..187
                        note = IFN epsilon
source                  1..187
                        mol_type = protein
                        organism = synthetic construct
SEQUENCE: 61
LDLKLIIFQQ RQVNQESLKL LNKLQTLSIQ QCLPHRKNFL LPQKSLSPQQ YQKGHTLAIL     60
HEMLQQIFSL FRANISLDGW EENHTEKFLI QLHQQLEYLE ALMGLEAEKL SGTLGSDNLR    120
LQVKMYFRRI HDYLENQDYS TCAWAIVQVE ISRCLFFVFS LTEKLSKQGR PLNDMKQELT    180
TEFRSPR                                                              187

SEQ ID NO: 62           moltype = AA   length = 628
FEATURE                 Location/Qualifiers
REGION                  1..628
                        note = antiCD40_hIgG2 dK_HC--HL--IFN alpha 2A
source                  1..628
                        mol_type = protein
                        organism = synthetic construct
SEQUENCE: 62
QVQLVQSGAE VKKPGASVKV SCKASGYTFT GYYMHWVRQA PGQGLEWMGW INPDSGGTNY     60
AQKFQGRVTM TRDTSISTAY MELNRLRSDD TAVYYCARDQ PLGYCTNGVC SYFDYWGQGT    120
LVTVSSASTK GPSVFPLAPC SRSTSESTAA LGCLVKDYFP EPVTVSWNSG ALTSGVHTFP    180
AVLQSSGLYS LSSVVTVPSS NFGTQTYTCN VDHKPSNTKV DKTVERKCCV ECPPCPAPPV    240
AGPSVFLFPP KPKDTLMISR TPEVTCVVVD VSHEDPEVQF NWYVDGVEVH NAKTKPREEQ    300
FNSTFRVVSV LTVVHQDWLN GKEYKCKVSN KGLPAPIEKT ISKTKGQPRE PQVYTLPPSR    360
EEMTKNQVSL TCLVKGFYPS DIAVEWESNG QPENNYKTTP PMLDSDGSFF LYSKLTVDKS    420
RWQQGNVFSC SVMHEALHNH YTQKSLSLSP GAEAAAKEAA AKCDLPQTH SLGSRRTLML     480
LAQMRKISLF SCLKDRHDFG FPQEEFGNQF QKAETIPVLH EMIQQIFNLF STKDSSAAWD    540
ETLLDKFYTE LYQQLNDLEA CVIQGVGVTE TPLMKEDSIL AVRKYFQRIT LYLKEKKYSP    600
CAWEVVRAEI MRSFSLSTNL QESLRSKE                                       628

SEQ ID NO: 63           moltype = AA   length = 398
FEATURE                 Location/Qualifiers
REGION                  1..398
                        note = antiCD40_LC-derivative--HL--IFN alpha 2A
```

```
                                 source          1..398
                                                 mol_type = protein
                                                 organism = synthetic construct
SEQUENCE: 63
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEKSLSLSP GAEAAAKEAA AKACDLPQTH   240
SLGSRRTLML LAQMRKISLF SCLKDRHDFG FPQEEFGNQF QKAETIPVLH EMIQQIFNLF   300
STKDSSAAWD ETLLDKFYTE LYQQLNDLEA CVIQGVGVTE TPLMKEDSIL AVRKYFQRIT   360
LYLKEKKYSP CAWEVVRAEI MRSFSLSTNL QESLRSKE                          398

SEQ ID NO: 64                    moltype = AA  length = 377
FEATURE                          Location/Qualifiers
REGION                           1..377
                                 note = antiCD40_LC--(G4S)4--IFN gamma
                                 source          1..377
                                                 mol_type = protein
                                                 organism = synthetic construct
SEQUENCE: 64
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGGGGSG GGGSGGGGSG GGGSQDPYVK   240
EAENLKKYFN AGHSDVADNG TLFLGILKNW KEESDRKIMQ SQIVSFYFKL FKNFKDDQSI   300
QKSVETIKED MNVKFFNSNK KKRDDFEKLT NYSVTDLNVQ RKAIHELIQV MAELSPAAKT   360
GKRKRSQMLF RGRRASQ                                                 377

SEQ ID NO: 65                    moltype = AA  length = 614
FEATURE                          Location/Qualifiers
REGION                           1..614
                                 note = antiCD40_hIgG2 dK_HC--(G4S)4--IFN gamma
                                 source          1..614
                                                 mol_type = protein
                                                 organism = synthetic construct
SEQUENCE: 65
QVQLVQSGAE VKKPGASVKV SCKASGYTFT GYYMHWVRQA PGQGLEWMGW INPDSGGTNY    60
AQKFQGRVTM TRDTSISTAY MELNRLRSDD TAVYYCARDQ PLGYCTNGVC SYFDYWGQGT   120
LVTVSSASTK GPSVFPLAPC SRSTSESTAA LGCLVKDYFP EPVTVSWNSG ALTSGVHTFP   180
AVLQSSGLYS LSSVVTVPSS NFGTQTYTCN VDHKPSNTKV DKTVERKCCV ECPPCPAPPV   240
AGPSVFLFPP KPKDTLMISR TPEVTCVVVD VSHEDPEVQF NWYVDGVEVH NAKTKPREEQ   300
FNSTFRVVSV LTVVHQDWLN GKEYKCKVSN KGLPAPIEKT ISKTKGQPRE PQVYTLPPSR   360
EEMTKNQVSL TCLVKGFYPS DIAVEWESNG QPENNYKTTP PMLDSDGSFF LYSKLTVDKS   420
RWQQGNVFSC SVMHEALHNH YTQKSLSLSP GGGGSGGGG SGGGGSGGGG SQDPYVKEAE   480
NLKKYFNAGH SDVADNGTLF LGILKNWKEE SDRKIMQSQI VSFYFKLFKN FKDDQSIQKS   540
VETIKEDMNV KFFNSNKKKR DDFEKLTNYS VTDLNVQRKA IHELIQVMAE LSPAAKTGKR   600
KRSQMLFRGR RASQ                                                   614

SEQ ID NO: 66                    moltype = AA  length = 409
FEATURE                          Location/Qualifiers
REGION                           1..409
                                 note = antiCD40_LC--(G4S)4--IFN lambda 2
                                 source          1..409
                                                 mol_type = protein
                                                 organism = synthetic construct
SEQUENCE: 66
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGGGGSG GGGSGGGGSG GGGSVPVARL   240
HGALPDARGC HIAQFKSLSP QELQAFKRAK DALEESLLLK DCRCHSRLFP RTWDLRQLQV   300
RERPMALEAE LALTLKVLEA TADTDPALVD VLDQPLHTLH HILSQFRACI QPQPTAGPRT   360
RGRLHHWLYR LQEAPKKESP GCLEASVTFN LFRLLTRDLN CVASGDLCV              409

SEQ ID NO: 67                    moltype = AA  length = 646
FEATURE                          Location/Qualifiers
REGION                           1..646
                                 note = antiCD40_hIgG2 dK_HC--(G4S)4--IFN lambda 2
                                 source          1..646
                                                 mol_type = protein
                                                 organism = synthetic construct
SEQUENCE: 67
QVQLVQSGAE VKKPGASVKV SCKASGYTFT GYYMHWVRQA PGQGLEWMGW INPDSGGTNY    60
AQKFQGRVTM TRDTSISTAY MELNRLRSDD TAVYYCARDQ PLGYCTNGVC SYFDYWGQGT   120
LVTVSSASTK GPSVFPLAPC SRSTSESTAA LGCLVKDYFP EPVTVSWNSG ALTSGVHTFP   180
AVLQSSGLYS LSSVVTVPSS NFGTQTYTCN VDHKPSNTKV DKTVERKCCV ECPPCPAPPV   240
AGPSVFLFPP KPKDTLMISR TPEVTCVVVD VSHEDPEVQF NWYVDGVEVH NAKTKPREEQ   300
FNSTFRVVSV LTVVHQDWLN GKEYKCKVSN KGLPAPIEKT ISKTKGQPRE PQVYTLPPSR   360
EEMTKNQVSL TCLVKGFYPS DIAVEWESNG QPENNYKTTP PMLDSDGSFF LYSKLTVDKS   420
```

```
RWQQGNVFSC SVMHEALHNH YTQKSLSLSP GGGGGSGGGG SGGGGSGGGG SVPVARLHGA     480
LPDARGCHIA QFKSLSPQEL QAFKRAKDAL EESLLLKDCR CHSRLFPRTW DLRQLQVRER     540
PMALEAELAL TLKVLEATAD TDPALVDVLD QPLHTLHHIL SQFRACIQPQ PTAGPRTRGR     600
LHHWLYRLQE APKKESPGCL EASVTFNLFR LLTRDLNCVA SGDLCV                    646

SEQ ID NO: 68          moltype = AA   length = 408
FEATURE                Location/Qualifiers
REGION                 1..408
                       note = antiCD40_LC--(G4S)4--IFN omega
source                 1..408
                       mol_type = protein
                       organism = synthetic construct
SEQUENCE: 68
DIQMTQSPSS VSASVGDRVT ITCRASQGIY SWLAWYQQKP GKAPNLLIYT ASTLQSGVPS     60
RFSGSGSGTD FTLTISSLQP EDFATYYCQQ ANIFPLTFGG GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGECGGGGSG GGGSGGGGSG GGGSLGCDLP     240
QNHGLLSRNT LVLLHQMRRI SPFLCLKDRR DFRFPQEMVK GSQLQKAHVM SVLHEMLQQI     300
FSLFHTERSS AAWNMTLLDQ LHTGLHQQLQ HLETCLLQVV GEGESAGAIS SPALTLRRYF     360
QGIRVYLKEK KYSDCAWEVV RMEIMKSLFL STNMQERLRS KDRDLGSS                  408

SEQ ID NO: 69          moltype = AA   length = 658
FEATURE                Location/Qualifiers
REGION                 1..658
                       note = antiCD40_hIgG2 dK_HC--(G4S)4--IFN epsilon
source                 1..658
                       mol_type = protein
                       organism = synthetic construct
SEQUENCE: 69
QVQLVQSGAE VKKPGASVKV SCKASGYTFT GYYMHWVRQA PGQGLEWMGW INPDSGGTNY     60
AQKFQGRVTM TRDTSISTAY MELNRLRSDD TAVYYCARDQ PLGYCTNGVC SYFDYWGQGT     120
LVTVSSASTK GPSVFPLAPC SRSTSESTAA LGCLVKDYFP EPVTVSWNSG ALTSGVHTFP     180
AVLQSSGLYS LSSVVTVPSS NFGTQTYTCN VDHKPSNTKV DKTVERKCCV ECPPCPAPPV     240
AGPSVFLFPP KPKDTLMISR TPEVTCVVVD VSHEDPEVQF NWYVDGVEVH NAKTKPREEQ     300
FNSTFRVVSV LTVVHQDWLN GKEYKCKVSN KGLPAPIEKT ISKTKGQPRE PQVYTLPPSR     360
EEMTKNQVSL TCLVKGFYPS DIAVEWESNG QPENNYKTTP PMLDSDGSFF LYSKLTVDKS     420
RWQQGNVFSC SVMHEALHNH YTQKSLSLSP GGGGGSGGGG SGGGGSGGGG SLDLKLIIFQ     480
QRQVNQESLK LLNKLQTLSI QQCLPHRKNF LLPQKSLSPQ QYQKGHTLAI LHEMLQQIFS     540
LFRANISLDG WEENHTEKFL IQLHQQLEYL EALMGLEAEK LSGTLGSDNL RLQVKMYFRR     600
IHDYLENQDY STCAWAIVQV EISRCLFFVF SLTEKLSKQG RPLNDMKQEL TTEFRSPR      658

SEQ ID NO: 70          moltype = DNA   length = 19
FEATURE                Location/Qualifiers
source                 1..19
                       mol_type = other DNA
                       organism = synthetic construct
SEQUENCE: 70
cctcaccata ctgcactca                                                   19

SEQ ID NO: 71          moltype = DNA   length = 20
FEATURE                Location/Qualifiers
source                 1..20
                       mol_type = other DNA
                       organism = synthetic construct
SEQUENCE: 71
gagggagttc ttcttctagg                                                  20

SEQ ID NO: 72          moltype = DNA   length = 24
FEATURE                Location/Qualifiers
source                 1..24
                       mol_type = other DNA
                       organism = synthetic construct
SEQUENCE: 72
agtgtggatt cgcactcctc cagc                                             24
```

INTERFERON-ASSOCIATED ANTIGEN BINDING PROTEINS AND USES THEREOF

CROSS-REFERENCE TO RELATED APPLICATIONS

This application is a continuation of U.S. application Ser. No. 17/756,803 filed on 2 Jun. 2022, which is the U.S. National Stage application of PCT/EP2020/083745 filed 27 Nov. 2020, which claims priority to European Patent Application No. EP19306552.1 filed 3 Dec. 2019 and European Patent Application No. EP19306573.7 filed 4 Dec. 2019, the entire disclosures of which are herein incorporated by reference.

SEQUENCE LISTING

11 January The instant application contains a Sequence Listing which has been submitted electronically in XML format and is hereby incorporated by reference in its entirety. Said XML copy, created on 9 Nov. 2023, is named DFMP_134_US_CON_T1_SL.xml and is 112,873 bytes in size.

FIELD OF THE INVENTION

The present invention relates to novel interferon-associated antigen binding proteins based on the agonistic anti-CD40 antibody CP870,893 as well as nucleic acids, vectors and vector systems encoding such interferon-associated antigen binding proteins. The present invention also relates to compositions comprising such interferon-associated antigen binding proteins, nucleic acids, vectors and vector systems. The novel interferon-associated antigen binding proteins afford beneficial improvements over the current state of the art, for example in that they effectively disrupt viral replication and thereby reduce HBV viral load. Thus, the present invention also provides medical uses of such interferon-associated antigen binding proteins, nucleic acids, vectors, vector systems and compositions, e.g., in the treatment of hepatitis B virus (HBV) infection and/or for decreasing one or more symptoms of HBV infection in a subject. The present invention further provides host cells comprising such nucleic acids, vectors and vector systems as well as methods of making the interferon-associated antigen binding proteins according to the invention using said host cells.

BACKGROUND

HBV infects more than 300 million people worldwide and is a common cause of liver disease and liver cancer (Liang (2009) Hepatology 49:S13). HBV is a small DNA virus with unusual features similar to retroviruses, which replicates through an RNA intermediate (pre-genomic RNA, pgRNA) and can integrate into the host genome. The unique features of the HBV replication cycle confer a distinct ability of the virus to persist in infected cells. HBV infection leads to a wide spectrum of liver disease ranging from acute (including fulminant hepatic failure) to chronic hepatitis, cirrhosis and hepatocellular carcinoma. Acute HBV infection can be either asymptomatic or present with symptomatic acute hepatitis. 90-95% of children and 5-10% of adults infected with HBV are unable to clear the virus and become chronically infected. Many chronically infected persons have mild liver disease with little or no long-term morbidity or mortality. Other individuals with chronic HBV infection develop active disease, which can progress to cirrhosis and liver cancer. These patients require careful monitoring and warrant therapeutic intervention.

Novel methods for treating HBV infection by modulating HBV infection in a cell are needed. In particular, methods for effectively disrupting viral replication, reducing HBV viral load of HBV-infected cells, reducing transcription of covalently closed circular HBV DNA in HBV-infected cells, and/or reducing the amount of pre-genomic HBV RNA in HBV-infected cells are needed.

SUMMARY OF THE INVENTION

The invention relates to an interferon-associated antigen binding protein comprising (I) an agonistic anti-CD40 antibody or an agonistic antigen binding fragment thereof, and (II) an Interferon (IFN) or a functional fragment thereof, wherein the agonistic anti-CD40 antibody, or the agonistic antigen binding fragment thereof, comprises (a) three light chain complementarity determining regions (CDRs) that are at least 90% identical to the CDRL1, CDRL2 and CDRL3 sequences within SEQ ID NO 3; and three heavy chain CDRs that are at least 90% identical to the CDRH1, CDRH2 and CDRH3 sequences within SEQ ID NO 6; wherein each CDR is defined in accordance with the Kabat definition, the Chothia definition, the AbM definition, or the contact definition of CDR; preferably wherein each CDR is defined in accordance with the CDR definition of Kabat or the CDR definition of Chothia;

(b) three light chain complementarity determining regions (CDRs) that are identical to the CDRL1, CDRL2 and CDRL3 sequences within SEQ ID NO 3; and three heavy chain CDRs that are identical to the CDRH1, CDRH2 and CDRH3 sequences within SEQ ID NO 6; wherein each CDR is defined in accordance with the Kabat definition, the Chothia definition, the AbM definition, or the contact definition of CDR; preferably wherein each CDR is defined in accordance with the CDR definition of Kabat or the CDR definition of Chothia;

(c) a heavy chain or a fragment thereof comprising a complementarity determining region (CDR) CDRH1 that is at least 90% identical to SEQ ID NO 56, a CDRH2 that is at least 90% identical to SEQ ID NO 57, and a CDRH3 that is at least 90% identical to SEQ ID NO 58; and a light chain or a fragment thereof comprising a CDRL1 that is at least 90% identical to SEQ ID NO 52, a CDRL2 that is at least 90% identical to SEQ ID NO 53, and a CDRL3 that is at least 90% identical to SEQ ID NO 54;

(d) a heavy chain or a fragment thereof comprising a complementarity determining region (CDR) CDRH1 that is identical to SEQ ID NO 56, a CDRH2 that is identical to SEQ ID NO 57, and a CDRH3 that is identical to SEQ ID NO 58; and a light chain or a fragment thereof comprising a CDRL1 that is identical to SEQ ID NO 52, a CDRL2 that is identical to SEQ ID NO 53, and a CDRL3 that is identical to SEQ ID NO 54;

(e) a light chain variable region $V_L$ comprising the sequence as set forth in SEQ ID NO 51, or a sequence at least 90% identical thereto; and/or a heavy chain variable region $V_H$ comprising the sequence as set forth in SEQ ID NO 55, or a sequence at least 90% identical thereto;

(f) a Fab region heavy chain comprising an amino acid sequence as set forth in SEQ ID NO 12, or a sequence at least 90% identical thereto; or (g) a light chain (LC) that comprises a sequence as set forth in SEQ ID NO 3, or a sequence at least 90% identical thereto; and/or a heavy chain (HC) that comprises a sequence selected from the group consisting of SEQ ID NO 6, SEQ ID NO 9, SEQ ID NO 49 and SEQ ID NO 48, or a sequence at least 90% identical thereto.

According to this aspect of the invention, the IFN or the functional fragment thereof is selected from the group consisting of a Type I IFN, a Type II IFN and a Type III IFN, or a functional fragment thereof. In a preferred embodiment, the Type I IFN, or the functional fragment thereof, is IFNα or IFNβ, or a functional fragment thereof.

According to one embodiment, the IFN or the functional fragment thereof is IFNα2a, or a functional fragment thereof. Preferably, the IFNα2a comprises the sequence as set forth in SEQ ID NO 17, or a sequence at least 90% identical thereto.

According to another embodiment, the IFN or the functional fragment thereof is IFNβ, or a functional fragment thereof. In a preferred embodiment, the IFNβ comprises the sequence as set forth in SEQ ID NO 14, or a sequence at least 90% identical thereto.

According to a further embodiment, the IFN or the functional fragment thereof is fused to a light chain of the agonistic anti-CD40 antibody or the agonistic antigen binding fragment thereof. Preferably, the IFN or the functional fragment thereof is fused to a C-terminus of a light chain of the agonistic anti-CD40 antibody or the agonistic antigen binding fragment thereof.

According to another embodiment, the IFN or the functional fragment thereof is fused to a heavy chain of the agonistic anti-CD40 antibody or the agonistic antigen binding fragment thereof. In a preferred embodiment, the IFN or the functional fragment thereof is fused to a C-terminus of a heavy chain of the agonistic anti-CD40 antibody or the agonistic antigen binding fragment thereof.

According to another embodiment, the agonistic anti-CD40 antibody or the agonistic antigen binding fragment thereof, and the IFN or the functional fragment thereof, are fused to each other via a linker. In a preferred embodiment, the linker comprises a sequence as set forth in SEQ ID NO 20, SEQ ID NO 21, SEQ ID NO 24, SEQ ID NO 25 or SEQ ID NO 26.

According to another embodiment, the interferon-associated antigen binding protein comprises a sequence selected from the group consisting of SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44, SEQ ID NO 45, SEQ ID NO 46 and SEQ ID NO 47.

According to further embodiment, the interferon-associated antigen binding protein is an interferon-fused agonistic anti-CD40 antibody or an interferon-fused agonistic antigen binding fragment thereof comprising one of the sequence combinations disclosed in Table 8.

According to another aspect, the invention relates to a nucleic acid encoding the interferon-associated antigen binding protein according to the invention. In a preferred embodiment, the nucleic acid further encodes a secretory signal peptide.

According to a further aspect, the invention relates to a vector comprising said nucleic acid.

According to another aspect, the invention relates to a vector system comprising (I) a first vector comprising a nucleic acid encoding the IFN, or the functional fragment thereof, fused to a light chain of the agonistic anti-CD40 antibody, or the agonistic antigen binding fragment thereof, of the interferon-associated antigen binding protein of the present invention; and a second vector comprising a nucleic acid encoding a heavy chain of the agonistic anti-CD40 antibody, or the agonistic antigen binding fragment thereof, of the interferon-associated antigen binding protein of the present invention; or (II) a first vector comprising a nucleic acid encoding the IFN, or the functional fragment thereof, fused to a heavy chain of the agonistic anti-CD40 antibody, or the agonistic antigen binding fragment thereof, of the interferon-associated antigen binding protein of the present invention; and a second vector comprising a nucleic acid encoding a light chain of the agonistic anti-CD40 antibody, or the agonistic antigen binding fragment thereof, of the interferon-associated antigen binding protein of the present invention.

According to another aspect, the invention relates to a composition, preferably a pharmaceutical composition, comprising an interferon-associated antigen binding protein, a nucleic acid, a vector, or a vector system according to the invention.

According to further aspect, the invention relates to a host cell comprising a nucleic acid, a vector, or a vector system according to the invention. According to another aspect, the invention relates to a method of making an interferon-associated antigen binding protein according to the invention, comprising culturing said host cell and recovering said interferon-associated antigen binding protein.

According to another aspect, the invention relates to an interferon-associated antigen binding protein, a nucleic acid, a vector, a vector system, or a composition according to the invention for use as a medicament.

According to yet another aspect, the invention relates to an interferon-associated antigen binding protein, a nucleic acid, a vector, a vector system, or a composition according to the invention for use in treating hepatitis B virus (HBV) infection and/or for decreasing one or more symptoms of HBV infection in a subject.

BRIEF DESCRIPTION OF THE DRAWINGS

FIG. 2A depicts an exemplary map of a pcDNA3.1 plasmid encoding SEQ ID NO 32 under the control of the pCMV promoter. The nucleic acid sequence encoding for SEQ ID NO 32 (SEQ ID NO 59) is also shown on the right. Italic: signal peptide sequence; black color: CP870,893 heavy chain coding sequence; underlined: HL linker coding sequence; bold: IFNβ coding sequence.

FIG. 2B shows examples of SDS PAGE in reduced conditions of some Interferon-fused Antibodies (IFAs), with IFNα or IFNβ fused either at the heavy chain or the light chain. Migration of the parental CP870,893 is also shown on the left.

FIG. 3A-3B graphically depict a dose dependent effect of a number of IFA molecules with IFNβ fusions on activating the CD40-mediated NFκB pathway reporter assay in HEK-Blue™ CD40L cells. FIG. 3A shows examples of anti-CD40 activities for IFAs with IFNβ fused to the C-terminal part of the heavy chain (HC). FIG. 3B shows examples of anti-CD40 activities for IFAs with IFNβ fused to the N-terminal part of the LC (IFA34) or the HC (IFA36) and the corresponding fusions on the C-terminal part (IFA35 and IFA37). Purification yield of the latter group of IFAs was very low, thus to test their activity, the supernatants from HEK transfected cells were used and serially diluted to evaluate the anti-CD40 activity on HEK-Blue™ CD40L cells.

FIG. 3C-3D graphically depict a dose dependent effect of a number of IFA molecules with IFNβ fusions on activating the Type I IFN-pathway in reporter HEK-Blue-IFN-α/β cells. FIG. 3C shows examples of IFN activity for IFAs with IFNβ fused to the C-terminal part of the HC. FIG. 3D shows examples of IFN activity for IFAs with IFNβ fused to the N-terminal part of the LC (IFA34) or the HC (IFA36) and the corresponding fusions on the C-terminal part (IFA35 and IFA37). The same supernatants from HEK transfected cells as in FIG. 3B were used and serially diluted to evaluate the IFN activity. Parental antibody CP870,893 was used as negative control and recombinant human IFNβ was used as positive control. NS: Non Stimulated.

FIG. 6C depicts a dose response anti-viral activity (HBeAg release) of IFAs with HL linker (IFA38 and IFA39) on HBV-infected PHHs.

FIGS. 6D-6H depict a dose response anti-viral activity of 4 IFA molecules with fusion to IFNα via a peptide linker on primary human hepatocytes infected with HBV. FIG. 6D: Cartoon illustrating the study design. FIG. 6E: Effect of IFAs on HBeAg release in comparison to PEGASYS® (peginterferon alfa-2a). FIG. 6F: Effect of IFAs on HBsAg release in comparison to PEGASYS® (peginterferon alfa-2a). FIG. 6G: Effect of IFAs on pgRNA levels in comparison to PEGASYS® (peginterferon alfa-2a). FIG. 6H: Effect of IFAs on CXCL10 release in comparison to PEGASYS® (peginterferon alfa-2a).

Tables 9a-b: These tables summarize data obtained after in vitro stimulation of whole blood cells (WBCs) obtained from healthy volunteers. Each IFA was tested on WBCs from four different donors. WBCs were left Non-Treated (NT), treated with LPS (10 ng/mL) or with IFAs (1 µg/mL) for 24 h. Supernatants were collected and submitted to cytokines release quantification using the MSD u-Plex kit for human cytokines. Results represent the mean of two independent stimulations from each donor and are expressed in pg/mL (nd: not detected).

FIGS. 8A-8D: Pharmacokinetic profile of IFA25, IFA26, IFA27, IFA28, IFA29, and IFA30 after 0.5 mg/kg (IFAs) or 0.3 mg/kg (PEGASYS® (peginterferon alfa-2a))) intravenous bolus injection to mice. Data expressed as mean+/−SD on semi-logarithmic scale. Samples were collected up to 10 days after administration. ELISA assay using anti-IFNα as secondary antibody for quantification method was used for IFA27, IFA29 and IFA30 (FIG. 8A) and for IFA25, IFA26 and IFA28 (FIG. 8B). ELISA assay using anti-IgG2 as secondary antibody for quantification method was used for IFA25 and IFA27 (FIG. 8C). FIG. 8D: PEGASYS® (peginterferon alfa-2a) quantification was done using human IFNα matched antibody pairs. The marked line (LLOQ) denotes the limit of detection for the PEGASYS® (peginterferon alfa-2a) assay.

Table 10A: PK Report Summary: PK parameters for CP870,893, IFA27, IFA29 and IFA30 following single intravenous administration of 0.5 mg/kg to male CD1 Swiss mice. PK parameters for CP870,893 were explored in a 7-day experiment and those for IFA27, IFA29 and IFA30 in 10-day experiments (quantification for IFA27 was performed using 2 different ELISA approaches).

Table 10B: PK parameters for CP870,893, PEGASYS® (peginterferon alfa-2a) and for three different IFAs (IFA25, IFA26 and IFA28) following single intravenous bolus administration of 0.5 mg/kg to male CD1 Swiss mice. PK parameters for CP870,893 and IFA25, IFA26, IFA28 and PEGASYS® (peginterferon alfa-2a) were explored in 21-day experiments (quantification for IFA25 was performed using 2 different ELISA approaches).

Figure 9A:
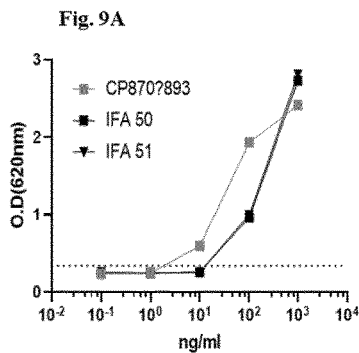
Figure 9B:
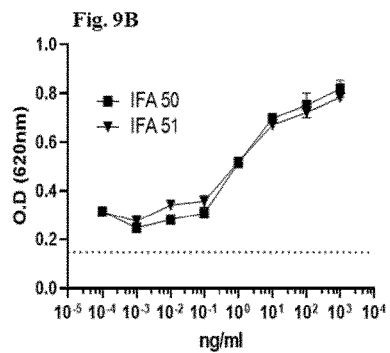
Figure 9C:
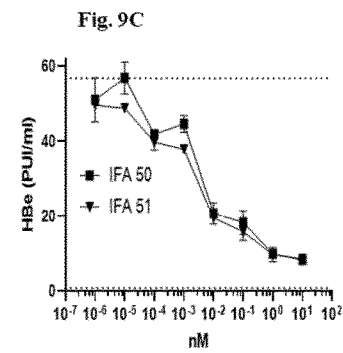

FIG. 9A depicts CD40 agonistic activity in a dose dependent manner of IFA50 and IFA51 with no Fc region in comparison to the parental anti-CD40 antibody in reporter HEK-Blue™ CD40L cells. FIG. 9B depicts the IFNα activity in a dose dependent manner of IFA50 and IFA51 in reporter HEK-Blue™ hIFN-α/β cells. FIG. 9C: Effect of IFA50 and IFA51 on HBeAg release from HBV-infected PHHs.

Figure 10A:
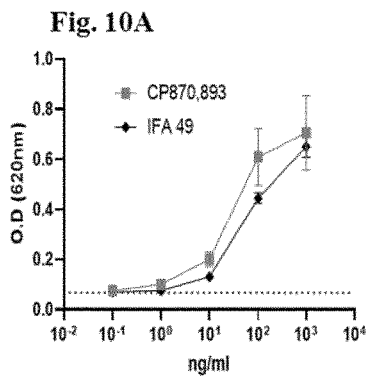
Figure 10B:
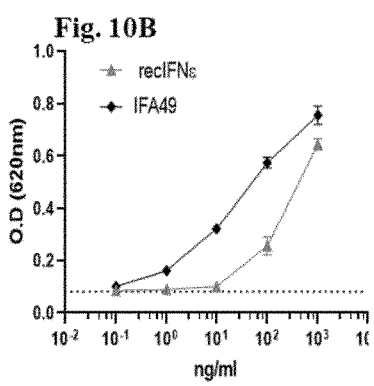
Figure 10C:
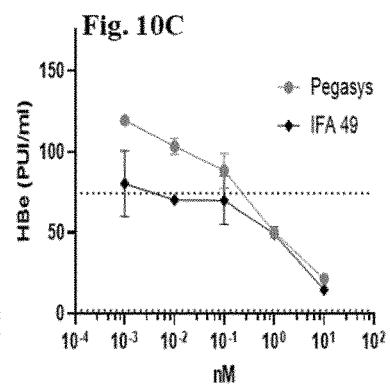

FIG. 10A depicts CD40 agonistic activity in a dose dependent manner of IFNε based IFA49, in comparison to parental anti-CD40 antibody, in HEK-Blue™ CD40L reporter cells. IFA49 corresponds to fusion of IFNε to the HC via a peptide linker. FIG. 10B depicts the IFN activity in a dose dependent manner of IFA49 on reporter HEK-Blue™ hIFN-α/β reporter cells which are activated by Type I interferons. FIG. 10C: Effect of IFA49 on HbeAg release from HBV-infected PHHs.

Figure 11A:
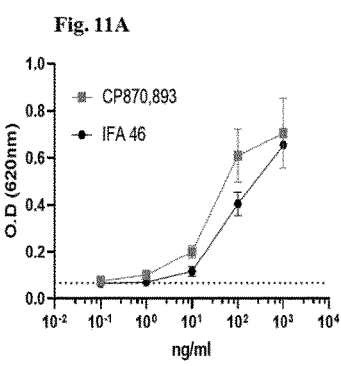
Figure 11B:
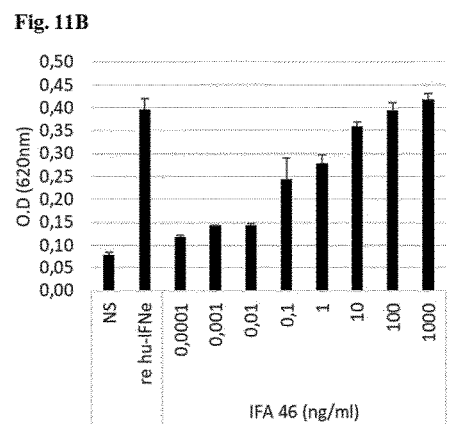
Figure 11C:
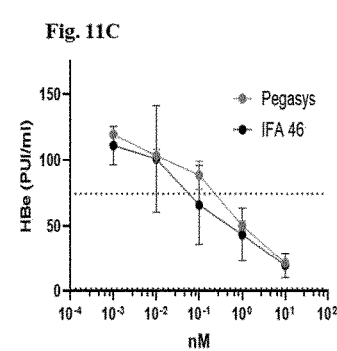

FIG. 11A depicts CD40 agonistic activity in a dose dependent manner of IFNω based IFA46, in comparison to parental anti-CD40 antibody, in HEK-Blue™ CD40L reporter cells. IFA46 corresponds to fusion of IFNω to the LC via a peptide linker. FIG. 11B depicts the IFN activity in a dose dependent manner of IFA46 on reporter HEK-Blue™ hIFN-α/β reporter cells which are activated by Type I interferons. FIG. 11C: Effect of IFA46 on HbeAg release from HBV-infected PHHs.

Figure 12A:
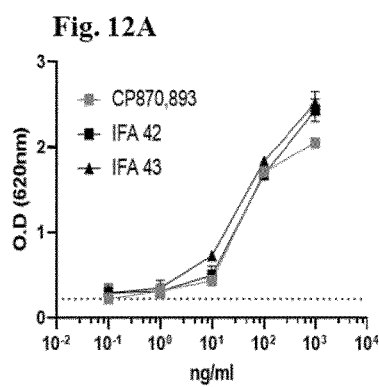
Figure 12B:
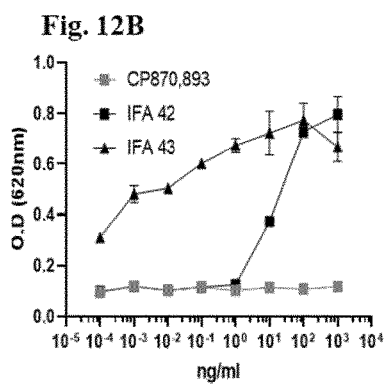
Figure 12C:
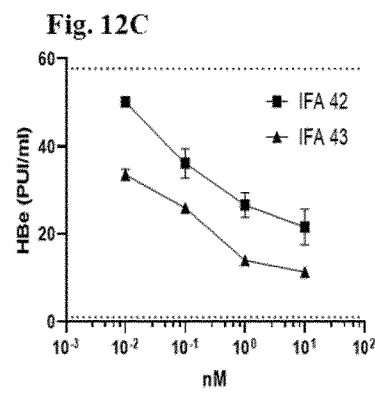

FIG. 12A depicts CD40 agonistic activity in a dose dependent manner of IFNγ based IFAs (IFA42 and IFA43), in comparison to parental anti-CD40 antibody, in HEK-Blue™ CD40L reporter cells. IFA42 corresponds to fusion of IFNγ to the LC via a peptide linker and IFA43 correspond to fusion of IFNγ to the HC via a peptide linker. FIG. 12B depicts the IFN activity in a dose dependent manner of IFA42 and IFA43 in reporter HEK-Blue-hIFNγ cells. FIG. 12C: Effect of IFA42 and IFA43 on HbeAg release from HBV-infected PHHs.

Figure 13A:
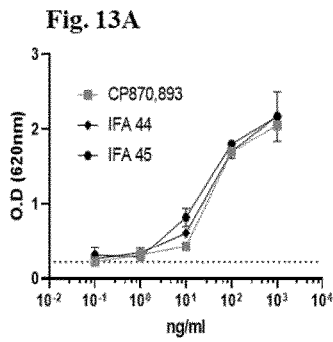
Figure 13B:
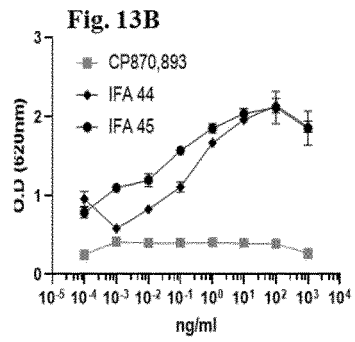
Figure 13C:
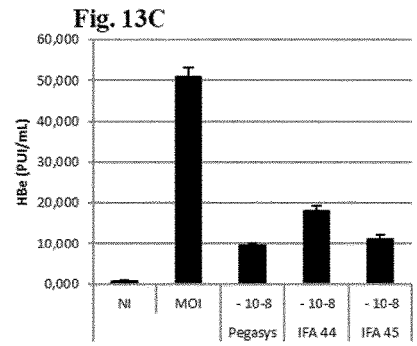

FIG. 13A depicts CD40 agonistic activity in a dose dependent manner of IFNλ based IFAs (IFA44 and IFA45), in comparison to parental anti-CD40 antibody, in HEK-Blue™ CD40L reporter cells. IFA44 corresponds to fusion of IFNλ to the LC via a peptide linker and IFA45 correspond to fusion of IFNλ to the HC via a peptide linker. FIG. 13B depicts the IFN activity in a dose dependent manner of IFA44 and IFA45 in reporter HEK-Blue-hIFNλ cells. FIG. 13C: Effect of the IFNλ based IFAs (IFA44 and IFA45) on HbeAg release from HBV-infected PHHs.

The foregoing and other features and advantages of the present invention will be more fully understood from the following detailed description of illustrative embodiments taken in conjunction with the accompanying drawings.

DETAILED DESCRIPTION

The present invention is based in part on the discovery of a therapy that is based on the use of "interferon-associated antigen-binding proteins", variants or derivatives thereof comprising (I) an agonistic anti-CD40 antibody or an agonistic antigen binding fragment thereof, and (II) an interferon (IFN) or a functional fragment thereof in hepatitis B virus (HBV) therapy. Said interferon-associated antigen-binding proteins inhibit transcription of hepatitis B virus covalently closed circular DNA (cccDNA) into pre-genomic HBV RNA (pgRNA) in HBV-infected cells, inhibit release of hepatitis B e-antigen (HBeAg) from HBV-infected cells, and enhance the IFN pathway in uninfected and HBV infected hepatocytes, in particular in uninfected and HBV infected primary human hepatocytes and in a synergistic fashion. HBV therapy comprising administering an interferon-associated antigen-binding protein to an HBV-infected cell, or a subject infected with HBV, is provided.

The invention may be more readily understood in the light of the selected terms defined below.

As used herein, the term "CD40" refers to "Cluster of differentiation 40", a member of the tumor necrosis factor receptor (TNFR) superfamily. CD40 is a costimulatory protein found on antigen presenting cells (e.g., B cells, dendritic cells, monocytes), hematopoietic precursors, endothelial cells, smooth muscle cells, epithelial cells, as well as the majority of human tumors (Grewal & Flavell, Ann. Rev. Immunol., 1996, 16: 111-35; Toes & Schoenberger, Seminars in Immunology, 1998, 10(6): 443-8). The binding of the natural ligand CD154 (CD40L) on $T_H$ cells to CD40 activates antigen presenting cells and induces a variety of downstream effects. The TNF-receptor associated factor adaptor proteins TRAF1, TRAF2, TRAF6 and TRAF5 interact with CD40 and serve as mediators of the signal transduction. Ultimately, CD40 signaling activates both the canonical and the noncanonical NF-κB pathways.

Agonistic Anti-CD40 Antibodies and Antigen Binding Fragments Thereof

As used herein, the term "antibody" refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated VH or $V_H$) and a heavy chain constant region (CH or $C_H$). The heavy chain constant region comprises three domains, CH1, CH2 and CH3. Each light chain comprises a light chain variable region (abbreviated VL or $V_L$) and a light chain constant region (CL or $C_L$). The light chain constant region comprises one domain (CL1). The VH and VL regions can be further subdivided into regions of hypervariability, termed "complementarity determining regions (CDRs)", interspersed with regions that are more conserved, termed "framework regions" (FR). Each VH and VL is composed of three CDRs and four FRs, arranged from amino-terminus to carboxy-terminus in the following order: FR1, CDR1, FR2, CDR2, FR3, CDR3, FR4. Framework regions can aid in maintaining the proper conformation of the CDRs to promote binding between the antigen binding region and an antigen.

The most commonly used immunoglobulin for therapeutic applications is immunoglobulin G (or IgG), a tetrameric glycoprotein. In a naturally-occurring immunoglobulin, each tetramer is composed of two identical pairs of polypeptide chains, each pair having one light (about 25 kDa) and one heavy chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Immunoglobulins can be assigned to different classes depending on the amino acid sequence of the constant domain of their heavy chains.

Heavy chains are classified as mu (μ), delta (δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes have antibody-dependent cellular cytotoxicity (ADCC) activity. In preferred embodiments, the agonistic anti-CD-40 antibodies or agonistic antigen binding fragments thereof comprised in the interferon-associated antigen binding proteins according to the invention are of the IgG class. In more preferred embodiments, the agonistic anti-CD40 antibodies or agonistic antigen binding fragments thereof comprised in the interferon-associated antigen binding proteins according to the invention are of the IgG1 or IgG3 subclasses. In specifically preferred embodiments, the agonistic anti-CD40 antibodies or agonistic antigen binding fragments thereof comprised in the interferon-associated antigen binding proteins according to the invention are of the IgG1 subclass. In other more preferred embodiments, the agonistic anti-CD40 antibodies or agonistic antigen binding fragments thereof comprised in the interferon-associated antigen binding proteins according to the invention are of the IgG2 or IgG4 subclasses. In specifically preferred embodiments, the agonistic anti-CD40 antibodies or agonistic antigen binding fragments thereof comprised in the interferon-associated antigen binding proteins according to the invention are of the IgG2 subclass.

Human light chains are classified as kappa (κ) and lambda (λ) light chains. Accordingly, in some embodiments, the agonistic anti-CD40 antibodies or agonistic antigen binding fragments thereof comprised in the interferon-associated antigen binding proteins according to the invention comprise a light chain of the κ class. In other embodiments, the agonistic anti-CD40 antibodies or agonistic antigen binding fragments thereof comprised in the interferon-associated antigen binding proteins according to the invention comprise a light chain of the λ class. Within light and heavy chains, the variable and constant regions are joined by a "J" region of about 12 or more amino acids, wherein the heavy chain additionally includes a "D" region of about 10 more amino acids. See generally, Fundamental Immunology, Ch. 7 (Paul, W., ed., 2nd ed. Raven Press, N.Y. (1989)).

The term "antibody" further includes, but is not limited to, monoclonal antibodies, bispecific antibodies, minibodies, domain antibodies, synthetic antibodies (sometimes referred to as "antibody mimetics"), chimeric antibodies, humanized antibodies, human antibodies, and fragments thereof, respectively. Unless otherwise indicated, the term "antibody" includes, in addition to antibodies comprising two full-length heavy chains and two full-length light chains, derivatives, variants, antigen binding fragments, and muteins thereof, examples of which are described below.

As used herein, the term "agonistic CD40 antibody" or "agonistic anti-CD40 antibody" refers to an antibody that binds to CD40 and mediates CD40 signaling. In a preferred embodiment, it binds to human CD40. As described below, binding to CD40 may be determined using surface plasmon resonance, preferably using the BIAcore® system. The agonistic anti-CD40 antibody may increase one or more CD40 activities by at least about 20% when added to a cell, tissue or organism expressing CD40. In some embodiments, the antibody activates CD40 activity by at least 40%, at least 50%, at least 60%, at least 70%, at least 80%, or at least 85%. CD40 activity of the agonistic anti-CD40 antibody may be measured using a whole blood surface molecule upregulation assay or using an in vitro reporter cell assay, e.g., using HEK-Blue™ CD40L cells (InvivoGen Cat. #: hkb-cd40), as described in greater detail in Example I. These reporter cells were generated by stable transfection of HEK293 cells with the human CD40 gene and an NFκB-inducible secreted embryonic alkaline phosphatase (SEAP) construct to measure the activity of CD40 agonists. Stimulation of CD40 leads to NFκB activation and thus to production of SEAP, which can be detected in the supernatant using chromogenic substrates such as QUANTI-Blue™.

In the context of the present invention, the interferon-associated antigen binding proteins activate both the CD40 and an IFN pathway. In certain embodiments, the interferon-associated antigen binding protein activates the CD40 pathway with an $EC_{50}$ of less than 400, 300, 200, 150, 100, 70, 60, 50, 40, 30, 25, 20, or 15 ng/mL. In more specific embodiments, the interferon-associated antigen binding protein activates the CD40 pathway with an $EC_{50}$ ranging from 10 to 200 ng/mL. In even more specific embodiments, the interferon-associated antigen binding protein activates the CD40 pathway with an $EC_{50}$ ranging from 10 to 50 ng/mL, preferably 10 to 30 ng/mL.

Exemplary light and heavy chain sequences of the agonistic anti-CD40 antibody CP870,893 are shown in Table 7.

As used herein, the term "agonistic antigen binding fragment" of an agonistic anti-CD40 antibody refers to a fragment of an agonistic anti-CD40 antibody that retains one or more functional activities of the original antibody, such as the ability to bind to and act as an agonist of CD40 signaling in a cell, e.g., it mediates CD40 pathway signaling. Such fragment may compete with the intact antibody for binding to CD40.

Agonistic antigen binding fragments of an agonistic anti-CD40 antibody can be produced by recombinant DNA techniques, or can be produced by enzymatic or chemical cleavage of an anti-CD40 antibody. Agonistic antigen binding fragments include, but are not limited to, a Fab fragment, a diabody (heavy chain variable domain on the same polypeptide as a light chain variable domain, connected via a short peptide linker that is too short to permit pairing between the two domains on the same chain), a Fab' fragment, a F(ab')$_2$ fragment, a Fv fragment, domain antibodies and single-chain antibodies, and can be derived from any mammalian source, including but not limited to human, mouse, rat, camelid or rabbit.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. Variable regions of different antibodies differ extensively in amino acid sequence even among antibodies derived from the same species or of the same class. Exemplary $V_L$ and $V_H$ domain sequences of the agonistic anti-CD40 antibody CP870,893 are shown in Table 1. The variable region of an antibody typically determines specificity of a particular antibody for its target as it contains the CDRs. Table 1 also shows exemplary CDR sequences of the agonistic anti-CD40 antibody CP870,893.

TABLE 1

Anti-CD40 antibody heavy/light chain variable regions and CDRs of the agonistic Anti--CD40 antibody CP870,893. Bold italic sequences correspond to CDR regions according to the Kabat definition.

| Anti-CD40 antibody regions | Sequence |
| --- | --- |
| Anti-CD40 Antibody $V_L$ domain (SEQ ID NO 51) | DIQMTQSPSSVSASVGDRVTITC*RASQGIYSWLA*WY QQKPGKAPNLLIY*TASTLQS*GVPSRFSGSGSGTDFTL TISSLQPEDFATYYC*QQANIFPLT*FGGGTKVEIK |
| Anti-CD40 Antibody CDRL1 (SEQ ID NO 52) | RASQGIYSWLA |
| Anti-CD40 Antibody CDRL2 (SEQ ID NO 53) | TASTLQS |

TABLE 1-continued

Anti-CD40 antibody heavy/light chain variable regions and CDRs of the agonistic Anti--CD40 antibody CP870,893. Bold italic sequences correspond to CDR regions according to the Kabat definition.

| Anti-CD40 antibody regions | Sequence |
|---|---|
| Anti-CD40 Antibody CDRL3 (SEQ ID NO 54) | QQANIFPLT |
| Anti-CD40 Antibody $V_H$ domain (SEQ ID NO 55) | QVQLVQSGAEVKKPGASVKVSCKASGYTFTGYYMH WVRQAPGQGLEWMGWINPDSGGTNYAQKFQGRVT MTRDTSISTAYMELNRLRSDDTAVYYCARDQPLGY CTNGVCSYFDYWGQGTLVTVSS |
| Anti-CD40 Antibody CDRH1 (SEQ ID NO 56) | TGYYMH |
| Anti-CD40 Antibody CDRH2 (SEQ ID NO 57) | WINPDSGGTNYAQKFQG |
| Anti-CD40 Antibody CDRH3 (SEQ ID NO 58) | DQPLGYCTNGVCSYFDY |

Delineation of a CDR and identification of residues comprising the binding site of an antibody may be accomplished by solving the structure of the antibody and/or solving the structure of the antibody-ligand complex. This can be accomplished by any of a variety of techniques known to those skilled in the art, such as X-ray crystallography. Various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

In certain embodiments, the complementarity determining regions (CDRs) of the light and heavy chain variable regions of an agonistic anti-CD40 antibody, or an agonistic antigen binding fragment thereof, can be grafted to framework regions (FRs) from the same, or another, species. In certain embodiments, the CDRs of the light and heavy chain variable regions of an agonistic anti-CD40 antibody, or an agonistic antigen binding fragment thereof, can be grafted to consensus human FRs. To create consensus human FRs, in certain embodiments, FRs from several human heavy chain or light chain amino acid sequences are aligned to identify a consensus amino acid sequence. In certain embodiments, the FRs of the heavy chain or light chain of an agonistic anti-CD40 antibody, or an agonistic antigen binding fragment thereof, are replaced with the FRs from a different heavy chain or light chain. In certain embodiments, rare amino acids in the FRs of the heavy and light chains of an agonistic anti-CD40 antibody, or an agonistic antigen binding fragment thereof, are not replaced, while the rest of the FR amino acids are replaced. Rare amino acids are specific amino acids that are in positions in which they are not usually found in FRs. In certain embodiments, the grafted variable regions from an agonistic anti-CD40 antibody, or an agonistic antigen binding fragment thereof, can be used with a constant region that is different from the constant region of an agonistic anti-CD40 antibody, or an agonistic antigen binding fragment thereof. In certain embodiments, the grafted variable regions are part of a single chain Fv antibody. CDR grafting is described, e.g., in U.S. Pat. Nos. 6,180,370, 6,054,297, 5,693,762, 5,859,205, 5,693,761, 5,565,332, 5,585,089, and 5,530,101, and in Jones et al., Nature, 321: 522-525 (1986); Riechmann et al., Nature, 332: 323-327 (1988); Verhoeyen et al., Science, 239:1534-1536 (1988), Winter, FEBS Letts., 430:92-94 (1998), which are hereby incorporated by reference for any purpose.

An "Fc" region typically comprises two heavy chain fragments comprising the $C_H2$ and $C_H3$ domains of an antibody. The two heavy chain fragments are held together by two or more disulfide bonds and by hydrophobic interactions of the $C_H3$ domains.

A "Fab fragment" comprises one full-length light chain as well as the $C_H1$ and variable regions of one heavy chain (the combination of the $V_H$ and $C_H1$ regions is referred to herein as "fab region heavy chain").

A "Fab' fragment" comprises one light chain and a portion of one heavy chain that contains the VH domain and the $C_H1$ domain and also the region between the $C_H1$ and $C_H2$ domains, such that an interchain disulfide bond can be formed between the two heavy chains of two Fab' fragments to form an F(ab')$_2$ molecule.

A "F(ab')2 fragment" contains two light chains and two heavy chains containing a portion of the constant region between the $C_H1$ and $C_H2$ domains, such that an interchain disulfide bond is formed between the two heavy chains. A F(ab')₂ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody can target the same or different antigens.

An antibody or antigen binding protein, such as an interferon-associated antigen binding protein according to the invention, preferably binds to its target antigen with a dissociation constant ($K_d$) of $\leq 10^{-7}$ M. The antibody or antigen binding protein binds its antigen with "high affinity" when the $K_d$ is $\leq 5 \times 10^{-9}$ M, and with "very high affinity" when the $K_d$ is $\leq 5 \times 10^{-10}$ M. More preferably, the antibody or antigen binding protein has a $K_d$ of $\leq 10^{-9}$ M. In some embodiment, the off-rate is $\leq 1 \times 10^{-5}$. In other embodiments, the antibody or antigen binding protein will bind to human CD40 with a $K_d$ of between about $10^{-9}$ M and $10^{-13}$ M, and in yet another embodiment the antibody or antigen binding protein will bind with a $K_d \leq 5 \times 10^{-10}$. As will be appreciated by one of skill in the art, in some embodiments, any or all of the antigen binding fragments can bind to CD40. Preferably, said constants are determined using surface plasmon resonance, more preferably using the BIAcore® system.

The term "surface plasmon resonance" means an optical phenomenon that allows for the analysis of real-time biospecific interactions by detection of alterations in protein concentrations within a biosensor matrix, for example using the BIAcore® system (BIAcore International AB, a GE Healthcare company, Uppsala, Sweden and Piscataway, N.J.). For further descriptions, see Jönsson et al. (1993) Ann. Biol. Clin. 51:19-26. The term "$K_{on}$" means the on rate constant for association of a binding protein (e.g., an antibody or antigen binding protein) to the antigen to form the, e.g., antigen binding protein/antigen complex. The term "$K_{on}$", or "on-rate" also means "association rate constant", or "ka", as is used interchangeably herein. This value indicating the binding rate of a binding protein to its target antigen or the rate of complex formation between a binding protein, e.g., an antibody or an antigen binding protein, and antigen also is shown by the equation below:

Antibody("$Ab$")+Antigen("$Ag$")→$Ab$–$Ag$

The term "$K_{off}$", or "off-rate", means the off rate constant for dissociation, or "dissociation rate constant", of a binding protein (e.g., an antibody or antigen binding protein) from the, e.g., antigen binding protein/antigen complex as is known in the art. This value indicates the dissociation rate of a binding protein, e.g., an antibody or an antigen binding protein, from its target antigen or separation of Ab–Ag complex over time into free antibody and antigen as shown by the equation below:

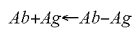

$Ab$+$Ag$←$Ab$–$Ag$

The terms "$K_d$" and "equilibrium dissociation constant" means the value obtained in a titration measurement at equilibrium, or by dividing the dissociation rate constant ($K_{off}$) by the association rate constant ($K_{on}$). The association rate constant, the dissociation rate constant and the equilibrium dissociation constant, are used to represent the binding affinity of a binding protein (e.g., an antibody or an antigen binding protein) to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay, can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.), can also be used.

An antigen binding protein according to the invention may bind to one target with an affinity at least one order of magnitude, preferably at least two orders of magnitude higher than for a second target.

The term "target" refers to a molecule or a portion of a molecule capable of being bound by an antigen binding protein. In certain embodiments, a target can have one or more epitopes. It will therefore be understood that the target may serve as "antigen" for the "antigen binding protein" of the present invention.

The term "epitope" includes any determinant capable of being bound by an antigen binding protein, such as an antibody. An epitope is a region of an antigen that is bound by an antigen binding protein that targets that antigen, and when the antigen is a protein, includes specific amino acids that directly contact the antigen binding protein. Most often, epitopes reside on proteins, but in some instances can reside on other kinds of molecules, such as nucleic acids. Epitope determinants can include chemically active surface groupings of molecules such as amino acids, sugar side chains, phosphoryl or sulfonyl groups, and can have specific three-dimensional structural characteristics, and/or specific charge characteristics. Generally, antibodies specific for a particular target antigen will preferentially/specifically recognize an epitope on the target antigen in a complex mixture of proteins and/or macromolecules.

In exemplary embodiments, the agonistic anti-CD40 antibody, or the agonistic antigen binding fragment thereof forming part (I) of the interferon-associated antigen binding proteins of the invention comprises three light chain complementarity determining regions (CDRs) that are at least 90% identical to the CDRL1, CDRL2 and CDRL3 sequences within SEQ ID NO 3; and three heavy chain CDRs that are at least 90% identical to the CDRH1, CDRH2 and CDRH3 sequences within SEQ ID NO 6. The agonistic anti-CD40 antibody, or the agonistic antigen binding fragment thereof, may also comprise three light chain complementarity determining regions (CDRs) that are identical to the CDRL1, CDRL2 and CDRL3 sequences within SEQ ID NO 3; and three heavy chain CDRs that are identical to the CDRH1, CDRH2 and CDRH3 sequences within SEQ ID NO 6. In such embodiments, each CDR is defined in accordance with the Kabat definition, the Chothia definition, the AbM definition, or the contact definition of CDR; preferably wherein each CDR is defined in accordance with the CDR definition of Kabat or the CDR definition of Chothia. In particular embodiments, each CDR is defined in accordance with the Kabat definition. In other particular embodiments, each CDR is defined in accordance with the Chothia definition.

Alternatively, the agonistic anti-CD40 antibody, or the agonistic antigen binding fragment thereof forming part (I) of the interferon-associated antigen binding proteins of the invention comprises (a) a heavy chain or a fragment thereof comprising a complementarity determining region (CDR) CDRH1 that is at least 90%, at least 95%, at least 98% or at least 99% identical to SEQ ID NO 56, a CDRH2 that is at least 90%, at least 95%, at least 98% or at least 99% identical to SEQ ID NO 57, and a CDRH3 that is at least 90%, at least 95%, at least 98% or at least 99% identical to SEQ ID NO 58; and (b) a light chain or a fragment thereof comprising a CDRL1 that is at least 90%, at least 95%, at least 98% or at least 99% identical to SEQ ID NO 52, a CDRL2 that is at least 90%, at least 95%, at least 98% or at least 99% identical to SEQ ID NO 53, and a CDRL3 that is at least 90%, at least 95%, at least 98% or at least 99% identical to SEQ ID NO 54.

In some embodiments, the agonistic anti-CD40 antibody, or the agonistic antigen binding fragment thereof, comprises (a) a heavy chain or a fragment thereof comprising a complementarity determining region (CDR) CDRH1 that is identical to SEQ ID NO 56, a CDRH2 that is identical to SEQ ID NO 57, and a CDRH3 that is identical to SEQ ID NO 58; and (b) a light chain or a fragment thereof comprising a CDRL1 that is identical to SEQ ID NO 52, a CDRL2 that is identical to SEQ ID NO 53, and a CDRL3 that is identical to SEQ ID NO 54.

More specifically the agonistic anti-CD40 antibody, or the agonistic antigen binding fragment thereof, comprises a light chain variable region $V_L$ comprising the sequence as set forth in SEQ ID NO 51, or a sequence at least 90%, at least 95%, at least 98% or at least 99% identical thereto; and/or a heavy chain variable region $V_H$ comprising the sequence as set forth in SEQ ID NO 55, or a sequence at least 90%, at least 95%, at least 98% or at least 99% identical thereto.

The interferon-associated antigen binding proteins of the invention may also comprise an agonistic anti-CD40 antibody or an agonistic antigen binding fragment thereof, comprising a Fab region heavy chain comprising an amino acid sequence as set forth in SEQ ID NO 12, or a sequence at least 90%, at least 95%, at least 98% or at least 99% identical thereto.

In some embodiments, the agonistic anti-CD40 antibody or the agonistic antigen binding fragment thereof comprises a light chain (LC) that comprises a sequence as set forth in SEQ ID NO 3, or a sequence at least 90%, at least 95%, at least 98% or at least 99% identical thereto; and/or a heavy chain (HC) that comprises a sequence selected from the group consisting of SEQ ID NO 6, SEQ ID NO 9, SEQ ID NO 49, SEQ ID NO 12 and SEQ ID NO 50, or a sequence at least 90%, at least 95%, at least 98% or at least 99% identical thereto.

In more specific embodiments, the agonistic anti-CD40 antibody or the agonistic antigen binding fragment thereof comprises a light chain (LC) that comprises a sequence as set forth in SEQ ID NO 3, or a sequence at least 90%, at least 95%, at least 98% or at least 99% identical thereto; and/or a heavy chain (HC) that comprises a sequence as set forth in SEQ ID NO 6, or a sequence at least 90%, at least 95%, at least 98% or at least 99% identical thereto.

In more specific embodiments, the agonistic anti-CD40 antibody or the agonistic antigen binding fragment thereof comprises a light chain (LC) that comprises a sequence as set forth in SEQ ID NO 3, or a sequence at least 90%, at least 95%, at least 98% or at least 99% identical thereto; and/or a heavy chain (HC) that comprises a sequence as set forth in SEQ ID NO 9, or a sequence at least 90%, at least 95%, at least 98% or at least 99% identical thereto.

In other more specific embodiments, the agonistic anti-CD40 antibody or the agonistic antigen binding fragment thereof comprises a light chain (LC) that comprises a sequence as set forth in SEQ ID NO 3, or a sequence at least 90%, at least 95%, at least 98% or at least 99% identical thereto; and/or a heavy chain (HC) that comprises a sequence as set forth in SEQ ID NO 49, or a sequence at least 90%, at least 95%, at least 98% or at least 99% identical thereto.

In other more specific embodiments, the agonistic anti-CD40 antibody or the agonistic antigen binding fragment thereof comprises a light chain (LC) that comprises a sequence as set forth in SEQ ID NO 3, or a sequence at least 90%, at least 95%, at least 98% or at least 99% identical thereto; and/or a heavy chain (HC) that comprises a sequence as set forth in SEQ ID NO 12, or a sequence at least 90%, at least 95%, at least 98% or at least 99% identical thereto.

In other more specific embodiments, the agonistic anti-CD40 antibody or the agonistic antigen binding fragment thereof comprises a light chain (LC) that comprises a sequence as set forth in SEQ ID NO 3, or a sequence at least 90%, at least 95%, at least 98% or at least 99% identical thereto; and/or a heavy chain (HC) that comprises a sequence as set forth in SEQ ID NO 50, or a sequence at least 90%, at least 95%, at least 98% or at least 99% identical thereto.

Variants and Derivatives of Interferon-Associated Antigen Binding Protein or Components Thereof A "variant" of a polypeptide (e.g., an interferon-associated antigen binding protein, an interferon-fused agonistic anti-CD40 antibody or an interferon-fused agonistic antigen binding fragment thereof, an antibody, an antigen binding protein, or an IFN, or components thereof) comprises an amino acid sequence wherein one, two, three, four, five or more amino acid residues are inserted into, deleted from and/or substituted into the amino acid sequence relative to another polypeptide sequence. Preferably, the variant comprises up to ten insertions, deletions and/or substitutions, more preferably up to eight insertions, deletions and/or substitutions. More specifically, the variant may comprise up to ten, more preferably up to eight insertions. The variant may also comprise up to ten, more preferably up to eight deletions. In even more preferred embodiments, the variant comprises up to ten substitutions, most preferably up to eight substitutions. In some embodiments, these substitutions are conservative amino acid substitution as described below.

A "variant" of a polynucleotide sequence (e.g., RNA or DNA) comprises one or more mutations within the polynucleotide sequence relative to another polynucleotide sequence, wherein one, two, three, four, five or more nucleic acid residues are inserted into, deleted from and/or substituted into the nucleic acid sequence. Preferably, the variant comprises up to ten insertions, deletions and/or substitutions, more preferably up to eight insertions, deletions and/or substitutions. More specifically, the variant may comprise up to ten, more preferably up to eight insertions. The variant may also comprise up to ten, more preferably up to eight deletions. In even more preferred embodiments, the variant comprises up to ten substitutions, most preferably up to eight substitutions. Said one, two, three, four, five or more mutations can cause one, two, three, four, five or more amino acid exchanges within the amino acid sequence the variant encodes for as compared to another amino acid sequence (i.e. a "non-silent mutation"). Variants also include nucleic acid sequences wherein one, two, three, four, five or more codons have been replaced by their synonyms which does not cause an amino acid exchange and is thus called a "silent mutation".

The term "identity" or "homology", in the context of variants of polypeptide or nucleotide sequences, refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. Preferably, identity is determined over the full length of a sequence. It is understood that the expression "at least 80% identical", includes embodiments wherein the claimed sequence is at least 85%, at least 90%, at least 95%, at least 98% or at least 99% identical to the reference sequence. The expression "at least 90% identical" includes embodiments wherein the claimed sequence is at least 90%, at least 91%, at least 92%, at least 93%, at least 94%, at least 95%, at least 96%, at least 97%, at least 98% or at least 99% identical to the reference sequence.

For the calculation of percent identity, gaps in alignments (if any) are preferably addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988*, SIAM J. Applied Math.* 48:1073.

In calculating percent identity, the sequences being compared are typically aligned in a way that gives the largest match between the sequences. One example of a computer program that can be used to determine percent identity is the GCG program package, which includes GAP (Devereux et al., 1984*, Nucl. Acid Res.* 12:387; Genetics Computer Group, University of Wisconsin, Madison, WI). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSum 62 are used in conjunction with the algorithm. In certain embodiments, a standard comparison matrix (see, Dayhoff et al., 1978*, Atlas of Protein Sequence and Structure* 5:345-352 for the PAM 250 comparison matrix; Henikoff et al., 1992*, Proc. Natl. Acad. Sci. U.S.A.* 89:10915-10919 for the BLOSum 62 comparison matrix) is also used by the algorithm.

Examples of parameters that can be employed in determining percent identity for polypeptides or nucleotide sequences using the GAP program are the following:

Algorithm: Needleman et al., 1970*, J. Mol. Biol.* 48:443-453

Comparison matrix: BLOSum 62 from Henikoff et al., 1992*, supra*

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or at least 100, preferably the entire length, of contiguous amino acids of the target polypeptide.

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues can be divided into classes based on common side chain properties:

1) hydrophobic: Norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the interferon-associated antigen binding protein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included.

Exemplary amino acid substitutions are set forth in Table 2.

TABLE 2

Amino Acid Substitutions.

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala, Gly | Ala |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

In light of the present invention, a skilled artisan will be able to determine suitable variants of the interferon-associated antigen binding proteins as set forth herein using well-known techniques. In certain embodiments, one skilled in the art can identify suitable areas of the molecule that may be changed without destroying activity by targeting regions not believed to be important for activity. In certain embodiments, one can identify residues and portions of the molecules that are conserved among similar polypeptides. In certain embodiments, even areas that can be important for biological activity or for structure can be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art can opt for chemically similar amino acid substitutions for such predicted important amino acid residues.

One skilled in the art can also analyze the three-dimensional structure and amino acid sequence in relation to that structure in similar proteins or protein domains. In view of such information, one skilled in the art can predict the alignment of amino acid residues of interferon-associated antigen binding protein, an antibody or an antigen binding fragment thereof or an interferon or a functional fragment thereof as described herein with respect to its three dimensional structure. In certain embodiments, one skilled in the art can choose not to make radical changes to amino acid residues predicted to be on the surface of the protein, since such residues can be involved in important interactions with other molecules. Moreover, one skilled in the art can generate test variants containing a single amino acid substitution at each desired amino acid residue. The variants can then be screened using activity assays known to those skilled in the art. Such variants can be used to gather information about suitable variants. For example, if one discovered that a change to a particular amino acid residue resulted in destroyed, undesirably reduced, or unsuitable activity, variants with such a change can be avoided. In other words, based on information gathered from such experiments, one skilled in the art can readily determine the amino acids where further substitutions should be avoided either alone or in combination with other mutations.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides. According to certain embodiments, single or multiple amino acid substitutions (in certain embodiments, conservative amino acid substitutions) can be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden & J. Tooze, eds., Garland Publishing, New York, N.Y. (1991)); and Thornton et al., Nature, 354:105 (1991), which are each incorporated herein by reference.

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified interferon-associated antigen binding protein can have a greater circulating half-life than an interferon-associated antigen binding protein that is not chemically modified. In certain embodiments, a chemically modified interferon-associated antigen binding protein can have improved targeting capacity for desired cells, tissues, and/or organs. In some embodiments, a derivative interferon-associated antigen binding protein is covalently modified to include one or more water-soluble polymer attachments, including, but not limited to, polyethylene glycol, polyoxyethylene glycol, or polypropylene glycol. See, e.g., U.S. Pat. Nos. 4,640,835, 4,496,689, 4,301, 144, 4,670,417, 4,791,192 and 4,179,337. In certain embodiments, a derivative interferon-associated antigen binding protein comprises one or more polymer, including, but not limited to, monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative of an interferon-associated antigen binding protein as described herein is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity of the interferon-associated antigen binding protein. Certain such methods are discussed, for example, in U.S. Pat. No. 6,133,426, which is hereby incorporated by reference for any purpose.

In certain embodiments, interferon-associated antigen binding protein variants include glycosylation variants wherein the number and/or type of glycosylation site has been altered compared to the amino acid sequences of a parent polypeptide. In certain embodiments, protein variants comprise a greater number of N-linked glycosylation sites than the native protein. In other embodiments, protein variants comprise a lesser number of N-linked glycosylation sites than the native protein. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one, two, three, four, five or more N-linked glycosylation sites (typically those that are naturally occurring) are eliminated and one or more new N-linked sites are created. Additional preferred variants include cysteine variants wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

HBV and HBV Marker

As used herein, "hepatitis B virus" or "HBV" refers to the double stranded DNA virus that causes hepatitis B, which belongs to a family of closely related DNA viruses called the Hepadnaviruses. Hepadnaviruses have a strong preference for infecting liver cells, but small amounts of hepadnaviral DNA can be found in kidney, pancreas, and mononuclear cells. However, infection at these sites is not linked to extra hepatic disease.

The HBV virion, i.e., the Dane particle, consists of an outer lipid envelope and an icosahedral nucleocapsid core composed of protein. The nucleocapsid encloses the viral DNA and a DNA polymerase that has reverse transcriptase activity similar to retroviruses. The outer envelope contains embedded proteins, which are involved in viral binding of, and entry into, susceptible cells. The virus is one of the smallest enveloped animal viruses with a virion diameter of 42 nm, but pleomorphic forms exist, including filamentous and spherical bodies lacking a core. These particles are not infectious and are composed of the lipid and protein that forms part of the surface of the virion, which is called the surface antigen (HBsAg), and is produced in excess during the life cycle of the virus. HBV comprises HBsAg, HBcAg (and its splice variant HBeAg), DNA polymerase and Hbx. HBV is one of a few known non-retroviral viruses which employ reverse transcription as a part of its replication process.

The HBV nucleocapsid contains a relatively small and partially duplex 3.2 kb circular DNA, viral polymerase and core protein. The genome has only four long open reading frames. The pre-S-S (pre-surface-surface) region of the genome encodes the three viral surface antigens by differential initiation of translation at each of three in-frame initiation codons.

The most abundant protein of HBV is the 24 kD S protein (which is known as HBsAg). The pre-C-C (pre-core-core) region encodes HBcAg (HBV core Antigen) and HBeAg (HBV e Antigen). HBeAg is not required for viral replication and plays no role in viral assembly but is nevertheless a useful indicator of active viral replication. Since HBeAg is secreted by HBV-infected hepatocytes, it can be detected in the blood via standard diagnostic tests (such as ELISA) and is thus used as a laboratory marker for a viremic HBV infection (Testoni et al., Serum hepatitis B core-related antigen (HBcrAg) correlates with covalently closed circular DNA. J. Hepatol. 2019, 70, 615-625. dx.doi.org/10.1016/j.jhep.2018.11.030).

The P-coding region is specific for the viral polymerase, a multifunctional enzyme involved in DNA synthesis and RNA encapsidation. The X open reading frame encodes the viral X protein (HBx), which modulates host-cell signal transduction and can directly and indirectly affect host and viral gene expression.

The life cycle of HBV is believed to begin when the virus attaches to the host cell membrane via its envelope proteins. It has been suggested that HBV binds to a receptor on the plasma membrane that is predominantly expressed on human hepatocytes via the pre-S1 domain of the large envelope protein as an initial step in HBV infection. However, the nature of the receptor remains controversial. Then, the viral membrane fuses with the cell membrane and the viral genome is released into the cells.

Replication of HBV can be regulated by a variety of factors, including hormones, growth factors, and cytokines. After the viral genome reaches the nucleus, the cellular DNA repair machinery convert the partial double-stranded DNA (dsDNA; also called relaxed circular HBV DNA (rcDNA)), genome into covalently closed circular DNA (cccDNA). The resulting cccDNA is the template for host RNA Pol-II for further transcription of pre-genomic RNA and sub-genomic RNA (Allweiss L and Dandri M, The Role of cccDNA in HBV Maintenance. Viruses 2017, 9(6):156; doi:10.3390/v9060156; Nur K. Mohd-Ismail, Zijie Lim, Jayantha Gunaratne and Yee-Joo Tan, Mapping the Interactions of HBV cccDNA with Host Factors. Int. J. Mol. Sci. 2019, 20(17):4276; doi:10.3390/ijms20174276).

The pre-genomic RNA is bifunctional, serving as both the template for viral DNA synthesis and as the messenger for pre-C, C, and P translation. The sub-genomic RNAs function exclusively for translation of the envelope and X protein. All viral RNA is transported to the cytoplasm, where its translation yields the viral envelope, core, and polymerase proteins, as well as HBx and HBcAg.

HBV core particles are assembled in the cytosol and during this process, a single molecule of pre-genomic RNA is incorporated into the assembling viral core. Once the viral RNA is encapsidated, reverse transcription begins. The synthesis of the two viral DNA strands is sequential. The first DNA strand is made from the encapsidated RNA template; during or after the synthesis of this strand, the RNA template is degraded and the synthesis of the second DNA strand proceeds, with the use of the newly made first DNA strand as a template. Some cores bearing the mature genome are transported back to the nucleus, where their newly minted DNA genomes can be converted to cccDNA to maintain a stable intranuclear pool of transcriptional templates.

HBV surface antigen (HBsAg) proteins are initially synthesized and polymerized in the rough endoplasmic reticulum. These proteins are transported to the post-ER and pre-Golgi compartments, where budding of the nucleocapsid follows. The assembled HBV virion and sub-viral particles are transported to the Golgi for further modification of glycans of the surface proteins, and then are secreted out of the host cell to finish the life cycle.

In particular embodiments, the interferon-associated antigen binding proteins, the nucleic acids, vectors, vector systems, methods and compositions described herein can be used to treat HBV infection. As used herein, "treat HBV infection" and "treatment of HBV infection" refers to one or more of: (i) reducing HBV viral load/viral titer; (ii) reducing the transcription of cccDNA; (iii) reducing the level of pre-genomic RNA in cells; (iv) decreasing one or more HBV-related disorders; and (v) decreasing one or more HBV-related symptoms in a subject.

The terms "viral load" and "viral titer" refer to the number of viral particles in a cell, an organ or a bodily fluid such as blood or serum. Viral load or viral titer is often expressed as viral particles, or infectious particles per mL depending on the type of assay. Today, viral load is usually measured using international units per milliliter (IU/mL). Viral load or viral titer may alternatively be determined as so-called viral genome equivalent. A higher viral burden, titer, or viral load often correlates with the severity of an active viral infection. Accordingly, reducing the viral load or viral titer correlates with a reduced number of infectious viral particles, e.g., in the serum. Viral load is usually determined using nucleic acid amplification based tests (NATs or NAATss). NAT/NAAT tests utilize, for example, PCR, (quantitative) reverse transcription polymerase chain reaction (RT-PCR or qRT-PCR), nucleic acid sequence based amplification (NASBA) or probe-based assays. Real-time PCR assays for hepatitis B virus DNA quantification are described, e.g., in Liu et al., *Virol J* 14, 94 (2017) doi:10.1186/s12985-017-0759-8. Due to the ease of detection of viral DNA using PCR, the viral load is useful in clinical settings to monitor success during treatment. A viral load of >10.000 copies/mL (2.000 IU/mL) is a strong risk predictor of hepatocellular carcinoma, independent of HBeAg status.

The terms "patient" and "subject" are used interchangeably and include human and non-human animal subjects, preferably human subjects, as well as those with formally diagnosed disorders, those without formally recognized disorders, those receiving medical attention, those at risk of developing the disorders, etc.

In particular embodiments, the interferon-associated antigen binding protein, the nucleic acids, vectors, vector systems, methods and compositions described herein can be used to reduce the HBV viral load/viral titer in an HBV-infected cell (such as in a cell culture, in an HBV-infected organ or in an HBV-infected patient). HBV viral load/viral titer may be reduced by about 20%, 25%, 30%, 35%, 40%, 45%, 50%, 55%, 60%, 65%, 70%, 75%, 80%, 85%, 90%, 95%, or 100% compared to an untreated HBV-infected cell culture or to the same patient before treatment. In some embodiments, HBV viral load/viral titer is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. Preferably, HBV viral load/viral titer is reduced by at least 35%, more preferably by at least 50%. In some embodiments, viral load/viral titer is determined by PCR or qRT-PCR.

In particular embodiments, the interferon-associated antigen binding protein, the nucleic acids, vectors, vector systems, methods and compositions described herein can be used to reduce transcription of HBV cccDNA in an HBV-infected cell (such as in a cell culture, in an HBV-infected organ or in an HBV-infected patient). cccDNA transcription may be reduced by about 20%, 25%, 30%, 35%, 40%, 45%, 50%, 55%, 60%, 65%, 70%, 75%, 80%, 85%, 90%, 95%, or 100% compared to an untreated HBV-infected cell culture or to the same patient before treatment. In some embodiments, transcription of HBV cccDNA is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. Preferably, transcription of HBV cccDNA is reduced by at least 35%, more preferably by at least 50%. In some embodiments, transcription of HBV cccDNA is determined by PCR or qPCR.

In particular embodiments, the interferon-associated antigen binding protein, the nucleic acids, vectors, vector systems, methods and compositions described herein can be used to reduce the level of pre-genomic HBV RNA in an HBV-infected cell (such as in a cell culture, in an HBV-infected organ or in an HBV-infected patient). Pre-genomic HBV RNA levels may be reduced by about 20%, 25%, 30%, 35%, 40%, 45%, 50%, 55%, 60%, 65%, 70%, 75%, 80%, 85%, 90%, 95%, or 100% compared to an untreated HBV-infected cell culture or to the same patient before treatment. In some embodiments, the level of pre-genomic HBV RNA is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. Preferably, the level of pre-genomic HBV RNA is reduced by at least 35%, more preferably by at least 50%. In some embodiments, the level of pre-genomic HBV RNA is determined by qRT-PCR.

As used herein, an "HBV-related disorder" refers to a disorder that results from infection of a subject by HBV. HBV-related disorders include, but are not limited to acute hepatitis, chronic hepatitis, icteric hepatitis, fulminant hepatitis, sub-fulminant hepatitis, and symptoms and/or complications arising from any of these disorders.

As used herein, an "HBV-related symptom," a "symptom of HBV infection" or an "HBV-related complication" includes one or more physical dysfunctions related to HBV infection. HBV symptoms and complications include, but are not limited to, cirrhosis, hepatocellular carcinoma (HCC), membranous glomerulonephritis (MGN), death, acute necrotizing vasculitis (polyarteritis nodosa), membranous glomerulonephritis, papular acrodermatitis of childhood (Gianotti-Crosti syndrome), HBV-associated nephropathy (e.g., membranous glomerulonephritis), immune-mediated hematological disorders (e.g., essential mixed cryoglobulinemia, aplastic anemia), portal hypertension, ascites, encephalopathy, jaundice, pruritus, pale stools, steatorrhea, polyarteritis nodosa, glomerular disease, abnormal ALT levels, abnormal AST levels, abnormal alkaline phosphatase levels, increased bilirubin levels, anorexia, malaise, fever, nausea, vomiting and the like.

Interferons

As used herein, an "interferon" or "IFN" refers to a cytokine, or derivative thereof, that is typically produced and released by cells in response to the presence of a pathogen or a tumor cell. IFNs include type I IFNs (e.g., IFNα, IFNβ, IFNε, IFNκ, IFNτ, IFNζ and IFNω), type II IFNs (e.g., IFNγ) and type III IFNs (e.g., IFNλ1, IFNλ2 and IFNλ3). The term "interferon" or "IFN" includes without limitation full-length IFN, a variant or a derivative thereof (e.g., a chemically (e.g., PEGylated) modified derivative or mutein), or a functionally active fragment thereof, that retains one or more signaling activities of a full-length IFN.

As used herein, the term "functional fragment" refers to a fragment of a substance that retains one or more functional activities of the original substance. For example, a functional fragment of an interferon refers to a fragment of an interferon that retains an IFN function as described herein, e.g., it mediates IFN pathway signaling.

The IFN may increase one or more IFN receptor activities by at least about 20% when added to a cell, tissue or organism expressing a cognate IFN receptor (IFNAR for IFNα, IFNBR for IFNβ, etc). In some embodiments, the interferon activates IFN receptor activity by at least 40%, at least 50%, at least 60%, at least 70%, at least 80%, or at least 85%. The activity of the IFN (i.e., the "IFN activity") may be measured, e.g., using an in vitro reporter cell assay, e.g., using HEK-Blue™ IFN-α/β cells (InvivoGen, Cat. #: hkb-ifnαβ), HEK-Blue™ IFN-λ (InvivoGen, Cat. #: hkb-ifnl) or HEK-Blue™ Dual IFN-γ cells (InvivoGen, Cat. #: hkb-ifng), as described in greater detail in Example I. These reporter cells were generated by stable transfection of HEK293 cells with human IFN receptor genes and an IFN-stimulated response element-controlled secreted embryonic alkaline phosphatase (SEAP) construct to measure the activity of IFNs. HEK-Blue™ IFN-cells are designed to monitor the activation of the JAK/STAT/ISGF3 pathways induced by type I, type II or type III interferons. Activation of these pathways induces the production and release of SEAP.

In the context of the present invention, the interferon-associated antigen binding proteins activate both the CD40 and an IFN pathway. In certain embodiments, the interferon-associated antigen binding protein activates the IFN pathway with an $EC_{50}$ of less than 100, 60, 50, 40, 30, 20, 10, or 1 ng/mL, preferably with an $EC_{50}$ of less than 11 ng/mL, more preferably with an $EC_{50}$ of less than 6 ng/mL. In some of these embodiments, the IFN pathway is the IFNα (interferon alpha), IFNβ (interferon beta), IFNε (interferon epsilon), IFNω (interferon omega), IFNγ (interferon gamma), or IFNλ, (interferon lambda) pathway.

According to certain exemplary embodiments, an interferon-associated antigen binding protein as described herein comprises full-length IFN, a variant or a derivative thereof (e.g., a chemically (e.g., PEGylated) modified derivative or mutein), or a functionally active fragment thereof, that retains one or more signaling activities of a full-length IFN. In certain embodiments, the IFN is a human IFN.

In certain embodiments, an interferon-associated antigen binding protein as described herein comprises an IFN or a functional fragment thereof selected from the group consisting of a Type I IFN, a Type II IFN and a Type III IFN, or a functional fragment thereof.

In particular embodiments, the IFN or the functional fragment thereof is a Type I IFN, or a functional fragment thereof. In specific embodiments, the type I IFN or the functional fragment thereof is IFNα, IFNβ, IFNω or IFNε, or a functional fragment thereof. In more specific embodiments, the type I IFN or the functional fragment thereof is IFNα or IFNβ, or a functional fragment thereof. In other more specific embodiments, the type I IFN or the functional fragment thereof is IFN α, or a functional fragment thereof. In other more specific embodiments, the type I IFN or the functional fragment thereof is IFN β, or a functional fragment thereof. In other more specific embodiments, the type I IFN or the functional fragment thereof is IFNω, or a functional fragment thereof. In other more specific embodiments, the type I IFN or the functional fragment thereof is IFNε, or a functional fragment thereof.

In particular embodiments, the IFN or the functional fragment thereof is IFNα, IFNβ, IFNγ, IFNε, IFNε or IFNω, or a functional fragment thereof. In specific embodiments, the IFN or a functional fragment thereof is IFNα or IFNβ, or a functional fragment thereof.

In some embodiments, the IFN or the functional fragment thereof is IFNα, or a functional fragment thereof. In more specific embodiments, the IFN or functional fragment thereof is IFNα2a, or a functional fragment thereof. The IFNα2a may comprise the sequence as set forth in SEQ ID NO 17, or a sequence at least 90% identical thereto.

In some embodiments, the IFN or the functional fragment thereof is IFNβ, or a functional fragment thereof. The IFNβ may comprise the sequence as set forth in SEQ ID NO 14, or a sequence at least 90% identical thereto. The IFNβ or the functional fragment thereof may comprise one or two amino acid substitution(s) relative to SEQ ID NO 14, selected from C17S and N80Q. In some embodiments, the IFNβ or the functional fragment thereof comprises the amino acid substitution C17S relative to SEQ ID NO 14. In some embodiments, the IFNβ comprises the amino acid sequence as set forth in SEQ ID NO 15. In other embodiments, the IFNβ comprises the amino acid substitutions C17S and N80Q relative to SEQ ID NO 14. In yet other embodiments, the IFNβ comprises the amino acid sequence as set forth in SEQ ID NO 16.

In some embodiments, the IFN or the functional fragment thereof is IFNγ or IFNε, or a functional fragment thereof. In specific embodiments, the IFN or functional fragment thereof is IFNγ, or a functional fragment thereof. In more specific embodiments, the IFNγ comprises the sequence as set forth in SEQ ID NO 19, or a sequence at least 90% identical thereto. In other specific embodiments, the IFN or functional fragment thereof is IFNε, or a functional fragment thereof. In more specific embodiments, the IFNε or the functional fragment thereof is IFNλ2, or a functional fragment thereof. The IFNλ2 may comprise the sequence as set forth in SEQ ID NO 18, or a sequence at least 90% identical thereto.

In some embodiments, the IFN or the functional fragment thereof is IFNε, or a functional fragment thereof. The IFNε may comprise the sequence as set forth in SEQ ID NO 61, or a sequence at least 90% identical thereto.

In some embodiments, the IFN or the functional fragment thereof is IFNω, or a functional fragment thereof. The IFNω may comprise the sequence as set forth in SEQ ID NO 60, or a sequence at least 90% identical thereto.

In certain embodiments, the expression level of one or more IFN signaling pathway biomarkers is altered, i.e., upregulated or downregulated, in an HBV-infected cell treated with an interferon-associated antigen binding protein described herein. According to certain exemplary embodiments, the expression level of one or more IFN pathway biomarkers is upregulated in an HBV-infected cell treated with an interferon-associated antigen binding protein described herein. In this context, a "biomarker" is to be understood as a characteristic that is objectively measured and evaluated as an indicator of normal biological processes, pathogenic processes, or pharmacologic responses to a therapeutic intervention.

According to certain embodiments, a suitable IFN pathway biomarker featured herein is a chemokine, e.g., a C—X—C chemokine, selected from the group consisting of CXCL9, CXCL10 and CXCL11. In certain exemplary embodiments, a suitable biomarker induced by the IFN pathway is CXCL9, CXCL10 and/or CXCL11, and also the interferon stimulated gene ISG20. Cytokine induction or release may be quantified using techniques known in the art, such as ELISA. Alternatively, induction may also be determined using RNA-based assays such as RNAseq or qRT-PCR. In certain embodiments, upregulation may refer to an at least at 1.5-fold, at least 2-fold, at least 2.5-fold, at least 3-fold, at least 4-fold, at least 5-fold or at least 10-fold increased expression or secretion of these cytokines.

In these or in other exemplary embodiments, the expression level of pro-inflammatory cytokines, e.g., IL10, IL1β and/or IL2 is not significantly upregulated in human Whole Blood cells upon treatment with an interferon-associated antigen binding protein of the invention. In some embodiments, the expression level of IL10 is not significantly upregulated in human Whole Blood cells upon treatment with an interferon-associated antigen binding protein of the invention. In some embodiments, the expression level of IL1β is not significantly upregulated in human Whole Blood cells upon treatment with an interferon-associated antigen binding protein of the invention. In some embodiments, the expression level of IL2 is not significantly upregulated in an HBV-infected cell upon treatment with an interferon-associated antigen binding protein of the invention. In some embodiments, the expression levels of IL10 and IL1β are not significantly upregulated in an HBV-infected cell upon treatment with an interferon-associated antigen binding protein of the invention. In some embodiments, the expression levels of IL10 and IL2 are not significantly upregulated in an HBV-infected cell upon treatment with an interferon-associated antigen binding protein of the invention. In some embodiments, the expression levels of IL1β and IL2 are not significantly upregulated in an HBV-infected cell upon treatment with an interferon-associated antigen binding protein of the invention. In some embodiments, the expression levels of IL10, IL1β and IL2 are not significantly upregulated in an HBV-infected cell upon treatment with an interferon-associated antigen binding protein of the invention.

Interferon-Associated Antigen Binding Proteins

The term "associated", as used herein, generally refers to a covalent or non-covalent linkage of two (or more) molecules. Associated proteins are created by joining two or more distinct peptides or proteins, resulting in a protein with one or more functional properties derived from each of the original proteins. In the context of the present invention, the interferon-associated antigen binding proteins activate both the CD40 and an IFN pathway. An associated protein encompasses monomeric and multimeric, e.g., dimeric, trimeric, tetrameric or the like, complexes of distinct associated or fused proteins. In this context, non-covalent linkage results from strong interactions between two protein surface regions, usually via ionic, Van-der-Waals, and/or hydrogen bond interactions. Covalent linkage, on the other hand, requires the presence of actual chemical bonds, such as peptide bonds, disulphide bridges, etc. The term "fused" as used herein, generally refers to the joining of two or more distinct peptides or proteins in a covalent fashion via a peptide bond. Thus, a "fused protein" refers to single protein created by joining two or more distinct peptides or proteins via a peptide bond with one or more functional properties derived from each of the original proteins. In certain embodiments, two or more distinct peptides or proteins may be fused to one another via one or more peptide linkers ("L").

In all aspects of the invention, an interferon-associated antigen binding protein is a protein comprising an agonistic anti-CD40 antibody or an agonistic antigen binding fragment thereof and an IFN or a functional fragment thereof.

In some embodiments, the IFN or the functional fragment thereof is non-covalently associated with the agonistic anti-CD40 antibody or the agonistic antigen binding fragment thereof. In more specific embodiments, the IFN or the functional fragment thereof is non-covalently associated with the agonistic anti-CD40 antibody or the agonistic antigen binding fragment thereof via ionic, Van-der-Waals, and/or hydrogen bond interactions.

In other embodiments, the IFN or the functional fragment thereof is covalently associated with the agonistic anti-CD40 antibody or the agonistic antigen binding fragment thereof. In preferred embodiments, the IFN or the functional fragment thereof is fused to the agonistic anti-CD40 antibody or the agonistic antigen binding fragment thereof. The IFN or the functional fragment thereof may be fused to a light chain of the agonistic anti-CD40 antibody or the agonistic antigen binding fragment thereof. In some embodiments, the IFN or the functional fragment thereof is fused to the N-terminus of a light chain of the agonistic anti-CD40 antibody or the agonistic antigen binding fragment thereof. In other embodiments, the IFN or the functional fragment thereof is fused to the C-terminus of a light chain of the agonistic anti-CD40 antibody or the agonistic antigen binding fragment thereof. The IFN or the functional fragment thereof may be also be fused to a heavy chain of the agonistic anti-CD40 antibody or the agonistic antigen binding fragment thereof. In some embodiments, the IFN or the functional fragment thereof is fused to the N-terminus of a heavy chain of the agonistic anti-CD40 antibody or the agonistic antigen binding fragment thereof. In other embodiments, the IFN or the functional fragment thereof is fused to the C-terminus of a heavy chain of the agonistic anti-CD40 antibody or the agonistic antigen binding fragment thereof. In any of these embodiments, the agonistic anti-CD40 antibody or an agonistic antigen binding fragment thereof, and the IFN or the functional fragment thereof may be fused to each other via a linker.

The term "linker" or "L," as used herein, refers to any moiety that covalently joins one or more agonistic anti-CD40 antibody or an agonistic antigen binding fragment thereof to one or more interferon, or a functional fragment thereof. In exemplary embodiments, a linker is a peptide linker. The term "peptide linker", as used herein, refers to a peptide adapted to link two or more moieties. A peptide linker referred to herein may have one or more of the properties outlined in the following. The sequences of peptide linker according to certain exemplary embodiments are set forth in Table 7.

A peptide linker may have any length, i.e., comprise any number of amino acid residues. In exemplary embodiments, the linker comprises at least 1, at least 2, at least 3, at least 4, at least 5 amino acids. The linker may comprise at least 4 amino acids. The linker may comprise at least 11 amino acids. The linker may comprise at least 12 amino acids. The linker may comprise at least 13 amino acids. The linker may comprise at least 15 amino acids. The linker may comprise at least 20 amino acids. The linker may comprise at least 21 amino acids. The linker may comprise at least 24 amino acids.

A linker is typically long enough to provide an adequate degree of flexibility to prevent the linked moieties from interfering with each other's activity, e.g., the ability of a moiety to bind to a receptor. In exemplary embodiments, the linker comprises up to 10, up to 20, up to 30, up to 40, up to 50, up to 60, up to 70, up to 80, up to 90, or up to 100 amino acids. The linker may comprise up to 80 amino acids. The linker may comprise up to 40 amino acids. The linker may comprise up to 24 amino acids. The linker may comprise up to 21 amino acids. The linker may comprise up to 20 amino acids. The linker may comprise up to 15 amino acids. The linker may comprise up to 13 amino acids. The linker may comprise up to 12 amino acids. The linker may comprise up to 11 amino acids. The linker may comprise up to 4 amino acids.

In some embodiments, the linker is selected from the group comprising rigid, flexible and/or helix-forming linkers. It is understood that helix-forming linkers can also be rigid linkers, since an α-helix has less degrees of freedom than a peptide assuming a more random-coil conformation. In some embodiments, the linker is a rigid linker. An exemplary rigid linker comprises a sequence as set forth in SEQ ID NO 20. Further exemplary rigid linkers comprise a sequence as set forth in SEQ ID NO 22 or SEQ ID NO 23. In related embodiments, the linker is a helix-forming linker. Exemplary helix-forming linkers comprise a sequence as set forth in SEQ ID NO 22 or SEQ ID NO 23. In other embodiments, the linker is a flexible linker. Exemplary flexible linkers comprise a sequence as set forth in SEQ ID NO 21, SEQ ID NO 24, SEQ ID NO 25 or SEQ ID NO 26.

The linker can also have different chemical properties. A linker can be selected from acidic, basic or neutral linkers. Typically, acidic linkers contain one or more acidic amino acid, such as Asp or Glu. Basic linkers typically contain one or more basic amino acids, such as Arg, His and Lys. Both types of amino acids are very hydrophilic. In some embodiments, the linker is an acidic linker. Exemplary acidic linkers comprise a sequence as set forth in SEQ ID NO 22 or SEQ ID NO 23. In other embodiments, the linker is a basic linker. In yet other embodiments, the linker is a neutral linker. Exemplary neutral linkers comprise a sequence as set forth in SEQ ID NO 20, SEQ ID NO 21, SEQ ID NO 24, SEQ ID NO 25 or SEQ ID NO 26.

In preferred embodiments, the linker is Gly-Ser or a Gly-Ser-Thr linker composed of multiple glycine, serine and, where applicable, threonine residues. In some of these embodiments, the linker comprises the amino acids glycine and serine. In more specific embodiments, the linker comprises the sequence as set forth in SEQ ID NO 21, SEQ ID NO 24, SEQ ID NO 25 or SEQ ID NO 26. In some embodiments, the linker further comprises the amino acid threonine. In a more specific embodiment, the linker comprises the sequence as set forth in SEQ ID NO 21.

In exemplary embodiments of the present invention, the interferon-associated antigen binding protein comprises a linker comprising a sequence selected from the sequences as set forth in SEQ ID NOs 20 to 26, preferably from the sequences as set forth in SEQ ID NO 24, SEQ ID NO 25 or SEQ ID NO 26. In a preferred embodiment, the linker comprises a sequence as set forth in SEQ ID NO 24. In another preferred embodiment, the linker comprises a sequence as set forth in SEQ ID NO 25. In another preferred embodiment, the linker comprises a sequence as set forth in SEQ ID NO 26.

In various embodiments of any one of the aspects of the invention, the interferon-associated antigen binding protein comprises no amino acids other than those forming (I) said agonistic anti-CD40 antibody, or agonistic antigen binding fragment thereof and (II) said IFN or functional fragment thereof. In related embodiments, the interferon-associated antigen binding protein comprises no amino acids other than those forming (I) said agonistic anti-CD40 antibody, or agonistic antigen binding fragment thereof, (II) said IFN or functional fragment thereof and (III) said linker.

Exemplary embodiments representing the various different configurations of (I) the agonistic anti-CD40 antibody or the agonistic antigen binding fragment thereof, (II) the interferon (IFN) or the functional fragment thereof and (III) the linker are outlined in the following.

In certain preferred embodiments, the IFN or a functional fragment thereof is fused to the C-terminus of a heavy chain of the agonistic anti-CD40 antibody, or the agonistic antigen binding fragment thereof, via the linker, as set forth in Table 3A or Table 3B. In these embodiments, the heavy chain of the agonistic anti-CD40 antibody, or the agonistic antigen binding fragment thereof, may comprise a sequence as set forth in SEQ ID NO 6, SEQ ID NO 9, SEQ ID NO 12, SEQ ID NO 48 or SEQ ID NO 49. The IFNα2a may comprise the sequence as set forth in SEQ ID NO 17. The IFNβ may comprise the sequence as set forth in SEQ ID NO 14, SEQ ID NO 15 or SEQ ID NO 16. The IFNβ may comprise the sequence as set forth in SEQ ID NO 14. The IFNβ_C17S may comprise the sequence as set forth in SEQ ID NO 15. The IFN3_C17S,N80Q may comprise the sequence as set forth in SEQ ID NO 16. The IFNγ may comprise the sequence as set forth in SEQ ID NO 19. The IFNλ2 may comprise the sequence as set forth in SEQ ID NO 18. The IFNε may comprise the sequence as set forth in SEQ ID NO 61. The IFNω may comprise the sequence as set forth in SEQ ID NO 60. The linkers referred to are those listed in Table 7.

In the embodiments where the IFN is fused to the C-terminus of the heavy chain of the agonistic anti-CD40 antibody, or the agonistic antigen binding fragment thereof, the interferon-associated antigen binding protein further comprises a light chain of an agonistic anti-CD40 antibody, or an agonistic antigen binding fragment thereof. In more specific embodiments, a heavy chain comprises a sequence as set forth in SEQ ID NO 6, SEQ ID NO 9, SEQ ID NO 12, SEQ ID NO 48, or SEQ ID NO 49 and a light chain comprises a sequence as set forth in SEQ ID NO 3.

TABLE 3

Interferon or a functional fragment thereof fused to the C-terminus of a heavy chain of the anti-CD40 antibody or an agonistic antigen binding fragment thereof.

| A | IFNα2a | IFNβ | IFNβ_C17S | IFNβ_C17S, N80Q | IFNγ | IFNλ2 |
|---|---|---|---|---|---|---|
| RL linker | antiCD40_HC--RL--IFNα2a | antiCD40_HC--RL--IFNβ | antiCD40_HC--RL--IFNβ_C17S | antiCD40_HC--RL--IFNβ_C17S, N80Q | antiCD40_HC--RL--IFNγ | antiCD40_HC--RL--IFNλ2 |
| GST linker | antiCD40_HC--GST--IFNα2a | antiCD40_HC--GST--IFNβ | antiCD40_HC--GST--IFNβ_C17S | antiCD40_HC--GST--IFNβ_C17S, N80Q | antiCD40_HC--GST--IFNγ | antiCD40_HC--GST--IFNλ2 |
| HL linker | antiCD40_HC--HL--IFNα2a | antiCD40_HC--HL--IFNβ | antiCD40_HC--HL--IFNβ_C17S | antiCD40_HC--HL--IFNβ_C17S, N80Q | antiCD40_HC--HL--IFNγ | antiCD40_HC--HL--IFNλ2 |
| HL2 linker | antiCD40_HC--HL2--IFNα2a | antiCD40_HC--HL2--IFNβ | antiCD40_HC--HL2--IFNβ_C17S | antiCD40_HC--HL2--IFNβ_C17S, N80Q | antiCD40_HC--HL2--IFNγ | antiCD40_HC--HL2--IFNλ2 |
| (G4S)2 linker | antiCD40_HC--(G4S)2--IFNα2a | antiCD40_HC--(G4S)2--IFNβ | antiCD40_HC--(G4S)2--IFNβ_C17S | antiCD40_HC--(G4S)2--IFNβ_C17S, N80Q | antiCD40_HC--(G4S)2--IFNγ | antiCD40_HC--(G4S)2--IFNλ2 |
| (G4S)3 linker | antiCD40_HC--(G4S)3--IFNα2a | antiCD40_HC--(G4S)3--IFNβ | antiCD40_HC--(G4S)3--IFNβ_C17S | antiCD40_HC--(G4S)3--IFNβ_C17S, N80Q | antiCD40_HC--(G4S)3--IFNγ | antiCD40_HC--(G4S)3--IFNλ2 |
| (G4S)4 linker | antiCD40_HC--(G4S)4--IFNα2a | antiCD40_HC--(G4S)4--IFNβ | antiCD40_HC--(G4S)4--IFNβ_C17S | antiCD40_HC--(G4S)4--IFNβ_C17S, N80Q | antiCD40_HC--(G4S)4--IFNγ | antiCD40_HC--(G4S)4--IFNλ2 |

| B | IFNε | IFNω |
|---|---|---|
| RL linker | antiCD40_HC--RL--IFNε | antiCD40_HC--RL--IFNω |
| GST linker | antiCD40_HC--GST--IFNε | antiCD40_HC--GST--IFNω |
| HL linker | antiCD40_HC--HL--IFNε | antiCD40_HC--HL--IFNω |
| HL2 linker | antiCD40_HC--HL2--IFNε | antiCD40_HC--HL2--IFNω |
| (G4S)2 linker | antiCD40_HC--(G4S)2--IFNε | antiCD40_HC--(G4S)2--IFNω |
| (G4S)3 linker | antiCD40_HC--(G4S)3--IFNε | antiCD40_HC--(G4S)3--IFNω |
| (G4S)4 linker | antiCD40_HC--(G4S)4--IFNε | antiCD40_HC--(G4S)4--IFNω |

In certain preferred embodiments, the IFN or a functional fragment thereof is fused to the N-terminus of a heavy chain of the agonistic anti-CD40 antibody, or the agonistic antigen binding fragment thereof, via the linker, as set forth in Table 4A or Table 4B. In these embodiments, the heavy chain of the agonistic anti-CD40 antibody, or the agonistic antigen binding fragment thereof, may comprise a sequence as set forth in SEQ ID NO 6, SEQ ID NO 9, SEQ ID NO 12, SEQ ID NO 48, SEQ ID NO 49 or SEQ ID NO 50. The IFNα2a may comprise the sequence as set forth in SEQ ID NO 17. The IFNβ may comprise the sequence as set forth in SEQ ID NO 14, SEQ ID NO 15 or SEQ ID NO 16. The IFNβ may comprise the sequence as set forth in SEQ ID NO 14. The IFNβ_C17S may comprise the sequence as set forth in SEQ ID NO 15. The IFNβ_C17S,N80Q may comprise the sequence as set forth in SEQ ID NO 16. The IFNγ may comprise the sequence as set forth in SEQ ID NO 19. The IFNλ2 may comprise the sequence as set forth in SEQ ID NO 18. The IFNε may comprise the sequence as set forth in SEQ ID NO 61. The IFNω may comprise the sequence as set forth in SEQ ID NO 60. The linkers referred to are those listed in Table 7.

In the embodiments where the IFN is fused to the N-terminus of a heavy chain of the agonistic anti-CD40 antibody, or the agonistic antigen binding fragment thereof, the interferon-associated antigen binding protein further comprises a light chain of an agonistic anti-CD40 antibody, or an agonistic antigen binding fragment thereof. In more specific embodiments, a heavy chain comprises a sequence as set forth in SEQ ID NO 6, SEQ ID NO 9, SEQ ID NO 12, SEQ ID NO 48, SEQ ID NO 49 or SEQ ID NO 50 and a light chain comprises a sequence as set forth in SEQ ID NO 3.

TABLE 4

Interferon or a functional fragment thereof fused to the N-terminus of a heavy chain of the anti-CD40 antibody or an agonistic antigen binding fragment thereof.

| A | IFNα2a | IFNβ | IFNβ_C17S | IFNβ_C17S, N80Q | IFNγ | IFNλ2 |
|---|---|---|---|---|---|---|
| RL linker | IFNα2a--RL--antiCD40_HC | IFNβ--RL--antiCD40_HC | IFNβ_C17S--RL--antiCD40_HC | IFNβ_C17S, N80Q--RL--antiCD40_HC | IFNγ--RL--antiCD40_HC | IFNλ2--RL--antiCD40_HC |
| GST linker | IFNα2a--GST--antiCD40_HC | IFNβ--GST--antiCD40_HC | IFNβ_C17S--GST--antiCD40_HC | IFNβ_C17S, N80Q--GST--antiCD40_HC | IFNγ--GST--antiCD40_HC | IFNλ2--GST--antiCD40_HC |
| HL linker | IFNα2a--HL--antiCD40_HC | IFNβ--HL--antiCD40_HC | IFNβ_C17S--HL--antiCD40_HC | IFNβ_C17S, N80Q--HL--antiCD40_HC | IFNγ--HL--antiCD40_HC | IFNλ2--HL--antiCD40_HC |
| HL2 linker | IFNα2a--HL2--antiCD40_HC | IFNβ--HL2--antiCD40_HC | IFNβ_C17S--HL2--antiCD40_HC | IFNβ_C17S, N80Q--HL2--antiCD40_HC | IFNγ--HL2--antiCD40_HC | IFNλ2--HL2--antiCD40_HC |

TABLE 4-continued

Interferon or a functional fragment thereof fused to the N-terminus of a heavy chain of the anti-CD40 antibody or an agonistic antigen binding fragment thereof.

| A | IFNα2a | IFNβ | IFNβ_C17S | IFNβ_C17S, N80Q | IFNγ | IFNλ2 |
|---|---|---|---|---|---|---|
| (G4S)2 linker | IFNα2a--(G4S)2--antiCD40_HC | IFNβ--(G4S)2--antiCD40_HC | IFNβ_C17S--(G4S)2--antiCD40_HC | IFNβ_C17S, N80Q--(G4S)2--antiCD40_HC | IFNγ--(G4S)2--antiCD40_HC | IFNλ2--(G4S)2--antiCD40_HC |
| (G4S)3 linker | IFNα2a--(G4S)3--antiCD40_HC | IFNβ--(G4S)3--antiCD40_HC | IFNβ_C17S--(G4S)3--antiCD40_HC | IFNβ_C17S, N80Q--(G4S)3--antiCD40_HC | IFNγ--(G4S)3--antiCD40_HC | IFNλ2--(G4S)3--antiCD40_HC |
| (G4S)4 linker | IFNα2a--(G4S)4--antiCD40_HC | IFNβ--(G4S)4--antiCD40_HC | IFNβ_C17S--(G4S)4--antiCD40_HC | IFNβ_C17S, N80Q--(G4S)4--antiCD40_HC | IFNγ--(G4S)4--antiCD40_HC | IFNλ2--(G4S)4--antiCD40_HC |

| B | IFNε | IFNω |
|---|---|---|
| RL linker | IFNε--RL--antiCD40_HC | IFNω--RL--antiCD40_HC |
| GST linker | IFNε--GST--antiCD40_HC | IFNω--GST--antiCD40_HC |
| HL linker | IFNε--HL--antiCD40_HC | IFNω--HL--antiCD40_HC |
| HL2 linker | IFNε--HL2--antiCD40_HC | IFNω--HL2--antiCD40_HC |
| (G4S)2 linker | IFNε--(G4S)2--antiCD40_HC | IFNω--(G4S)2--antiCD40_HC |
| (G4S)3 linker | IFNε--(G4S)3--antiCD40_HC | IFNω--(G4S)3--antiCD40_HC |
| (G4S)4 linker | IFNε--(G4S)4--antiCD40_HC | IFNω--(G4S)4--antiCD40_HC |

In certain preferred embodiments, the IFN is fused to the C-terminus of a light chain of the agonistic anti-CD40 antibody, or the agonistic antigen binding fragment thereof, via the linker, as set forth in Table 5A or Table 5B. In these embodiments, the light chain of the agonistic anti-CD40 antibody, or the agonistic antigen binding fragment thereof, may comprise a sequence as set forth in SEQ ID NO 3. The IFNα2a may comprise the sequence as set forth in SEQ ID NO 17. The IFNβ may comprise the sequence as set forth in SEQ ID NO 14, SEQ ID NO 15 or SEQ ID NO 16. The IFNβ may comprise the sequence as set forth in SEQ ID NO 14. The IFNβ_C17S may comprise the sequence as set forth in SEQ ID NO 15. The IFNβ_C17S,N80Q may comprise the sequence as set forth in SEQ ID NO 16. The IFNγ may comprise the sequence as set forth in SEQ ID NO 19. The IFNλ2 may comprise the sequence as set forth in SEQ ID NO 18. The IFNε may comprise the sequence as set forth in SEQ ID NO 61. The IFNω may comprise the sequence as set forth in SEQ ID NO 60. The linkers referred to are those listed in Table 7.

In the embodiments where the IFN is fused to the C-terminus of a light chain of the agonistic anti-CD40 antibody, or the agonistic antigen binding fragment thereof, the interferon-associated antigen binding protein further comprises a heavy chain of an agonistic anti-CD40 antibody, or an agonistic antigen binding fragment thereof. In more specific embodiments, a light chain comprises a sequence as set forth in SEQ ID NO 3 and a heavy chain comprises a sequence as set forth in SEQ ID NO 6, SEQ ID NO 9, SEQ ID NO 49, SEQ ID NO 48, SEQ ID NO 50 or SEQ ID NO 12.

TABLE 5

Interferon or a functional fragment thereof fused to the C-terminus of a light chain of the anti-CD40 antibody or an agonistic antigen binding fragment thereof.

| A | IFNα2a | IFNβ | IFNβ_C17S | IFNβ_C17S, N80Q | IFNγ | IFNλ2 |
|---|---|---|---|---|---|---|
| RL linker | antiCD40_LC-RL--IFNα2a | antiCD40_LC--RL--IFNβ | antiCD40_LC--RL--IFNβ_C17S | antiCD40_LC--RL--IFNβ_C17S, N80Q | antiCD40_LC--RL--IFNγ | antiCD40_LC--RL--IFNλ2 |
| GST linker | antiCD40_LC--GST--IFNα2a | antiCD40_LC--GST--IFNβ | antiCD40_LC--GST--IFNβ_C17S | antiCD40_LC--GST--IFNβ_C17S, N80Q | antiCD40_LC--GST--IFNγ | antiCD40_LC--GST--IFNλ2 |
| HL linker | antiCD40_LC--HL--IFNα2a | antiCD40_LC--HL--IFNβ | antiCD40_LC--HL--IFNβ_C17S | antiCD40_LC--HL--IFNβ_C17S, N80Q | antiCD40_LC--HL--IFNγ | antiCD40_LC--HL--IFNλ2 |
| HL2 linker | antiCD40_LC--HL2--IFNα2a | antiCD40_LC--HL2--IFNβ | antiCD40_LC--HL2--IFNβ_C17S | antiCD40_LC--HL2--IFNβ_C17S, N80Q | antiCD40_LC--HL2--IFNγ | antiCD40_LC--HL2--IFNλ2 |
| (G4S)2 linker | antiCD40_LC--(G4S)2--IFNα2a | antiCD40_LC--(G4S)2--IFNβ | antiCD40_LC--(G4S)2--IFNβ_C17S | antiCD40_LC--(G4S)2--IFNβ_C17S, N80Q | antiCD40_LC--(G4S)2--IFNγ | antiCD40_LC--(G4S)2--IFNλ2 |
| (G4S)3 linker | antiCD40_LC--(G4S)3--IFNα2a | antiCD40_LC--(G4S)3--IFNβ | antiCD40_LC--(G4S)3--IFNβ_C17S | antiCD40_LC--(G4S)3--IFNβ_C17S, N80Q | antiCD40_LC--(G4S)3--IFNγ | antiCD40_LC--(G4S)3--IFNλ2 |
| (G4S)4 linker | antiCD40_LC--(G4S)4--IFNα2a | antiCD40_LC--(G4S)4--IFNβ | antiCD40_LC--(G4S)4--IFNβ_C17S | antiCD40_LC--(G4S)4--IFNβ_C17S, N80Q | antiCD40_LC--(G4S)4--IFNγ | antiCD40_LC--(G4S)4--IFNλ2 |

| B | IFNε | IFNω |
|---|---|---|
| RL linker | antiCD40_LC--RL--IFNε | antiCD40_LC--RL--IFNω | or the agonistic antigen binding fragment thereof, the interferon-associated antigen binding protein further comprises a heavy chain of an agonistic anti-CD40 antibody, or an agonistic antigen binding fragment thereof. In more specific embodiments, a light chain comprises a sequence as set forth in SEQ ID NO 3 and a heavy chain comprises a sequence as set forth in SEQ ID NO 6, SEQ ID NO 9, SEQ ID NO 49, SEQ ID NO 48, SEQ ID NO 12 or SEQ ID NO 50.

TABLE 6

Interferon or a functional fragment thereof fused to the N-terminus of a light chain of the anti-CD40 antibody or an agonistic antigen binding fragment thereof.

| A | IFNα2a | IFNβ | IFNβ_C17S | IFNβ_C17S, N80Q | IFNγ | IFNλ2 |
|---|---|---|---|---|---|---|
| RL linker | IFNα2a--RL--antiCD40_LC | IFNβ--RL--antiCD40_LC | IFNβ_C17S--RL--antiCD40_LC | IFNβ_C17S, N80Q--RL--antiCD40_LC | IFNγ--RL--antiCD40_LC | IFNλ2--RL--antiCD40_LC |
| GST linker | IFNα2a--GST--antiCD40_LC | IFNβ--GST--antiCD40_LC | IFNβ_C17S--GST--antiCD40_LC | IFNβ_C17S, N80Q--GST--antiCD40_LC | IFNγ--GST--antiCD40_LC | IFNλ2--GST--antiCD40_LC |
| HL linker | IFNα2a--HL--antiCD40_LC | IFNβ--HL--antiCD40_LC | IFNβ_C17S--HL--antiCD40_LC | IFNβ_C17S, N80Q--HL--antiCD40_LC | IFNγ--HL--antiCD40_LC | IFNλ2--HL--antiCD40_LC |
| HL2 linker | IFNα2a--HL2--antiCD40_LC | IFNβ--HL2--antiCD40_LC | IFNβ_C17S--HL2--antiCD40_LC | IFNβ_C17S, N80Q--HL2--antiCD40_LC | IFNγ--HL2--antiCD40_LC | IFNλ2--HL2--antiCD40_LC |
| (G4S)2 linker | IFNα2a--(G4S)2--antiCD40_LC | IFNβ--(G4S)2--antiCD40_LC | IFNβ_C17S--(G4S)2--antiCD40_LC | IFNβ_C17S, N80Q--(G4S)2--antiCD40_LC | IFNγ--(G4S)2--antiCD40_LC | IFNλ2--(G4S)2--antiCD40_LC |
| (G4S)3 linker | IFNα2a--(G4S)3--antiCD40_LC | IFNβ--(G4S)3--antiCD40_LC | IFNβ_C17S--(G4S)3--antiCD40_LC | IFNβ_C17S, N80Q--(G4S)3--antiCD40_LC | IFNγ--(G4S)3--antiCD40_LC | IFNλ2--(G4S)3--antiCD40_LC |
| (G4S)4 linker | IFNα2a--(G4S)4--antiCD40_LC | IFNβ--(G4S)4--antiCD40_LC | IFNβ_C17S--(G4S)4--antiCD40_LC | IFNβ_C17S, N80Q--(G4S)4--antiCD40_LC | IFNγ--(G4S)4--antiCD40_LC | IFNλ2--(G4S)4--antiCD40_LC |

-continued

| B | IFNε | IFNω |
|---|---|---|
| GST linker | antiCD40_LC--GST--IFNε | antiCD40_LC--GST--IFNω |
| HL linker | antiCD40_LC--HL--IFNε | antiCD40_LC--HL--IFNω |
| HL2 linker | antiCD40_LC--HL2--IFNε | antiCD40_LC--HL2--IFNω |
| (G4S)2 linker | antiCD40_LC--(G4S)2--IFNε | antiCD40_LC--(G4S)2--IFNω |
| (G4S)3 linker | antiCD40_LC--(G4S)3--IFNε | antiCD40_LC--(G4S)3--IFNω |
| (G4S)4 linker | antiCD40_LC--(G4S)4--IFNε | antiCD40_LC--(G4S)4--IFNω |

In certain preferred embodiments, the IFN is fused to the N-terminus of a light chain of the agonistic anti-CD40 antibody, or the agonistic antigen binding fragment thereof, via the linker, as set forth in Table 6A or Table 6B. In these embodiments, the light chain of the agonistic anti-CD40 antibody, or the agonistic antigen binding fragment thereof, may comprise a sequence as set forth in SEQ ID NO 3. The IFNα2a may comprise the sequence as set forth in SEQ ID NO 17. The IFNβ may comprise the sequence as set forth in SEQ ID NO 14, SEQ ID NO 15 or SEQ ID NO 16. The IFNβ may comprise the sequence as set forth in SEQ ID NO 14. The IFNβ_C17S may comprise the sequence as set forth in SEQ ID NO 15. The IFNβ_C17S,N80Q may comprise the sequence as set forth in SEQ ID NO 16. The IFNγ may comprise the sequence as set forth in SEQ ID NO 19. The IFNλ2 may comprise the sequence as set forth in SEQ ID NO 18. The IFNε may comprise the sequence as set forth in SEQ ID NO 61. The IFNω may comprise the sequence as set forth in SEQ ID NO 60. The linkers referred to are those listed in Table 7.

In the embodiments where the IFN is fused to the N-terminus of a light chain of the agonistic anti-CD40 antibody,

| B | IFNε | IFNω |
|---|---|---|
| RL linker | IFNε--RL--antiCD40_LC | IFNω--RL--antiCD40_LC |
| GST linker | IFNε--GST--antiCD40_LC | IFNω--GST--antiCD40_LC |
| HL linker | IFNε--HL--antiCD40_LC | IFNω--HL--antiCD40_LC |
| HL2 linker | IFNε--HL2--antiCD40_LC | IFNω--HL2--antiCD40_LC |
| (G4S)2 linker | IFNε--(G4S)2--antiCD40_LC | IFNω--(G4S)2--antiCD40_LC |
| (G4S)3 linker | IFNε--(G4S)3--antiCD40_LC | IFNω--(G4S)3--antiCD40_LC |
| (G4S)4 linker | IFNε--(G4S)4--antiCD40_LC | IFNω--(G4S)4--antiCD40_LC |

Exemplary sequences comprised in interferon-associated antigen binding proteins of the invention or precursors thereof are listed in Table 7.

In exemplary preferred embodiments, the interferon-associated antigen binding protein comprises an interferon-fused agonistic anti-CD40 antibody or an interferon-fused agonistic antigen binding fragment thereof comprising a sequence selected from SEQ ID NOs 28-47. In other exemplary embodiments, the interferon-associated antigen binding protein comprises an interferon-fused agonistic anti-CD40 antibody or an interferon-fused agonistic antigen binding fragment thereof comprising a sequence selected from SEQ ID NOs 62-69. In exemplary preferred embodiments, the interferon-associated antigen binding protein is an interferon-fused agonistic anti-CD40 antibody or an interferon-fused agonistic antigen binding fragment thereof comprising a sequence selected from SEQ ID NOs 28-47. In other exemplary embodiments, the interferon-associated antigen binding protein is an interferon-fused agonistic anti-CD40 antibody or an interferon-fused agonistic antigen binding fragment thereof comprising a sequence selected from SEQ ID NOs 62-69.

In certain exemplary embodiments, the interferon-associated antigen binding protein comprises an interferon-fused agonistic anti-CD40 antibody or an interferon-fused agonistic binding fragment thereof comprising a sequence as set forth in SEQ ID NO 62. In another exemplary embodiment, the interferon-associated antigen binding protein is an interferon-fused agonistic anti-CD40 antibody or an interferon-fused agonistic binding fragment thereof comprising a sequence as set forth in SEQ ID NO 62.

In certain exemplary embodiments, the interferon-associated antigen binding protein comprises an interferon-fused agonistic anti-CD40 antibody or an interferon-fused agonistic binding fragment thereof comprising a sequence as set forth in SEQ ID NO 63. In another exemplary embodiment, the interferon-associated antigen binding protein is an interferon-fused agonistic anti-CD40 antibody or an interferon-fused agonistic binding fragment thereof comprising a sequence as set forth in SEQ ID NO 63.

In certain exemplary embodiments, the interferon-associated antigen binding protein comprises an interferon-fused agonistic anti-CD40 antibody or an interferon-fused agonistic binding fragment thereof comprising a sequence as set forth in SEQ ID NO 64. In another exemplary embodiment, the interferon-associated antigen binding protein is an interferon-fused agonistic anti-CD40 antibody or an interferon-fused agonistic binding fragment thereof comprising a sequence as set forth in SEQ ID NO 64.

In certain exemplary embodiments, the interferon-associated antigen binding protein comprises an interferon-fused agonistic anti-CD40 antibody or an interferon-fused agonistic binding fragment thereof comprising a sequence as set forth in SEQ ID NO 65. In another exemplary embodiment, the interferon-associated antigen binding protein is an interferon-fused agonistic anti-CD40 antibody or an interferon-fused agonistic binding fragment thereof comprising a sequence as set forth in SEQ ID NO 65.

In certain exemplary embodiments, the interferon-associated antigen binding protein comprises an interferon-fused agonistic anti-CD40 antibody or an interferon-fused agonistic binding fragment thereof comprising a sequence as set forth in SEQ ID NO 66. In another exemplary embodiment, the interferon-associated antigen binding protein is an interferon-fused agonistic anti-CD40 antibody or an interferon-fused agonistic binding fragment thereof comprising a sequence as set forth in SEQ ID NO 66.

In certain exemplary embodiments, the interferon-associated antigen binding protein comprises an interferon-fused agonistic anti-CD40 antibody or an interferon-fused agonistic binding fragment thereof comprising a sequence as set forth in SEQ ID NO 67. In another exemplary embodiment, the interferon-associated antigen binding protein is an interferon-fused agonistic anti-CD40 antibody or an interferon-fused agonistic binding fragment thereof comprising a sequence as set forth in SEQ ID NO 67.

In certain exemplary embodiments, the interferon-associated antigen binding protein comprises an interferon-fused agonistic anti-CD40 antibody or an interferon-fused agonistic binding fragment thereof comprising a sequence as set forth in SEQ ID NO 68. In another exemplary embodiment, the interferon-associated antigen binding protein is an interferon-fused agonistic anti-CD40 antibody or an interferon-fused agonistic binding fragment thereof comprising a sequence as set forth in SEQ ID NO 68.

In certain exemplary embodiments, the interferon-associated antigen binding protein comprises an interferon-fused agonistic anti-CD40 antibody or an interferon-fused agonistic binding fragment thereof comprising a sequence as set forth in SEQ ID NO 69. In another exemplary embodiment, the interferon-associated antigen binding protein is an interferon-fused agonistic anti-CD40 antibody or an interferon-fused agonistic binding fragment thereof comprising a sequence as set forth in SEQ ID NO 69.

In more preferred embodiments, the interferon-associated antigen binding protein comprises an interferon-fused agonistic anti-CD40 antibody or an interferon-fused agonistic antigen binding fragment thereof comprising a sequence selected from SEQ ID NO 38, SEQ ID NO 39, SEQ ID NO 40, SEQ ID NO 41, SEQ ID NO 42 or SEQ ID NO 43. In more preferred embodiments, the interferon-associated antigen binding protein is an interferon-fused agonistic anti-CD40 antibody or an interferon-fused agonistic antigen binding fragment thereof comprising a sequence selected from SEQ ID NO 38, SEQ ID NO 39, SEQ ID NO 40, SEQ ID NO 41, SEQ ID NO 42 or SEQ ID NO 43.

In an even more preferred embodiment, the interferon-associated antigen binding protein comprises an interferon-fused agonistic anti-CD40 antibody or an interferon-fused agonistic binding fragment thereof comprising a sequence as set forth in SEQ ID NO 38. In still another even more preferred embodiment, the interferon-associated antigen binding protein is an interferon-fused agonistic anti-CD40 antibody or an interferon-fused agonistic binding fragment thereof comprising a sequence as set forth in SEQ ID NO 38.

In another even more preferred embodiment, the interferon-associated antigen binding protein comprises an interferon-fused agonistic anti-CD40 antibody or an interferon-fused agonistic binding fragment thereof comprising a sequence as set forth in SEQ ID NO 39. In another even more preferred embodiment, the interferon-associated antigen binding protein is an interferon-fused agonistic anti-CD40 antibody or an interferon-fused agonistic binding fragment thereof comprising a sequence as set forth in SEQ ID NO 39.

In another even more preferred embodiment, the interferon-associated antigen binding protein comprises an interferon-fused agonistic anti-CD40 antibody or an interferon-fused agonistic binding fragment thereof comprising a sequence as set forth in SEQ ID NO 40. In another even more preferred embodiment, the interferon-associated antigen binding protein is an interferon-fused agonistic anti-CD40 antibody or an interferon-fused agonistic binding fragment thereof comprising a sequence as set forth in SEQ ID NO 40.

In another even more preferred embodiment, the interferon-associated antigen binding protein comprises an interferon-fused agonistic anti-CD40 antibody or an interferon-fused agonistic binding fragment thereof comprising a sequence as set forth in SEQ ID NO 41. In another even more preferred embodiment, the interferon-associated antigen binding protein is an interferon-fused agonistic anti-CD40 antibody or an interferon-fused agonistic binding fragment thereof comprising a sequence as set forth in SEQ ID NO 41.

In another even more preferred embodiment, the interferon-associated antigen binding protein comprises an interferon-fused agonistic anti-CD40 antibody or an interferon-fused agonistic binding fragment thereof comprising a sequence as set forth in SEQ ID NO 42. In another even more preferred embodiment, the interferon-associated antigen binding protein is an interferon-fused agonistic anti-CD40 antibody or an interferon-fused agonistic binding fragment thereof comprising a sequence as set forth in SEQ ID NO 42.

In another even more preferred embodiment, the interferon-associated antigen binding protein comprises an interferon-fused agonistic anti-CD40 antibody or an interferon-fused agonistic binding fragment thereof comprising a sequence as set forth in SEQ ID NO 43. In another even more preferred embodiment, the interferon-associated antigen binding protein is an interferon-fused agonistic anti-CD40 antibody or an interferon-fused agonistic binding fragment thereof comprising a sequence as set forth in SEQ ID NO 43.

TABLE 7

Sequences of exemplary interferon-associated Anti-gen binding protein and components thereof based on the Anti-CD40 antibody CP870,893. Italic sequences correspond to signal peptides. Bold italic sequences in SEQ ID NOs 3 and 6 correspond to CDR regions. Bold non-italic sequences correspond to linkers. Mutated amino acids are underlined.

| Name/SEQ ID Number | Sequence |
| --- | --- |
| Signal peptide 1 (SEQ ID NO 1) | *MGWSCHIILFLVATATGVHS* |
| Signal peptide 2 (SEQ ID NO 2) | *MDMRVPAQLLGLLLLWLRGARC* |
| Anti-CD40 antibody light chain (SEQ ID NO 3) | DIQMTQSPSSVSASVGDRVTITC*RASQGIYSWLA*WYQQKPGKAP NLLIY*TASTLQS*GVPSRFSGSGSGTDFTLTISSLQPEDFATYYC*QQ ANIFPLT*FGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGEC |
| Anti-CD40 antibody light chain with signal peptide 1 (SEQ ID NO 4) | *MGWSCIILFLVATATGVHS*DIQMTQSPSSVSASVGDRVTITCRASQ GIYSWLAWYQQKPGKAPNLLIYTASTLQSGVPSRFSGSGSGTDF TLTISSLQPEDFATYYCQQANIFPLTFGGGTKVEIKRTVAAPSVFI FPPSDEQLKSGTASVVCLLNNFYPREAKVQWKVDNALQSGNSQ ESVTEQDSKDSTYSLSSTLTLSKADYEKHKVYACEVTHQGLSSP VTKSFNRGEC |
| Anti-CD40 antibody light chain with signal peptide 2 (SEQ ID NO 5) | *MDMRVPAQLLGLLLLWLRGARC*DIQMTQSPSSVSASVGDRVTITC RASQGIYSWLAWYQQKPGKAPNLLIYTASTLQSGVPSRFSGSGS GTDFTLTISSLQPEDFATYYCQQANIFPLTFGGGTKVEIKRTVAAP SVFIFPPSDEQLKSGTASVVCLLNNFYPREAKVQWKVDNALQSG NSQESVTEQDSKDSTYSLSSTLTLSKADYEKHKVYACEVTHQGL SSPVTKSFNRGEC |
| Anti-CD40 antibody heavy chain hIgG2 dK (SEQ ID NO 6) | QVQLVQSGAEVKKPGASVKVSCKASGYTF*TGYYMH*WVRQAPG QGLEWMG*WINPDSGGTNYAQKFQG*RVTMTRDTSISTAYMELNR LRSDDTAVYYCARD*QPLGYCTNGVCSYFDY*WGQGTLVTVSSAS TKGPSVFPLAPCSRSTSESTAALGCLVKDYFPEPVTVSWNSGALT SGVHTFPAVLQSSGLYSLSSVVTVPSSNFGTQTYTCNVDHKPSNT KVDKTVERKCCVECPPCPAPPVAGPSVFLFPPKPKDTLMISRTPE VTCVVVDVSHEDPEVQFNWYVDGVEVHNAKTKPREEQFNSTFR VVSVLTVVHQDWLNGKEYKCKVSNKGLPAPIEKTISKTKGQPRE PQVYTLPPSREEMTKNQVSLTCLVKGFYPSDIAVEWESNGQPEN NYKTTPPMLDSDGSFFLYSKLTVDKSRWQQGNVFSCSVMHEAL HNHYTQKSLSLSPG |
| Anti-CD40 antibody heavy chain hIgG2 dK with signal peptide 1 (SEQ ID NO 7) | *MGWSCIILFLVATATGVHS*QVQLVQSGAEVKKPGASVKVSCKASG YTFTGYYMHWVRQAPGQGLEWMGWINPDSGGTNYAQKFQGR VTMTRDTSISTAYMELNRLRSDDTAVYYCARDQPLGYCTNGVC SYFDYWGQGTLVTVSSASTKGPSVFPLAPCSRSTSESTAALGCLV KDYFPEPVTVSWNSGALTSGVHTFPAVLQSSGLYSLSSVVTVPSS NFGTQTYTCNVDHKPSNTKVDKTVERKCCVECPPCPAPPVAGPS VFLFPPKPKDTLMISRTPEVTCVVVDVSHEDPEVQFNWYVDGVE VHNAKTKPREEQFNSTFRVVSVLTVVHQDWLNGKEYKCKVSN KGLPAPIEKTISKTKGQPREPQVYTLPPSREEMTKNQVSLTCLVK GFYPSDIAVEWESNGQPENNYKTTPPMLDSDGSFFLYSKLTVDK SRWQQGNVFSCSVMHEALHNHYTQKSLSLSPG |
| Anti-CD40 antibody heavy chain hIgG2 dK with signal peptide 2 (SEQ ID NO 8) | *MDMRVPAQLLGLLLLWLRGARC*QVQLVQSGAEVKKPGASVKVSC KASGYTFTGYYMHWVRQAPGQGLEWMGWINPDSGGTNYAQK FQGRVTMTRDTSISTAYMELNRLRSDDTAVYYCARDQPLGYCT NGVCSYFDYWGQGTLVTVSSASTKGPSVFPLAPCSRSTSESTAA LGCLVKDYFPEPVTVSWNSGALTSGVHTFPAVLQSSGLYSLSSV VTVPSSNFGTQTYTCNVDHKPSNTKVDKTVERKCCVECPPCPAP PVAGPSVFLFPPKPKDTLMISRTPEVTCVVVDVSHEDPEVQFNW YVDGVEVHNAKTKPREEQFNSTFRVVSVLTVVHQDWLNGKEY KCKVSNKGLPAPIEKTISKTKGQPREPQVYTLPPSREEMTKNQVS LTCLVKGFYPSDIAVEWESNGQPENNYKTTPPMLDSDGSFFLYS KLTVDKSRWQQGNVFSCSVMHEALHNHYTQKSLSLSPG |

TABLE 7-continued

Sequences of exemplary interferon-associated Anti-gen binding protein and components thereof based on the Anti-CD40 antibody CP870,893. Italic sequences correspond to signal peptides. Bold italic sequences in SEQ ID NOs 3 and 6 correspond to CDR regions. Bold non-italic sequences correspond to linkers. Mutated amino acids are underlined.

| Name/SEQ ID Number | Sequence |
| --- | --- |
| Anti-CD40 antibody heavy chain hIgG2 (SEQ ID NO 9) | QVQLVQSGAEVKKPGASVKVSCKASGYTFTGYYMHWVRQAPG QGLEWMGWINPDSGGTNYAQKFQGRVTMTRDTSISTAYMELN RLRSDDTAVYYCARDQPLGYCTNGVCSYFDYWGQGTLVTVSSA STKGPSVFPLAPCSRSTSESTAALGCLVKDYFPEPVTVSWNSGAL TSGVHTFPAVLQSSGLYSLSSVVTVPSSNFGTQTYTCNVDHKPSN TKVDKTVERKCCVECPPCPAPPVAGPSVFLFPPKPKDTLMISRTP EVTCVVVDVSHEDPEVQFNWYVDGVEVHNAKTKPREEQFNSTF RVVSVLTVVHQDWLNGKEYKCKVSNKGLPAPIEKTISKTKGQPR EPQVYTLPPSREEMTKNQVSLTCLVKGFYPSDIAVEWESNGQPE NNYKTTPPMLDSDGSFFLYSKLTVDKSRWQQGNVFSCSVMHEA LHNHYTQKSLSLSPGK |
| Anti-CD40 antibody heavy chain hIgG2 with signal peptide 1 (SEQ ID NO 10) | *MGWSCIILFLVATATGVHS*QVQLVQSGAEVKKPGASVKVSCKASG YTFTGYYMHWVRQAPGQGLEWMGWINPDSGGTNYAQKFQGR VTMTRDTSISTAYMELNRLRSDDTAVYYCARDQPLGYCTNGVC SYFDYWGQGTLVTVSSASTKGPSVFPLAPCSRSTSESTAALGCLV KDYFPEPVTVSWNSGALTSGVHTFPAVLQSSGLYSLSSVVTVPSS NFGTQTYTCNVDHKPSNTKVDKTVERKCCVECPPCPAPPVAGPS VFLFPPKPKDTLMISRTPEVTCVVVDVSHEDPEVQFNWYVDGVE VHNAKTKPREEQFNSTFRVVSVLTVVHQDWLNGKEYKCKVSN KGLPAPIEKTISKTKGQPREPQVYTLPPSREEMTKNQVSLTCLVK GFYPSDIAVEWESNGQPENNYKTTPPMLDSDGSFFLYSKLTVDK SRWQQGNVFSCSVMHEALHNHYTQKSLSLSPGK |
| Anti-CD40 antibody heavy chain hIgG2 with signal peptide 2 (SEQ ID NO 11) | *MDMRVPAQLLGLLLLWLRGARC*QVQLVQSGAEVKKPGASVKVSC KASGYTFTGYYMHWVRQAPGQGLEWMGWINPDSGGTNYAQK FQGRVTMTRDTSISTAYMELNRLRSDDTAVYYCARDQPLGYCT NGVCSYFDYWGQGTLVTVSSASTKGPSVFPLAPCSRSTSESTAA LGCLVKDYFPEPVTVSWNSGALTSGVHTFPAVLQSSGLYSLSSV VTVPSSNFGTQTYTCNVDHKPSNTKVDKTVERKCCVECPPCPAP PVAGPSVFLFPPKPKDTLMISRTPEVTCVVVDVSHEDPEVQFNW YVDGVEVHNAKTKPREEQFNSTFRVVSVLTVVHQDWLNGKEY KCKVSNKGLPAPIEKTISKTKGQPREPQVYTLPPSREEMTKNQVS LTCLVKGFYPSDIAVEWESNGQPENNYKTTPPMLDSDGSFFLYS KLTVDKSRWQQGNVFSCSVMHEALHNHYTQKSLSLSPGK |
| Anti-CD40 antibody hIgG1 heavy chain- NNAS (SEQ ID NO 48) | QVQLVQSGAEVKKPGASVKVSCKASGYTFTGYYMHWVRQAPG QGLEWMGWINPDSGGTNYAQKFQGRVTMTRDTSISTAYMELN RLRSDDTAVYYCARDQPLGYCTNGVCSYFDYWGQGTLVTVSSA STKGPSVFPLAPSSKSTSGGTAALGCLVKDYFPEPVTVSWNSGAL TSGVHTFPAVLQSSGLYSLSSVVTVPSSSLGTQTYICNVNHKPSN TKVDKKVEPKSCDKTHTCPPCPAPELLGGPSVFLFPPKPKDTLMI SRTPEVTCVVVDVSHEDPEVKFNWYVDGVEVHNAKTKPREEQY <u>NNAS</u>RVVSVLTVLHQDWLNGKEYKCKVSNKALPAPIEKTISKA <u>K</u>GQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPGK |
| Anti-CD40 antibody hIgG1 heavy chain- NNAS-dK (SEQ ID NO 49) | QVQLVQSGAEVKKPGASVKVSCKASGYTFTGYYMHWVRQAPG QGLEWMGWINPDSGGTNYAQKFQGRVTMTRDTSISTAYMELN RLRSDDTAVYYCARDQPLGYCTNGVCSYFDYWGQGTLVTVSSA STKGPSVFPLAPSSKSTSGGTAALGCLVKDYFPEPVTVSWNSGAL TSGVHTFPAVLQSSGLYSLSSVVTVPSSSLGTQTYICNVNHKPSN TKVDKKVEPKSCDKTHTCPPCPAPELLGGPSVFLFPPKPKDTLMI SRTPEVTCVVVDVSHEDPEVKFNWYVDGVEVHNAKTKPREEQY <u>NNAS</u>RVVSVLTVLHQDWLNGKEYKCKVSNKALPAPIEKTISKA <u>K</u>GQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPG |
| Anti-CD40 antibody hIgG2 Fab region heavy chain (SEQ ID NO 12) | QVQLVQSGAEVKKPGASVKVSCKASGYTFTGYYMHWVRQAPG QGLEWMGWINPDSGGTNYAQKFQGRVTMTRDTSISTAYMELN RLRSDDTAVYYCARDQPLGYCTNGVCSYFDYWGQGTLVTVSSA STKGPSVFPLAPCSRSTSESTAALGCLVKDYFPEPVTVSWNSGAL TSGVHTFPAVLQSSGLYSLSSVVTVPSSNFGTQTYTCNVDHKPSN TKVDKTVERKCCVE |
| Anti-CD40 antibody hIgG2 Fab region heavy chain with signal | *MGWSCIILFLVATATGVHS*QVQLVQSGAEVKKPGASVKVSCKASG YTFTGYYMHWVRQAPGQGLEWMGWINPDSGGTNYAQKFQGR VTMTRDTSISTAYMELNRLRSDDTAVYYCARDQPLGYCTNGVC SYFDYWGQGTLVTVSSASTKGPSVFPLAPCSRSTSESTAALGCLV |

TABLE 7-continued

Sequences of exemplary interferon-associated Anti-gen binding protein and components thereof based on the Anti-CD40 antibody CP870,893. Italic sequences correspond to signal peptides. Bold italic sequences in SEQ ID NOs 3 and 6 correspond to CDR regions. Bold non-italic sequences correspond to linkers. Mutated amino acids are underlined.

| Name/SEQ ID Number | Sequence |
| --- | --- |
| peptide 1 (SEQ ID NO 13) | KDYFPEPVTVSWNSGALTSGVHTFPAVLQSSGLYSLSSVVTVPSS NFGTQTYTCNVDHKPSNTKVDKTVERKCCVE |
| Anti-CD40 antibody hIgG2 Fab region heavy chain --TEV--6His tag (SEQ ID NO 50) | QVQLVQSGAEVKKPGASVKVSCKASGYTFTGYYMHWVRQAPG QGLEWMGWINPDSGGTNYAQKFQGRVTMTRDTSISTAYMELN RLRSDDTAVYYCARDQPLGYCTNGVCSYFDYWGQGTLVTVSSA STKGPSVFPLAPCSRSTSESTAALGCLVKDYFPEPVTVSWNSGAL TSGVHTFPAVLQSSGLYSLSSVVTVPSSNFGTQTYTCNVDHKPSN TKVDKTVERKCCVEENLYFQSHHHHHH |
| IFNß (SEQ ID NO 14) | MSYNLLGFLQRSSNFQCQKLLWQLNGRLEYCLKDRMNFDIPEEI KQLQQFQKEDAALTIYEMLQNIFAIFRQDSSSTGWNETIVENLLA NVYHQINHLKTVLEEKLEKEDFTRGKLMSSLHLKRYYGRILHYL KAKEYSHCAWTIVRVEILRNFYFINRLTGYLRN |
| IFNß C17S (SEQ ID NO 15) | MSYNLLGFLQRSSNFQSQKLLWQLNGRLEYCLKDRMNFDIPEEI KQLQQFQKEDAALTIYEMLQNIFAIFRQDSSSTGWNETIVENLLA NVYHQINHLKTVLEEKLEKEDFTRGKLMSSLHLKRYYGRILHYL KAKEYSHCAWTIVRVEILRNFYFINRLTGYLRN |
| IFNß C17S, N80Q (SEQ ID NO 16) | MSYNLLGFLQRSSNFQSQKLLWQLNGRLEYCLKDRMNFDIPEEI KQLQQFQKEDAALTIYEMLQNIFAIFRQDSSSTGWQETIVENLLA NVYHQINHLKTVLEEKLEKEDFTRGKLMSSLHLKRYYGRILHYL KAKEYSHCAWTIVRVEILRNFYFINRLTGYLRN |
| IFNα2a (SEQ ID NO 17) | CDLPQTHSLGSRRTLMLLAQMRKISLFSCLKDRHDFGFPQEEFG NQFQKAETIPVLHEMIQQIFNLFSTKDSSAAWDETLLDKFYTELY QQLNDLEACVIQGVGVTETPLMKEDSILAVRKYFQRITLYLKEK KYSPCAWEVVRAEIMRSFSLSTNLQESLRSKE |
| IFNλ2 (SEQ ID NO 18) | VPVARLHGALPDARGCHIAQFKSLSPQELQAFKRAKDALEESLL LKDCRCHSRLFPRTWDLRQLQVRERPMALEAELALTLKVLEAT ADTDPALVDVLDQPLHTLHHILSQFRACIQPQPTAGPRTRGRLHH WLYRLQEAPKKESPGCLEASVTFNLFRLLTRDLNCVASGDLCV |
| IFNγ (SEQ ID NO 19) | QDPYVKEAENLKKYFNAGHSDVADNGTLFLGILKNWKEESDRK IMQSQIVSFYFKLFKNFKDDQSIQKSVETIKEDMNVKFFNSNKKK RDDFEKLTNYSVTDLNVQRKAIHELIQVMAELSPAAKTGKRKRS QMLFRGRRASQ |
| IFNω (SEQ ID NO 60) | LGCDLPQNHGLLSRNTLVLLHQMRRISPFLCLKDRRDFRFPQEM VKGSQLQKAHVMSVLHEMLQQIFSLFHTERSSAAWNMTLLDQL HTGLHQQLQHLETCLLQVVGEGESAGAISSPALTLRRYFQGIRV YLKEKKYSDCAWEVVRMEIMKSLFLSTNMQERLRSKDRDLGSS |
| IFNε (SEQ ID NO 61) | LDLKLIIFQQRQVNQESLKLLNKLQTLSIQQCLPHRKNFLLPQKSL SPQQYQKGHTLAILHEMLQQIFSLFRANISLDGWEENHTEKFLIQ LHQQLEYLEALMGLEAEKLSGTLGSDNLRLQVKMYFRRIHDYL ENQDYSTCAWAIVQVEISRCLFFVFSLTEKLSKQGRPLNDMKQE LTTEFRSPR |
| RL linker (SEQ ID NO 20) | PAPA |
| GST linker (SEQ ID NO 21) | SGGTSGSTSGTGS |
| HL linker (SEQ ID NO 22) | AEAAAKEAAAKA |
| HL2 linker (SEQ ID NO 23) | AEAAAKEAAAKAAEAAAKEAAAKA |
| (G4S)2 linker (SEQ ID NO 24) | GGGGSGGGGS |
| (G4S)3 linker (SEQ ID NO 25) | GGGGSGGGGSGGGGS |
| (G4S)4 linker (SEQ ID NO 26) | GGGGSGGGGSGGGGSGGGGS |

TABLE 7-continued

Sequences of exemplary interferon-associated Anti-gen binding protein and components thereof based on the Anti-CD40 antibody CP870,893. Italic sequences correspond to signal peptides. Bold italic sequences in SEQ ID NOs 3 and 6 correspond to CDR regions. Bold non-italic sequences correspond to linkers. Mutated amino acids are underlined.

| Name/SEQ ID Number | Sequence |
| --- | --- |
| TEV-6His tag (SEQ ID NO 27) | ENLYFQSHHHHHH |
| Anti-CD40_LC--HL--IFNß (SEQ ID NO 28) | DIQMTQSPSSVSASVGDRVTITCRASQGIYSWLAWYQQKPGKAP NLLIYTASTLQSGVPSRFSGSGSGTDFTLTISSLQPEDFATYYCQQ ANIFPLTFGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGECAEAAAKEAA AKAMSYNLLGFLQRSSNFQCQKLLWQLNGRLEYCLKDRMNFDI PEEIKQLQQFQKEDAALTIYEMLQNIFAIFRQDSSSTGWNETIVEN LLANVYHQINHLKTVLEEKLEKEDFTRGKLMSSLHLKRYYGRIL HYLKAKEYSHCAWTIVRVEILRNFYFINRLTGYLRN |
| Anti-CD40_LC--HL--IFNß_C17S (SEQ ID NO 29) | DIQMTQSPSSVSASVGDRVTITCRASQGIYSWLAWYQQKPGKAP NLLIYTASTLQSGVPSRFSGSGSGTDFTLTISSLQPEDFATYYCQQ ANIFPLTFGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGECAEAAAKEAA AKAMSYNLLGFLQRSSNFQSQKLLWQLNGRLEYCLKDRMNFDI PEEIKQLQQFQKEDAALTIYEMLQNIFAIFRQDSSSTGWNETIVEN LLANVYHQINHLKTVLEEKLEKEDFTRGKLMSSLHLKRYYGRIL HYLKAKEYSHCAWTIVRVEILRNFYFINRLTGYLRN |
| Anti-CD40 hIgG2 dK_HC--RL--IFNß (SEQ ID NO 30) | QVQLVQSGAEVKKPGASVKVSCKASGYTFTGYYMHWVRQAPG QGLEWMGWINPDSGGTNYAQKFQGRVTMTRDTSISTAYMELN RLRSDDTAVYYCARDQPLGYCTNGVCSYFDYWGQGTLVTVSSA STKGPSVFPLAPCSRSTSESTAALGCLVKDYFPEPVTVSWNSGAL TSGVHTFPAVLQSSGLYSLSSVVTVPSSNFGTQTYTCNVDHKPSN TKVDKTVERKCCVECPPCPAPPVAGPSVFLFPPKPKDTLMISRTP EVTCVVVDVSHEDPEVQFNWYVDGVEVHNAKTKPREEQFNSTF RVVSVLTVVHQDWLNGKEYKCKVSNKGLPAPIEKTISKTKGQPR EPQVYTLPPSREEMTKNQVSLTCLVKGFYPSDIAVEWESNGQPE NNYKTTPPMLDSDGSFFLYSKLTVDKSRWQQGNVFSCSVMHEA LHNHYTQKSLSLSPGPAPAMSYNLLGFLQRSSNFQCQKLLWQL NGRLEYCLKDRMNFDIPEEIKQLQQFQKEDAALTIYEMLQNIFAI FRQDSSSTGWNETIVENLLANVYHQINHLKTVLEEKLEKEDFTR GKLMSSLHLKRYYGRILHYLKAKEYSHCAWTIVRVEILRNFYFI NRLTGYLRN |
| Anti-CD40_hIgG2_dK_HC--RL--IFNß_C17S (SEQ ID NO 31) | QVQLVQSGAEVKKPGASVKVSCKASGYTFTGYYMHWVRQAPG QGLEWMGWINPDSGGTNYAQKFQGRVTMTRDTSISTAYMELN RLRSDDTAVYYCARDQPLGYCTNGVCSYFDYWGQGTLVTVSSA STKGPSVFPLAPCSRSTSESTAALGCLVKDYFPEPVTVSWNSGAL TSGVHTFPAVLQSSGLYSLSSVVTVPSSNFGTQTYTCNVDHKPSN TKVDKTVERKCCVECPPCPAPPVAGPSVFLFPPKPKDTLMISRTP EVTCVVVDVSHEDPEVQFNWYVDGVEVHNAKTKPREEQFNSTF RVVSVLTVVHQDWLNGKEYKCKVSNKGLPAPIEKTISKTKGQPR EPQVYTLPPSREEMTKNQVSLTCLVKGFYPSDIAVEWESNGQPE NNYKTTPPMLDSDGSFFLYSKLTVDKSRWQQGNVFSCSVMHEA LHNHYTQKSLSLSPGPAPAMSYNLLGFLQRSSNFQSQKLLWQLN GRLEYCLKDRMNFDIPEEIKQLQQFQKEDAALTIYEMLQNIFAIF RQDSSSTGWNETIVENLLANVYHQINHLKTVLEEKLEKEDFTRG KLMSSLHLKRYYGRILHYLKAKEYSHCAWTIVRVEILRNFYINR LTGYLRN |
| Anti-CD40_hIgG2_dK_HC--HL--IFNß (SEQ ID NO 32) | QVQLVQSGAEVKKPGASVKVSCKASGYTFTGYYMHWVRQAPG QGLEWMGWINPDSGGTNYAQKFQGRVTMTRDTSISTAYMELN RLRSDDTAVYYCARDQPLGYCTNGVCSYFDYWGQGTLVTVSSA STKGPSVFPLAPCSRSTSESTAALGCLVKDYFPEPVTVSWNSGAL TSGVHTFPAVLQSSGLYSLSSVVTVPSSNFGTQTYTCNVDHKPSN TKVDKTVERKCCVECPPCPAPPVAGPSVFLFPPKPKDTLMISRTP EVTCVVVDVSHEDPEVQFNWYVDGVEVHNAKTKPREEQFNSTF RVVSVLTVVHQDWLNGKEYKCKVSNKGLPAPIEKTISKTKGQPR EPQVYTLPPSREEMTKNQVSLTCLVKGFYPSDIAVEWESNGQPE NNYKTTPPMLDSDGSFFLYSKLTVDKSRWQQGNVFSCSVMHEA LHNHYTQKSLSLSPGAEAAAKEAAAKAMSYNLLGFLQRSSNFQ CQKLLWQLNGRLEYCLKDRMNFDIPEEIKQLQQFQKEDAALTIY EMLQNIFAIFRQDSSSTGWNETIVENLLANVYHQINHLKTVLEEK LEKEDFTRGKLMSSLHLKRYYGRILHYLKAKEYSHCAWTIVRVE ILRNFYFINRLTGYLRN |

TABLE 7-continued

Sequences of exemplary interferon-associated Anti-gen binding protein and components thereof based on the Anti-CD40 antibody CP870,893. Italic sequences correspond to signal peptides. Bold italic sequences in SEQ ID NOs 3 and 6 correspond to CDR regions. Bold non-italic sequences correspond to linkers. Mutated amino acids are underlined.

| Name/SEQ ID Number | Sequence |
| --- | --- |
| Anti-CD40_hIgG2_dK_HC--HL--IFNß_C17S (SEQ ID NO 33) | QVQLVQSGAEVKKPGASVKVSCKASGYTFTGYYMHWVRQAPG QGLEWMGWINPDSGGTNYAQKFQGRVTMTRDTSISTAYMELN RLRSDDTAVYYCARDQPLGYCTNGVCSYFDYWGQGTLVTVSSA STKGPSVFPLAPCSRSTSESTAALGCLVKDYFPEPVTVSWNSGAL TSGVHTFPAVLQSSGLYSLSSVVTVPSSNFGTQTYTCNVDHKPSN TKVDKTVERKCCVECPPCPAPPVAGPSVFLFPPKPKDTLMISRTP EVTCVVVDVSHEDPEVQFNWYVDGVEVHNAKTKPREEQFNSTF RVVSVLTVVHQDWLNGKEYKCKVSNKGLPAPIEKTISKTKGQPR EPQVYTLPPSREEMTKNQVSLTCLVKGFYPSDIAVEWESNGQPE NNYKTTPPMLDSDGSFFLYSKLTVDKSRWQQGNVFSCSVMHEA LHNHYTQKSLSLSPGAEAAAKEAAAKAMSYNLLGFLQRSSNFQ SQKLLWQLNGRLEYCLKDRMNFDIPEEIKQLQQFQKEDAALTIY EMLQNIFAIFRQDSSSTGWNETIVENLLANVYHQINHLKTVLEEK LEKEDFTRGKLMSSLHLKRYYGRILHYLKAKEYSHCAWTIVRVE ILRNFYFINRLTGYLRN |
| Anti-CD40_LC--RL--IFNß (SEQ ID NO 34) | DIQMTQSPSSVSASVGDRVTITCRASQGIYSWLAWYQQKPGKAP NLLIYTASTLQSGVPSRFSGSGSGTDFTLTISSLQPEDFATYYCQQ ANIFPLTFGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGECPAPAMSYNL LGFLQRSSNFQCQKLLWQLNGRLEYCLKDRMNFDIPEEIKQLQQ FQKEDAALTIYEMLQNIFAIFRQDSSSTGWNETIVENLLANVYHQ INHLKTVLEEKLEKEDFTRGKLMSSLHLKRYYGRILHYLKAKEY SHCAWTIVRVEILRNFYFINRLTGYLRN |
| Anti-CD40_LC--RL--IFNß_C17S (SEQ ID NO 35) | DIQMTQSPSSVSASVGDRVTITCRASQGIYSWLAWYQQKPGKAP NLLIYTASTLQSGVPSRFSGSGSGTDFTLTISSLQPEDFATYYCQQ ANIFPLTFGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGECPAPAMSYNL LGFLQRSSNFQSQKLLWQLNGRLEYCLKDRMNFDIPEEIKQLQQ FQKEDAALTIYEMLQNIFAIFRQDSSSTGWNETIVENLLANVYHQ INHLKTVLEEKLEKEDFTRGKLMSSLHLKRYYGRILHYLKAKEY SHCAWTIVRVEILRNFYFINRLTGYLRN |
| Anti-CD40_LC--GST--IFNß_C17S (SEQ ID NO 36) | DIQMTQSPSSVSASVGDRVTITCRASQGIYSWLAWYQQKPGKAP NLLIYTASTLQSGVPSRFSGSGSGTDFTLTISSLQPEDFATYYCQQ ANIFPLTFGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGECSGGTSGSTS GTGSMSYNLLGFLQRSSNFQSQKLLWQLNGRLEYCLKDRMNFD IPEEIKQLQQFQKEDAALTIYEMLQNIFAIFRQDSSSTGWNETIVE NLLANVYHQINHLKTVLEEKLEKEDFTRGKLMSSLHLKRYYGRI LHYLKAKEYSHCAWTIVRVEILRNFYFINRLTGYLRN |
| Anti-CD40_LC--HL2--IFNß_C17S (SEQ ID NO 37) | DIQMTQSPSSVSASVGDRVTITCRASQGIYSWLAWYQQKPGKAP NLLIYTASTLQSGVPSRFSGSGSGTDFTLTISSLQPEDFATYYCQQ ANIFPLTFGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGECAEAAAKEAA AKAAEAAAKEAAAKAMSYNLLGFLQRSSNFQSQKLLWQLNGR LEYCLKDRMNFDIPEEIKQLQQFQKEDAALTIYEMLQNIFAIFRQ DSSSTGWNETIVENLLANVYHQINHLKTVLEEKLEKEDFTRGKL MSSLHLKRYYGRILHYLKAKEYSHCAWTIVRVEILRNFYFINRLT GYLRN |
| Anti-CD40_hIgG2_dK_HC--(G4S)2--IFNα2a (SEQ ID NO 38) | QVQLVQSGAEVKKPGASVKVSCKASGYTFTGYYMHWVRQAPG QGLEWMGWINPDSGGTNYAQKFQGRVTMTRDTSISTAYMELN RLRSDDTAVYYCARDQPLGYCTNGVCSYFDYWGQGTLVTVSSA STKGPSVFPLAPCSRSTSESTAALGCLVKDYFPEPVTVSWNSGAL TSGVHTFPAVLQSSGLYSLSSVVTVPSSNFGTQTYTCNVDHKPSN TKVDKTVERKCCVECPPCPAPPVAGPSVFLFPPKPKDTLMISRTP EVTCVVVDVSHEDPEVQFNWYVDGVEVHNAKTKPREEQFNSTF RVVSVLTVVHQDWLNGKEYKCKVSNKGLPAPIEKTISKTKGQPR EPQVYTLPPSREEMTKNQVSLTCLVKGFYPSDIAVEWESNGQPE NNYKTTPPMLDSDGSFFLYSKLTVDKSRWQQGNVFSCSVMHEA LHNHYTQKSLSLSPGGGGGSGGGGSCDLPQTHSLGSRRTLMLL AQMRKISLFSCLKDRHDFGFPQEEFGNQFQKAETIPVLHEMIQQI FNLFSTKDSSAAWDETLLDKFYTELYQQLNDLEACVIQGVGVTE TPLMKEDSILAVRKYFQRITLYLKEKKYSPCAWEVVRAEIMRSFS LSTNLQESLRSKE |

TABLE 7-continued

Sequences of exemplary interferon-associated Anti-gen binding protein and components thereof based on the Anti-CD40 antibody CP870,893. Italic sequences correspond to signal peptides. Bold italic sequences in SEQ ID NOs 3 and 6 correspond to CDR regions. Bold non-italic sequences correspond to linkers. Mutated amino acids are underlined.

| Name/SEQ ID Number | Sequence |
| --- | --- |
| Anti-CD40_hIgG2_dK_HC--(G4S)3--IFNα2a (SEQ ID NO 39) | QVQLVQSGAEVKKPGASVKVSCKASGYTFTGYYMHWVRQAPG QGLEWMGWINPDSGGTNYAQKFQGRVTMTRDTSISTAYMELN RLRSDDTAVYYCARDQPLGYCTNGVCSYFDYWGQGTLVTVSSA STKGPSVFPLAPCSRSTSESTAALGCLVKDYFPEPVTVSWNSGAL TSGVHTFPAVLQSSGLYSLSSVVTVPSSNFGTQTYTCNVDHKPSN TKVDKTVERKCCVECPPCPAPPVAGPSVFLFPPKPKDTLMISRTP EVTCVVVDVSHEDPEVQFNWYVDGVEVHNAKTKPREEQFNSTF RVVSVLTVVHQDWLNGKEYKCKVSNKGLPAPIEKTISKTKGQPR EPQVYTLPPSREEMTKNQVSLTCLVKGFYPSDIAVEWESNGQPE NNYKTTPPMLDSDGSFFLYSKLTVDKSRWQQGNVFSCSVMHEA LHNHYTQKSLSLSPGGGGGSGGGGSGGGGSCDLPQTHSLGSRR TLMLLAQMRKISLFSCLKDRHDFGFPQEEFGNQFQKAETIPVLHE MIQQIFNLFSTKDSSAAWDETLLDKFYTELYQQLNDLEACVIQG VGVTETPLMKEDSILAVRKYFQRITLYLKEKKYSPCAWEVVRAE IMRSFSLSTNLQESLRSKE |
| Anti-CD40_hIgG2_dK_HC--(G4S)4--IFNα2a (SEQ ID NO 40) | QVQLVQSGAEVKKPGASVKVSCKASGYTFTGYYMHWVRQAPG QGLEWMGWINPDSGGTNYAQKFQGRVTMTRDTSISTAYMELN RLRSDDTAVYYCARDQPLGYCTNGVCSYFDYWGQGTLVTVSSA STKGPSVFPLAPCSRSTSESTAALGCLVKDYFPEPVTVSWNSGAL TSGVHTFPAVLQSSGLYSLSSVVTVPSSNFGTQTYTCNVDHKPSN TKVDKTVERKCCVECPPCPAPPVAGPSVFLFPPKPKDTLMISRTP EVTCVVVDVSHEDPEVQFNWYVDGVEVHNAKTKPREEQFNSTF RVVSVLTVVHQDWLNGKEYKCKVSNKGLPAPIEKTISKTKGQPR EPQVYTLPPSREEMTKNQVSLTCLVKGFYPSDIAVEWESNGQPE NNYKTTPPMLDSDGSFFLYSKLTVDKSRWQQGNVFSCSVMHEA LHNHYTQKSLSLSPGGGGGSGGGGSGGGGSGGGGSCDLPQTH SLGSRRTLMLLAQMRKISLFSCLKDRHDFGFPQEEFGNQFQKAE TIPVLHEMIQQIFNLFSTKDSSAAWDETLLDKFYTELYQQLNDLE ACVIQGVGVTETPLMKEDSILAVRKYFQRITLYLKEKKYSPCAW EVVRAEIMRSFSLSTNLQESLRSKE |
| Anti-CD40_LC--(G4S)2--IFNα2a (SEQ ID NO 41) | DIQMTQSPSSVSASVGDRVTITCRASQGIYSWLAWYQQKPGKAP NLLIYTASTLQSGVPSRFSGSGSGTDFTLTISSLQPEDFATYYCQQ ANIFPLTFGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGECGGGGSGGG GSCDLPQTHSLGSRRTLMLLAQMRKISLFSCLKDRHDFGFPQEEF GNQFQKAETIPVLHEMIQQIFNLFSTKDSSAAWDETLLDKFYTEL YQQLNDLEACVIQGVGVTETPLMKEDSILAVRKYFQRITLYLKE KKYSPCAWEVVRAEIMRSFSLSTNLQESLRSKE |
| Anti-CD40_LC--(G4S)3--IFNα2a (SEQ ID NO 42) | DIQMTQSPSSVSASVGDRVTITCRASQGIYSWLAWYQQKPGKAP NLLIYTASTLQSGVPSRFSGSGSGTDFTLTISSLQPEDFATYYCQQ ANIFPLTFGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGECGGGGSGGG GSGGGGSCDLPQTHSLGSRRTLMLLAQMRKISLFSCLKDRHDFG FPQEEFGNQFQKAETIPVLHEMIQQIFNLFSTKDSSAAWDETLLD KFYTELYQQLNDLEACVIQGVGVTETPLMKEDSILAVRKYFQRI TLYLKEKKYSPCAWEVVRAEIMRSFSLSTNLQESLRSKE |
| Anti-CD40_LC--(G4S)4--IFNα2a (SEQ ID NO 43) | DIQMTQSPSSVSASVGDRVTITCRASQGIYSWLAWYQQKPGKAP NLLIYTASTLQSGVPSRFSGSGSGTDFTLTISSLQPEDFATYYCQQ ANIFPLTFGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGECGGGGSGGG GSGGGGSGGGGSCDLPQTHSLGSRRTLMLLAQMRKISLFSCLK DRHDFGFPQEEFGNQFQKAETIPVLHEMIQQIFNLFSTKDSSAAW DETLLDKFYTELYQQLNDLEACVIQGVGVTETPLMKEDSILAVR KYFQRITLYLKEKKYSPCAWEVVRAEIMRSFSLSTNLQESLRSKE |
| IFNβ--(G4S)3--Anti-CD40_LC) (SEQ ID NO 44) | MSYNLLGFLQRSSNFQCQKLLWQLNGRLEYCLKDRMNFDIPEEI KQLQQFQKEDAALTIYEMLQNIFAIFRQDSSTGWNETIVENLLA NVYHQINHLKTVLEEKLEKEDFTRGKLMSSLHLKRYYGRILHYL KAKEYSHCAWTIVRVEILRNFYFINRLTGYLRNGGGGSGGGGS GGGGSDIQMTQSPSSVSASVGDRVTITCRASQGIYSWLAWYQQ KPGKAPNLLIYTASTLQSGVPSRFSGSGSGTDFTLTISSLQPEDFA TYYCQQANIFPLTFGGGTKVEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |

TABLE 7-continued

Sequences of exemplary interferon-associated Anti-gen binding protein and components thereof based on the Anti-CD40 antibody CP870,893. Italic sequences correspond to signal peptides. Bold italic sequences in SEQ ID NOs 3 and 6 correspond to CDR regions. Bold non-italic sequences correspond to linkers. Mutated amino acids are underlined.

| Name/SEQ ID Number | Sequence |
| --- | --- |
| Anti-CD40_LC--<br>(G4S)4--IFNß<br>(SEQ ID NO 45) | DIQMTQSPSSVSASVGDRVTITCRASQGIYSWLAWYQQKPGKAP<br>NLLIYTASTLQSGVPSRFSGSGSGTDFTLTISSLQPEDFATYYCQQ<br>ANIFPLTFGGGTKVEIKRTVAAPSVFIFPPSDEQLKSGTASVVCLL<br>NNFYPREAKVQWKVDNALQSGNSQESVTEQDSKDSTYSLSSTLT<br>LSKADYEKHKVYACEVTHQGLSSPVTKSFNRGECGGGGSGGG<br>GSGGGGSGGGGSMSYNLLGFLQRSSNFQCQKLLWQLNGRLEY<br>CLKDRMNFDIPEEIKQLQQFQKEDAALTIYEMLQNIFAIFRQDSSS<br>TGWNETIVENLLANVYHQINHLKTVLEEKLEKEDFTRGKLMSSL<br>HLKRYYGRILHYLKAKEYSHCAWTIVRVEILRNFYFINRLTGYLRN |
| IFNß--(G4S)3--<br>Anti-CD40_HC_Ig<br>G1_NNAS-dK<br>(SEQ ID NO 46) | MSYNLLGFLQRSSNFQCQKLLWQLNGRLEYCLKDRMNFDIPEEI<br>KQLQQFQKEDAALTIYEMLQNIFAIFRQDSSTGWNETIVENLLA<br>NVYHQINHLKTVLEEKLEKEDFTRGKLMSSLHLKRYYGRILHYL<br>KAKEYSHCAWTIVRVEILRNFYFINRLTGYLRNGGGGSGGGGS<br>GGGGSQVQLVQSGAEVKKPGASVKVSCKASGYTFTGYYMHW<br>VRQAPGQGLEWMGWINPDSGGTNYAQKFQGRVTMTRDTSISTA<br>YMELNRLRSDDTAVYYCARDQPLGYCTNGVCSYFDYWGQGTL<br>VTVSSASTKGPSVFPLAPSSKSTSGGTAALGCLVKDYFPEPVTVS<br>WNSGALTSGVHTFPAVLQSSGLYSLSSVVTVPSSSLGTQTYICNV<br>NHKPSNTKVDKKVEPKSCDKTHTCPPCPAPELLGGPSVFLFPPKP<br>KDTLMISRTPEVTCVVVDVSHEDPEVKFNWYVDGVEVHNAKTK<br>PREEQY<u>NN</u>A<u>S</u>RVVSVLTVLHQDWLNGKEYKCKVSNKALPAPIE<br>KTISKA<u>K</u>GQPREPQVYTLPPSRDELTKNQVSLTCLVKGFYPSDIA<br>VEWESNGQPENNYKTTPPVLDSDGSFFLYSKLTVDKSRWQQGN<br>VFSCSVMHEALHNHYTQKSLSLSPG |
| Anti-CD40_HC_Ig<br>G1_NNAS_dK--<br>(G4S)4--IFNß<br>(SEQ ID NO 47) | QVQLVQSGAEVKKPGASVKVSCKASGYTFTGYYMHWVRQAPG<br>QGLEWMGWINPDSGGTNYAQKFQGRVTMTRDTSISTAYMELN<br>RLRSDDTAVYYCARDQPLGYCTNGVCSYFDYWGQGTLVTVSSA<br>STKGPSVFPLAPSSKSTSGGTAALGCLVKDYFPEPVTVSWNSGAL<br>TSGVHTFPAVLQSSGLYSLSSVVTVPSSSLGTQTYICNVNHKPSN<br>TKVDKKVEPKSCDKTHTCPPCPAPELLGGPSVFLFPPKPKDTLMI<br>SRTPEVTCVVVDVSHEDPEVKFNWYVDGVEVHNAKTKPREEQY<br><u>NN</u>A<u>S</u>RVVSVLTVLHQDWLNGKEYKCKVSNKALPAPIEKTISKA<br><u>K</u>GQPREPQVYTLPPSRDELTKNQVSLTCLVKGFYPSDIAVEWES<br>NGQPENNYKTTPPVLDSDGSFFLYSKLTVDKSRWQQGNVFSCSV<br>MHEALHNHYTQKSLSLSPGGGGGSGGGGSGGGGSGGGGSMS<br>YNLLGFLQRSSNFQCQKLLWQLNGRLEYCLKDRMNFDIPEEIKQ<br>LQQFQKEDAALTIYEMLQNIFAIFRQDSSTGWNETIVENLLANV<br>YHQINHLKTVLEEKLEKEDFTRGKLMSSLHLKRYYGRILHYLKA<br>KEYSHCAWTIVRVEILRNFYFINRLTGYLRN |
| Anti-CD40_hIgG2<br>dK_HC--HL--<br>IFNα2A<br>(SEQ ID NO 62) | QVQLVQSGAEVKKPGASVKVSCKASGYTFTGYYMHWVRQAPG<br>QGLEWMGWINPDSGGTNYAQKFQGRVTMTRDTSISTAYMELN<br>RLRSDDTAVYYCARDQPLGYCTNGVCSYFDYWGQGTLVTVSSA<br>STKGPSVFPLAPCSRSTSESTAALGCLVKDYFPEPVTVSWNSGAL<br>TSGVHTFPAVLQSSGLYSLSSVVTVPSSNFGTQTYTCNVDHKPSN<br>TKVDKTVERKCCVECPPCPAPPVAGPSVFLFPPKPKDTLMISRTP<br>EVTCVVVDVSHEDPEVQFNWYVDGVEVHNAKTKPREEQFNSTF<br>RVVSVLTVVHQDWLNGKEYKCKVSNKGLPAPIEKTISKTKGQPR<br>EPQVYTLPPSREEMTKNQVSLTCLVKGFYPSDIAVEWESNGQPE<br>NNYKTTPPMLDSDGSFFLYSKLTVDKSRWQQGNVFSCSVMHEA<br>LHNHYTQKSLSLSPGAEAAAKEAAAKACDLPQTHSLGSRRTLM<br>LLAQMRKISLFSCLKDRHDFGFPQEEFGNQFQKAETIPVLHEMIQ<br>QIFNLFSTKDSSAAWDETLLDKFYTELYQQLNDLEACVIQGVGV<br>TETPLMKEDSILAVRKYFQRITLYLKEKKYSPCAWEVVRAEIMR<br>SFSLSTNLQESLRSKE |
| Anti-CD40_LC-<br>derivative--HL--<br>IFNα2A<br>(SEQ ID NO 63) | DIQMTQSPSSVSASVGDRVTITCRASQGIYSWLAWYQQKPGKAP<br>NLLIYTASTLQSGVPSRFSGSGSGTDFTLTISSLQPEDFATYYCQQ<br>ANIFPLTFGGGTKVEIKRTVAAPSVFIFPPSDEQLKSGTASVVCLL<br>NNFYPREAKVQWKVDNALQSGNSQESVTEQDSKDSTYSLSSTLT<br>LSKADYEKHKVYACEVTHQGLSSPVTKSFNRGEKSLSLSPGAEA<br>AAKEAAAKACDLPQTHSLGSRRTLMLLAQMRKISLFSCLKDRH<br>DFGFPQEEFGNQFQKAETIPVLHEMIQQIFNLFSTKDSSAAWDET<br>LLDKFYTELYQQLNDLEACVIQGVGVTETPLMKEDSILAVRKYF<br>QRITLYLKEKKYSPCAWEVVRAEIMRSFSLSTNLQESLRSKE |
| Anti-CD40_LC--<br>(G4S)4--IFNγ<br>(SEQ ID NO 64) | DIQMTQSPSSVSASVGDRVTITCRASQGIYSWLAWYQQKPGKAP<br>NLLIYTASTLQSGVPSRFSGSGSGTDFTLTISSLQPEDFATYYCQQ<br>ANIFPLTFGGGTKVEIKRTVAAPSVFIFPPSDEQLKSGTASVVCLL |

TABLE 7-continued

Sequences of exemplary interferon-associated Anti-gen binding protein and components thereof based on the Anti-CD40 antibody CP870,893. Italic sequences correspond to signal peptides. Bold italic sequences in SEQ ID NOs 3 and 6 correspond to CDR regions. Bold non-italic sequences correspond to linkers. Mutated amino acids are underlined.

| Name/SEQ ID Number | Sequence |
| --- | --- |
|  | NNFYPREAKVQWKVDNALQSGNSQESVTEQDSKDSTYSLSSTLT<br>LSKADYEKHKVYACEVTHQGLSSPVTKSFNRGECGGGGSGGG<br>GSGGGGSGGGGSQDPYVKEAENLKKYFNAGHSDVADNGTLFL<br>GILKNWKEESDRKIMQSQIVSFYFKLFKNFKDDQSIQKSVETIKE<br>DMNVKFFNSNKKKRDDFEKLTNYSVTDLNVQRKAIHELIQVMA<br>ELSPAAKTGKRKRSQMLFRGRRASQ |
| Anti-CD40_hIgG2<br>dK_HC--(G4S)4--<br>IFNγ<br>(SEQ ID NO 65) | QVQLVQSGAEVKKPGASVKVSCKASGYTFTGYYMHWVRQAPG<br>QGLEWMGWINPDSGGTNYAQKFQGRVTMTRDTSISTAYMELN<br>RLRSDDTAVYYCARDQPLGYCTNGVCSYFDYWGQGTLVTVSSA<br>STKGPSVFPLAPCSRSTSESTAALGCLVKDYFPEPVTVSWNSGAL<br>TSGVHTFPAVLQSSGLYSLSSVVTVPSSNFGTQTYTCNVDHKPSN<br>TKVDKTVERKCCVECPPCPAPPVAGPSVFLFPPKPKDTLMISRTP<br>EVTCVVVDVSHEDPEVQFNWYVDGVEVHNAKTKPREEQFNSTF<br>RVVSVLTVVHQDWLNGKEYKCKVSNKGLPAPIEKTISKTKGQPR<br>EPQVYTLPPSREEMTKNQVSLTCLVKGFYPSDIAVEWESNGQPE<br>NNYKTTPPMLDSDGSFFLYSKLTVDKSRWQQGNVFSCSVMHEA<br>LHNHYTQKSLSLSPGGGGGSGGGGSGGGGSGGGGSQDPYVKE<br>AENLKKYFNAGHSDVADNGTLFLGILKNWKEESDRKIMQSQIVS<br>FYFKLFKNFKDDQSIQKSVETIKEDMNVKFFNSNKKKRDDFEKL<br>TNYSVTDLNVQRKAIHELIQVMAELSPAAKTGKRKRSQMLFRG<br>RRASQ |
| Anti-CD40_LC--<br>(G4S)4--IFNλ2<br>(SEQ ID NO 66) | DIQMTQSPSSVSASVGDRVTITCRASQGIYSWLAWYQQKPGKAP<br>NLLIYTASTLQSGVPSRFSGSGSGTDFTLTISSLQPEDFATYYCQQ<br>ANIFPPLTFGGGTKVEIKRTVAAPSVFIFPPSDEQLKSGTASVVCLL<br>NNFYPREAKVQWKVDNALQSGNSQESVTEQDSKDSTYSLSSTLT<br>LSKADYEKHKVYACEVTHQGLSSPVTKSFNRGECGGGGSGGG<br>GSGGGGSGGGGSVPVARLHGALPDARGCHIAQFKSLSPQELQA<br>FKRAKDALEESLLLKDCRCHSRLFPRTWDLRQLQVRERPMALE<br>AELALTLKVLEATADTDPALVDVLDQPLHTLHHILSQFRACIQPQ<br>PTAGPRTRGRLHHWLYRLQEAPKKESPGCLEASVTFNLFRLLTR<br>DLNCVASGDLCV |
| Anti-CD40_hIgG2<br>dK_HC--(G4S)4--<br>IFNλ2<br>(SEQ ID NO 67) | QVQLVQSGAEVKKPGASVKVSCKASGYTFTGYYMHWVRQAPG<br>QGLEWMGWINPDSGGTNYAQKFQGRVTMTRDTSISTAYMELN<br>RLRSDDTAVYYCARDQPLGYCTNGVCSYFDYWGQGTLVTVSSA<br>STKGPSVFPLAPCSRSTSESTAALGCLVKDYFPEPVTVSWNSGAL<br>TSGVHTFPAVLQSSGLYSLSSVVTVPSSNFGTQTYTCNVDHKPSN<br>TKVDKTVERKCCVECPPCPAPPVAGPSVFLFPPKPKDTLMISRTP<br>EVTCVVVDVSHEDPEVQFNWYVDGVEVHNAKTKPREEQFNSTF<br>RVVSVLTVVHQDWLNGKEYKCKVSNKGLPAPIEKTISKTKGQPR<br>EPQVYTLPPSREEMTKNQVSLTCLVKGFYPSDIAVEWESNGQPE<br>NNYKTTPPMLDSDGSFFLYSKLTVDKSRWQQGNVFSCSVMHEA<br>LHNHYTQKSLSLSPGGGGGSGGGGSGGGGSGGGGSVPVARLH<br>GALPDARGCHIAQFKSLSPQELQAFKRAKDALEESLLLKDCRCH<br>SRLFPRTWDLRQLQVRERPMALEAELALTLKVLEATADTDPALV<br>DVLDQPLHTLHHILSQFRACIQPQPTAGPRTRGRLHHWLYRLQE<br>APKKESPGCLEASVTFNLFRLLTRDLNCVASGDLCV |
| Anti-CD40_LC--<br>(G4S)4--IFNω<br>(SEQ ID NO 68) | DIQMTQSPSSVSASVGDRVTITCRASQGIYSWLAWYQQKPGKAP<br>NLLIYTASTLQSGVPSRFSGSGSGTDFTLTISSLQPEDFATYYCQQ<br>ANIFPPLTFGGGTKVEIKRTVAAPSVFIFPPSDEQLKSGTASVVCLL<br>NNFYPREAKVQWKVDNALQSGNSQESVTEQDSKDSTYSLSSTLT<br>LSKADYEKHKVYACEVTHQGLSSPVTKSFNRGECGGGGSGGG<br>GSGGGGSGGGGSLGCDLPQNHGLLSRNTLVLLHQMRRISPFLC<br>LKDRRDFRFPQEMVKGSQLQKAHVMSVLHEMLQQIFSLFHTERS<br>SAAWNMTLLDQLHTGLHQQLQHLETCLLQVVGEGESAGAISSP<br>ALTLRRYFQGIRVYLKEKKYSDCAWEVVRMEIMKSLFLSTNMQ<br>ERLRSKDRDLGSS |
| Anti-CD40_hIgG2<br>dK_HC--(G4S)4--<br>IFNε<br>(SEQ ID NO 69) | QVQLVQSGAEVKKPGASVKVSCKASGYTFTGYYMHWVRQAPG<br>QGLEWMGWINPDSGGTNYAQKFQGRVTMTRDTSISTAYMELN<br>RLRSDDTAVYYCARDQPLGYCTNGVCSYFDYWGQGTLVTVSSA<br>STKGPSVFPLAPCSRSTSESTAALGCLVKDYFPEPVTVSWNSGAL<br>TSGVHTFPAVLQSSGLYSLSSVVTVPSSNFGTQTYTCNVDHKPSN<br>TKVDKTVERKCCVECPPCPAPPVAGPSVFLFPPKPKDTLMISRTP<br>EVTCVVVDVSHEDPEVQFNWYVDGVEVHNAKTKPREEQFNSTF<br>RVVSVLTVVHQDWLNGKEYKCKVSNKGLPAPIEKTISKTKGQPR<br>EPQVYTLPPSREEMTKNQVSLTCLVKGFYPSDIAVEWESNGQPE<br>NNYKTTPPMLDSDGSFFLYSKLTVDKSRWQQGNVFSCSVMHEA<br>LHNHYTQKSLSLSPGGGGGSGGGGSGGGGSGGGGSLDLKLIIF |

TABLE 7-continued

Sequences of exemplary interferon-associated Anti-gen binding protein and components thereof based on the Anti-CD40 antibody CP870,893. Italic sequences correspond to signal peptides. Bold italic sequences in SEQ ID NOs 3 and 6 correspond to CDR regions. Bold non-italic sequences correspond to linkers. Mutated amino acids are underlined.

| Name/SEQ ID Number | Sequence |
|---|---|
|  | QQRQVNQESLKLLNKLQTLSIQQCLPHRKNFLLPQKSLSPQQYQ KGHTLAILHEMLQQIFSLFRANISLDGWEENHTEKFLIQLHQQLE YLEALMGLEAEKLSGTLGSDNLRLQVKMYFRRIHDYLENQDYS TCAWAIVQVEISRCLFFVFSLTEKLSKQGRPLNDMKQELTTEFRSPR |

In preferred embodiments, the interferon-associated antigen binding proteins described herein are interferon-fused antigen binding proteins comprising polypeptides derived from those specified in Table 8, in particular Table 8A or Table 8B, more particularly Table 8A below, and especially from the polypeptides of SEQ ID NO 38, SEQ ID NO 39, SEQ ID NO 40, SEQ ID NO 41, SEQ ID NO 42 or SEQ ID NO 43 above. In preferred embodiments, the interferon-associated antigen binding proteins described herein are interferon-fused antigen binding proteins consisting of polypeptides derived from those specified in Table 8, in particular Table 8A or Table 8B, more particularly Table 8A below, and especially from the polypeptides of SEQ ID NO 38, SEQ ID NO 39, SEQ ID NO 40, SEQ ID NO 41, SEQ ID NO 42 or SEQ ID NO 43 above. In more preferred embodiments, the interferon-fused antibody comprises the sequences as set forth in SEQ ID NO 38 and SEQ ID NO 3. In other more preferred embodiments, the interferon-fused antibody comprises the sequences as set forth in SEQ ID NO 39 and SEQ ID NO 3. In other more preferred embodiments, the interferon-fused antibody comprises the sequences as set forth in SEQ ID NO 40 and SEQ ID NO 3. In other more preferred embodiments, the interferon-fused antibody comprises the sequences as set forth in SEQ ID NO 41 and SEQ ID NO 9. In other more preferred embodiments, the interferon-fused antibody comprises the sequences as set forth in SEQ ID NO 42 and SEQ ID NO 9. In other more preferred embodiments, the interferon-fused antibody comprises the sequences as set forth in SEQ ID NO 43 and SEQ ID NO 9.

TABLE 8

Polypeptide combinations found in preferred interferon-fused antigen binding proteins of the invention, their mean $EC_{50}$ values with regard to the activation of CD40 and IFN-pathways and their productivity (i.e., yield per liter culture). Each sequence combination as indicated is comprised twice in the respective IFA.

A

| Interferon-fused Antibody (IFA) | Sequence combination | CD40 $EC_{50}$ (ng/mL) | IFNβ $EC_{50}$ (ng/mL) | IFNα $EC_{50}$ (ng/ml) | productivity (mg/L) |
|---|---|---|---|---|---|
| IFA1 | (SEQ ID NO 28) + (SEQ ID NO 9) | 74.1 | 1.64 |  | 16.7 |
| IFA2 | (SEQ ID NO 29) + (SEQ ID NO 9) | 111 | 0.14 |  | 17.8 |
| IFA8 | (SEQ ID NO 30) + (SEQ ID NO 3) | 39.7 | 2.9 |  | 6.45 |
| IFA9 | (SEQ ID NO 31) + (SEQ ID NO 3) | 42.6 | 0.7 |  | 3.4 |
| IFA10 | (SEQ ID NO 32) + (SEQ ID NO 3) | 26.5 | 4.5 |  | 6.9 |
| IFA11 | (SEQ ID NO 33) + (SEQ ID NO 3) | 42.8 | 1.78 |  | 5.1 |
| IFA12 | (SEQ ID NO 34) + (SEQ ID NO 9) | 105 | 3.64 |  | 21.2 |
| IFA13 | (SEQ ID NO 35) + (SEQ ID NO 9) | 192 | 0.7 |  | 11.5 |
| IFA19 | (SEQ ID NO 36) + (SEQ ID NO 9) | 110 | 1.3 |  | 5.6 |
| IFA20 | (SEQ ID NO 37) + (SEQ ID NO 9) | 182 | 2.34 |  | 4.2 |
| IFA25 | (SEQ ID NO 38) + (SEQ ID NO 3) | 13.3 |  | 5.1 | 21 |
| IFA26 | (SEQ ID NO 39) + (SEQ ID NO 3) | 15.35 |  | 4 | 8.6 |
| IFA27 | (SEQ ID NO 40) + (SEQ ID NO 3) | 17 |  | 2.4 | 9.3 |
| IFA28 | (SEQ ID NO 41) + (SEQ ID NO 9) | 12.8 |  | 4.5 | 75 |
| IFA29 | (SEQ ID NO 42) + (SEQ ID NO 9) | 11.1 |  | 2 | 56.6 |
| IFA30 | (SEQ ID NO 43) + (SEQ ID NO 9) | 11.3 |  | 1.6 | 46.6 |

TABLE 8-continued

Polypeptide combinations found in preferred interferon-fused antigen binding proteins of the invention, their mean EC$_{50}$ values with regard to the activation of CD40 and IFN-pathways and their productivity (i.e., yield per liter culture). Each sequence combination as indicated is comprised twice in the respective IFA.

A

| Interferon-fused Antibody (IFA) | Sequence combination | CD40 EC$_{50}$ (ng/mL) | IFNβ EC$_{50}$ (ng/mL) | IFNα EC$_{50}$ (ng/ml) | productivity (mg/L) |
|---|---|---|---|---|---|
| IFA34 | (SEQ ID NO 44) + (SEQ ID NO 49) | active (SN) | active (SN) | | no significant production |
| IFA35 | (SEQ ID NO 45) + (SEQ ID NO 49) | active (SN) | active (SN) | | no significant production |
| IFA36 | (SEQ ID NO 46) + (SEQ ID NO 3) | active (SN) | active (SN) | | no significant production |
| IFA37 | (SEQ ID NO 47) + (SEQ ID NO 3) | active (SN) | active (SN) | | no significant production |

SN: supernatant.

B

| Interferon-fused Antibody (IFA) | Sequence combination | CD40 EC$_{50}$ (ng/mL) | IFNα EC$_{50}$ (ng/mL) | IFNλ EC$_{50}$ (ng/mL) | IFNγ EC$_{50}$ (ng/mL) | IFNε EC$_{50}$ (ng/mL) | IFNω EC$_{50}$ (ng/mL) | productivity (mg/L) |
|---|---|---|---|---|---|---|---|---|
| IFA38 | (SEQ ID NO 62) + (SEQ ID NO 3) | 22.7 | 3.77 | | | | | 1.32 |
| IFA39 | (SEQ ID NO 63) + (SEQ ID NO 9) | 17.5 | 2.95 | | | | | 1.25 |
| IFA42 | (SEQ ID NO 64) + (SEQ ID NO 9) | 65.6 | | | 15.4 | | | 0.72 |
| IFA43 | (SEQ ID NO 65) + (SEQ ID NO 3) | 50.8 | | | <0.001 | | | 0.55 |
| IFA44 | (SEQ ID NO 66) + (SEQ ID NO 9) | 41.4 | | 0.153 | | | | 0.91 |
| IFA45 | (SEQ ID NO 67) + (SEQ ID NO 3) | 25.8 | | <0.001 | | | | 1.09 |
| IFA46 | (SEQ ID NO 68) + (SEQ ID NO 9) | 86.3 | | | | | 0.493 | 0.89 |
| IFA49 | (SEQ ID NO 69) + (SEQ ID NO 3) | 65.8 | | | | 78.2 | | 0.61 |
| IFA50 | (SEQ ID NO 41) + (SEQ ID NO 50) | 128 | 1.36 | | | | | 0.57 |
| IFA51 | (SEQ ID NO 42) + (SEQ ID NO 50) | 123 | 1.43 | | | | | 0.48 |

Nucleic Acids and Expression Vectors

In one aspect, a combination of polynucleotides encoding an interferon-associated antigen binding protein is provided. Methods of making an interferon-associated antigen binding protein comprising expressing these polynucleotides are also provided.

In some embodiments, a nucleic acid encoding an IFN or a functional fragment thereof being fused to an agonistic anti-CD40 antibody or an agonistic antigen binding fragment thereof, as disclosed herein is provided. In certain exemplary embodiments, the nucleic acid is encoding an IFN or a functional fragment thereof fused to an agonistic anti-CD40 antibody or an agonistic antigen binding fragment thereof according to any of the sequences set forth in SEQ ID NOs 62 to 69, or a nucleic acid sequence at least 80%, at least 85%, at least 90%, at least 95%, at least 98% or at least 99% identical to a nucleic acid encoding any of these sequences. In certain exemplary embodiments, said nucleic acid is at least 95%, at least 98% or at least 99% identical to a nucleic acid encoding any of SEQ ID NOs 62 to 69. In preferred embodiments, the nucleic acid is encoding an IFN or a functional fragment thereof fused to an agonistic anti-CD40 antibody or an agonistic antigen binding fragment thereof according to any of the sequences set forth in SEQ ID NOs 28 to 47, or a nucleic acid sequence at least 80%, at least 85%, at least 90%, at least 95%, at least 98% or at least 99% identical to a nucleic acid encoding any of these sequences. In even more specific embodiments, said nucleic acid is at least 95%, at least 98% or at least 99% identical to a nucleic acid encoding any of SEQ ID NOs 28 to 47.

In those embodiments wherein a nucleic acid encodes an IFN or a functional fragment thereof being fused to a light chain of the agonistic anti-CD40 antibody or the agonistic antigen binding fragment thereof, the nucleic acid may further encode a heavy chain of the agonistic anti-CD40 antibody or the agonistic antigen binding fragment thereof. In more specific embodiments, the heavy chain of the agonistic anti-CD40 antibody or the agonistic antigen binding fragment thereof comprises a sequence as set forth in SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 48, SEQ ID NO 49, or SEQ ID NO 50, or a nucleic acid sequence at least 80%, at least 85%, at least 90%, at least 95%, at least 98% or at least 99% identical to a nucleic acid encoding any of these sequences. In even more specific embodiments, said nucleic acid is at least 95%, at least 98% or at least 99% identical to a nucleic acid encoding SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 48, SEQ ID NO 49, or SEQ ID NO 50.

In those embodiments where a nucleic acid encodes an IFN or a functional fragment thereof being fused to the heavy chain of the agonistic anti-CD40 antibody or the agonistic antigen binding fragment thereof, the nucleic acid may further encode a light chain of the agonistic anti-CD40 antibody or the agonistic antigen binding fragment thereof. In more specific embodiments, the light chain of the agonistic anti-CD40 antibody or the agonistic antigen binding fragment thereof comprises a sequence as set forth in SEQ ID NO 3, SEQ ID NO 4 or SEQ ID NO 5, or a nucleic acid sequence at least 80%, at least 85%, at least 90%, at least 95%, at least 98% or at least 99% identical to a nucleic acid encoding any of these sequences. In even more specific embodiments, said nucleic acid is at least 95%, at least 98% or at least 99% identical to a nucleic acid encoding SEQ ID NO 3, SEQ ID NO 4 or SEQ ID NO 5.

In certain embodiments, the nucleic acids described herein may comprise a sequence encoding a sequence to increase the yield (e.g. a solubility tag) or facilitate purification of the expressed proteins (i.e., a purification tag). Purification tags are known to a person skilled in the art and may be selected from glutathione S-transferase (GST) tags, maltose binding protein (MBP) tags, calmodulin binding peptide (CBP) tags, intein-chitin binding domain (intein-CBD) tags, Streptavidin/Biotin-based tags (such as biotinylation signal peptide (BCCP) tags, Streptavidin-binding peptide (SBP) tags, His-patch ThioFusion tags, tandem affinity purification (TAP) tags, Small ubiquitin-like modifier (SUMO) tags, HaloTag® (Promega), Profinity eXact™ system (Bio-Rad). In some embodiments, the purification tag may be a polyhistidine tag (e.g., a $His_6$-, $His_7$-, $His_8$-, $His_9$- or $His_{10}$-tag). In other embodiments, the purification tag may be a Strep-tag (e.g., a Strep-Tag® or a Strep-tag II@; IBA Life Sciences). In yet other embodiments, the purification tag may be a maltose binding protein (MBP) tag.

In some embodiments, the nucleic acid sequence may further comprise a sequence encoding a cleavage site for removal of the purification tag. Such cleavage sequences are known to a person skilled in the art and may be selected from a sequence recognized and cleaved by an endoprotease or an exoprotease. In some embodiments, an endoprotease for the removal of a purification tag may be selected from: Enteropeptidase, Thrombin, Factor Xa, TEV protease or Rhinovirus 3C protease. In some embodiments, an exoprotease for the removal of a purification tag may be selected from: Carboxypeptidase A, Carboxypeptidase B or DAPase. In preferred embodiments, the protease for the removal of a purification tag is TEV protease. In a more specific preferred embodiment, the nucleic acid comprises a sequence encoding a $His_6$-tag and a TEV cleavage site. In an even more specific preferred embodiment, said nucleic acid comprises a sequence encoding a sequence as set forth in SEQ ID NO 27.

The nucleic acid molecules of the invention may also comprise a sequence encoding a signal peptide. The skilled person is aware of the various signal peptides available to direct the expressed protein to the desired site of folding, assembly and/or maturation as well as to effect secretion of the final protein into the medium to facilitate downstream processing. Thus, in some embodiments, the signal peptide is a secretory signal peptide. The encoded signal peptide may comprise a sequence as set forth in SEQ ID NO: 1 or SEQ ID NO: 2. In some embodiments, the signal peptide comprises the sequence as set forth in SEQ ID NO: 1. In other embodiments, the signal peptide comprises the sequence as set forth in SEQ ID NO: 2.

Signal peptide 1 (SEQ ID NO 1) was used for synthesis of the polypeptide sequences as set forth in SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID 36, SEQ ID NO 37, SEQ ID NO 44, SEQ ID NO 45, SEQ ID NO 46, SEQ ID NO 47 or SEQ ID NO 50. Such signal peptide that is initially present at the N-terminus of the respective sequence of the polypeptide is cleaved during synthesis.

Signal peptide 2 (SEQ ID NO 2) was used for synthesis of the polypeptide sequences as set forth in SEQ ID NO 38, SEQ ID NO 39, SEQ ID NO 40, SEQ ID NO 41, SEQ ID NO 42 and SEQ ID NO 43. Such signal peptide that is initially present at the N-terminus of the respective sequence of the polypeptide is cleaved during synthesis.

For the synthesis of the polypeptide sequences as set forth in SEQ ID NO 62, SEQ ID NO 63, SEQ ID NO 64, SEQ ID NO 65, SEQ ID NO 66, SEQ ID NO 67, SEQ ID 68 and SEQ ID NO 69 the signal peptide MGWSCIILFL-VATATGVHS (SEQ ID NO 1) was used. Such signal peptide that is initially present at the N-terminus of the respective sequence of the polypeptide is cleaved during synthesis.

Polynucleotides encoding an IFN or a functional fragment thereof being fused to the agonistic anti-CD40 antibody or the agonistic antigen binding fragment thereof as disclosed herein are typically inserted in an expression vector for introduction into host cells that may be used to produce the desired quantity of the claimed interferon-associated antigen binding proteins. Accordingly, in certain aspects, the invention provides expression vectors comprising polynucleotides disclosed herein and host cells comprising these vectors and polynucleotides.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the present invention will comprise a selection marker, appropriate restriction sites to facilitate cloning of the desired gene and the ability to enter and/or replicate in eukaryotic or prokaryotic cells.

Numerous expression vector systems may be employed for the purposes of this invention. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals. In some embodiments the cloned variable region genes, one of them fused with a gene encoding an IFN or a functional fragment thereof, are inserted into an expression vector along with the heavy and light chain constant region genes (such as human genes) synthesized as discussed above.

In other embodiments, a vector system of the invention may comprise more than one vector. In some embodiments, a vector system may comprise a first vector for the expression of an IFN or a functional fragment thereof fused to a light chain of the agonistic anti-CD40 antibody or the agonistic antigen binding fragment thereof and a second vector for expression of a heavy chain of the agonistic anti-CD40 antibody or the agonistic antigen binding fragment thereof. Alternatively, such a vector system may comprise a first vector for the expression of an IFN or a functional fragment thereof fused to a heavy chain of the agonistic anti-CD40 antibody or the agonistic antigen binding fragment thereof and a second vector for expression of a light chain of the agonistic anti-CD40 antibody or the agonistic antigen binding fragment thereof.

In other embodiments, an interferon-associated antigen binding protein as described herein may be expressed using polycistronic constructs. In such expression systems, multiple gene products of interest such as those encoding an IFN or a functional fragment thereof being fused to a heavy chain of an agonistic anti-CD40 antibody or the agonistic antigen binding fragment thereof and encoding a light chain of said antibody, or those encoding an IFN or a functional fragment thereof being fused to a light chain of an agonistic anti-CD40 antibody or an agonistic antigen binding fragment thereof and encoding a heavy chain of said antibody or an agonistic antigen binding fragment thereof may be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980, which is incorporated by reference herein. Those skilled in the art will appreciate that such expression systems may be used to effectively produce the full range of polypeptides disclosed in the instant application.

More generally, once a vector or a DNA sequence encoding an interferon-associated antigen binding protein of the present invention has been prepared, the expression vector may be introduced into an appropriate host cell. That is, the host cell may be transformed. Introduction of a plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, e.g., Ridgway, A. A. G. "Mammalian Expression Vectors" Chapter 24.2, pp. 470-472 Vectors, Rodriguez and Denhardt, Eds. (Butterworths, Boston, MA 1988). The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refer to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of the interferon-associated antigen binding protein unless it is clearly specified otherwise. In other words, recovery of polypeptide from the "cells" may mean either from spun down whole cells, or from the cell culture containing both the medium and the suspended cells.

In one embodiment, the host cell line used for expression of an interferon-associated antigen binding protein is of eukaryotic or prokaryotic origin. As used herein, the term "expression" may include the transcription and translation of more than one polypeptide chain (such as a heavy and a light chain of the antibody moiety of an interferon-associated antigen binding protein), which associate to form the final interferon-associated antigen binding protein. In one embodiment, the host cell line used for expression of an interferon-associated antigen binding protein is of bacterial origin. In one embodiment, the host cell line used for expression of an interferon-associated antigen binding protein is of mammalian origin; those skilled in the art can determine particular host cell lines which are best suited for the desired gene product to be expressed therein. Exemplary host cell lines include, but are not limited to, CHO K1 GS knockout from Horizon, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), BFA-1c1BPT (bovine endothelial cells), RAJI (human lymphocyte), HEK 293 (human kidney). In a preferred embodiment, HEK FS S11/254 cells may be used. In another preferred embodiment, CHO K1 GS from Horizon may be used. In one embodiment, the cell line provides for altered glycosylation, e.g., afucosylation, of the antibody expressed therefrom (e.g., PER.C6® (Crucell) or FUT8-knock-out CHO cell lines (POTELLIGENT™ cells) (Biowa, Princeton, NJ)). In one embodiment NSO cells may be used. Host cell lines are typically available from commercial services, the American Tissue Culture Collection or from published literature.

In one embodiment, the host used for expression of an interferon-associated antigen binding protein is a non-human transgenic animal or transgenic plant.

Interferon-associated antigen binding proteins of the invention can also be produced transgenically through the generation of a non-human animal (e.g., mammal) or plant that is transgenic for the sequences of interest and production of the interferon-associated antigen binding protein in a recoverable form therefrom. In connection with the transgenic production in mammals, interferon-associated antigen binding proteins can be produced in, and recovered from, the milk of goats, cows, or other mammals. See, e.g., U.S. Pat. Nos. 5,827,690, 5,756,687, 5,750,172, and 5,741,957. Exemplary plant hosts are Nicotiana, Arabidopsis, duckweed, corn, wheat, potato, etc. Methods for expressing antibodies in plants, including a description of promoters and vectors, as well as transformation of plants is known in the art. See, e.g., U.S. Pat. No. 6,517,529, herein incorporated by reference. In some embodiments, non-human transgenic animals or plants are produced by introducing one or more nucleic acid molecules encoding an interferon-associated antigen binding protein of the invention into the animal or plant by standard transgenic techniques. See Hogan and U.S. Pat. No. 6,417,429. The transgenic cells used for making the transgenic animal can be embryonic stem cells or somatic cells. The transgenic non-human organisms can be chimeric, nonchimeric heterozygotes, and nonchimeric homozygotes. See, e.g., Hogan et al., Manipulating the Mouse Embryo: A Laboratory Manual 2nd ed., Cold Spring Harbor Press (1999); Jackson et al., Mouse Genetics and Transgenics: A Practical Approach, Oxford University Press (2000); and Pinkert, Transgenic Animal Technology: A Laboratory Handbook, Academic Press (1999). In some embodiments, the transgenic non-human animals have a targeted disruption and replacement by a targeting construct that encodes the sequence(s) of interest. The interferon-associated antigen binding proteins may be made in any transgenic animal. In a preferred embodiment, the non-human animals are mice, rats, sheep, pigs, goats, cattle or horses. The non-human transgenic animal expresses said interferon-associated antigen binding proteins in blood, milk, urine, saliva, tears, mucus and other bodily fluids.

In vitro production allows scale-up to give large amounts of the desired interferon-associated antigen binding proteins. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges. If necessary and/or desired, a solution of an interferon-associated antigen binding protein, can be purified by the customary chromatography methods, for example gel filtration, ion-exchange chromatography, chromatography over DEAE-cellulose and/or (immuno-) affinity chromatography.

One or more genes encoding an interferon-associated antigen binding protein can also be expressed in non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, interferon-associated antigen binding proteins according to the invention or components thereof (i.e., agonistic anti-CD40 antibodies or agonistic antigen binding fragments thereof, and IFNs or functional fragments of IFNs) can become part of inclusion bodies. The desired interferon-associated antigen binding proteins may then need to be isolated, optionally also refolded, and purified.

In addition to prokaryotes, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene, which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan.

Therapeutic Vectors

A nucleic acid sequence encoding an interferon-associated antigen binding protein can be inserted into a vector and used as a therapeutic vector, e.g., a vector that expresses an interferon-associated antigen binding protein of the invention. The construction of suitable, functional expression constructs and therapeutic expression vectors is known to one of ordinary skill in the art. Thus, in certain embodiments, the interferon-associated antigen binding protein may be administered to a subject by means of genetic delivery with RNA or DNA sequences, a vector or vector system encoding the interferon-associated antigen binding protein.

Therapeutic vectors can be delivered to a subject by, for example, intravenous injection, local administration (see U.S. Pat. No. 5,328,470) or by stereotactic injection (see, e.g., Chen et al., PNAS 91:3054-3057 (1994)). The pharmaceutical preparation of a therapeutic vector can include the vector in an acceptable diluent.

An interferon-associated antigen binding protein encoding nucleic acid, or nucleic acids, can be incorporated into a gene construct to be used as a part of a therapy protocol to deliver nucleic acids encoding an interferon-associated antigen binding protein. Expression vectors for in vivo transfection and expression of an interferon-associated antigen binding protein are provided.

Expression constructs of such components may be administered in any biologically effective carrier, e.g., any formulation or composition capable of effectively delivering the component nucleic acid sequence to cells in vivo, as are known to one of ordinary skill in the art. Approaches include, but are not limited to, insertion of the subject nucleic acid sequence(s) in viral vectors including, but not limited to, recombinant retroviruses, adenovirus, adeno-associated virus and herpes simplex virus-1, recombinant bacterial or eukaryotic plasmids and the like.

Retrovirus vectors and adeno-associated viral vectors can be used as a recombinant delivery system for the transfer of exogenous nucleic acid sequences in vivo, particularly into humans. Such vectors provide efficient delivery of genes into cells, and the transferred nucleic acids can be stably integrated into the chromosomal DNA of the host.

The development of specialized cell lines (termed "packaging cells") which produce only replication-defective retroviruses has increased the utility of retroviruses for gene therapy, and defective retroviruses are characterized for use in gene transfer for gene therapy purposes (for a review see, e.g., Miller, Blood 76:271-78 (1990)). A replication-defective retrovirus can be packaged into virions, which can be used to infect a target cell through the use of a helper virus by standard techniques. Protocols for producing recombinant retroviruses and for infecting cells in vitro or in vivo with such viruses can be found in Current Protocols in Molecular Biology, Ausubel, et al., (eds.) Greene Publishing Associates, (1989), Sections 9.10-9.14, and other standard laboratory manuals. Non-limiting examples of suitable retroviruses include pLJ, pZIP, pWE and pEM, which are known to those of ordinary skill in the art. Examples of suitable packaging virus lines include *Crip, *Cre, *2 and *Am. (See, for example, Eglitis, et al., Science 230:1395-1398 (1985); Danos and Mulligan, Proc. Natl. Acad. Sci. USA 85:6460-6464 (1988); Wilson, et al., Proc. Natl. Acad. Sci. USA 85:3014-3018 (1988); Armentano, et al., Proc. Natl. Acad. Sci. USA 87:6141-6145 (1990); Huber, et al., Proc. Natl. Acad. Sci. USA 88:8039-8043 (1991); Ferry, et al., Proc. Natl. Acad. Sci. USA 88:8377-8381 (1991); Chowdhury, et al., Science 254:1802-1805 (1991); van Beusechem, et al., Proc. Natl. Acad. Sci. USA 89:7640-7644 (1992); Kay, et al., Human Gene Therapy 3:641-647 (1992);

Dai, et al., Proc. Natl. Acad. Sci. USA 89:10892-10895 (1992); Hwu, et al., J. Immunol. 150:4104-4115 (1993); U.S. Pat. Nos. 4,868,116; 4,980,286; PCT Application WO 89/07136; PCT Application WO 89/02468; PCT Application WO 89/05345; and PCT Application WO 92/07573).

In another embodiment, adenovirus-derived delivery vectors are provided. The genome of an adenovirus can be manipulated such that it encodes and expresses a gene product of interest but is inactivated in terms of its ability to replicate in a normal lytic viral life cycle. See, for example, Berkner, et al., BioTechniques 6:616 (1988); Rosenfeld, et al., Science 252:431-434 (1991); and Rosenfeld, et al., Cell 68:143-155 (1992). Suitable adenoviral vectors derived from the adenovirus strain Ad type 5 d1324 or other strains of adenovirus (e.g., Ad2, Ad3, Ad7 etc.) are known to those of ordinary skill in the art. Recombinant adenoviruses can be advantageous in certain circumstances in that they are not capable of infecting non-dividing cells and can be used to infect a wide variety of cell types, including epithelial cells (Rosenfeld, et al. (1992), supra). Furthermore, the virus particle is relatively stable and amenable to purification and concentration and, as above, can be modified so as to affect the spectrum of infectivity. Additionally, introduced adenoviral DNA (and foreign DNA contained therein) is not integrated into the genome of a host cell, but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other delivery vectors (Berkner, et al. (1998), supra; Haj-Ahmand and Graham, J. Virol. 57:267 (1986)).

Yet another viral vector system useful for delivery of a nucleic acid sequence encoding an interferon-associated antigen binding protein, is the adeno-associated virus (AAV). AAV is a naturally occurring defective virus that requires another virus, such as an adenovirus or a herpes virus, as a helper virus for efficient replication and a productive life cycle. (For a review see Muzyczka, et al., Curr. Topics in Micro. and Immunol. 158:97-129 (1992)). It is also one of the few viruses that may integrate its DNA into non-dividing cells, and exhibits a high frequency of stable integration (see for example Flotte, et al., Am. J. Respir. Cell. Mol. Biol. 7:349-356 (1992); Samulski, et al., J. Virol. 63:3822-3828 (1989); and McLaughlin, et al., J. Virol. 62:1963-1973 (1989)). Vectors containing as little as 300 base pairs of AAV can be packaged and can integrate. Space for exogenous DNA is limited to about 4.5 kb. An AAV vector such as that described in Tratschin, et al., Mol. Cell. Biol. 5:3251-3260 (1985) can be used to introduce DNA into cells. A variety of nucleic acids have been introduced into different cell types using AAV vectors (see for example Hermonat, et al., Proc. Natl. Acad. Sci. USA 81:6466-6470 (1984); Tratschin, et al., Mol. Cell. Biol. 4:2072-2081 (1985); Wondisford, et al., Mol. Endocrinol. 2:32-39 (1988); Tratschin, et al., J. Virol. 51:611-619 (1984); and Flotte, et al., J. Biol. Chem. 268:3781-3790 (1993)).

In addition to viral transfer methods, non-viral methods can also be employed to cause expression of a nucleic acid sequence encoding an interferon-associated antigen binding protein in the tissue of a subject. Most non-viral methods of gene transfer rely on normal mechanisms used by mammalian cells for the uptake and intracellular transport of macromolecules. In some embodiments, non-viral delivery systems rely on endocytic pathways for the uptake of the subject gene by the targeted cell. Exemplary delivery systems of this type include liposomal derived systems, poly-lysine conjugates, and artificial viral envelopes. Other embodiments include plasmid injection systems such as are described in Meuli, et al., J. Invest. Dermatol. 116 (1):131-135 (2001); Cohen, et al., Gene Ther 7 (22):1896-905 (2000); or Tam, et al., Gene Ther. 7 (21):1867-74 (2000).

In clinical settings, the delivery systems can be introduced into a subject by any of a number of methods, each of which is familiar in the art. For instance, a pharmaceutical preparation of the delivery system can be introduced systemically, e.g., by intravenous injection. Specific transduction of the protein in the target cells occurs predominantly from specificity of transfection provided by the delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the delivery vehicle can be introduced by catheter (see, U.S. Pat. No. 5,328,470) or by stereotactic injection (e.g., Chen, et al., PNAS 91: 3054-3057 (1994)).

The pharmaceutical preparation of the therapeutic construct can consist essentially of the delivery system in an acceptable diluent, or can comprise a slow release matrix in which the delivery vehicle is imbedded. Alternatively, where the complete delivery system can be produced intact from recombinant cells, e.g., retroviral vectors, the pharmaceutical preparation can comprise one or more cells, which produce the delivery system.

Methods of Treatment

In one aspect, the invention provides methods of treating a patient in need thereof (e.g., a patient infected with HBV) comprising administering an effective amount of an interferon-associated antigen binding protein, or a nucleic acid sequence (e.g., mRNA) that encodes an interferon-associated antigen binding protein, as disclosed herein. The invention also provides for a use of an interferon-associated antigen binding protein, or a nucleic acid sequence (e.g., mRNA) that encodes an interferon-associated antigen binding protein, as disclosed herein, in the preparation of a medicament. More specifically, the invention provides for a use of an interferon-associated antigen binding protein, or a nucleic acid sequence (e.g., mRNA) that encodes an interferon-associated antigen binding protein, as disclosed herein, in the preparation of a medicament for the treatment of disorders and/or symptoms, e.g., HBV-related disorders and/or HBV-related symptoms. In certain embodiments, the present invention provides kits and methods for the treatment of disorders and/or symptoms, e.g., HBV-related disorders and/or HBV-related symptoms, in a mammalian subject in need of such treatment. In certain exemplary embodiments, the subject is a human.

The interferon-associated antigen binding proteins, or nucleic acid sequences that encode them, of the present invention are useful in a number of different applications. For example, in one embodiment, the subject interferon-associated antigen binding proteins, or nucleic acid sequences that encode them, are useful for reducing HBeAg release from an HBV-infected cell. In some embodiments, the interferon-associated antigen binding proteins of the invention reduce HBeAg release by primary hepatocytes in vitro by at least 10% at 1 ng/mL, at least 20% at 1 ng/mL, at least 30% at 1 ng/mL, at least 40% at 1 ng/mL, at least 50% at 1 ng/mL, at least 60% at 1 ng/mL, at least 70% at 1 ng/mL, at least 80% at 1 ng/mL, or at least 85% at 1 ng/mL. In some embodiments, the interferon-associated antigen binding proteins of the invention reduce HBeAg release by primary hepatocytes in vitro by at least 12% at 1 ng/mL. In some embodiments, the interferon-associated antigen binding proteins of the invention reduce HBeAg release by primary hepatocytes in vitro by up to 90% at 1 ng/mL. In related embodiments, the interferon-associated antigen binding protein reduces HBeAg release with an $EC_{50}$ of less than 30 ng/mL, preferably with an $EC_{50}$ of less than 10 ng/mL, more preferably with an $EC_{50}$ of less than 1 ng/mL.

In another embodiment, the subject interferon-associated antigen binding proteins, or nucleic acid sequences that encode them, are useful for reducing pgRNA transcription of cccDNA in an HBV-infected cell.

In another embodiment, the subject interferon-associated antigen binding proteins, or nucleic acid sequences that encode them, are useful for reducing one or more symptoms and/or complications associated with HBV infection, as described herein (infra).

In certain embodiments, the subject interferon-associated antigen binding proteins, or nucleic acid sequences that encode them, are useful for reducing one or more disorders, symptoms and/or complications associated with chronic HBV infection, e.g., chronic inflammation of the liver (chronic hepatitis), leading to cirrhosis over a period of several years; hepatocellular carcinoma (HCC); development of membranous glomerulonephritis (MGN); risk of death; acute necrotizing vasculitis (polyarteritis nodosa), membranous glomerulonephritis, and papular acrodermatitis of childhood (Gianotti-Crosti syndrome); HBV-associated nephropathy (e.g., membranous glomerulonephritis); immune-mediated hematological disorders (e.g., essential mixed cryoglobulinemia, aplastic anemia); and the like.

In certain embodiments, the subject interferon-associated antigen binding proteins, or nucleic acid sequences that encode them, are useful for reducing one or more symptoms and/or complications associated with acute HBV infection, e.g., acute viral hepatitis (which begins with general ill-health, loss of appetite, nausea, vomiting, body aches, mild fever, and dark urine, and then progresses to development of jaundice, fulminant hepatic failure, and/or serum-sickness-like syndrome); loss of appetite; joint and muscle pain; low-grade fever; stomach pain; nausea; vomiting; jaundice; bloated stomach; and the like.

Accordingly, this invention also relates to a method of treating one or more disorders, symptoms and/or complications associated with HBV infection in a human or other animal by administering to such human or animal an effective, non-toxic amount of an interferon-associated antigen binding protein, or a nucleic acid sequence that encodes it. One skilled in the art would be able, by routine experimentation, to determine what an effective, non-toxic amount of an interferon-associated antigen binding protein, or a nucleic acid sequence that encodes it, would be for the purpose of treating HBV infection.

For example, a "therapeutically active amount" of an interferon-associated antigen binding protein of the present invention may vary according to factors such as the disease stage (e.g., acute vs. chronic), age, sex, medical complications (e.g., HIV co-infection, immunosuppressed conditions or diseases) and weight of the subject, and the ability of the interferon-associated antigen binding protein to elicit a desired response in the subject. The dosage regimen may be adjusted to provide the optimum therapeutic response. For example, several divided doses may be administered daily, or the dose may be proportionally reduced as indicated by the exigencies of the therapeutic situation.

In general, the compositions provided in the current invention may be used to prophylactically treat non-infected cells or therapeutically treat any HBV-infected cells comprising an antigenic marker that allows for the targeting of the HBV-infected cells by an interferon-associated antigen binding protein.

Pharmaceutical Compositions and Administration Thereof

In certain embodiments, the interferon-associated antigen binding proteins of the invention or nucleic acid sequences (including vectors or vector systems) that encode them are comprised in a pharmaceutical composition. Methods of preparing and administering interferon-associated antigen binding proteins, or nucleic acid sequences that encode them, of the current invention to a subject are well known to or can be readily determined by those skilled in the art using this specification and the knowledge in the art as a guide. The route of administration of the interferon-associated antigen binding proteins, or nucleic acid sequences that encode them, of the current invention may be oral, parenteral, by inhalation or topical. The term "parenteral", as used herein, includes intravenous, intraarterial, intraperitoneal, intramuscular, subcutaneous, rectal or vaginal administration. While all these forms of administration are clearly contemplated as being within the scope of the current invention, a form for administration would be a solution for injection, in particular for intravenous or intraarterial injection or drip. Usually, a suitable pharmaceutical composition for injection may comprise a buffering agent (e.g. acetate, phosphate or citrate buffer), a surfactant (e.g. polysorbate), optionally a stabilizing agent (e.g. human albumin), etc. In some embodiments, the buffering agent is acetate. In another embodiment, the buffering agent is formate. In yet another embodiment, the buffering agent is citrate. In related embodiments, the surfactant may be selected from the list comprising pluronics, PEG, sorbitan esters, polysorbates, triton, tromethamine, lecithin, cholesterol and tyloxapal. In preferred embodiments, the surfactant is polysorbate. In more preferred embodiments, the surfactant is polysorbate 20, polysorbate 40, polysorbate 60, polysorbate 80 or polysorbate 100, preferably polysorbate 20 or polysorbate 80.

In some embodiments, the interferon-associated antigen binding proteins, or nucleic acid sequences that encode them, can be delivered directly to the site of the adverse cellular population (e.g., the liver) thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the compositions and methods of the current invention, pharmaceutically acceptable carriers include, but are not limited to, 0.01-0.1 M, e.g., 0.05 M phosphate buffer, or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water-soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will typically be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, isotonic agents will be included, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound such as an interferon-associated antigen binding protein, or a nucleic acid sequence encoding said interferon-associated antigen binding protein, of the present invention by itself or in combination with other active agents in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, exemplary methods of preparation include vacuum drying and freeze-drying, which yields a powder of an active ingredient plus any additional desired ingredient from a previously sterile-filtered solution thereof. The preparations for injections are processed, filled into containers such as ampules, bags, bottles, syringes or vials, and sealed under aseptic conditions according to methods known in the art. Further, the preparations may be packaged and sold in the form of a kit. Such articles of manufacture will typically have labels or package inserts indicating that the associated compositions are useful for treating a subject suffering from HBV infection.

Effective doses of the compositions of the present invention, for the treatment of the above described HBV infection-related conditions vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals, in particular non-human primates, can also be treated. Treatment dosages may be titrated using routine methods known to those of skill in the art to optimize safety and efficacy.

For treatment with an interferon-associated antigen binding protein, the dosage can range, e.g., from about 0.0001 to about 100 mg/kg, and more usually about 0.01 to about 5 mg/kg (e.g., about 0.02 mg/kg, about 0.25 mg/kg, about 0.5 mg/kg, about 0.75 mg/kg, about 1 mg/kg, about 2 mg/kg, etc.), of the host body weight. For example, dosages can be about 1 mg/kg body weight or about 10 mg/kg body weight or within the range of about 1 to about 10 mg/kg, e.g., at least about 1 mg/kg. Doses intermediate in the above ranges are also intended to be within the scope of the current invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration about once per every two weeks or about once a month or about once every 3 to 6 months. Exemplary dosage schedules include about 1 to about 10 mg/kg or about 15 mg/kg on consecutive days, about 30 mg/kg on alternate days or about 60 mg/kg weekly.

Interferon-associated antigen binding proteins, or nucleic acid sequences expressing any of these, can be administered on multiple occasions. Intervals between single dosages can be weekly, monthly or yearly. Intervals can also be irregular as indicated by measuring blood levels of interferon-associated antigen binding proteins of components thereof in the patient. Alternatively, interferon-associated antigen binding proteins, or nucleic acid sequences expressing any of these can be administered as a sustained release formulation, in which case less frequent administration is required. Dosage and frequency vary depending on the half-life of the interferon-associated antigen binding proteins in the patient.

The term "half-life" or "$t_{1/2}$", as referred to herein, relates to the stability and/or the rate of excretion of a compound, such as the interferon-associated antigen binding proteins of the invention. In practice, the half-life of a compound is usually measured in the serum and denotes the time after administration that the serum concentration is 50% of the serum concentration at the time of administration. The interferon-associated antigen binding proteins of the invention are characterized by a long serum half-life in mice. In some embodiments, the half-life of the interferon-associated antigen binding protein is at least 50 h, at least 60 h, at least 70 h, at least 80 h, at least 90 h or at least 100 h. In some embodiments, the half-life of the interferon-associated antigen binding protein is at least 100 h. In preferred embodiments, the half-life of the interferon-associated antigen binding protein in mice ranges from 116 to 158 h.

The half-life of a protein is related to its clearance. The term "clearance" or "clearance rate", as used herein, refers to the volume of plasma cleared of the protein per unit time. Clearance of the interferon-associated antigen binding proteins of the invention is low. In some embodiments, clearance of the interferon-associated antigen binding protein is below 10 mL/h/kg, below 5 mL/h/kg, below 2.5 mL/h/kg, below 1 mL/h/kg, or below 0.5 mL/h/kg. In some embodiments, clearance of the interferon-associated antigen binding protein is below 5 mL/h/kg. In some embodiments, clearance of the interferon-associated antigen binding protein is below 1 mL/h/kg. In some embodiments, clearance of the interferon-associated antigen binding protein in mice ranges from 0.28 to 0.49 mL/h/kg.

The terms "volume of distribution", "$V_D$", "$V_{ss}$" or "apparent volume of distribution" as used herein refer to the theoretical volume that would be necessary to contain the total amount of an administered compound such as the interferon-associated antigen binding protein of the invention at the same concentration that it is observed in the blood plasma and relates to the distribution of said compound between plasma and the rest of the body after oral or parenteral dosing. In certain embodiments, the volume of distribution Vss of the interferon-associated antigen binding protein is below 500 mL/kg, below 400 mL/kg, below 300 mL/kg, below 200 mL/kg, or below 100 mL/kg. In some embodiments, the volume of distribution Vss of the interferon-associated antigen binding protein is below 100 mL/kg. In some embodiments, the volume of distribution Vss of the interferon-associated antigen binding protein in mice ranges from 50 to 98 mL/kg.

Another related pharmacokinetic parameter is the systemic exposure. As used herein, the terms "systemic exposure", "AUC" or "area under the curve" refer to the integral of the concentration-time curve. Systemic exposure might be represented by plasma (serum or blood) concentrations or the AUCs of parent compound and/or metabolite(s). The interferon-associated antigen binding proteins of the invention circulate in the blood with higher systemic exposure (AUC (0-inf)) than their parental antibody (CP870,893). In some embodiments, the systemic exposure of the interferon-associated antigen binding protein is at least 600 µg*h/mL, at least 700 µg*h/mL, at least 800 µg*h/mL, at least 900 µg*h/mL or at least 1000 µg*h/mL, preferably at least 1000 µg*h/mL. In some embodiments, the systemic exposure of the interferon-associated antigen binding protein in mice ranges from 1033 µg*h/mL to 1793 µg*h/mL.

As previously discussed, an interferon-associated antigen binding protein of the present invention may be administered in a pharmaceutically effective amount for the in vivo treatment of mammalian disorders. In this regard, it will be appreciated that as disclosed an interferon-associated antigen binding protein, will be formulated to facilitate administration and promote stability of the active agent.

A pharmaceutical composition in accordance with the present invention can comprise a pharmaceutically acceptable, non-toxic, sterile carrier such as physiological saline, nontoxic buffers, preservatives and the like. A pharmaceutically effective amount of an interferon-associated antigen binding protein typically is an amount sufficient to mediate one or more of: a reduction of HBeAg release from an HBV-infected cell; a reduction of pgRNA transcription in an HBV-infected cell; and a stimulation of the IFN signaling pathway in an infected cell. Of course, the pharmaceutical compositions of the present invention may be administered in single or multiple doses to provide for a pharmaceutically effective amount of the interferon-associated antigen binding protein.

In keeping with the scope of the present invention, interferon-associated antigen binding proteins, or nucleic acid sequences expressing any of them, may be administered to a human or other animal in accordance with the aforementioned methods of treatment in an amount sufficient to produce a therapeutic effect. The interferon-associated antigen binding proteins, or nucleic acid sequences expressing any of them, can be administered to such human or other animal in a conventional dosage form prepared by combining the interferon-associated antigen binding proteins, or nucleic acid sequences expressing any of them, with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of interferon-associated antigen binding proteins, or nucleic acid sequences expressing any of them, described in the current invention may prove to be effective.

It is to be understood that the methods described in this invention are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included," is not limiting. The use of the term "comprising" shall include the term "consisting of" unless stated otherwise.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The section headings used herein are for organizational purposes only and are not to be construed as limiting the subject matter described. The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention using this disclosure as a guide. Having now described certain embodiments in detail, the same will be more clearly understood by reference to the following examples, which are included for purposes of illustration only and are not intended to be limiting.

EXAMPLES

Example I

Generation of Interferon-Fused Antibodies (IFA) and Characterization on Reporter Cells I.a—IFA Design The sequence combinations of exemplary IFAs, designed with CP870,893 agonistic anti-CD40 antibody as backbone antibody, with the location of IFNs and the nature of the linkers are listed in Table 7 and Table 8. IFN was fused via a linker at the N- or the C-terminal part of the Light Chain (LC) or the Heavy Chain (HC), as indicated in Table 7. Nucleic acids encoding the HC, the LC or the fusions were synthesized with optimized mammalian expression codons and cloned into a eukaryotic expression vector such as pcDNA3.1 (Invitrogen). FIG. 2A depicts an exemplary map of a pcDNA3.1 plasmid encoding Seq ID NO 32 under the control of the pCMV promoter.

I.b—IFA Production

The Freestyle 293-F cells (Invitrogen) were transiently cotransfected with plasmids encoding both HC and LC at a HC/LC ratio of 4/6. Six days after transfection, the supernatant was collected, centrifuged and filtered through 0.22 µm filters. Purification process was performed in two purification steps, on AktaExpress chromatography system (GE Healthcare) using Protein A MabSelect Sure 5 mL 1.6/2.5 cm column (GE Healthcare) at a Flow rate of 5 mL/min. Sample binding was done in D-PBS1× pH 7.5 buffer, and elution with Glycine/HCl 0.1 M pH 3.0 buffer. Elution peak was stored in a loop then injected on HiTrap desalting 26/10 column (GE Healthcare) with a flow rate of 10 mL/min in D-PBS1× pH 7.5 buffer. Elution peak was collected on a 96-well microplate (2 mL fractions). Pool was performed according to the UV peak profile. After filtration on 0.22 µm filters (Sartorius MiniSart), quality control was performed including Bacterial Endotoxins using Endosafe® nexgen-PTS™ (Charles River), size exclusion Chromatography: using SEC 200 Increase 10/300 column (GE Healthcare) to determine purity and oligomers and SDS-PAGE under reducing and non-reducing conditions on NuPAGE gel System (Invitrogen) in MES SDS running buffer. The production yield is indicated in Table 8. For some IFAs, the production yield was very low. In that case, the agonistic CD40 activity and the IFN activity were assessed directly using the supernatant containing IFAs without any further purification.

Reduced SDS-PAGE analysis of purified IFAs indicated the presence of two major bands corresponding to the HC and the LC. When the IFN (whatever the IFN family member) was fused to the HC, a shift of its molecular weight was observed and the same phenomenon was observed for the LCs fused with any IFN (FIG. 2B).

I.c—IFA Characterization on Reporter Cells

HEK-Blue™ CD40L cells (InvivoGen Cat. #: hkb-cd40) or HEK-Blue™ IFNα/β cells (InvivoGen, Cat. #: hkb-ifnαβ), were used to monitor, respectively, the activation of the NFκB pathway by CD40 agonists or of the IFN pathway induced by type I-IFN.

HEK-Blue™ CD40L cells were generated by stable transfection of HEK293 cells with the human CD40 gene and a NFκB-inducible Secreted Embryonic Alkaline Phosphatase (SEAP) construct (Invivogen) to measure the bioactivity of CD40 agonists. Stimulation of CD40 leads to NFκB induction and then production of SEAP, which is detected in the supernatant using QUANTI-Blue™ (Invivogen, Cat. #repqbs2).

HEK-Blue™ IFN-cells are designed to monitor the activation of the JAK/STAT/ISGF3 pathways induced by type I-IFNs. Activation of this pathway induces the production and release of SEAP. Levels of SEAP are readily assessable in the supernatant using QUANTI-Blue™.

HEK-Blue™ IFN-α/β are used to monitor the activity of human IFNα or IFNβ.

Cells were seeded in 96-well plates (50,000 cells per well) and stimulated with the indicated concentration for each IFA or controls and incubated at 37° C. for 24 h. Supernatants were then collected and levels of SEAP were quantified after incubation of the supernatant for about 30 min with QuantiBlue™ and Optical Density (O.D.) assessment at 620 nm on an Ensight plate reader or PheraStar (Lab Biotech).

HEK-Blue™ Dual IFN-γ cells (InvivoGen, Cat. #: hkb-ifng) or HEK-Blue™ IFN-λ (InvivoGen, Cat. #: hkb-ifnl) may be used to respectively monitor the activity of type II- and type III-IFNs. HEK-Blue™ IFN-λ cells are designed to monitor the activity of IFNλ. HEK-Blue™ Dual IFN-γ cells allow the detection of bioactive human IFNγ.

I.d—Functional Activities of IFNα/β-based IFAs on Reporter Cells

FIG. 3 shows examples of dose responses of IFAs, where IFNβ or a mutated version thereof as specified in Table 7 was fused to the HC as indicated in Table 7, on HEK-Blue™ CD40L (FIGS. 3A-3B) and HEK-Blue™ IFN-α/β cells (FIGS. 3C-3D). Agonistic anti-CD40 activities of IFAs are summarized in Table 8 and examples are shown in FIG. 3A and FIG. 3B. Results indicate that all tested IFAs are functional to activate both the CD40 pathway and the IFN-α/β pathway in a dose dependent manner. For fusions to the C-terminus of the HC or LC, the $EC_{50}$ values for agonistic CD40 are ranging from 11.1 ng/mL to 192 ng/mL (Table 8). The mean $EC_{50}$ value for the parental antibody is 48 ng/mL and 57 ng/mL in the experiment shown in FIG. 3. IFAs with the IFN fused to the N-terminus of the HC or the LC were also able to activate the CD40 pathway, but the precise $EC_{50}$ values could not be determined for these IFAs since the activity was directly determined from the supernatant and not using purified proteins (FIG. 3B).

The IFN activity of various IFAs is summarized in Table 8 and examples are shown in FIGS. 3C to 3D. For fusions of IFNβ or mutated IFNβ (as specified in Table 7) to the C-terminus of the HC or LC, the IFN activity is variable depending on the linker sequence with $EC_{50}$ values ranging from 0.14 ng/mL to 4.5 ng/mL (FIG. 3C and Table 8). FIG. 3D shows that IFAs with IFNβ fused to the N-terminal part exhibit high IFN activity. The parental antibody used as negative control did not show any activity, whereas recombinant IFNβ did show a strong dose-dependent response. Altogether, these results demonstrate that fusion of IFNβ or a mutated version thereof as specified in Table 7 to an antibody, regardless the location, maintain both biological functions, although with differences in terms of potencies.

Figure 1:
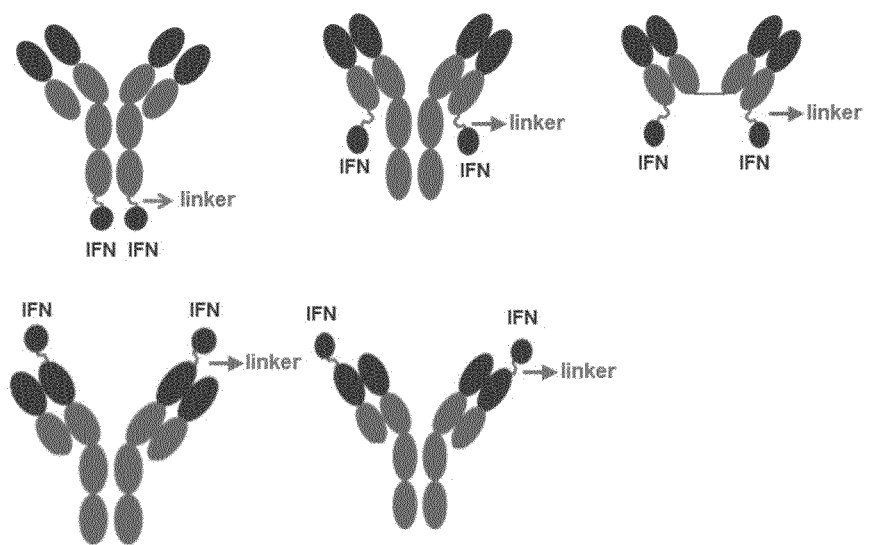
FIG. 1: This schematic drawing depicts exemplary interferon-associated antigen binding protein formats. The interferon-associated antigen binding protein is an interferon-fused agonistic anti-CD40 antibody or an interferon-fused agonistic antigen binding fragment thereof. IFNs are associated via linkers to different positions on the antibody or the antigen binding fragment thereof: N-terminal or C-terminal part of the light chain (LC) or the heavy chain (HC). In particular, IFNs are chosen from Type I, Type II and Type III interferon families.
Figure 4A:
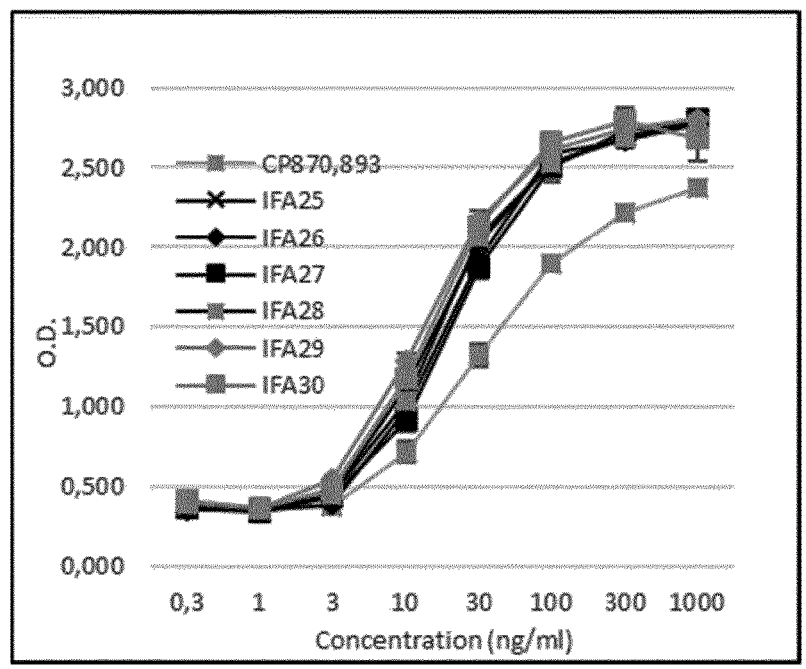
FIG. 4A graphically depicts a dose effect of a number of IFA molecules with IFNα fusions on activating the CD40-mediated NFκB pathway reporter assay in HEK-Blue™ CD40L cells.
Figure 4B:
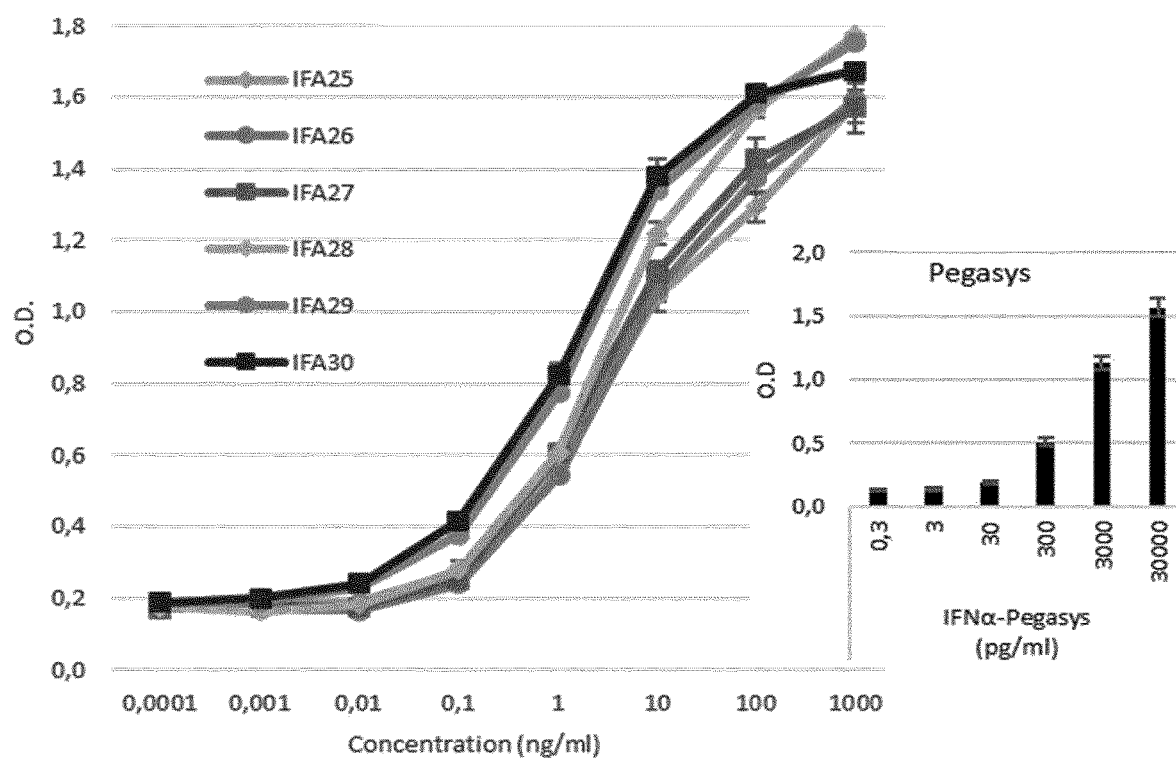
FIG. 4B graphically depicts a dose effect of a number of IFA molecules with IFNα fusions on activating the Type I IFN-mediated pathway in reporter HEK-Blue-IFN-α/β cells. The activity of PEGASYS® (peginterferon alfa-2a) is indicated in the insert in the lower right corner.
Figure 4C:
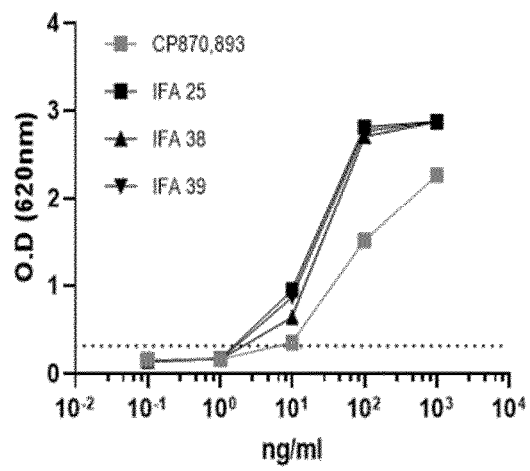
FIG. 4C graphically depicts the effect of IFA molecules with IFNα fusions and HL linker on HC (IFA38) or LC (IFA39) on activating the CD40-mediated NFκB pathway reporter assay in HEK-Blue™ CD40L cells.
Figure 4D:
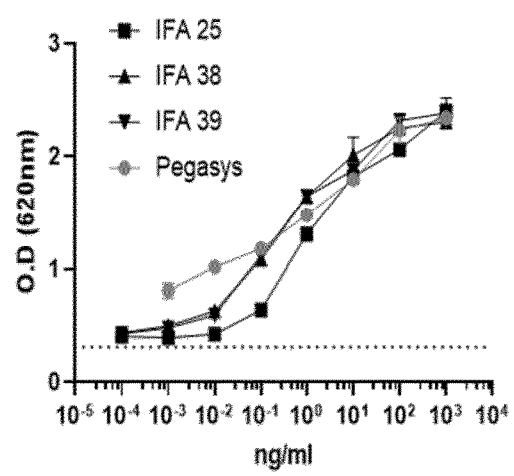
FIG. 4D graphically depicts the effect of IFA38 and IFA39 on activation of the Type I IFN-pathway in reporter HEK-Blue-IFNα/β cells.

FIG. 4 shows examples of dose responses of IFAs, where IFNα was fused to the HC or the LC as indicated in Table 7, on HEK-Blue™ CD40L (FIGS. 4A and 4C) and HEK-Blue™ IFN-α/β cells (FIG. 4B and FIG. 4D). Results indicate that all tested IFAs are functional to activate both the CD40 pathway and the IFNα/β pathway in a dose-dependent manner. Surprisingly, for all the IFNα-based IFAs, the potency on CD40 pathway was reproducibly higher than that of the parental antibody. The $EC_{50}$ values for IFNα-based IFAs ranged from 11.1 ng/mL to 22.7 ng/mL and the $EC_{50}$ for CP870,893 ranged from 30 ng/mL to 80 ng/mL (mean $EC_{50}$ value: 48 ng/mL).

The IFN activity of IFAs is variable depending on the linker sequence with $EC_{50}$ values ranging from 1.6 ng/mL to 5.1 ng/mL. In the same assay, PEGylated IFNα2a (PEGASYS® (peginterferon alfa-2a)) was also active in a dose-dependent manner with an $EC_{50}$ value of around 1 ng/mL.

I.e—Generation and Characterization of IFAs without the Fc Region

Suitable constructs according to the invention can also be interferon-associated antigen binding proteins without an Fc region. A construct encoding the heavy chain of the fab fragment of CP870,893 fused to a TEV-His tag was designed (SEQ ID NO 50) and cloned into the expression plasmid pcDNA3.1. This construct is cotransfected in HEK cells as described earlier, with LCs fused via different linkers to different IFNs such as SEQ ID NO 28, SEQ ID NO 29, SEQ ID NO 34, SEQ ID NO 35, SEQ ID NO 36, SEQ ID NO 37, SEQ ID NO 41, SEQ ID NO 42, or SEQ ID NO 43. Proteins and/or supernatants are evaluated in reporter cells and/or their effect on HBV infection in PHHs. It will be understood by one of skill in the art that constructs for use in therapy will no longer contain the TEV-His tag. These constructs are likewise embodiments of the invention. Interferon-associated antigen binding proteins without the Fc part will be active against HBV infection. Two IFAs were then produced and their functional characterization is described in Example V: IFA50: (SEQ ID NO 41)+(SEQ ID NO 50) and IFA51: (SEQ ID NO 42)+(SEQ ID NO 50).

Example II

Effect of IFAs on HBV Infected Primary Hepatocytes

II.a—Effect of IFAs on HBV Infection in Primary Human Hepatocytes

The effect of IFAs on HBV infection in primary human hepatocytes (PHHs) was investigated. PHH cells were plated in 96-well plates (70,000 cells/well) in William's E GlutaMAX media (32551-020, Gibco) supplemented with 10% fetal calf serum (FCS) (SH30066.02, Hyclone), insulin (19278-5ML, Sigma), hydrocortisone (H2270-100MG, Sigma) and Penicillin/Streptomycin (15140, Gibco). Four hours later, cells were rinsed and media was replaced. The next day, media was replaced by matrigel-containing media (0.25 mg/mL; 356231, Corning). Cells were infected 48 hours after plating with a MOI (Multiplicity Of Infection) of 500 to 1,000 vge/cell (viral genome equivalent) in InVitroGRO HI medium (Z99009, Bioreclamation IVT) supplemented with 5% FCS, 4% PEG 8000 (81268, Sigma), 2% DMSO (DMSO-100ML, Sigma) and 1% Penicillin/Streptomycin. Sixteen hours post-infection, cells were washed three times with PBS. Four days after infection, cells were kept untreated or treated with serially diluted IFAs as indicated in the figures. Three days after treatment, culture supernatants were collected and kept at −80° C. for further protein detection.

II.b.—HBV e-Antigen (HBeAg) Release Assessment

HBV e-antigen (HBeAg) levels in the cell culture supernatant were measured using ELISA as described by the manufacturer and results expressed in PEI Units (HBeAg CLIA 96T/K: CL0312-2; Autobio) or in luminescence.

II.c.—HBV s-Antigen (HBsAg) Release Assessment

Quantification of the HBsAg in the supernatant was carried out by following the protocol of the AutoBio HBsAg CLIA kit (#CL0310-2), the main steps were: first the samples were diluted 1/5 in 1×PBS. Then 50 µL of standards, controls, and diluted samples were placed in the wells. 50 µL of "Enzyme conjugate" solution were added to each well, followed by an incubation of one hour at 37° C. Subsequently, the plates were washed 6 times with 300 µL of washing solution from the kit using the plate washer. Then 50 µL of "Substrate Solution" (volume-to-volume mix in reagents A and B) was added in each well and an incubation of 10 minutes in the dark was carried out. The plates were then read on a PHERASTAR microplate reader (BMG Labtech) in Luminescence mode.

II.d.—pgRNA Quantification

The qPCR technique was used to compare the level of expression of pgRNA from infected cells treated with test compounds. pgRNA quantification from infected cells was done in 96-well plates with the QuantStudio 12K Flex. The cDNA was obtained by RT, followed by qPCR with TaqMan Fast Virus assay in one step (ThermoFisher cat #4444434). The results were processed by the AACt method and normalized with the housekeeping gene GUSB in duplex. The pgRNA was amplified using the following primers and probe: (forward: CCTCACCATACTGCACTCA SEQ ID NO: 70, reverse: GAGGGAGTTCTTCTTCTAGG SEQ ID NO: 71, AGTGTGGATTCGCACTCCTCCAGC SEQ ID NO: 72 as a probe). The GUSB gene was amplified using the TaqMan assay from Thermo Fisher (Hs99999908-m1).

II.e.—CXCL10 release

CXCL10 release was assessed using an ELISA kit according to the manufacturer's instruction (BioLegend 439904). Samples were diluted 1/50 and luminescence was assessed on an EnSight microplate reader at 450 nm.

II.f—Effect of IFNα/β Based IFAs on HBV Infection

Figure 5:
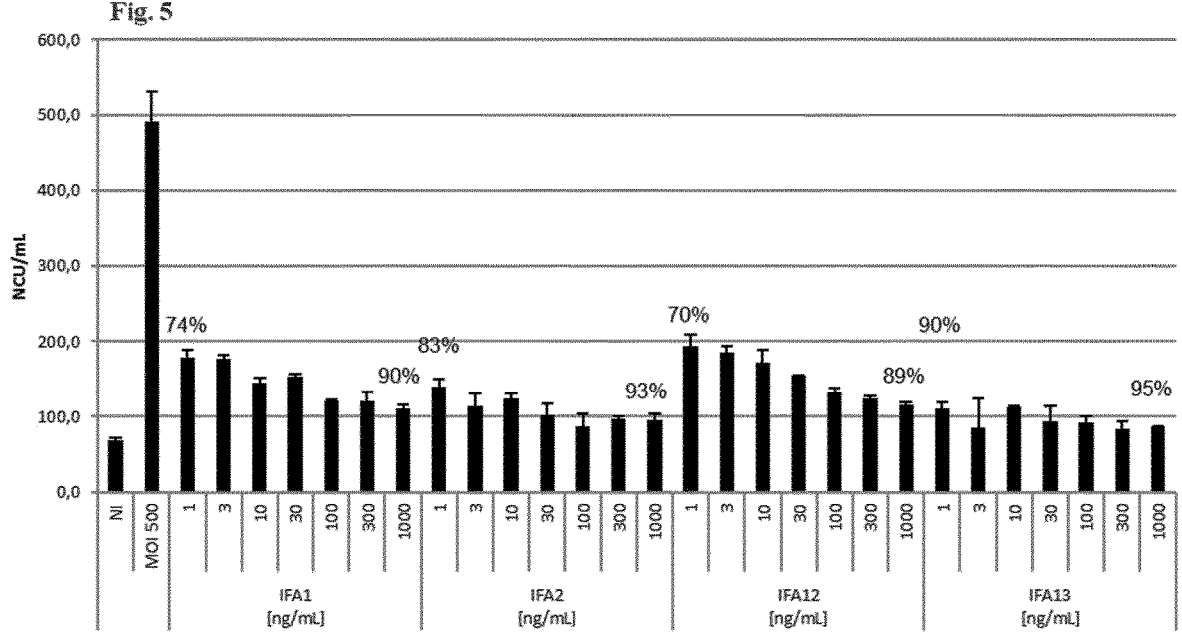
FIG. 5 depicts the effect of IFNβ based IFAs in a dose dependent manner on HBeAg release from primary hepatocytes infected with HBV. IFA1, IFA12: fusion of IFNβ to the C-terminus of LC via HL or RL linkers, respectively. IFA2 and IFA13: fusion of IFNβ_C17S to the C-terminus of the LC via HL or RL linkers, respectively.

Several IFAs were tested for their abilities to reduce HBeAg secretion after infection of PHH with HBV. In FIG. 5, IFAs with IFNβ or a mutated version thereof fused at the C-terminus of the LC were used. Results indicate that all the tested IFAs strongly reduce HBeAg release. Indeed, even at the lowest concentration tested (1 ng/mL), depending on the IFA, 70% to 90% inhibition of HBeAg release was observed, demonstrating that they are endowed with potent anti-viral effect. It is noteworthy that 100% inhibition could not be reached in this experiment, since treatment started four days after infection and at that time an existing pool of HBeAg (mRNA and protein) is already present in the cell and continue to be produced thereafter.

Figure 6A:
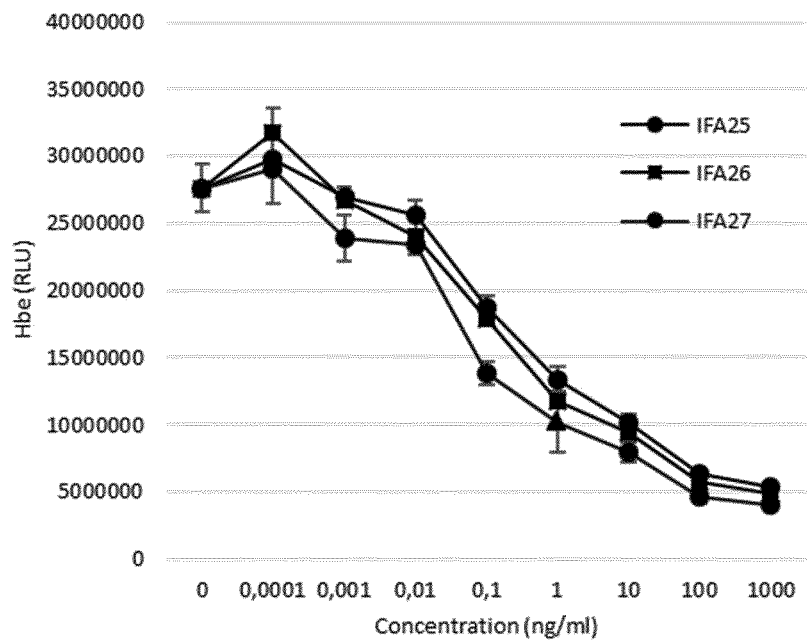
FIG. 6A depicts the effect of IFA25, IFA26 and IFA27 in a dose dependent manner on HBeAg release from primary human hepatocytes infected by HBV.
Figure 6B:
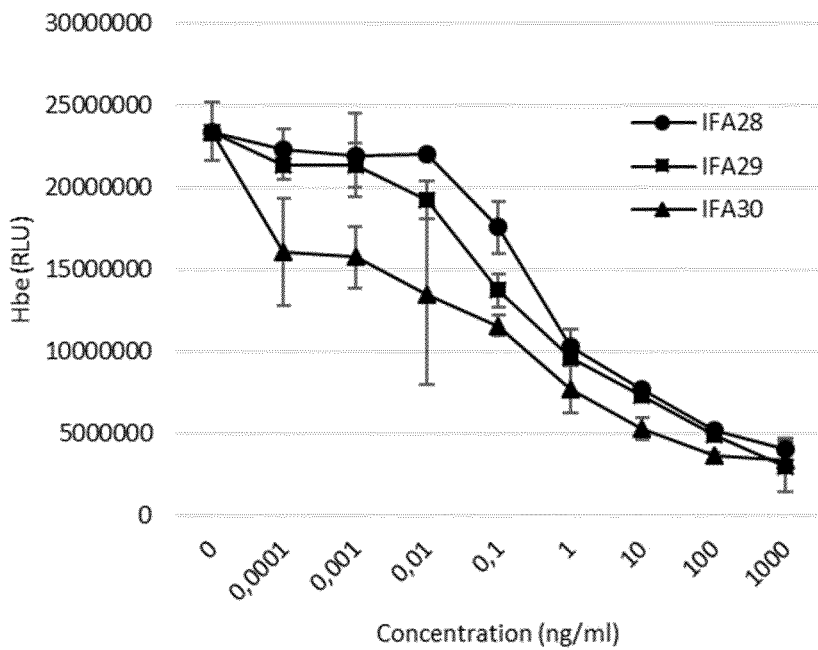
FIG. 6B depicts the effect of IFA28, IFA29 and IFA30 in a dose dependent manner on HBeAg release from primary human hepatocytes infected by HBV.

The effect of IFAs fused to IFNα were also tested in HBV-infected PHHs. FIG. 6 shows that these IFAs are very potent on HBV infection with $EC_{50}$ values ranging from 0.06 ng/mL to 0.2 ng/mL for IFAs with IFNα2a fused at the C-terminus of the HC (IFA25: 0.16 ng/mL, IFA26: 0.1 ng/mL; IFA27: 0.06 ng/mL; and IFA38: ~0.2 ng/mL (~2.2 pM); FIG. 6A and FIG. 6C) and from 0.15 ng/mL to 0.36 ng/mL for IFAs with IFNα2a fused at the C-terminus of the LC (IFA28: 0.36 ng/mL; IFA29: 0.15 ng/mL; IFA30: 0.31 ng/mL; and IFA39: ~0.3 ng/mL (~3 pM); FIG. 6B and FIG. 6C). To compare the antiviral effect of PEGASYS® (peginterferon alfa-2a) to IFA38 and IFA39, results are expressed in pM and indicate that $EC_{50}$ for PEGASYS® (peginterferon alfa-2a) is ~250 pM in comparison to ~2.2 pM for IFA38 and ~3 pM for IFA39, indicating that IFAs are much more potent than PEGASYS® (peginterferon alfa-2a).

II.g—Short Terms Treatment is Sufficient to Induce Potent Anti-Viral Activity

To assess the effect of short term IFA treatment of primary hepatocytes infected with HBV, cells were infected and incubated for 4 days, treated with IFA25, IFA27, IFA28, IFA30 or with PEGASYS® (peginterferon alfa-2a) in a dose dependent manner for 24 h, washed and then incubated with fresh medium without any treatment. After 3 days, supernatants were collected to assess the level of HBeAG (FIG. 6E), HBsAG (FIG. 6F) and CXCL10 (FIG. 6H) release and cells were lysed and RNA extracted for the quantification of pgRNA (FIG. 6G). Results indicate that all tested IFAs were able to inhibit HbeAG and HBsAG release as well as pgRNA expression in a dose dependent manner. PEGASYS® (peginterferon alfa-2a) alone was only able to inhibit HBeAG release and reduce pgRNA levels. In this respect, IFAs are at least 2 logs more active than PEGASYS® (peginterferon alfa-2a) on viral parameters. Surprisingly, although all tested IFAs showed a dose dependent inhibition of HBsAg release, no reduction was observed with PEGASYS® (peginterferon alfa-2a) even at the highest concentration. Analysis of CXCL10, a biomarker of the IFN pathway, showed that IFAs are also much more potent than PEGASYS® (peginterferon alfa-2a).

Example III

Cytokine Release
III.a—Cytokine Release Assessment (CRA) from Human Whole Blood Cells Whole blood cells (WBC) ex vivo stimulation assay was used to investigate release of cytokines following IFA stimulation. WBC were collected from four healthy donors, diluted 1/3 in RPMI1640 (72400-021, Gibco) and distributed in sterile reaction tubes (300 µl). Cells were left unstimulated, stimulated with LPS (LipoPolySaccharide) K12 (tlrl-eklps, Invivogen) at 10 ng/mL as a positive control or with IFAs at 1 µg/ml and incubated for 24 h at 37° C. Supernatants were then collected and frozen at −20° C. until the day of analysis.

Human pro-inflammatory cytokines were analyzed using multiplexing MSD assay (K15067L-4) which measures Tumor Necrosis Factor (TNF)-α, Interleukin (IL)-1β, IL-2, IL-6, IL-8, IL-10, IL-12/IL-23p40 and IFNγ. MSD plates were analyzed on the 1300 MESO QuickPlex SQ120 apparatus (MSD).

Figure 7:
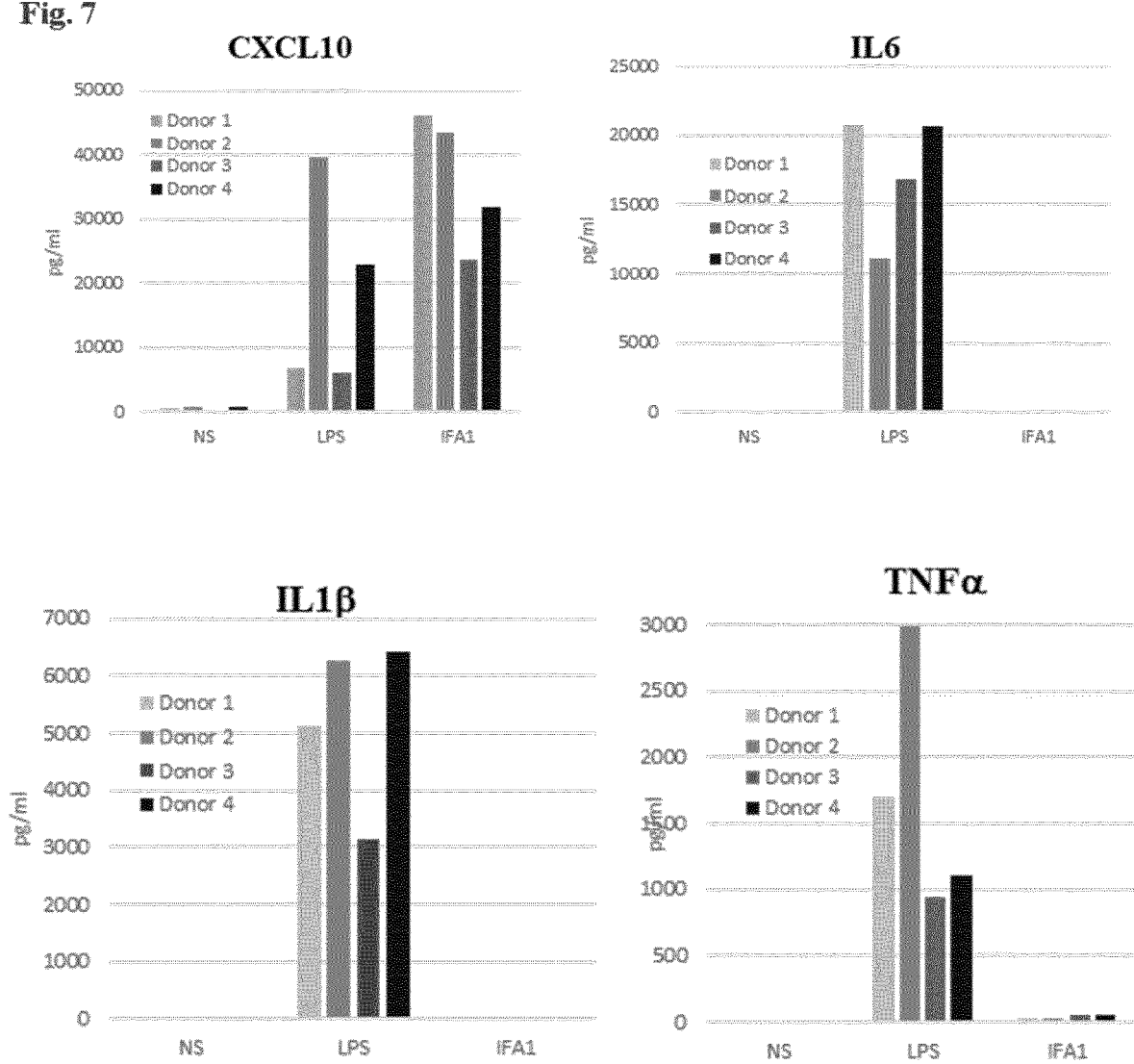
FIG. 7 depicts results from an in vitro Cytokines Release Assay of Human Whole Blood Cells (WBCs): Example of data obtained after stimulation of WBCs from 4 healthy volunteer donors. WBC were left Non-Stimulated (NS), treated with LPS (10 ng/mL) or with IFA1 (1 µg/mL) for 24 h. Supernatants were collected and submitted to cytokines release quantification using the MSD u-Plex kit for human cytokines. Results represent the mean of two independent stimulations from each donor. The profile of CXCL10 (IP10), IL6, IL1β and TNFα are shown.

FIG. 7 depicts exemplary results from an in vitro Cytokine Release Assessment of Human WBC either non-stimulated, treated with LPS or with IFA1.

Further results from testing IFNβ-/mutated IFNβ- and IFNα-based IFAs are summarized in Tables 9a and 9b. Results show that for all donors, LPS induces very high level of the inflammatory cytokines (IL-1β, TNF-α, IL-6, IL-12p40 and IFNγ). It also induced IP10 (CXCL10) which is a biomarker of the IFN pathway and moderate level of IL-10. Two IFNβ- (Table 9a) and six IFNα- (Table 9b) based IFAs were tested. All of them induced the biomarker IP10. However, they did not induce IL-10, IL-1β and IL-2, and they induced only very low to moderate level of IFNγ, IL-6 and TNF-α, thus suggesting a favorable safety profile with regard to the induction of inflammatory cytokines.

Example IV

Pharmacokinetic Studies
IV.a—ELISA Assay Development for IFA Quantifications

For the ELISA quantification 96-wells plates (PLATES 96 wells Maxisorp, THERMO Scientifique; 442404) were coated overnight at 4° C. with 100 µl of recombinant human CD40/TNFRSF5 Fc Chimera Protein, consisting of the extracellular domain of human CD40 fused to the Fc part of human IgG1 (CD40-Fc; R&D Systems; 1493-CDB-050) at 0.5 µg/mL in Sodium Carbonate (0.05 M, pH 9.6, C-3041, Sigma). After emptying by flipping, plates were then incubated for 1 hour at 37° C. with PBS-0.05% Tween20-1% Milk (SIGMA; 70166-500 g) followed by washing with PBS-0.05% Tween20. Samples and controls (100 µl of 1/2 serial dilutions) were then incubated for 90 minutes at 37° C. followed by three washes (PBS-0.05% Tween20) and incubation with a secondary anti-IgG2-conjugate HRP (1/5000, ab99779, Abcam) antibody or anti-IFNα conjugate HRP (1/1000, eBIOSCIENCE/Invitrogen; BMS216MST) in PBS-0.05% Tween20-1% Milk. After three washes with PBS, 0.05% Tween2, TMB (Tetramethylbenzidin, Tebu Bio; TMBW-1000-01) was added and the plates incubated for 20 minutes in the dark. The reaction was stopped by adding 1M HCl. Plates were read at 450-650 nm with an Ensight plate reader (Perkin Elmer). Quantification of PEGASYS® (peginterferon alfa-2a) was assessed using similar protocol steps but using human IFN-α matched antibody pairs from eBioscience/Invitrogen. Capture was performed using 100 µL of human anti-IFNα antibody (eBioscience/Invitrogen; BMS216MST), at 1 µg/mL in sodium carbonate (0.05 M, pH 9.6, C-3041, Sigma). For the detection, a secondary anti-IFNα conjugate HRP antibody (1/1000, Affymetrix eBioscience/BMS216MST; 15501707) in PBS-0.05% Tween20-1% Milk was applied.

IV.b—In Vivo Bioavailability in Mice

To determine the PK parameters, CP870,893, IFA25, IFA26, IFA27, IFA28, IFA29 and IFA30 were administrated at 0.5 mg/kg and PEGASYS® (peginterferon alfa-2a) at 0.3 mg/kg i.v. bolus to male CD1-Swiss mice and blood samples were collected at different time points. Examples of quantification of circulating molecules using the ELISA approach described above and revealed with anti-IFNα-conjugated HRP are shown in FIGS. 8A and 8B, while examples of quantification revealed with anti-IgG2-conjugated HRP are shown in FIG. 8C; PEGASYS® (peginterferon alfa-2a) quantification is shown in FIG. 8D. In one set of experiments summarized in Table 10A, PK parameters for CP870,893 were explored in a 7-day experiment and those for IFA27, IFA29 and IFA30 in 10-day experiments (quantification for IFA27 was performed using 2 different ELISA approaches). In another set of experiments summarized in Table 10B, the PK parameters for CP870,893 and IFA25, IFA26, IFA28 and PEGASYS® (peginterferon alfa-2a) were explored in 21-day experiments (quantification for IFA25 was performed using 2 different ELISA approaches).

After a short distribution phase, the pharmacokinetic profiles of IFAs are characterized by a long serum half-life ranging from 116 to 218 h (Table 10A and Table 10B). Very similar PK profiles were obtained for the 6 tested IFAs with high circulating level even ten days after single dose administration. The pharmacokinetic parameters summarized in Table 10A/B indicate that these IFAs surprisingly circulate in the blood with higher systemic exposure (AUC (0-inf)) ranging from 1033 µg·h/mL to 2552 µg·h/mL for IFAs in comparison to 590 or 797 µg·h/mL, respectively, for the parental antibody CP870,893 (up to 3.2 fold), also reflecting lower clearance values for IFAs. The volume of distribution Vss was low and ranked from 50 to 105 mL/kg, slightly higher than the plasma vascular volume (50 mL/kg) in this species. For all IFAs, the clearance was ranked as low (0.28 to 0.49 mL/h/kg). Interestingly, the clearance of PEGASYS® (peginterferon alfa-2a) (1.4 mL/hr/kg) is up to 7 fold higher than clearance of IFAs (e.g., 0.2 mL/hr/kg for IFA27) demonstrating a higher systemic exposure of IFAs.

Example V

V.a—Functional Activities of IFAs without Fc Region on Reporter Cells and HBV Infection To determine whether the Fc part of IFAs is needed for activity, fusions of IFNα to the C-terminal part of the LC associated with a Fab fragment of the HC were designed and produced. IFNα was linked to the LC part with a (G4S)2 (IFA50) or (G4S)3 (IFA51) linker.

Evaluation on HEK-Blue™ CD40L cells demonstrated that such IFAs still exhibit agonistic CD40 activity (FIG. 9A) and activate the CD40 pathway with an $EC_{50}$ value of about 128 ng/ml (IFA50) and 123 ng/mL (IFA51), respectively.

Evaluation of the IFN activity on HEK-Blue™ IFN-α/β cells showed that both tested IFAs exhibit IFN activity (FIG. 9B). $EC_{50}$ values are reported in Table 8B and are about 1.36 ng/ml for IFA50 and 1.43 ng/mL for IFA51.

Both IFAs were tested on HBV infection as described earlier and both IFAs exhibit potent anti-viral activity with $EC_{50}$ values of about 4.1 pM (IFA50) and 2.7 pM (IFA51), respectively.

V.b—Functional Activities of IFNε Based IFAs on Reporter Cells and on HBV Infection Fusions of CP870,893 to a third type I interferon (IFN epsilon; IFNε) have also been designed and produced. Such IFAs were tested on HEK-Blue™ CD40L cells and it could be demonstrated that they maintain agonistic CD40 activity. Results for one such IFA (IFA49) are shown in FIG. 10A. Evaluation on HEK-Blue™ hIFN-α/β cells (which are in fact activated by any type I interferon) showed that IFA49 is also able to activate the IFN-I-pathways (FIG. 10B). $EC_{50}$ values are reported in Table 8B. In addition, IFA49 was also tested on HBV infection in primary hepatocytes and showed similar activity to PEGASYS® (peginterferon alfa-2a) (FIG. 10C).

These results demonstrate that IFAs with IFNε maintain both IFN and agonistic CD40 activity (i.e., are bifunctional) and have antiviral activity.

V.c—Functional Activities of IFNω Based IFAs on Reporter Cells and on HBV Infection Fusions of CP870,893 to a fourth type I interferon (IFN omega; IFNω) have also been designed and produced. Such IFAs were tested on HEK-Blue™ CD40L cells and results demonstrated that they maintain agonistic CD40 activity. Results for one such IFA (IFA46) are shown in FIG. 11A. Evaluation on HEK-Blue™ hIFN-α/β cells (which are in fact activated by any type I interferon) showed that IFA46 is also able to activate the IFN-I-pathways (FIG. 11B). $EC_{50}$ values are reported in Table 8B. In addition, IFA46 was also tested on HBV infection in primary hepatocytes and showed similar activity to PEGASYS® (peginterferon alfa-2a) (FIG. 11C).

These results demonstrate that IFAs with IFNω maintain both IFN and agonistic CD40 activity (i.e., are bifunctional) and have antiviral activity.

V.d—Functional Activities of IFNγ Based IFAs on Reporter Cells on HBV Infection

Fusions of CP870,893 to type II Interferon (IFN gamma; IFNγ) have also been designed and produced. Evaluation of these IFAs on HEK-Blue™ CD40L cells demonstrate that they maintain agonistic CD40 activity, regardless of whether IFNγ is linked to the C-terminal part of the LC (IFA42) or of the HC (IFA43) (FIG. 12A). Evaluation of these IFAs on HEK-Blue™-IFNγ cells (FIG. 12B) showed that they are also able to activate the IFNγ-pathway. IFNγ activity differed somewhat between IFA42 ($EC_{50}$: 15 ng/ml) and IFA43 ($EC_{50}$: <0.01 ng/ml). $EC_{50}$ values are reported in Table 8B. In addition, IFA42 and IFA43 were tested in a dose dependent manner on HBV infection in primary hepatocytes as described earlier. Results indicate that both IFAs reduce HbeAg release in a dose dependent manner (FIG. 12C), indicating that IFAs with type II-IFN are active on HBV infection.

Taken together, these results demonstrate that IFAs with IFNγ maintain both IFN and agonistic CD40 activity (i.e., are bifunctional) and have anti-viral activity.

V.e—Functional Activities of IFNλ Based IFAs on Reporter Cells and on HBV Infection Fusions of CP870,893 to type III Interferon (IFN lambda; IFNλ) have also been designed and produced. These IFAs were tested on HEK-Blue™ CD40L cells and results demonstrated that they also maintain agonistic CD40 activity, regardless of whether IFNλ is linked to the C-terminal part of the LC (IFA44) or of the HC (IFA45) (FIG. 13A). Evaluation of these IFAs on HEK-Blue™-IFNλ cells showed that they are also able to activate the IFNλ-pathway (FIG. 13B). $EC_{50}$ values are reported in Table 8B. These results also demonstrate that IFAs with IFNλ maintain both IFN and agonistic CD40 activity (i.e., are bifunctional).

IFA44 and IFA45 were tested in a single dose in comparison to PEGASYS® (peginterferon alfa-2a) on HBV infection in primary hepatocytes as described earlier. Results indicate that both types of IFAs reduce HbeAg release by 65% and 78%, respectively. Under these condition PEGASYS® (peginterferon alfa-2a) inhibited HbeAg release by 81%. These results indicate that IFAs with type III IFN are active on HBV infection with $EC_{50}$ values for both tested IFAs<10 nM (FIG. 13C).

EQUIVALENTS

The invention may be embodied in other specific forms without departing from the spirit or essential characteristics thereof. The foregoing embodiments are therefore to be considered in all respects illustrative rather than limiting of the invention. Scope of the invention is thus indicated by the appended claims rather than by the foregoing description, and all changes that come within the meaning and range of equivalency of the claims are therefore intended to be embraced herein.

Items

In view of the above, it will be appreciated that the present invention also relates to the following items:

1. An interferon-associated antigen binding protein comprising
   (I) an agonistic anti-CD40 antibody or an agonistic antigen binding fragment thereof, and
   (II) an Interferon (IFN) or a functional fragment thereof, wherein the agonistic anti-CD40 antibody, or the agonistic antigen binding fragment thereof, comprises
      (a) three light chain complementarity determining regions (CDRs) that are at least 90% identical to the CDRL1, CDRL2 and CDRL3 sequences within SEQ ID NO 3; and three heavy chain CDRs that are at least 90% identical to the CDRH1, CDRH2 and CDRH3 sequences within SEQ ID NO 6; wherein each CDR is defined in accordance with the Kabat definition, the Chothia definition, the AbM definition, or the contact definition of CDR; preferably wherein each CDR is defined in accordance with the CDR definition of Kabat or the CDR definition of Chothia;
  (b) three light chain complementarity determining regions (CDRs) that are identical to the CDRL1, CDRL2 and CDRL3 sequences within SEQ ID NO 3; and three heavy chain CDRs that are identical to the CDRH1, CDRH2 and CDRH3 sequences within SEQ ID NO 6; wherein each CDR is defined in accordance with the Kabat definition, the Chothia definition, the AbM definition, or the contact definition of CDR; preferably wherein each CDR is defined in accordance with the CDR definition of Kabat or the CDR definition of Chothia;
  (c) a heavy chain or a fragment thereof comprising a complementarity determining region (CDR) CDRH1 that is at least 90% identical to SEQ ID NO 56, a CDRH2 that is at least 90% identical to SEQ ID NO 57, and a CDRH3 that is at least 90% identical to SEQ ID NO 58; and a light chain or a fragment thereof comprising a CDRL1 that is at least 90% identical to SEQ ID NO 52, a CDRL2 that is at least 90% identical to SEQ ID NO 53, and a CDRL3 that is at least 90% identical to SEQ ID NO 54;
  (d) a heavy chain or a fragment thereof comprising a complementarity determining region (CDR) CDRH1 that is identical to SEQ ID NO 56, a CDRH2 that is identical to SEQ ID NO 57, and a CDRH3 that is identical to SEQ ID NO 58; and a light chain or a fragment thereof comprising a CDRL1 that is identical to SEQ ID NO 52, a CDRL2 that is identical to SEQ ID NO 53, and a CDRL3 that is identical to SEQ ID NO 54;
  (e) a light chain variable region $V_L$ comprising the sequence as set forth in SEQ ID NO 51, or a sequence at least 90% identical thereto; and/or a heavy chain variable region $V_H$ comprising the sequence as set forth in SEQ ID NO 55, or a sequence at least 90% identical thereto;
  (f) a Fab region heavy chain comprising an amino acid sequence as set forth in SEQ ID NO 12, or a sequence at least 90% identical thereto; or
  (g) a light chain (LC) that comprises a sequence as set forth in SEQ ID NO 3, or a sequence at least 90% identical thereto; and/or a heavy chain (HC) that comprises a sequence selected from the group consisting of SEQ ID NO 6, SEQ ID NO 9, SEQ ID NO 49 and SEQ ID NO 48, or a sequence at least 90% identical thereto.

2. The interferon-associated antigen binding protein according to item 1, wherein the HC comprises the sequence as set forth in SEQ ID NO 6, or a sequence at least 90% identical thereto.

3. The interferon-associated antigen binding protein according to item 1, wherein the HC comprises the sequence as set forth in SEQ ID NO 9, or a sequence at least 90% identical thereto.

4. The interferon-associated antigen binding protein according to item 1, wherein the HC comprises the sequence as set forth in SEQ ID NO 49, or a sequence at least 90% identical thereto.

5. The interferon-associated antigen binding protein according to item 1, wherein the HC comprises the sequence as set forth in SEQ ID NO 48, or a sequence at least 90% identical thereto.

6. The interferon-associated antigen binding protein according to any one of the preceding items, wherein the IFN or the functional fragment thereof is a human interferon.

7. The interferon-associated antigen binding protein according to any one of the preceding items, wherein the IFN or the functional fragment thereof is selected from the group consisting of a Type I IFN, a Type II IFN and a Type III IFN, or a functional fragment thereof.

8. The interferon-associated antigen binding protein according to any one of the preceding items, wherein the IFN or the functional fragment thereof is a Type I IFN, or a functional fragment thereof.

9. The interferon-associated antigen binding protein according to item 8, wherein the type I IFN or the functional fragment thereof is IFNα, IFNβ, IFNω, or IFNε, or a functional fragment thereof.

10. The interferon-associated antigen binding protein according to item 8, wherein the type I IFN or the functional fragment thereof is IFNα or IFNβ, or a functional fragment thereof.

11. The interferon-associated antigen binding protein according to item 8, wherein the type I IFN or the functional fragment thereof is IFNω, or a functional fragment thereof.

12. The interferon-associated antigen binding protein according to item 8, wherein the type I IFN or the functional fragment thereof is IFNε, or a functional fragment thereof.

13. The interferon-associated antigen binding protein according to any one of the items 1 to 6, wherein the IFN or the functional fragment thereof is IFNα, IFNβ, IFNγ, IFNλ, IFNω or IFNε, or a functional fragment thereof.

14. The interferon-associated antigen binding protein according to item 13, wherein the IFN or the functional fragment thereof is IFNα or IFNβ, or a functional fragment thereof.

15. The interferon-associated antigen binding protein according to item 14, wherein the IFN or the functional fragment thereof is IFNα, or a functional fragment thereof.

16. The interferon-associated antigen binding protein according to item 15, wherein the IFN or functional fragment thereof is IFNα2a, or a functional fragment thereof.

17. The interferon-associated antigen binding protein according to item 16, wherein the IFNα2a comprises the sequence as set forth in SEQ ID NO 17, or a sequence at least 90% identical thereto.

18. The interferon-associated antigen binding protein according to item 14, wherein the IFN or the functional fragment thereof is IFNβ, or a functional fragment thereof.

19. The interferon-associated antigen binding protein according to item 18, wherein the IFNβ comprises the sequence as set forth in SEQ ID NO 14, or a sequence at least 90% identical thereto.

20. The interferon-associated antigen binding protein according to item 18, wherein the IFNβ or the functional fragment thereof comprises one or two amino acid substitution(s) relative to SEQ ID NO 14, selected from C17S and N80Q.

21. The interferon-associated antigen binding protein according to item 20, wherein the IFNβ or the functional fragment thereof comprises the amino acid substitution C17S relative to SEQ ID NO 14.

22. The interferon-associated antigen binding protein according to item 21, wherein the IFNβ comprises the amino acid sequence as set forth in SEQ ID NO 15.

23. The interferon-associated antigen binding protein according to item 20, wherein the IFNβ or the functional fragment thereof comprises the amino acid substitutions C17S and N80Q relative to SEQ ID NO 14.

24. The interferon-associated antigen binding protein according to item 23, wherein the IFNβ comprises the amino acid sequence as set forth in SEQ ID NO 16.

25. The interferon-associated antigen binding protein according to item 13, wherein the IFN or a functional fragment thereof is IFNγ or IFNλ, or a functional fragment thereof.

26. The interferon-associated antigen binding protein according to item 25, wherein the IFN or a functional fragment thereof is IFNγ, or a functional fragment thereof.

27. The interferon-associated antigen binding protein according to item 26, wherein the IFNγ comprises the sequence as set forth in SEQ ID NO 19, or a sequence at least 90% identical thereto.

28. The interferon-associated antigen binding protein according to item 25, wherein the IFN or a functional fragment thereof is IFNλ, or a functional fragment thereof.

29. The interferon-associated antigen binding protein according to item 28, wherein the IFNλ or the functional fragment thereof is IFNλ2, or a functional fragment thereof.

30. The interferon-associated antigen binding protein according to item 29, wherein the IFNλ2 comprises the sequence as set forth in SEQ ID NO 18, or a sequence at least 90% identical thereto.

31. The interferon-associated antigen binding protein according to any one of the preceding items, wherein the IFN or the functional fragment thereof is non-covalently associated with the agonistic anti-CD40 antibody or the agonistic antigen binding fragment thereof.

32. The interferon-associated antigen binding protein according to item 31, wherein the IFN or the functional fragment thereof is non-covalently associated with the agonistic anti-CD40 antibody or the agonistic antigen binding fragment thereof via ionic, Van-der-Waals, and/or hydrogen bond interactions.

33. The interferon-associated antigen binding protein according to any one of items 1 to 30, wherein the IFN or the functional fragment thereof is covalently associated with the agonistic anti-CD40 antibody or the agonistic antigen binding fragment thereof.

34. The interferon-associated antigen binding protein according to item 33, wherein the IFN or the functional fragment thereof is fused to the agonistic anti-CD40 antibody or the agonistic antigen binding fragment thereof.

35. The interferon-associated antigen binding protein according to item 34, wherein the IFN or the functional fragment thereof is fused to a light chain of the agonistic anti-CD40 antibody or the agonistic antigen binding fragment thereof.

36. The interferon-associated antigen binding protein according to item 35, wherein the IFN or the functional fragment thereof is fused to the N-terminus of the light chain of the agonistic anti-CD40 antibody or the agonistic antigen binding fragment thereof.

37. The interferon-associated antigen binding protein according to item 35, wherein the IFN or the functional fragment thereof is fused to the C-terminus of the light chain of the agonistic anti-CD40 antibody or the agonistic antigen binding fragment thereof.

38. The interferon-associated antigen binding protein according to item 34, wherein the IFN or the functional fragment thereof is fused to a heavy chain of the agonistic anti-CD40 antibody or the agonistic antigen binding fragment thereof.

39. The interferon-associated antigen binding protein according to item 38, wherein the IFN or the functional fragment thereof is fused to the N-terminus of the heavy chain of the agonistic anti-CD40 antibody or the agonistic antigen binding fragment thereof.

40. The interferon-associated antigen binding protein according to item 38, wherein the IFN or the functional fragment thereof is fused to the C-terminus of the heavy chain of the agonistic anti-CD40 antibody or the agonistic antigen binding fragment thereof.

41. The interferon-associated antigen binding protein according to any one of items 34 to 40, wherein the agonistic anti-CD40 antibody or an agonistic antigen binding fragment thereof, and the IFN or the functional fragment thereof are fused to each other via a linker.

42. The interferon-associated antigen binding protein according to item 41, wherein the interferon-associated antigen binding protein comprises no amino acids other than those forming (I) said agonistic anti-CD40 antibody, or agonistic antigen binding fragment thereof, (II) said IFN or functional fragment thereof and (III) said linker.

43. The interferon-associated antigen binding protein according to any one of items 1 to 41, wherein the interferon-associated antigen binding protein comprises no amino acids other than those forming (I) said agonistic anti-CD40 antibody, or agonistic antigen binding fragment thereof and (II) said IFN or functional fragment thereof.

44. The interferon-associated antigen binding protein according to any one of items 41 to 42, wherein the linker is a peptide linker.

45. The interferon-associated antigen binding protein according to item 44, wherein the linker comprises at least 1, at least 2, at least 3, at least 4, or at least 5 amino acids.

46. The interferon-associated antigen binding protein according to item 45, wherein the linker comprises at least 4 amino acids.

47. The interferon-associated antigen binding protein according to item 45, wherein the linker comprises at least 11 amino acids.

48. The interferon-associated antigen binding protein according to item 45, wherein the linker comprises at least 12 amino acids.

49. The interferon-associated antigen binding protein according to item 45, wherein the linker comprises at least 13 amino acids.

50. The interferon-associated antigen binding protein according to item 45, wherein the linker comprises at least 15 amino acids.

51. The interferon-associated antigen binding protein according to item 45, wherein the linker comprises at least 20 amino acids.

52. The interferon-associated antigen binding protein according to item 45, wherein the linker comprises at least 21 amino acids.

53. The interferon-associated antigen binding protein according to item 45, wherein the linker comprises at least 24 amino acids.

54. The interferon-associated antigen binding protein according to item 44, wherein the linker comprises up to 10, up to 20, up to 30, up to 40, up to 50, up to 60, up to 70, up to 80, up to 90, or up to 100 amino acids.

55. The interferon-associated antigen binding protein according to item 54, wherein the linker comprises up to 80 amino acids.

56. The interferon-associated antigen binding protein according to item 54, wherein the linker comprises up to 40 amino acids.

57. The interferon-associated antigen binding protein according to item 54, wherein the linker comprises up to 24 amino acids.

58. The interferon-associated antigen binding protein according to item 54, wherein the linker comprises up to 21 amino acids.

59. The interferon-associated antigen binding protein according to item 54, wherein the linker comprises up to 20 amino acids.

60. The interferon-associated antigen binding protein according to item 54, wherein the linker comprises up to 15 amino acids.

61. The interferon-associated antigen binding protein according to item 54, wherein the linker comprises up to 13 amino acids.

62. The interferon-associated antigen binding protein according to item 54, wherein the linker comprises up to 12 amino acids.

63. The interferon-associated antigen binding protein according to item 54, wherein the linker comprises up to 11 amino acids.

64. The interferon-associated antigen binding protein according to item 54, wherein the linker comprises up to 4 amino acids.

65. The interferon-associated antigen binding protein according to any one of items 44 to 64, wherein the linker is selected from the group comprising acidic, basic and neutral linkers.

66. The interferon-associated antigen binding protein according to item 65, wherein the linker is an acidic linker.

67. The interferon-associated antigen binding protein according to item 65 or 66, wherein the linker comprises a sequence as set forth in SEQ ID NO 22 or SEQ ID NO 23.

68. The interferon-associated antigen binding protein according to item 65, wherein the linker is a basic linker.

69. The interferon-associated antigen binding protein according to item 65, wherein the linker is a neutral linker.

70. The interferon-associated antigen binding protein according to item 65 or 69, wherein the linker comprises a sequence as set forth in SEQ ID NO 20, SEQ ID NO 21, SEQ ID NO 24, SEQ ID NO 25 or SEQ ID NO 26.

71. The interferon-associated antigen binding protein according to any one of items 44 to 70, wherein the linker is selected from the group comprising rigid, flexible and helix-forming linkers.

72. The interferon-associated antigen binding protein according to item 71, wherein the linker is a rigid linker.

73. The interferon-associated antigen binding protein according to item 71 or 72, wherein the linker comprises a sequence as set forth in SEQ ID NO 20, SEQ ID NO 22 or SEQ ID NO 23.

74. The interferon-associated antigen binding protein according to item 71, wherein the linker is a flexible linker.

75. The interferon-associated antigen binding protein according to item 71 or 74, wherein the linker comprises a sequence as set forth in SEQ ID NO 21, SEQ ID NO 24, SEQ ID NO 25 or SEQ ID NO 26.

76. The interferon-associated antigen binding protein according to item 71, wherein the linker is a helix-forming linker.

77. The interferon-associated antigen binding protein according to item 71 or 76, wherein the linker comprises a sequence as set forth in SEQ ID NO 22 or SEQ ID NO 23.

78. The interferon-associated antigen binding protein according to any one of items 44 to 66, 68, 69, 71, 72, 74 or 76, wherein the linker comprises the amino acids glycine and serine.

79. The interferon-associated antigen binding protein according to item 78, wherein the linker comprises the sequence as set forth in SEQ ID NO 21, SEQ ID NO 24, SEQ ID NO 25, or SEQ ID NO 26.

80. The interferon-associated antigen binding protein according to item 78, wherein the linker further comprises the amino acid threonine.

81. The interferon-associated antigen binding protein according to item 80, wherein the linker comprises the sequence as set forth in SEQ ID NO 21.

82. The interferon-associated antigen binding protein according to item 44, wherein the linker comprises a sequence selected from the sequences as set forth in SEQ ID NOs 20 to 26.

83. The interferon-associated antigen binding protein according to item 82, wherein the linker comprises a sequence selected from the sequences as set forth in SEQ ID NO 24, SEQ ID NO 25 or SEQ ID NO 26.

84. The interferon-associated antigen binding protein according to item 83, wherein the linker comprises a sequence as set forth in SEQ ID NO 24.

85. The interferon-associated antigen binding protein according to item 83, wherein the linker comprises a sequence as set forth in SEQ ID NO 25.

86. The interferon-associated antigen binding protein according to item 83, wherein the linker comprises a sequence as set forth in SEQ ID NO 26.

87. The interferon-associated antigen binding protein according to any one of items 41, 42 or 44 to 86, wherein the IFN or a functional fragment thereof is fused to the C-terminus of a heavy chain of the agonistic anti-CD40 antibody, or the agonistic antigen binding fragment thereof, via the linker as set forth in Table 3, in particular Table 3A or Table 3B, more particularly Table 3A.

88. The interferon-associated antigen binding protein according to item 87, wherein the heavy chain of the agonistic anti-CD40 antibody, or the agonistic antigen binding fragment thereof, comprises a sequence as set forth in SEQ ID NO 6, SEQ ID NO 9, SEQ ID NO 49, SEQ ID NO 48, or SEQ ID NO 12.

89. The interferon-associated antigen binding protein according to items 87 or 88, wherein the IFNα2a comprises the sequence as set forth in SEQ ID NO 17.

90. The interferon-associated antigen binding protein according to items 87 or 88, wherein the IFNβ comprises the sequence as set forth in SEQ ID NO 14, SEQ ID NO 15 or SEQ ID NO 16.

91. The interferon-associated antigen binding protein according to item 90, wherein the IFNβ comprises the sequence as set forth in SEQ ID NO 14.

92. The interferon-associated antigen binding protein according to item 90, wherein the IFNβ comprises the sequence as set forth in SEQ ID NO 15.

93. The interferon-associated antigen binding protein according to item 90, wherein the IFNβ comprises the sequence as set forth in SEQ ID NO 16.

94. The interferon-associated antigen binding protein according to item 87 or 88, wherein the IFNγ comprises the sequence as set forth in SEQ ID NO 19.

95. The interferon-associated antigen binding protein according to item 87 or 88, wherein the IFNλ2 comprises the sequence as set forth in SEQ ID NO 18.

96. The interferon-associated antigen binding protein according to any one of items 87 to 95, wherein the interferon-associated antigen binding protein further comprises a light chain of an agonistic anti-CD40 antibody, or an agonistic antigen binding fragment thereof.

97. The interferon-associated antigen binding protein according to item 96, wherein the light chain comprises a sequence as set forth in SEQ ID NO 3.

98. The interferon-associated antigen binding protein according to any one of items 41, 42 or 44 to 86, wherein the IFN or a functional fragment thereof is fused to the N-terminus of a heavy chain of the agonistic anti-CD40 antibody, or the agonistic antigen binding fragment thereof, via the linker as set forth in Table 4, in particular Table 4A or Table 4B, more particularly Table 4A.

99. The interferon-associated antigen binding protein according to item 98, wherein the heavy chain of the agonistic anti-CD40 antibody, or the agonistic antigen binding fragment thereof, comprises a sequence as set forth in SEQ ID NO 6, SEQ ID NO 9, SEQ ID NO 12, SEQ ID NO 48, SEQ ID NO 49 or SEQ ID NO 50, preferably a sequence as set forth in SEQ ID NO 6, SEQ ID NO 9, SEQ ID NO 12, SEQ ID NO 48 or SEQ ID NO 49.

100. The interferon-associated antigen binding protein according to items 98 or 99, wherein the IFNα2a comprises the sequence as set forth in SEQ ID NO 17.

101. The interferon-associated antigen binding protein according to items 98 or 99, wherein the IFNβ comprises the sequence as set forth in SEQ ID NO 14, SEQ ID NO 15 or SEQ ID NO 16.

102. The interferon-associated antigen binding protein according to item 101, wherein the IFNβ comprises the sequence as set forth in SEQ ID NO 14.

103. The interferon-associated antigen binding protein according to item 101, wherein the IFNβ comprises the sequence as set forth in SEQ ID NO 15.

104. The interferon-associated antigen binding protein according to item 101, wherein the IFNβ comprises the sequence as set forth in SEQ ID NO 16.

105. The interferon-associated antigen binding protein according to items 98 or 99, wherein the IFNγ comprises the sequence as set forth in SEQ ID NO 19.

106. The interferon-associated antigen binding protein according to items 98 or 99, wherein the IFNλ2 comprises the sequence as set forth in SEQ ID NO 18.

107. The interferon-associated antigen binding protein according to any one of items 98 to 106, wherein the interferon-associated antigen binding protein further comprises a light chain of an agonistic anti-CD40 antibody, or an agonistic antigen binding fragment thereof.

108. The interferon-associated antigen binding protein according to item 107, wherein the light chain comprises a sequence as set forth in SEQ ID NO 3.

109. The interferon-associated antigen binding protein according to any one of items 41, 42 or 44 to 86, wherein the IFN or a functional fragment thereof is fused to the C-terminus of a light chain of the agonistic anti-CD40 antibody, or the agonistic antigen binding fragment thereof, via the linker as set forth in Table 5, in particular Table 5A or Table 5B, more particularly Table 5A.

110. The interferon-associated antigen binding protein according to item 109, wherein the light chain of the agonistic anti-CD40 antibody, or the agonistic antigen binding fragment thereof, comprises a sequence as set forth in SEQ ID NO 3.

111. The interferon-associated antigen binding protein according to items 109 or 110, wherein the IFNα2a comprises the sequence as set forth in SEQ ID NO 17.

112. The interferon-associated antigen binding protein according to items 109 or 110, wherein the IFNβ comprises the sequence as set forth in SEQ ID NO 14, SEQ ID NO 15 or SEQ ID NO 16.

113. The interferon-associated antigen binding protein according to item 112, wherein the IFNβ comprises the sequence as set forth in SEQ ID NO 14.

114. The interferon-associated antigen binding protein according to item 112, wherein the IFNβ comprises the sequence as set forth in SEQ ID NO 15.

115. The interferon-associated antigen binding protein according to item 112, wherein the IFNβ comprises the sequence as set forth in SEQ ID NO 16.

116. The interferon-associated antigen binding protein according to items 109 or 110, wherein the IFNγ comprises the sequence as set forth in SEQ ID NO 19.

117. The interferon-associated antigen binding protein according to items 109 or 110, wherein the IFNλ2 comprises the sequence as set forth in SEQ ID NO 18.

118. The interferon-associated antigen binding protein according to any one of items 109 to 117, wherein the interferon-associated antigen binding protein further comprises a heavy chain of an agonistic anti-CD40 antibody, or an agonistic antigen binding fragment thereof.

119. The interferon-associated antigen binding protein according to item 118, wherein the heavy chain of the agonistic anti-CD40 antibody comprises a sequence as set forth in SEQ ID NO 6, SEQ ID NO 9, SEQ ID NO 12, SEQ ID NO 48, SEQ ID NO 49 or SEQ ID NO 50, preferably a sequence as set forth in SEQ ID NO 6, SEQ ID NO 9, SEQ ID NO 12, SEQ ID NO 48 or SEQ ID NO 49.

120. The interferon-associated antigen binding protein according to any one of items 41, 42 or 44 to 86, wherein the IFN is fused to the N-terminus of a light chain of the agonistic anti-CD40 antibody, or the agonistic antigen binding fragment thereof, via the linker as set forth in Table 6, in particular Table 6A or Table 6B, more particularly Table 6A.

121. The interferon-associated antigen binding protein according to item 120, wherein the light chain of the agonistic anti-CD40 antibody, or the agonistic antigen binding fragment thereof, comprises a sequence as set forth in SEQ ID NO 3.

122. The interferon-associated antigen binding protein according to items 120 or 121, wherein the IFNα2a comprises the sequence as set forth in SEQ ID NO 17.

123. The interferon-associated antigen binding protein according to items 120 or 121, wherein the IFNβ comprises the sequence as set forth in SEQ ID NO 14, SEQ ID NO 15 or SEQ ID NO 16.

124. The interferon-associated antigen binding protein according to item 123, wherein the IFNβ comprises the sequence as set forth in SEQ ID NO 14.

125. The interferon-associated antigen binding protein according to item 123, wherein the IFNβ comprises the sequence as set forth in SEQ ID NO 15.

126. The interferon-associated antigen binding protein according to item 123, wherein the IFNβ comprises the sequence as set forth in SEQ ID NO 16.

127. The interferon-associated antigen binding protein according to items 120 or 121, wherein the IFNγ comprises the sequence as set forth in SEQ ID NO 19.

128. The interferon-associated antigen binding protein according to items 120 or 121, wherein the IFNλ2 comprises the sequence as set forth in SEQ ID NO 18.

129. The interferon-associated antigen binding protein according to any one of items 120 to 128, wherein the interferon-associated antigen binding protein further comprises a heavy chain of an anti-CD40 antibody, or an agonistic antigen binding fragment thereof.

130. The interferon-associated antigen binding protein according to item 129, wherein the heavy chain of the agonistic anti-CD40 antibody comprises a sequence as set forth in SEQ ID NO 6, SEQ ID NO 9, SEQ ID NO 12, SEQ ID NO 48, SEQ ID NO 49 or SEQ ID NO 50, preferably a sequence as set forth in SEQ ID NO 6, SEQ ID NO 9, SEQ ID NO 12, SEQ ID NO 48 or SEQ ID NO 49.

131. The interferon-associated antigen binding protein according to any one of items 1 to 130, wherein the interferon-associated antigen binding protein comprises a sequence selected from SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44, SEQ ID NO 45, SEQ ID NO 46 and SEQ ID NO 47.

132. The interferon-associated antigen binding protein according to item 131, wherein the interferon-associated antigen binding protein comprises a sequence selected from SEQ ID NO 38, SEQ ID NO 39, SEQ ID NO 40, SEQ ID NO 41, SEQ ID NO 42 or SEQ ID NO 43.

133. The interferon-associated antigen binding protein according to items 131 or 132, wherein the interferon-associated antigen binding protein is an interferon-fused agonistic anti-CD40 antibody or an interferon-fused agonistic antigen binding fragment thereof comprising one of the sequence combinations disclosed in Table 8, in particular Table 8A or Table 8B, more particularly Table 8A.

134. The interferon-associated antigen binding protein according to item 133, wherein the interferon-associated antigen binding protein is an interferon-fused agonistic anti-CD40 antibody or an interferon-fused agonistic antigen binding fragment thereof comprising the sequences as set forth in SEQ ID NO 38 and SEQ ID NO 3.

135. The interferon-associated antigen binding protein according to item 133, wherein the interferon-associated antigen binding protein is an interferon-fused agonistic anti-CD40 antibody or an interferon-fused agonistic antigen binding fragment thereof comprising the sequences as set forth in SEQ ID NO 39 and SEQ ID NO 3.

136. The interferon-associated antigen binding protein according to item 133, wherein the interferon-associated antigen binding protein is an interferon-fused agonistic anti-CD40 antibody or an interferon-fused agonistic antigen binding fragment thereof comprising the sequences as set forth in SEQ ID NO 40 and SEQ ID NO 3.

137. The interferon-associated antigen binding protein according to item 133, wherein the interferon-associated antigen binding protein is an interferon-fused agonistic anti-CD40 antibody or an interferon-fused agonistic antigen binding fragment thereof comprising the sequences as set forth in SEQ ID NO 41 and SEQ ID NO 9.

138. The interferon-associated antigen binding protein according to item 133, wherein the interferon-associated antigen binding protein is an interferon-fused agonistic anti-CD40 antibody or an interferon-fused agonistic antigen binding fragment thereof comprising the sequences as set forth in SEQ ID NO 42 and SEQ ID NO 9.

139. The interferon-associated antigen binding protein according to item 133, wherein the interferon-associated antigen binding protein is an interferon-fused agonistic anti-CD40 antibody or an interferon-fused agonistic antigen binding fragment thereof comprising the sequences as set forth in SEQ ID NO 43 and SEQ ID NO 9.

140. The interferon-associated antigen binding protein according to any one of items 1 to 139, wherein the interferon-associated antigen binding protein activates both the CD40 and an IFN pathway.

141. The interferon-associated antigen binding protein according to item 140, wherein CD40 activity is determined using a whole blood surface molecule upregulation assay or an in vitro reporter cell assay.

142. The interferon-associated antigen binding protein according to item 141, wherein CD40 activity is determined using an in vitro reporter cell assay, optionally using HEK-Blue™ CD40L cells.

143. The interferon-associated antigen binding protein according to any one of items 140 to 142, wherein the interferon-associated antigen binding protein activates the CD40 pathway with an $EC_{50}$ of less than 400, 300, 200, 150, 100, 70, 60, 50, 40, 30, 25, 20, or 15 ng/mL.

144. The interferon-associated antigen binding protein according to item 143, wherein the interferon-associated antigen binding protein activates the CD40 pathway with an $EC_{50}$ ranging from 10 to 200 ng/mL.

145. The interferon-associated antigen binding protein according to item 144, wherein the interferon-associated antigen binding protein activates the CD40 pathway with an $EC_{50}$ ranging from 10 to 50 ng/mL, preferably 10 to 30 ng/mL.

146. The interferon-associated antigen binding protein according to any one of items 140 to 145, wherein the interferon-associated antigen binding protein activates the IFN pathway with an $EC_{50}$ of less than 100, 60, 50, 40, 30, 20, 10, or 1 ng/mL.

147. The interferon-associated antigen binding protein according to any one of items 140 to 146, wherein the interferon-associated antigen binding protein activates the IFN pathway with an $EC_{50}$ of less than 11 ng/mL, preferably less than 6 ng/mL.

148. The interferon-associated antigen binding protein according to any one of items 140 to 147, wherein the IFN pathway is the IFNα, IFNβ, IFNε, IFNγ, IFNω or IFNλ pathway.

149. The interferon-associated antigen binding protein according to item 148, wherein IFNβ activity is determined using an in vitro reporter cell assay, optionally using HEK-Blue™ IFN-α/β cells.

150. The interferon-associated antigen binding protein according to item 148, wherein IFNα activity is determined using an in vitro reporter cell assay, optionally using HEK-Blue™ IFN-α/β cells.

151. The interferon-associated antigen binding protein according to item 148, wherein IFNγ activity is determined using an in vitro reporter cell assay, optionally using HEK-Blue™ Dual IFN-γ cells.

152. The interferon-associated antigen binding protein according to item 148, wherein IFN, activity is determined using an in vitro reporter cell assay, optionally using HEK-Blue™ IFN-λ cells.

153. The interferon-associated antigen binding protein according to any one of the preceding items, wherein the interferon-associated antigen binding protein reduces HBeAg release by primary hepatocytes in vitro by at least 12% at 1 ng/mL.

154. The interferon-associated antigen binding protein for the use of item 153, wherein the interferon-associated antigen binding protein reduces HBeAg release by primary hepatocytes in vitro by up to 90% at 1 ng/mL.

155. The interferon-associated antigen binding protein according to item 153, wherein the interferon-associated antigen binding protein reduces HBeAg release with an $EC_{50}$ of less than 30 ng/mL.

156. The interferon-associated antigen binding protein according to item 155, wherein the interferon-associated antigen binding protein reduces HBeAg release with an $EC_{50}$ of less than 10 ng/mL.

157. The interferon-associated antigen binding protein according to item 156, wherein the interferon-associated antigen binding protein reduces HBeAg release with an $EC_{50}$ of less than 1 ng/mL.

158. The interferon-associated antigen binding protein according to item 156, wherein the interferon-associated antigen binding protein reduces HBeAg release with an $EC_{50}$ of less than 0.1 ng/mL.

159. The interferon-associated antigen binding protein according to any one of the preceding items, wherein the interferon-associated antigen binding protein is capable of upregulating the expression level of one or more IFN pathway biomarkers in an HBV-infected cell, preferably at least 1.5-fold, more preferably at least 2-fold, most preferably at least 3-fold.

160. The interferon-associated antigen binding protein according to item 159, wherein the IFN pathway biomarker is a chemokine.

161. The interferon-associated antigen binding protein according to item 160, wherein the IFN pathway biomarker is the interferon stimulated gene ISG20.

162. The interferon-associated antigen binding protein according to item 160, wherein the IFN pathway biomarker is a C-X-C chemokine, selected from the group consisting of CXCL9, CXCL10 and CXCL11.

163. The interferon-associated antigen binding protein according to item 162, wherein the IFN pathway biomarker is CXCL10.

164. The interferon-associated antigen binding protein according to any one of the preceding items, wherein the interferon-associated antigen binding protein does not significantly upregulate the expression level of one or more of IL10, IL1β and IL2 in an HBV-infected cell.

165. The interferon-associated antigen binding protein according to any one of the preceding items, wherein the systemic exposure of the interferon-associated antigen binding protein is increased compared to antibody CP870,893, preferably by at least 10%, more preferably by at least 15%, most preferably by at least 25%.

166. The interferon-associated antigen binding protein according to any one of the preceding items, wherein the systemic exposure of the interferon-associated antigen binding protein is at least 1000 μg*h/mL.

167. The interferon-associated antigen binding protein according to item 166, wherein the systemic exposure of the interferon-associated antigen binding protein ranges from 1033 μg*h/mL to 1793 μg*h/mL.

168. The interferon-associated antigen binding protein according to any one of the preceding items, wherein the half-life of the interferon-associated antigen binding protein is at least 100 h.

169. The interferon-associated antigen binding protein according to item 168, wherein the half-life of the interferon-associated antigen binding protein ranges from 116 to 158 h.

170. The interferon-associated antigen binding protein according to any one of the preceding items, wherein the clearance rate of the interferon-associated antigen binding protein is below 0.5 mL/h/kg.

171. The interferon-associated antigen binding protein according to item 170, wherein the clearance of the interferon-associated antigen binding protein ranges from 0.28 to 0.49 mL/h/kg.

172. The interferon-associated antigen binding protein according to any one of the preceding items, wherein the volume of distribution Vss of the interferon-associated antigen binding protein is below 100 mL/kg.

173. The interferon-associated antigen binding protein according to item 172, wherein the volume of distribution Vss of the interferon-associated antigen binding protein ranges from 50 to 98 mL/kg.

174. The interferon-associated antigen binding protein according to any one of the preceding items, wherein the interferon-associated antigen binding protein is suitable for administration to a subject in need thereof by means of genetic delivery with nucleic acid sequences encoding the interferon-associated antigen binding protein, or a vector or vector system encoding the interferon-associated antigen binding protein.

175. A nucleic acid encoding the interferon-associated antigen binding protein as recited in any one of the preceding items.

176. A nucleic acid encoding the IFN or the functional fragment thereof being fused to the agonistic anti-CD40 antibody or the agonistic antigen binding fragment thereof as recited in any one of items 34 to 174.

177. The nucleic acid according to item 176 encoding the IFN or the functional fragment thereof being fused to the light chain of the agonistic anti-CD40 antibody or the agonistic antigen binding fragment thereof, and further encoding a heavy chain of the agonistic anti-CD40 antibody or the agonistic antigen binding fragment thereof.

178. The nucleic acid according to item 177, wherein the heavy chain of the agonistic anti-CD40 antibody or the agonistic antigen binding fragment thereof comprises a sequence as set forth in SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 48, SEQ ID NO 49 or SEQ ID NO 50, or a nucleic acid sequence at least 95% identical to a nucleic acid encoding any of these sequences.

179. The nucleic acid according to item 176 encoding the IFN or the functional fragment thereof being fused to the heavy chain of the agonistic anti-CD40 antibody or the agonistic antigen binding fragment thereof, and further encoding a light chain of the agonistic anti-CD40 antibody or the agonistic antigen binding fragment thereof.

180. The nucleic acid according to item 179, wherein the light chain of the agonistic anti-CD40 antibody or the agonistic antigen binding fragment thereof comprises a sequence as set forth in SEQ ID NO 3, SEQ ID NO 4 or SEQ ID NO 5, or a nucleic acid sequence at least 95% identical to a nucleic acid encoding any of these sequences.

181. A nucleic acid encoding an IFN or a functional fragment thereof fused to an agonistic anti-CD40 antibody or an agonistic antigen binding fragment thereof according to any of the sequences set forth in SEQ ID NOs 28 to 47, or a nucleic acid sequence at least 95% identical to a nucleic acid encoding any of these sequences.

182. The nucleic acid according to items 175 to 181, wherein the nucleic acid further encodes a purification tag.

183. The nucleic acid according to item 182, wherein the purification tag is a His-tag.

184. The nucleic acid according to items 182 or 183, wherein the nucleic acid further encodes a cleavage site to cleave off the purification tag.

185. The nucleic acid according to item 184, wherein the nucleic acid comprises a sequence encoding the amino acid sequence as set forth in SEQ ID NO 27.

186. The nucleic acid according to items 175 to 185, wherein the nucleic acid further encodes a signal peptide.

187. The nucleic acid according to item 186, wherein the signal peptide is a secretory signal peptide.

188. The nucleic acid according to item 186 or 187, wherein the signal peptide comprises the sequence as set forth in SEQ ID NO: 1 or SEQ ID NO: 2.

189. The nucleic acid according to item 188, wherein the signal peptide comprises the sequence as set forth in SEQ ID NO: 1.

190. The nucleic acid according to item 188, wherein the signal peptide comprises the sequence as set forth in SEQ ID NO: 2.

191. A vector or a vector system comprising the nucleic acid according to any one of items 175 to 190.

192. A vector system comprising
(I) a first vector comprising a nucleic acid encoding an IFN or a functional fragment thereof fused to a light chain of the agonistic anti-CD40 antibody or the agonistic antigen binding fragment thereof of the interferon-associated antigen binding protein of any of items 1 to 174 and a second vector comprising a nucleic acid encoding a heavy chain of the agonistic anti-CD40 antibody or the agonistic antigen binding fragment thereof of the interferon-associated antigen binding protein of any one of items 1 to 174; or
(II) a first vector comprising a nucleic acid encoding an IFN or a functional fragment thereof fused to a heavy chain of the agonistic anti-CD40 antibody or the agonistic antigen binding fragment thereof of the interferon-associated antigen binding protein of any of items 1 to 174 and a second vector comprising a nucleic acid encoding a light chain of the agonistic anti-CD40 antibody or the agonistic antigen binding fragment thereof of the interferon-associated antigen binding protein of any one of items 1 to 174.

193. A vector system comprising
(I) a first vector according to item 191 for the expression of the IFN or the functional fragment thereof fused to the light chain of the agonistic anti-CD40 antibody or the agonistic antigen binding fragment thereof and a second vector for expression of the heavy chain of the agonistic anti-CD40 antibody or the agonistic antigen binding fragment thereof; or
(II) a first vector according to item 191 for the expression of the IFN or the functional fragment thereof fused to the heavy chain of the agonistic anti-CD40 antibody or the agonistic antigen binding fragment thereof and a second vector for expression of the light chain of the agonistic anti-CD40 antibody or the agonistic antigen binding fragment thereof.

194. A composition comprising the interferon-associated antigen binding protein according to any one of items 1 to 174, the nucleic acid according to any one of items 175 to 190, the vector according to item 191 or the vector system according to any one of items 191 to 193.

195. The composition according to item 194, wherein the composition is a pharmaceutical composition.

196. The composition according to item 195, wherein the pharmaceutical composition is suitable for oral, parenteral, or topical administration or for administration by inhalation.

197. The composition according to item 196, wherein the pharmaceutical composition is suitable for oral administration.

198. The composition according to item 196, wherein the pharmaceutical composition is suitable for topical administration.

199. The composition according to item 196, wherein the pharmaceutical composition is suitable for administration by inhalation.

200. The composition according to item 196, wherein the pharmaceutical composition is suitable for parenteral administration.

201. The composition according to item 200, wherein the pharmaceutical composition is suitable for intravenous, intraarterial, intraperitoneal, intramuscular, subcutaneous, rectal or vaginal administration.

202. The composition according to item 201, wherein the pharmaceutical composition is suitable for injection, preferably for intravenous or intraarterial injection or drip.

203. The composition according to any one of items 195 to 202 comprising at least one buffering agent.

204. The composition according to item 203, wherein the buffering agent is acetate, formate or citrate.

205. The composition according to item 204, wherein the buffering agent is acetate.

206. The composition according to item 204, wherein the buffering agent is formate.

207. The composition according to item 204, wherein the buffering agent is citrate.

208. The composition according to any one of items 195 to 207, wherein the pharmaceutical formulation comprises a surfactant.

209. The composition according to item 208, wherein the surfactant is selected from the list comprising pluronics, PEG, sorbitan esters, polysorbates, triton, tromethamine, lecithin, cholesterol and tyloxapal.

210. The composition according to item 209, wherein the surfactant is polysorbate.

211. The composition according to item 210, wherein the surfactant is polysorbate 20, polysorbate 40, polysorbate 60, polysorbate 80 or polysorbate 100.

212. The composition according to item 211, wherein the surfactant is polysorbate 20.

213. The composition according to item 211, wherein the surfactant is polysorbate 80.

214. The composition according to any one of items 195 to 213 comprising a stabilizing agent, optionally wherein the stabilizing agent is albumin.

215. A host cell comprising the nucleic acid according to any one of items 175 to 190, the vector according to item 191 or the vector system according to any one of items 191 to 193.

216. A method of making the interferon-associated antigen binding protein according to any one of items 1 to 174, comprising culturing the host cell according to item 215 and recovering said interferon-associated antigen binding protein.

217. A non-human transgenic animal or transgenic plant comprising the nucleic acid according to any one of items 175 to 190, the vector according to item 191 or the vector system according to any one of items 191 to 193, wherein the non-human transgenic animal or transgenic plant expresses said nucleic acid.

218. A method of making the interferon-associated antigen binding protein according to any one of items 1 to 174, comprising the step of isolating the interferon-associated antigen binding protein from the non-human transgenic animal or transgenic plant according to item 217.

219. The interferon-associated antigen binding protein according to any one of items 1 to 174, the nucleic acid according to any one of items 175 to 190, the vector according to item 191, the vector system according to any one of items 191 to 193 or the composition according to any one of items 195 to 214 for use as a medicament.

220. The interferon-associated antigen binding protein according to any one of items 1 to 174, the nucleic acid according to any one of items 175 to 190, the vector according to item 191, the vector system according to any one of items 191 to 193 or the composition according to any one of items 195 to 214 for use in treating hepatitis B virus (HBV) infection and/or for decreasing one or more symptoms of HBV infection in a patient.

221. The interferon-associated antigen binding protein, the nucleic acid, the vector, the vector system or the composition for the use of item 220, wherein treating hepatitis B virus (HBV) infection comprises decreasing one or more symptoms of HBV infection in the patient.

222. The interferon-associated antigen binding protein according to any one of items 1 to 174, the nucleic acid according to any one of items 175 to 190, the vector according to item 191, the vector system according to any one of items 191 to 193 or the composition according to any one of items 195 to 214 for use in reducing the HBV viral load in an HBV-infected cell culture or an HBV-infected patient compared to an untreated HBV-infected cell culture or to the same patient before treatment.

223. The interferon-associated antigen binding protein, the nucleic acid, the vector, the vector system or the composition for the use of item 222, wherein the HBV viral load is reduced by about 20%, 25%, 30%, 35%, 40%, 45%, 50%, 55%, 60%, 65%, 70%, 75%, 80%, 85%, 90%, 95%, or 100%.

224. The interferon-associated antigen binding protein, the nucleic acid, the vector, the vector system or the composition for the use of item 222 or 223, wherein the HBV viral load is determined by PCR or qRT-PCR.

225. The interferon-associated antigen binding protein according to any one of items 1 to 174, the nucleic acid according to any one of items 175 to 190, the vector according to item 191, the vector system according to any one of items 191 to 193 or the composition according to any one of items 195 to 214 for use in reducing the HBV viral titer in an HBV-infected cell culture or an HBV-infected patient compared to an untreated HBV-infected cell culture or to the same patient before treatment.

226. The interferon-associated antigen binding protein, the nucleic acid, the vector, the vector system or the composition for the use of item 225, wherein the HBV viral titer is reduced by about 20%, 25%, 30%, 35%, 40%, 45%, 50%, 55%, 60%, 65%, 70%, 75%, 80%, 85%, 90%, 95%, or 100%.

227. The interferon-associated antigen binding protein, the nucleic acid, the vector, the vector system or the composition for the use of item 225 or 226, wherein the HBV viral titer is determined by PCR or qRT-PCR.

228. The interferon-associated antigen binding protein according to any one of items 1 to 174, the nucleic acid according to any one of items 175 to 190, the vector according to item 191, the vector system according to any one of items 191 to 193 or the composition according to any one of items 195 to 214 for use in reducing transcription of HBV cccDNA in an HBV-infected cell culture or an HBV-infected patient compared to an untreated HBV-infected cell culture or to the same patient before treatment.

229. The interferon-associated antigen binding protein, the nucleic acid, the vector, the vector system or the composition for the use of item 228, wherein transcription of cccDNA is reduced by about 20%, 25%, 30%, 35%, 40%, 45%, 50%, 55%, 60%, 65%, 70%, 75%, 80%, 85%, 90%, 95%, or 100%.

230. The interferon-associated antigen binding protein, the nucleic acid, the vector, the vector system or the composition for the use of item 228 or 229, wherein cccDNA transcription is determined by qPCR.

231. The interferon-associated antigen binding protein according to any one of items 1 to 174, the nucleic acid according to any one of items 175 to 190, the vector according to item 191, the vector system according to any one of items 191 to 193 or the composition according to any one of items 195 to 214 for use in reducing the level of pre-genomic HBV RNA in an HBV-infected cell culture or an HBV-infected patient compared to an untreated HBV-infected cell culture or to the same patient before treatment.

232. The interferon-associated antigen binding protein, the nucleic acid, the vector, the vector system or the composition for the use of item 231, wherein the level of pre-genomic HBV RNA is reduced by about 20%, 25%, 30%, 35%, 40%, 45%, 50%, 55%, 60%, 65%, 70%, 75%, 80%, 85%, 90%, 95%, or 100%.

233. The interferon-associated antigen binding protein, the nucleic acid, the vector, the vector system or the composition for the use of item 231 or 232, wherein the level of pre-genomic HBV RNA is determined by qRT-PCR.

TABLE 9a

| | | IFN-β-based IFAs | | | | | | | |
|---|---|---|---|---|---|---|---|---|---|
| | | IFN-γ | IL10 | IL12p40 | IL1β | IL2 | IL6 | IP10 | TFNα |
| NT | donor 1 | nd | nd | nd | nd | nd | nd | 457.0 | nd |
| | donor 2 | nd | nd | 101.4 | nd | nd | nd | 672.7 | 4.6 |
| | donor 3 | nd | nd | nd | nd | nd | nd | 302.3 | nd |
| | donor 4 | nd | nd | 104.0 | nd | nd | nd | 648.2 | nd |
| LP9 | donor 1 | 2023.0 | 148.0 | 7757.1 | 5116.0 | nd | 20709.6 | 6646.7 | 1706.3 |
| | donor 2 | 4675.6 | 57.2 | 6265.6 | 6263.7 | 20.7 | 11070.1 | 39539.4 | 2987.1 |
| | donor 3 | 1537.3 | 192.9 | 1750.0 | 3137.6 | nd | 16837.7 | 6141.0 | 944.9 |
| | donor 4 | 2360.7 | 299.7 | 1676.5 | 6423.0 | 18.6 | 20654.0 | 22848.2 | 1107.2 |
| IFA1 | donor 1 | 98.1 | nd | nd | nd | nd | 16.3 | 46033.6 | 43.7 |
| | donor 2 | nd | nd | 118.8 | nd | nd | 11.8 | 43545.5 | 36.6 |
| | donor 3 | nd | nd | nd | nd | nd | nd | 23562.1 | 34.0 |
| | donor 4 | nd | nd | nd | nd | nd | nd | 31922.5 | 57.1 |

TABLE 9a-continued

| | | IFN-β-based IFAs | | | | | | | |
|---|---|---|---|---|---|---|---|---|---|
| | | IFN-γ | IL10 | IL12p40 | IL1β | IL2 | IL6 | IP10 | TFNα |
| IFA2 | donor 1 | nd | nd | nd | nd | nd | 18.6 | 43382.3 | 41.0 |
| | donor 2 | nd | nd | 114.2 | nd | nd | 17.4 | 43283.4 | 33.8 |
| | donor 3 | nd | nd | nd | nd | nd | nd | 25961.4 | 32.2 |
| | donor 4 | 109.4 | nd | nd | nd | nd | nd | 38445.0 | 66.0 |

TABLE 9b

| | | IFN-α-based IFAs | | | | | | | |
|---|---|---|---|---|---|---|---|---|---|
| | | IFN-γ | IL10 | IL12p40 | IL1β | IL2 | IL6 | IP10 | TFNα |
| NT | donor 5 | 12.6 | 0.6 | 91.6 | 0.9 | 0.9 | 3.9 | 270.3 | 2.1 |
| | donor 6 | 5.0 | 1.1 | 129.9 | 19.9 | #DIV/0! | 423.2 | 1052.7 | 16.0 |
| | donor 7 | 16.5 | 2.0 | 143.7 | 22.1 | 2.1 | 426.9 | 1025.0 | 12.6 |
| | donor 8 | 9.7 | 0.1 | 58.3 | 1.8 | #DIV/0! | 2.6 | 594.2 | 2.2 |
| LPS | donor 5 | 10848.1 | 46.6 | 8463.3 | 8712.3 | 10.5 | 30713.2 | 20538.9 | 1738.3 |
| | donor 6 | 2467.1 | 175.6 | 5364.9 | 6557.9 | 3.3 | 31735.5 | 17262.6 | 2583.3 |
| | donor 7 | 3310.1 | 248.6 | 6814.8 | 9123.9 | 16.6 | 39139.8 | 59939.2 | 6270.1 |
| | donor 8 | 2555.6 | 138.5 | 2942.9 | 6767.5 | 9.6 | 31756.7 | 20062.7 | 1265.5 |
| IFA25 | donor 5 | 495.5 | 1.5 | 99.5 | 1.9 | 5.5 | 30.5 | 39637.5 | 30.4 |
| | donor 6 | 312.2 | 2.0 | 129.8 | 16.5 | 4.0 | 51.8 | 61963.8 | 71.4 |
| | donor 7 | 271.2 | 2.9 | 130.3 | 9.1 | 4.4 | 75.0 | 133442.5 | 30.3 |
| | donor 8 | 441.6 | 1.9 | 74.8 | 6.8 | 3.2 | 44.3 | 95647.9 | 87.4 |
| IFA26 | donor 5 | 330.4 | 2.0 | 98.1 | 2.1 | 6.4 | 29.3 | 37880.2 | 32.1 |
| | donor 6 | 303.7 | 3.3 | 150.8 | 17.1 | 3.1 | 53.0 | 72944.8 | 45.7 |
| | donor 7 | 180.3 | 2.0 | 135.6 | 9.2 | 4.9 | 75.2 | 154696.3 | 29.7 |
| | donor 8 | 421.4 | 2.8 | 95.7 | 6.8 | 4.1 | 42.1 | 79768.5 | 89.1 |
| IFA27 | donor 5 | 430.7 | 2.2 | 127.8 | 3.1 | 7.1 | 32.9 | 40214.1 | 61.3 |
| | donor 6 | 286.5 | 2.0 | 148.5 | 16.8 | 2.1 | 66.0 | 83445.0 | 70.1 |
| | donor 7 | 350.3 | 4.7 | 117.6 | 9.3 | 4.4 | 73.5 | 195844.6 | 105.6 |
| | donor 8 | 440.1 | 2.6 | 68.6 | 8.9 | 0.6 | 46.9 | 102676.8 | 43.4 |
| IFA28 | donor 5 | 620.1 | 2.7 | 127.3 | 3.4 | 8.7 | 35.0 | 40958.5 | 24.6 |
| | donor 6 | 264.7 | 2.0 | 170.3 | 13.6 | 2.4 | 45.7 | 62333.3 | 33.0 |
| | donor 7 | 289.6 | 2.7 | 144.4 | 13.7 | 3.9 | 77.1 | 176521.8 | 59.6 |
| | donor 8 | 436.2 | 2.5 | 74.4 | 4.9 | 2.3 | 36.8 | 79217.6 | 37.6 |
| IFA29 | donor 5 | 692.7 | 1.3 | 108.7 | 2.3 | 3.7 | 33.9 | 55062.8 | 30.3 |
| | donor 6 | 183.1 | 2.2 | 158.8 | 11.6 | 0.4 | 44.4 | 58665.4 | 44.3 |
| | donor 7 | 235.5 | 2.6 | 127.6 | 9.6 | 2.0 | 65.6 | 136893.2 | 90.5 |
| | donor 8 | 301.1 | 3.0 | 77.7 | 5.8 | 0.6 | 33.8 | 69226.3 | 48.0 |
| IFA30 | donor 5 | 709.7 | 1.2 | 110.6 | 2.9 | 5.5 | 38.0 | 63040.7 | 36.5 |
| | donor 6 | 122.9 | 2.0 | 153.0 | 14.9 | 1.7 | 46.1 | 67861.2 | 37.4 |
| | donor 7 | 64.6 | 1.0 | 114.0 | 10.0 | 2.9 | 75.5 | 149093.0 | 32.7 |
| | donor 8 | 206.0 | 1.9 | 71.1 | 6.8 | 1.8 | 37.9 | 85986.9 | 40.5 |

TABLE 10A

| Matrix | Compound | Dose In-life period | Method | C0 (μg/mL) | AUC (0-last) (μg·h/mL) | $T_{last}$ (h) | AUC (0-inf) (μg·h/mL) | % Extrapolation | $T_{1/2t}$ (h) | CI (mL/hr/kg) | $V_D$ (mL/kg) |
|---|---|---|---|---|---|---|---|---|---|---|---|
| Serum | CP870,893 | 0.5 mg/kg 168 h | ELISA-IgG2 | 7.15 | 241 | 168 | 590 | 59 | 264 (long) | 0.35 (Low) | 296 (Low) |
| Serum | IFA27 | 0.5 mg/kg 240 h | ELISA-IgG2 | 14.7 | 1501 | 240 | 2552 | 41 | 218 (long) | 0.20 (Low) | 55 (Low) |
| Serum | IFA27 | 0.5 mg/kg 240 h | ELISA-IFN | 16.9 | 1318 | 240 | 1793 | 26 | 125 (long) | 0.28 (Low) | 50 (Low) |
| Serum | IFA29 | 0.5 mg/kg 240 h | ELISA-IFN | 11.6 | 804 | 240 | 1033 | 22 | 116 (long) | 0.49 (Low) | 78 (Low) |
| Serum | IFA30 | 0.5 mg/kg 240 h | ELISA-IFN | 8.12 | 741 | 240 | 1089 | 31 | 158 (long) | 0.46 (Low) | 98 (Low) |

TABLE 10B

| Matrix | Compound | Dose In-life period | Method | C0 (μg/mL) | AUC (0-last) (μg·h/mL) | T$_{last}$ (h) | AUC (0-inf) (μg·h/mL) | % Extrapolation | T$_{1/2t}$ (h) | Cl (mL/hr/kg) | V$_D$ (mL/kg) |
|---|---|---|---|---|---|---|---|---|---|---|---|
| Serum | IFA25 | 0.5 mg/kg 504 h | ELISA-IFN | 7.45 | 1328 | 504 | 1500 | 11 | 154 (long) | 0.34 (Low) | 73 (Low) |
| Serum | IFA26 | 0.5 mg/kg 504 h | ELISA-IFN | 8.20 | 988 | 336 | 1027 | 3.8 | 59 (long) | 0.49 (Low) | 57 (Low) |
| Serum | IFA28 | 0.5 mg/kg 504 h | ELISA-IFN | 9.38 | 1048 | 504 | 1264 | 17 | 213 (long) | 0.40 (Low) | 105 (Low) |
| Serum | Pegasys | 0.3 mg/kg 504 h | ELISA-IFNa specific | 8.3 | 210 | 168 | 215 | 2 | 30 (moderate) | 1.4 (Low) | 62 (Low) |
| Serum | CP870,893 | 0.5 mg/kg 504 h | ELISA-IgG2 | 11.9 | 527 | 168 | 797 | 34 | 116 (long) | 0.63 (Low) | 96 (Low) |
| Serum | IFA25 | 0.5 mg/kg 504 h | ELISA-IgG2 | 11.8 | 1292 | 240 | 1971 | 34 | 155 (long) | 0.26 (Low) | 56 (Low) |

The invention claimed is:

1. A pharmaceutical composition comprising an interferon-associated antigen binding protein comprising:
   (I) an agonistic anti-CD40 antibody or an agonistic antigen binding fragment thereof, fused to (II) an Interferon-α2a (IFNα2a) or a functional fragment thereof, optionally fused via a linker, wherein the functional fragment mediates interferon pathway signaling,
   wherein the agonistic anti-CD40 antibody, or the agonistic antigen binding fragment thereof, comprises a heavy chain or a fragment thereof and a light chain or a fragment thereof,
   wherein the heavy chain or the fragment thereof comprises a complementarity determining region 1 (CDRH1) comprising the amino acid sequence of SEQ ID NO: 56; a complementarity determining region 2 (CDRH2) comprising the amino acid sequence of SEQ ID NO: 57; and a complementarity determining region 3 (CDRH3) comprising the amino acid sequence of SEQ ID NO: 58; and
   wherein the light chain or the fragment thereof comprises a complementarity determining region 1 (CDRL1) comprising the amino acid sequence of SEQ ID NO: 52; a complementarity determining region 2 (CDRL2) comprising the amino acid sequence of SEQ ID NO: 53; and a complementarity determining region 3 (CDRL3) comprising the amino acid sequence of SEQ ID NO: 54.

2. The pharmaceutical composition of claim 1, wherein the heavy chain or the fragment thereof comprises a heavy chain variable domain comprising the amino acid sequence of SEQ ID NO: 55 and the light chain or the fragment thereof comprises a light chain variable domain comprising the amino acid sequence of SEQ ID NO: 51.

3. The pharmaceutical composition of claim 1, wherein the heavy chain comprises the amino acid sequence of SEQ ID NO: 6 and the light chain comprises the amino acid sequence of SEQ ID NO: 3.

4. The pharmaceutical composition of claim 1, wherein the agonistic anti-CD40 antibody, or the agonistic antigen binding fragment thereof, comprises a Fab region heavy chain comprising the amino acid sequence of SEQ ID NO: 12.

5. The pharmaceutical composition of claim 1, wherein the IFNα2a or the functional fragment thereof is fused to the light chain or the fragment thereof of the agonistic anti-CD40 antibody or the agonistic antigen binding fragment thereof, optionally via a linker.

6. The pharmaceutical composition of claim 1, wherein the IFNα2a or the functional fragment thereof is fused to a C-terminus of the light chain or the fragment thereof of the agonistic anti-CD40 antibody or the agonistic antigen binding fragment thereof, optionally via a linker.

7. The pharmaceutical composition of claim 1, wherein the IFNα2a or the functional fragment thereof is fused to the heavy chain or the fragment thereof of the agonistic anti-CD40 antibody or the agonistic antigen binding fragment thereof, optionally via a linker.

8. The pharmaceutical composition of claim 1, wherein the IFNα2a or the functional fragment thereof is fused to a C-terminus of the heavy chain or the fragment thereof of the agonistic anti-CD40 antibody or the agonistic antigen binding fragment thereof, optionally via a linker.

9. The pharmaceutical composition of claim 1, wherein the agonistic anti-CD40 antibody or the agonistic antigen binding fragment thereof is fused to the IFNα2a or the functional fragment thereof via a linker.

10. The pharmaceutical composition of claim 9, wherein the linker comprises the amino acid sequence of SEQ ID NO: 24, SEQ ID NO: 25 or SEQ ID NO: 26.

11. The pharmaceutical composition of claim 1, wherein the IFNα2a comprises the amino acid sequence of SEQ ID NO: 17 or an amino acid sequence having at least 90% identity to SEQ ID NO: 17.

12. The pharmaceutical composition of claim 1, wherein the composition comprises an amount of the interferon-associated binding protein sufficient to mediate a reduction of HBV e-antigen (HBeAg) release from an HBV-infected primary human hepatocyte and/or a reduction of pre-genomic RNA (pgRNA) transcription in an HBV-infected primary human hepatocyte.

13. A pharmaceutical composition comprising an interferon-associated antigen binding protein comprising:
   (I) an agonistic anti-CD40 antibody comprising a heavy chain and a light chain, and (II) an Interferon-α2a (IFNα2a) or a functional fragment thereof, wherein the functional fragment mediates interferon pathway signaling,
   wherein the light chain comprises the amino acid sequence of SEQ ID NO: 3 and the heavy chain comprises the amino acid sequence of SEQ ID NO: 6, wherein the IFNα2a or the functional fragment thereof is fused to the C-terminus of the heavy chain via a linker, wherein the linker comprises the amino acid sequence of SEQ ID NO: 24 or SEQ ID NO: 26.

14. The pharmaceutical composition of claim 13, wherein the linker comprises the amino acid sequence of SEQ ID NO: 24.

15. The pharmaceutical composition of claim 13, wherein the linker comprises the amino acid sequence of SEQ ID NO: 26.

16. The pharmaceutical composition of claim 14, wherein the IFNα2a or the functional fragment thereof comprises the amino acid sequence of SEQ ID NO: 17 or an amino acid sequence having at least 90% identity to SEQ ID NO: 17.

17. The pharmaceutical composition of claim 15, wherein the IFNα2a or the functional fragment thereof comprises the amino acid sequence of SEQ ID NO: 17 or an amino acid sequence having at least 90% identity to SEQ ID NO: 17.

18. The pharmaceutical composition of claim 13, wherein the fusion of the IFNα2a to the C-terminus of the heavy chain via the linker comprises the amino acid sequence of SEQ ID NO: 38.

19. The pharmaceutical composition of claim 13, wherein the fusion of the IFNα2a to the C-terminus of the heavy chain via the linker comprises the amino acid sequence of SEQ ID NO: 40.

20. The pharmaceutical composition of claim 13, wherein the composition comprises an amount of the interferon-associated binding protein sufficient to mediate a reduction of HBV e-antigen (HBeAg) release from an HBV-infected cell and/or a reduction of pre-genomic RNA (pgRNA) transcription in an HBV-infected cell.

21. The pharmaceutical composition of claim 13, wherein the interferon-associated binding protein demonstrates a potency on an HBV infection of primary human hepatocytes in vitro with $EC_{50}$ values ranging from 0.06 ng/mL to 0.16 ng/mL.

22. A method for treating hepatitis B virus (HBV) infection and/or reducing one or more symptoms of HBV infection in an HBV-infected subject comprising:
   administering an effective amount of the pharmaceutical composition of claim 1.

23. A method for treating hepatitis B virus (HBV) infection and/or reducing one or more symptoms of HBV infection in an HBV-infected subject, comprising administering an effective amount of the pharmaceutical composition of claim 14.

24. A method for treating hepatitis B virus (HBV) infection and/or reducing one or more symptoms of HBV infection in an HBV-infected subject, comprising administering an effective amount of the pharmaceutical composition of claim 15.

25. A method for treating hepatitis B virus (HBV) infection and/or reducing one or more symptoms of HBV infection in an HBV-infected subject, comprising administering an effective amount of the pharmaceutical composition of claim 18.

26. A method for treating hepatitis B virus (HBV) infection and/or reducing one or more symptoms of HBV infection in an HBV-infected subject, comprising administering an effective amount of the pharmaceutical composition of claim 19.

27. The method of claim 22, wherein the one or more symptoms of HBV infection are associated with chronic inflammation of the liver, hepatocellular carcinoma, development of membranous glomerulonephritis, risk of death, acute necrotizing vasculitis, papular acrodermatitis of childhood, HBV-associated nephropathy, and/or immune-mediated hematological disorders.

28. The method of claim 22, wherein the one or more symptoms of HBV infection are associated with acute viral hepatitis.

29. The method of claim 28, wherein the one or more symptoms of HBV infection associated with acute viral hepatitis symptoms comprise a loss of appetite, nausea, vomiting, body aches, dark urine, jaundice, fulminant hepatic failure, low-grade fever, stomach pain, and/or bloated stomach.

30. The method of claim 25, wherein the subject is a human.

31. The method of claim 26, wherein the subject is a human.

* * * * *